(12) United States Patent
Liu et al.

(10) Patent No.: US 8,685,969 B2
(45) Date of Patent: Apr. 1, 2014

(54) CARBOLINE CARBOXAMIDE COMPOUNDS USEFUL AS KINASE INHIBITORS

(75) Inventors: Chunjian Liu, Pennington, NJ (US); James Lin, Lawrenceville, NJ (US); George V. DeLucca, Pennington, NJ (US); Douglas G. Batt, Wilmington, DE (US); Qingjie Liu, Newtown, PA (US)

(73) Assignee: Bristol-Myers Squibb Company, Princeton, NJ (US)

( * ) Notice: Subject to any disclaimer, the term of this patent is extended or adjusted under 35 U.S.C. 154(b) by 0 days.

(21) Appl. No.: 13/704,297

(22) PCT Filed: Jun. 16, 2011

(86) PCT No.: PCT/US2011/040615
§ 371 (c)(1),
(2), (4) Date: Dec. 14, 2012

(87) PCT Pub. No.: WO2011/159857
PCT Pub. Date: Dec. 22, 2011

(65) Prior Publication Data
US 2013/0096118 A1    Apr. 18, 2013

Related U.S. Application Data

(60) Provisional application No. 61/355,275, filed on Jun. 16, 2010.

(51) Int. Cl.
*C07D 471/04* (2006.01)
*C07D 487/04* (2006.01)

(52) U.S. Cl.
USPC .......... 514/234.5; 514/232.8; 514/235.2; 514/248; 514/256; 514/264.1; 514/266.21; 514/266.22; 514/269; 514/292; 544/119; 544/126; 544/234; 544/279; 544/298; 544/333; 546/87

(58) Field of Classification Search
None
See application file for complete search history.

(56) References Cited

U.S. PATENT DOCUMENTS

| 2002/0099068 A1 | 7/2002 | Ritzeler et al. |
| 2006/0084650 A1 | 4/2006 | Dong et al. |
| 2009/0163545 A1 | 6/2009 | Goldfarb |

FOREIGN PATENT DOCUMENTS

| WO | WO 03/030901 | 4/2003 |
| WO | WO 2005/005429 | 1/2005 |
| WO | WO 2005/014599 | 2/2005 |
| WO | WO 2005/047290 | 5/2005 |
| WO | WO 2006/034317 | 3/2006 |
| WO | WO 2006/053121 | 5/2006 |
| WO | WO 2006/099075 | 9/2006 |
| WO | WO 2007/038314 | 4/2007 |
| WO | WO 2007/061764 | 5/2007 |
| WO | WO 2008/033858 | 3/2008 |
| WO | WO 2010/080481 | 7/2010 |

OTHER PUBLICATIONS

International Search Report issued Dec. 19, 2012.
Janetka, J.W., "Checkpoint kinase inhibitors: a review of the patent literature," Expert Opin Ther. Patents, vol. 19, No. 2, pp. 165-197 (2009).
Chemical Journal of Chinese Universities, vol. 19, No. 12, pp. 1964-1969 (1998)—No English Translation.
Sun, Hai-Ying, et al., "Synthesis and properties of new dibenzocyclobromonium salts," Gaodeng Xuexiao Huaxue Xuebao, vol. 19, No. 12, (1998).

*Primary Examiner* — Janet L Andres
*Assistant Examiner* — Timothy R Rozof
(74) *Attorney, Agent, or Firm* — Hong Liu; Mark K. VanAtten; Gary D. Greenblatt

(57) ABSTRACT

Compounds having formula (I), and enantiomers, and diastereomers, stereoisomers, pharmaceutically-acceptable salts thereof, formula (I) are useful as kinase modulators, including Btk modulation.

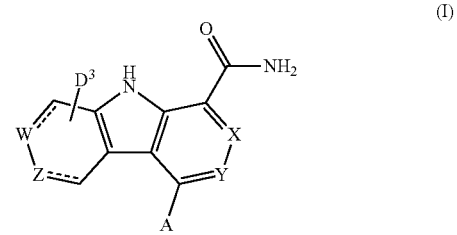

15 Claims, No Drawings

CARBOLINE CARBOXAMIDE COMPOUNDS USEFUL AS KINASE INHIBITORS

CROSS-REFERENCE TO RELATED APPLICATIONS

This application claims the benefit of U.S. Provisional Application Ser. No. 61/355,275, filed Jun. 16, 2010, which is incorporated herein in its entirety.

FIELD OF THE INVENTION

This invention relates to carboline carboxamide compounds useful as kinase inhibitors, including the modulation of Bruton's tyrosine kinase (Btk) and other Tec family kinases such as Itk. Provided herein are carboline carboxamide compounds, compositions comprising such compounds, and methods of their use. The invention further pertains to pharmaceutical compositions containing at least one compound according to the invention that are useful for the treatment of conditions related to kinase modulation and methods of inhibiting the activity of kinases, including Btk and other Tec family kinases such as Itk, in a mammal.

BACKGROUND OF THE INVENTION

Protein kinases, the largest family of human enzymes, encompass well over 500 proteins. Btk is a member of the Tec family of tyrosine kinases, and is a regulator of early B-cell development, as well as mature B-cell activation, signaling and survival.

B-cell signaling through the B-cell receptor (BCR) leads to a wide range of biological outputs, which in turn depend on the developmental stage of the B-cell. The magnitude and duration of BCR signals must be precisely regulated. Aberrant BCR-mediated signaling can cause disregulated B-cell activation and/or the formation of pathogenic auto-antibodies leading to multiple autoimmune and/or inflammatory diseases. Mutation of Btk in humans results in X-linked agammaglobulinaemia (XLA). This disease is associated with the impaired maturation of B-cells, diminished immunoglobulin production, compromised T-cell-independent immune responses and marked attenuation of the sustained calcium signal upon BCR stimulation.

Evidence for the role of Btk in allergic disorders and/or autoimmune disease and/or inflammatory disease has been established in Btk-deficient mouse models. For example, in standard murine preclinical models of systemic lupus erythematosus (SLE), Btk deficiency has been shown to result in a marked amelioration of disease progression. Moreover, Btk deficient mice are also resistant to developing collagen-induced arthritis and are less susceptible to Staphylococcus-induced arthritis.

A large body of evidence supports the role of B-cells and the humoral immune system in the pathogenesis of autoimmune and/or inflammatory diseases. Protein-based therapeutics (such as RITUXAN®) developed to deplete B-cells, represent an important approach to the treatment of a number of autoimmune and/or inflammatory diseases. Because of Btk's role in B-cell activation, inhibitors of Btk can be useful as inhibitors of B-cell mediated pathogenic activity (such as autoantibody production).

Btk is also expressed in mast cells and monocytes and has been shown to be important for the function of these cells. For example, Btk deficiency in mice is associated with impaired IgE-mediated mast cell activation (marked diminution of TNF-alpha and other inflammatory cytokine release), and Btk deficiency in humans is associated with greatly reduced TNF-alpha production by activated monocytes.

Thus, inhibition of Btk activity can be useful for the treatment of allergic disorders and/or autoimmune and/or inflammatory diseases including, but not limited to: SLE, rheumatoid arthritis, multiple vasculitides, idiopathic thrombocytopenic purpura (ITP), myasthenia gravis, allergic rhinitis, multiple sclerosis (MS), transplant rejection, type I diabetes, membranous nephritis, inflammatory bowel disease, autoimmune hemolytic anemia, autoimmune thyroiditis, cold and warm agglutinin diseases, Evan's syndrome, hemolytic uremic syndrome/thrombotic thrombocytopenic purpura (HUS/TTP), sarcoidosis, Sjögren's syndrome, peripheral neuropathies (e.g., Guillain-Barre syndrome), pemphigus vulgaris, and asthma.

In addition, Btk has been reported to play a role in controlling B-cell survival in certain B-cell cancers. For example, Btk has been shown to be important for the survival of BCR-Abl-positive B-cell acute lymphoblastic leukemia cells. Thus inhibition of Btk activity can be useful for the treatment of B-cell lymphoma and leukemia.

In view of the numerous conditions that are contemplated to benefit by treatment involving modulation of protein kinases, it is immediately apparent that new compounds capable of modulating protein kinases such as Btk and methods of using these compounds should provide substantial therapeutic benefits to a wide variety of patients.

Inhibitors of protein kinases are widely sought and a number of publications report compounds effective in modulating protein kinases. For example, patent publications WO 2005/047290, WO 2005/014599, WO 2005/005429, WO 2006/099075, WO 2006/053121, and US 2006/0183746 disclose certain imidazopyrazine compounds that are said to inhibit protein kinase activity, including Btk activity. Patent publication WO 2008/033858 discloses methods of inhibiting Btk activity with various Btk binding chemical compounds. Patent publication US 2006/0084650 discloses that fused heterocyclic compounds exemplified by imidazopyrimidines and pyrrolotriazines may be used as protein kinase inhibitors. In addition, new imidazopyridazine and imidazotriazine compounds are disclosed in WO 2007/038314 (published Apr. 5, 2007) and WO 2008/0045536 (published Feb. 21, 2008), both of which are assigned to the present assignee. Also assigned to the present assignee, WO 2010/080481 (published Jul. 15, 2010) discloses certain carbazole carboxamides useful as Btk inhibitors.

The present invention relates to a new class of substituted carboline carboxamide compounds found to be effective inhibitors of protein kinases including Btk and other Tec family kinases such as Itk.

SUMMARY OF THE INVENTION

Modulators of kinase activity which may generally be described as substituted β-carboline carboxamides, γ-aza-β-carboline carboxamides, and related compounds are provided herein.

The invention is directed to compounds of Formula (I), or stereoisomers, tautomers, pharmaceutically acceptable salts, solvates or prodrugs thereof, useful as inhibitors of Btk in the treatment of proliferative diseases, allergic diseases, autoimmune diseases and inflammatory diseases.

The present invention also provides processes and intermediates for making the compounds of the present invention or stereoisomers, tautomers, pharmaceutically acceptable salts, solvates, or prodrugs thereof.

The present invention also provides pharmaceutical compositions comprising a pharmaceutically acceptable carrier and at least one of the compounds of the present invention or stereoisomers, tautomers, pharmaceutically acceptable salts, solvates, or prodrugs thereof.

The present invention also provides methods for inhibition of Btk comprising administering to a host in need of such treatment a therapeutically effective amount of at least one of the compounds of the present invention or stereoisomers, tautomers, pharmaceutically acceptable salts, solvates, or prodrugs thereof.

The present invention also provides methods for treating proliferative diseases, allergic diseases, autoimmune diseases and inflammatory diseases, comprising administering to a host in need of such treatment a therapeutically effective amount of at least one of the compounds of the present invention or stereoisomers, tautomers, pharmaceutically acceptable salts, solvates, or prodrugs thereof.

The present invention also provides the compounds of the present invention or stereoisomers, tautomers, pharmaceutically acceptable salts, solvates, or prodrugs thereof, for use in therapy.

The present invention also provides the use of the compounds of the present invention or stereoisomers, tautomers, pharmaceutically acceptable salts, solvates, or prodrugs thereof, for the manufacture of a medicament for the treatment of cancers.

These and other features of the invention will be set forth in the expanded form as the disclosure continues.

DETAILED DESCRIPTION OF EMBODIMENTS OF THE INVENTION

Provided herein is at least one chemical entity chosen from compounds of formula (I):

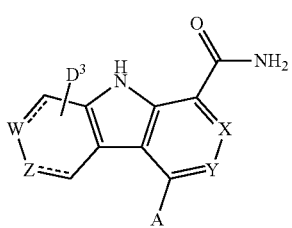

or enantiomers, diastereomers, stereoisomers, prodrugs, or pharmaceutically-acceptable salts thereof, wherein X is $CR^3$ or N;
Y is $CR^3$ or N;
Z is $CD^1$ or N;
W is $CD^2$ or N;
— is an optional bond; provided when the two optional bonds are absent, Z is $CHD^1$, W is $ND^2$ or Z is $ND^1$, W is $CHD^2$;

A is $C_{3-10}$ carbocycle substituted with 0-3 B, $C_{6-10}$ mono- or bicyclic aryl substituted with 0-3 B, a 5-14 membered heterocyclyl containing 1-4 heteroatoms selected from N, O, and S, substituted with 0-3 B, a 5-10 membered heteroaryl containing 1-4 heteroatoms selected from N, O, and S, substituted with 0-3 B;

B is $R^1$, halogen, cyano, nitro, $-OR^1$, $-C(=O)R^1$, $-C(=O)OR^1$, $-C(=O)NR^{11}R^1$, $-S(=O)_2R^1$, $-NR^{11}C(=O)R^1$, $-NR^{11}C(=O)NR^{11}R^1$, $-NR^{11}C(=O)OR^1$, $-N(C(=O)OR^1)_2$, $-NR^{11}S(=O)_2R^1$, $-N(S(=O)_2R^1)_2$, or $-NR^{11}R^1$;

$R^1$ is hydrogen, $C_{1-6}$ alkyl substituted with 0-3 $R^{1a}$, $C_{1-6}$ haloalkyl, $C_{2-6}$ alkenyl substituted with 0-3 $R^{1a}$, $C_{2-6}$ alkynyl substituted with 0-3 $R^{1a}$, $C_{3-10}$ cycloalkyl substituted with 0-3 $R^{1a}$, $C_{6-10}$ aryl substituted with 0-3 $R^{1a}$, a 5-10 membered heterocyclyl containing 1-4 heteroatoms selected from N, O, and S, substituted with 0-3 $R^{1a}$, a 5-10 membered heteroaryl containing 1-4 heteroatoms selected from N, O, and S, substituted with 0-3 $R^{1a}$;

$R^{1a}$ is hydrogen, =O, F, Cl, Br, $OCF_3$, $CF_3$, $CHF_2$, CN, $NO_2$, $-(CH_2)_rOR^b$, $-(CH_2)_rSR^b$, $-(CH_2)_rC(O)R^b$, $-(CH_2)_rC(O)OR^b$, $-(CH_2)_rOC(O)R^b$, $-(CH_2)_rNR^{11}R^{11}$, $-(CH_2)_rC(O)NR^{11}R^{11}$, $-(CH_2)_rNR^bC(O)R^c$, $-(CH_2)_rNR^bC(O)OR^c$, $-NR^bC(O)NR^{11}R^{11}$, $-S(O)_pNR^{11}R^{11}$, $-NR^bS(O)_pR^c$, $-S(O)R^c$, $-S(O)_2R^c$, $C_{1-6}$ alkyl substituted with 0-2 $R^a$, $C_{1-6}$ haloalkyl, $-(CH_2)_r$-3-14 membered carbocycle substituted with 0-1 $R^a$, or $-(CH_2)_r$-5-7 membered heterocycle comprising carbon atoms and 1-4 heteroatoms selected from N, O, and $S(O)_p$ substituted with 0-1 $R^a$;

$D^1$ and $D^2$ are independently $R^2$, halogen, $-(C(R^{11})_2)_rR^2$, $-OR^2$, $-C(=O)R^2$, $-C(=O)OR^2$, $-C(=O)NR^{11}R^2$, $-S(=O)_2R^2$, $-S(=O)R^2$, $-SR^2$, $-NR^{11}C(=O)R^2$, $-NR^{11}C(=O)NR^{11}R^2$, $-NR^{11}C(=O)OR^2$, $-NR^{11}S(=O)_2R^2$, $-NR^{11}R^2$, $-C(=O)NR^{11}OR^2$, $-OC(=O)OR^2$, $-O^1C(=O)R^2$, or CH=N—OH; alternatively $D^1$ and $D^2$ join to form $-O-CH_2-O-$;

$D^3$ is hydrogen, halogen, $C_{1-3}$ alkyl, $C_{1-3}$ alkoxy, or CN;

$R^2$ is hydrogen, $C_{1-6}$ alkyl substituted with 0-3 $R^{2a}$, $C_{2-6}$ alkenyl substituted with 0-3 $R^{2a}$, $C_{2-6}$ alkynyl substituted with 0-3 $R^{2a}$, $C_{3-10}$ cycloalkyl substituted with 0-3 $R^{2a}$, $C_{6-10}$ aryl substituted with 0-3 $R^{2a}$, a 5-10 membered heterocyclyl containing 1-4 heteroatoms selected from N, O, and S, substituted with 0-3 $R^{2a}$, a 5-10 membered heteroaryl containing 1-4 heteroatoms selected from N, O, and S, substituted with 0-3 $R^{2a}$;

$R^{2a}$ is hydrogen, =O, F, Cl, Br, $OCF_3$, CN, $NO_2$, $-(CH_2)_rOR^b$, $-(CH_2)_rSR^b$, $-(CH_2)_rC(O)R^b$, $-(CH_2)_rC(O)OR^b$, $-(CH_2)_rOC(O)R^b$, $-(CH_2)_rNR^{11}R^{11}$, $-(CH_2)_rC(O)NR^{11}R^{11}$, $-(CH_2)_rNR^bC(O)R^c$, $-(CH_2)_rNR^bC(O)OR^c$, $-NR^bC(O)NR^{11}R^{11}$, $-S(O)_pNR^{11}R^{11}$, $-NR^bS(O)_pR^c$, $-S(O)R^c$, $-S(O)_2R^c$, $C_{1-6}$ alkyl substituted with 0-2 $R^a$, $C_{1-6}$ haloalkyl, $-(CH_2)_r$-3-14 membered carbocycle substituted with 0-1 $R^a$, or $-(CH_2)_r$-5-7 membered heterocycle comprising carbon atoms and 1-4 heteroatoms selected from N, O, and $S(O)_p$ substituted with 0-2 $R^a$;

$R^{11}$ is independently hydrogen or $C_{1-4}$ alkyl substituted with 0-1 $R^f$, $CH_2$-phenyl, or $-(CH_2)_r$-5-7 membered heterocycle comprising carbon atoms and 1-4 heteroatoms selected from N, O, and $S(O)_p$;

alternatively, $R^{11}$ along with another $R^{11}$, $R^1$, or $R^2$ on the same nitrogen atom may join to form an optionally substituted azetidinyl, pyrrolidinyl, piperidinyl, morpholinyl, or 4-($C_{1-6}$ alkyl)piperazinyl;

$R^3$ is hydrogen or $C_{1-6}$ alkyl;

$R^a$ is hydrogen, F, Cl, Br, $OCF_3$, $CF_3$, $CHF_2$, CN, $NO_2$, $-(CH_2)_rOR^b$, $-(CH_2)_rSR^b$, $-(CH_2)_rC(O)R^b$, $-(CH_2)_rC(O)OR^b$, $-(CH_2)_rOC(O)R^b$, $-(CH_2)_rNR^{11}R^{11}$, $-(CH_2)_rC(O)NR^{11}R^{11}$, $-(CH_2)_rNR^bC(O)R^c$, $-(CH_2)_rNR^bC(O)OR^c$, $-NR^bC(O)NR^{11}R^{11}$, $-S(O)_pNR^{11}R^{11}$, $-NR^bS(O)_pR^c$, $-S(O)R^c$, $-S(O)_2R^c$, $C_{1-6}$ alkyl substituted with 0-1 $R^f$, $C_{1-6}$ haloalkyl, $-(CH_2)_r$-3-14 membered carbocycle, or $-(CH_2)_r$-5-7 membered heterocycle comprising carbon atoms and 1-4 heteroatoms selected from N, O, and $S(O)_p$, alternatively two $R^a$ on adjacent or the same carbon atom form a cyclic acetal of the formula $-O-(CH_2)_n-O-$, or $-O-CF_2-O-$, wherein n is selected from 1 or 2;

$R^b$ is hydrogen, $C_{1-6}$ alkyl substituted with 0-2 $R^d$, $C_{1-6}$ haloalkyl, $C_{3-6}$ cycloalkyl substituted with 0-2 $R^d$, or $(CH_2)_r$-phenyl substituted with 0-2 $R^d$;

$R^c$ is $C_{1-6}$ alkyl substituted with 0-1 $R^f$, $C_{3-6}$ cycloalkyl, or $(CH_2)_r$-phenyl substituted with 0-1 $R^f$;

$R^d$ is hydrogen, F, Cl, Br, $OCF_3$, $CF_3$, CN, $NO_2$, —$OR^e$, —$(CH_2)_rC(O)R^c$, —$NR^eR^e$, —$NR^eC(O)OR^c$, $C_{1-6}$ alkyl, or $(CH_2)_r$-phenyl;

$R^e$ is hydrogen, $C_{1-6}$ alkyl, $C_{3-6}$ cycloalkyl, or $(CH_2)_r$-phenyl;

$R^f$ is hydrogen, halo, $NH_2$, OH, or $OCH_3$;

r is 0, 1, 2, 3, or 4; and p is 0, 1, or 2.

In another embodiment there are provided compounds of formula (I), wherein $D^1$ and $D^2$ are independently $R^2$, —$(CH_2)_rR^2$, —$OR^2$, —$C(=O)R^2$, —$C(=O)OR^2$, —$C(=O)NR^{11}R^2$, —$S(=O)_2R^2$, —$S(=O)R^2$, $SR^2$, —$NR^{11}C(=O)R^2$, —$NR^{11}C(=O)NR^{11}R^2$, —$NR^{11}C(=O)OR^2$, —$NR^{11}S(=O)_2R^2$, or —$NR^{11}R^2$;

$R^2$ is hydrogen, $C_{1-6}$ alkyl substituted with 0-3 $R^{2a}$, $C_{2-6}$ alkenyl substituted with 0-3 $R^{2a}$, $C_{3-10}$ cycloalkyl substituted with 0-3 $R^{2a}$, —$C_{6-10}$ aryl substituted with 0-3 $R^{2a}$, a 5-10 membered heterocyclyl containing 1-4 heteroatoms selected from N, O, and S, substituted with 0-3 $R^{2a}$, a 5-10 membered heteroaryl containing 1-4 heteroatoms selected from N, O, and S, substituted with 0-3 $R^{2a}$;

$R^{2a}$ is hydrogen, =O, F, Cl, Br, $OCF_3$, $CF_3$, $CHF_2$, CN, $NO_2$, $OR^b$, $SR^b$, —$C(O)R^b$, —$C(O)OR^b$, —$OC(O)R^b$, —$NR^{11}R^{11}$, —$C(O)NR^{11}R^{11}$, —$NR^bC(=O)R^c$, —$NR^bC(O)OR^c$, —$NR^bC(O)NR^{11}R^{11}$, —$S(=O)_pNR^{11}R^{11}$, —$NR^bS(O)_p)R^c$, —$S(O)R^c$, —$S(O)_2R^c$, $C_{1-6}$ alkyl substituted with 0-2 $R^a$, —$(CH_2)_r$-3-14 membered carbocycle substituted with 0-1 $R^a$, wherein the carbocycle is cyclopropyl, cyclobutyl, cyclopentyl or cyclohexyl; or —$(CH_2)_r$-5-7 membered heterocycle comprising carbon atoms and 1-4 heteroatoms selected from N, O, and $S(O)_p$ substituted with 0-2 $R^a$; and r is 0, 1, or 2.

In another embodiment there are provided compounds of formula (I), wherein

A is $C_{3-10}$ carbocycle substituted with 0-3 B, $C_{6-10}$ mono- or bicyclic aryl substituted with 0-3-B;

B is $R^1$, halogen, cyano, nitro, —$OR^1$, —$C(=O)R^1$, —$C(=O)OR^1$, —$C(=O)NR^{11}R^1$, —$S(=O)_2R^1$, —$NR^{11}C(=O)R^1$, —$NR^{11}C(=O)NR^{11}R^1$, —$NR^{11}S(=O)_2R^1$, —$N(S(=O)_2R^1)_2$, or —$NR^{11}R^1$; and $R^1$ is hydrogen, $C_{1-6}$ alkyl substituted with 0-3 $R^{1a}$, $C_{1-6}$ haloalkyl, $C_{6-10}$ aryl substituted with 0-3 $R^{1a}$, a 5-10 membered heterocyclyl containing 1-4 heteroatoms selected from N, O, and S, substituted with 0-3 $R^{1a}$, a 5-10 membered heteroaryl containing 1-4 heteroatoms selected from N, O, and S, substituted with 0-3 $R^{1a}$.

In another embodiment there are provided compounds of formula (I), wherein $R^2$ is hydrogen, $C_{1-6}$ alkyl substituted with 0-3 $R^{2a}$, ethenyl, $C_{3-10}$ cycloalkyl substituted with 0-3 $R^{2a}$, $C_{6-10}$ aryl substituted with 0-3 $R^{2a}$, a 5-10 membered heterocyclyl containing 1-4 heteroatoms selected from N, O, and S, substituted with 0-3 $R^{2a}$, wherein the heterocyclyl is pyrrolidinyl, piperidinyl, morpholinyl or piperazinyl, tetrahydrofuranyl, tetrahydropyranyl; a 5-10 membered heteroaryl containing 1-4 heteroatoms selected from N, O, and S, substituted with 0-3 $R^{2a}$, wherein the heteroaryl is pyrimidinyl, imidazolyl, pyrazinyl, thiadiazolyl, pyridinyl, quinolinyl, isoquinolinyl, or thiazolyl.

In another embodiment there are provided compounds of formula (I), wherein

A is $C_6$ carbocycle substituted with 0-3 B, $C_{6-10}$ mono- or bicyclic aryl substituted with 0-3-B; and $R^1$ is hydrogen, $C_{1-6}$ alkyl substituted with 0-3 $R^{1a}$, $C_{1-6}$ haloalkyl, $C_{6-10}$ aryl substituted with 0-3 $R^{1a}$, a 5-10 membered heterocyclyl containing 1-4 heteroatoms selected from N, O, and S, substituted with 0-3 $R^{1a}$, wherein the heterocyclyl is isoquinolin-1(2H)-one, isoindolinyl, isoindoline-1,3-dione, quinolinyl, quinazolinyl, quinazolin-4(3H)-one, or pyrido[3,2-d]pyrimidine.

In another embodiment there are provided compounds according to formula (Ia), (Ib) or (Ic):

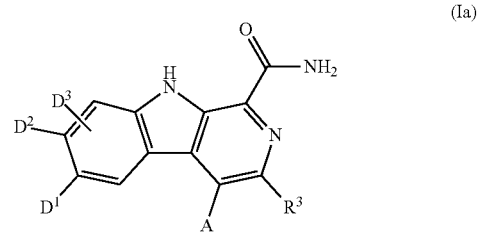

(Ia)

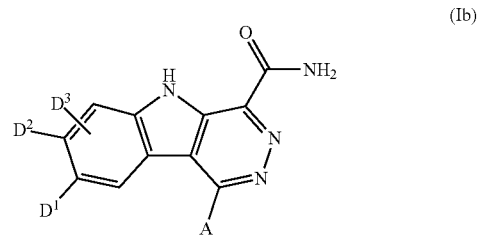

(Ib)

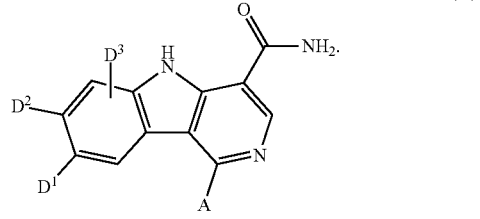

(Ic)

In another embodiment there are provided compounds according to formula (Id) or (Ie):

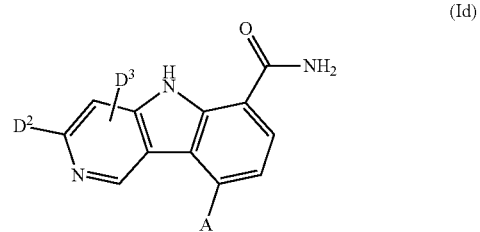

(Id)

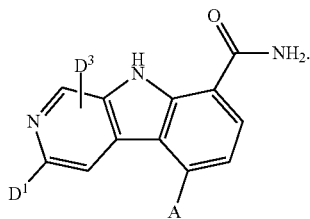

(Ie)

In another embodiment there are provided compounds according to formula (If) or (Ig):

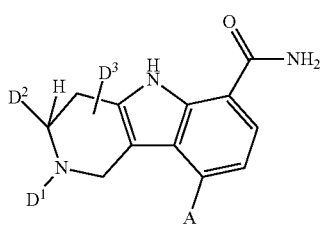

(If)

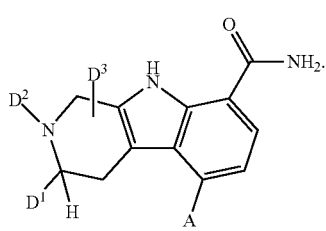

(Ig)

In another embodiment there are provided compounds of formula (I), wherein $R^a$ is hydrogen, F, Cl, Br, $OCF_3$, $CF_3$, $CHF_2$, CN, $NO_2$, —$OR^b$, —$SR^b$, —$C(O)R^b$, —$C(O)OR^b$, —$OC(O)R^b$, —$NR^{11}R^{11}$, —$C(O)NR^{11}R^{11}$, —$NR^bC(O)R^c$, —$NR^bC(O)OR^c$, —$NR^bC(O)NR^{11}R^{11}$, —$S(O)_pNR^{11}R^{11}$, —$NR^bS(O)_pR^c$, —$S(O)R^c$, —$S(O)_2R^c$, $C_{1-6}$ alkyl substituted with 0-1 $R^f$, $C_{1-6}$ haloalkyl, —$(CH_2)_r$-3-6 membered carbocycle, or —$(CH_2)_r$-5-7 membered heterocycle comprising carbon atoms and 1-4 heteroatoms selected from N, O, and $S(O)_p$, wherein the heterocycle is pyrrolidinyl, pyrrolyl, pyrazolyl, imidazolyl, oxazolyl, isoxazolyl, thiazolyl, isothiazolyl, furyl, thienyl, pyridyl, pyrazinyl, pyrimidinyl, morpholinyl, thiamorpholinyl, triazolyl, indolyl, benzothiazolyl, benzoxazolyl, benzothienyl, quinolinyl, isoquinolinyl, tetrahydroisoquinolinyl, benzimidazolyl, benzopyranyl, benzofuryl, benzisothiazolyl, benzisoxazolyl, benzodiazinyl, or benzofurazanyl;

$R^b$ is hydrogen, $C_{1-6}$ alkyl substituted with 0-2 $R^d$, $C_{1-6}$ haloalkyl, $C_{3-6}$ cycloalkyl substituted with 0-2 $R^d$, or $(CH_2)_r$-phenyl substituted with 0-2 $R^d$;

$R^c$ is $C_{1-6}$ alkyl substituted with 0-1 $R^f$, $C_{3-6}$ cycloalkyl, or $(CH_2)_r$-phenyl substituted with 0-1 $R^f$;

$R^d$ is hydrogen, F, Cl, Br, $OCF_3$, $CF_3$, CN, NO2, —$OR^e$, —$C(O)R^e$, —$NR^eR^e$, —$NR^eC(O)OR^c$, $C_{1-6}$ alkyl, or $(CH_2)_r$-phenyl;

$R^e$ is hydrogen, $C_{1-6}$ alkyl, $C_{3-6}$ cycloalkyl, or $(CH_2)_r$-phenyl;

$R^f$ is hydrogen, halo, or $NH_2$; and r is 0 or 1.

In another embodiment there are provided compounds of formula (I), wherein $R^a$ is hydrogen, F, Cl, Br, $OCF_3$, $CF_3$, $CHF_2$, CN, $NO_2$, —$OR^b$, —$SR^b$, —$C(O)R^b$, —$C(O)OR^b$, —$OC(O)R^b$, —$NR^{11}R^{11}$, —$C(O)NR^{11}R^{11}$, —$NR^bC(O)R^c$, —$NR^bC(O)OR^c$, —$NR^bC(O)NR^{11}R^{11}$, —$S(O)_pNR^{11}R^{11}$, —$NR^bS(O)_pR^c$, —$S(O)R^c$, —$S(O)_2R^c$, $C_{1-6}$ alkyl, $C_{1-6}$ haloalkyl, —$(CH_2)_r$-3-6 membered carbocycle phenyl, or —$(CH_2)_r$-5-7 membered heterocycle comprising carbon atoms and 1-4 heteroatoms selected from N, O, and $S(O)_p$, wherein the heterocycle is thiazolyl, pyridinyl, piperidinyl, morpholinyl, piperazinyl, pyrrolidinyl, pyrrolidin-one;

$R^b$ is hydrogen, $C_{1-6}$ alkyl substituted with 0-2 $R^d$, $C_{1-6}$ haloalkyl, $C_{3-6}$ cycloalkyl substituted with 0-2 $R^d$, or $(CH_2)_r$-phenyl substituted with 0-2 $R^d$;

$R^c$ is $C_{1-6}$ alkyl, $C_{3-6}$ cycloalkyl, or $(CH_2)_r$-phenyl;

$R^d$ is hydrogen, F, Cl, Br, $OCF_3$, $CF_3$, CN, NO2, —$OR^e$, —$C(O)R^e$, —$NR^eR^e$, —$NR^eC(O)OR^c$, $C_{1-6}$ alkyl, or $(CH_2)_r$-phenyl; and $R^e$ is hydrogen, $C_{1-6}$ alkyl, $C_{3-6}$ cycloalkyl, or $(CH_2)_r$-phenyl.

In another embodiment there are provided compounds of formula (I), wherein

A is $C_6$ carbocycle substituted with 0-3 B, wherein the carbocycle is cyclohexyl or cyclohexenyl, $C_{6-10}$ mono- or bicyclic aryl substituted with 0-3-B, wherein the aryl group is phenyl or naphthyl;

B is $R^1$, halogen, —$C(=O)OR^1$, —$S(=O)_2R^1$, —$NR^{11}C(=O)R^1$, —$NR^{11}C(=O)NR^{11}R^1$, —$NR^{11}S(=O)_2R^1$, $N(S(=O)_2R^1)_2$, or —$NR^{11}R^1$;

$R^1$ is hydrogen, trifluoromethyl, $C_{1-4}$ alkyl substituted with 0-1 $R^{1a}$, phenyl substituted with 0-3 $R^{1a}$, a 5-10 membered heteroaryl containing 1-4 heteroatoms selected from N, O, and S, substituted with 0-3 $R^{1a}$, wherein the heteroaryl is pyridyl or thiazolyl;

one of $D^1$ and $D^2$ is $R^2$, —$C(=O)R^2$, —$OR^2$, —$C(=O)NR^{11}R^2$, $NR^{11}C(=O)R^2$, $NR^{11}C(=O)NR^{11}R^2$, $NR^{11}S(=O)_2R^2$, or —$NR^{11}R^2$; and the other is hydrogen;

alternatively $D^1$ and $D^2$ join to form —O—$CH_2$—O—;

$R^2$ is hydrogen, $C_{2-6}$ alkyl substituted with 0-3 $R^{2a}$, a 5-10 membered heterocyclyl containing 1-4 heteroatoms selected from N, O, and S, substituted with 0-3 $R^{2a}$ where the heterocyclyl is tetrazolyl, pyrrolidinyl, piperidinyl, piperazinyl or morpholinyl; and $R^{2a}$ is OH, $C_{1-4}$ alkyl, wherein the alkyl is methyl, ethyl, propyl, i-propyl, butyl, and t-butyl, substituted with 0-1 $R^a$.

In another embodiment there are provided compounds of formula (II):

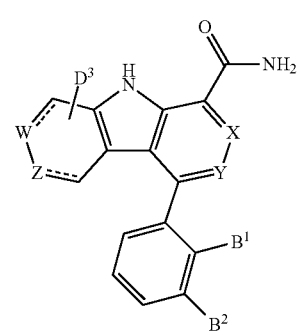

(II)

or enantiomers, diastereomers, stereoisomers, prodrugs, or pharmaceutically-acceptable salts thereof, wherein X is $CR^3$ or N;

Y is $CR^3$ or N;

Z is $CD^1$ or N;

W is $CD^2$ or N;

— is an optional bond; provided when the two optional bonds are absent, Z is $CHD^1$, W is $ND^2$ or Z is $ND^1$ and W is $CHD^2$;

$B^1$ is hydrogen, halogen, cyano, nitro, —OH, $C_{1-6}$ alkyl substituted with 0-3 $R^{1a}$;

$B^2$ is $R^1$, —C(=O)$R^1$, —C(=O)O$R^1$, —C(=O)N$R^{11}R^1$, —S(=O)$_2R^1$, —N$R^{11}$C(=O)$R^1$, —N$R^{11}$C(=O)N$R^{11}R^1$, —N$R^{11}$C(=O)O$R^1$, —N(C(=O)O$R^1$)$_2$, —N$R^{11}$S(=O)$_2$ $R^1$, —N(S(=O)$_2R^1$)$_2$, or —N$R^{11}R^1$;

$R^1$ is hydrogen, $C_{1-6}$ alkyl substituted with 0-3 $R^{1a}$, $C_{1-6}$ haloalkyl, $C_{2-6}$ alkenyl substituted with 0-3 $R^{1a}$, $C_{2-6}$ alkynyl substituted with 0-3 $R^{1a}$, $C_{3-10}$ cycloalkyl substituted with 0-3 $R^{1a}$, $C_{6-10}$ aryl substituted with 0-3 $R^{1a}$, a 5-10 membered heterocyclyl containing 1-4 heteroatoms selected from N, O, and S, substituted with 0-3 $R^{1a}$, a 5-10 membered heteroaryl containing 1-4 heteroatoms selected from N, O, and S, substituted with 0-3 $R^{1a}$;

$R^{1a}$ is hydrogen, =O, F, Cl, Br, OCF$_3$, CF$_3$, CHF$_2$, CN, NO$_2$, —(CH$_2$)$_r$O$R^b$, —(CH$_2$)$_r$S$R^b$, —(CH$_2$)$_r$C(O)$R^b$, —(CH$_2$)$_1$C(O)O$R^b$, —(CH$_2$)$_r$OC(O)$R^b$, —(CH$_2$)$_r$N$R^{11}R^{11}$, —(CH$_2$)$_r$C(O)N$R^{11}R^{11}$, —(CH$_2$)$_r$N$R^b$C(O)$R^c$, —(CH$_2$)$_r$N$R^b$C(O)O$R^c$, —N$R^b$C(O)N$R^{11}R^{11}$, —S(O)$_p$N$R^{11}R^{11}$, —N$R^b$S(O)$_p R^c$, —S(O)$R^c$, —S(O)$_2R^c$, $C_{1-6}$ alkyl substituted with 0-2 $R^d$, $C_{1-6}$ haloalkyl, —(CH$_2$)$_r$-3-14 membered carbocycle substituted with 0-1 $R^a$, or —(CH$_2$)$_r$-5-7 membered heterocycle comprising carbon atoms and 1-4 heteroatoms selected from N, O, and S(O)$_p$ substituted with 0-1 $R^a$;

$D^1$ and $D^2$ are independently $R^2$, halogen, —(C(R$^{11}$)$_2$)$_r R^2$, —(C(R$^{11}$)$_2$)$_r$O$R^2$, —C(=O)$R^2$, —C(=O)O$R^2$, —C(=O)N$R^{11}R^2$, —S(=O)$_2R^2$, —S(=O)$R^2$, —S$R^2$, —N$R^{11}$C(=O)$R^2$, —N$R^{11}$C(=O)N$R^{11}R^2$, —N$R^{11}$C(=O)O$R^2$, —N$R^{11}$S(=O)$_2R^2$, —N$R^{11}R^2$, —C(=O)N$R^{11}$O$R^2$, —OC(=O)O$R^2$, —OC(=O)$R^2$, or CH=N—OH; alternatively $D^1$ and $D^2$ join to form —O—CH$_2$—O—;

$D^3$ is hydrogen, halogen, $C_{1-3}$ alkyl, $C_{1-3}$ alkoxy, or CN;

$R^2$ is hydrogen, $C_{1-6}$ alkyl substituted with 0-3 $R^{2a}$, $C_{2-6}$ alkenyl substituted with 0-3 $R^{2a}$, $C_{2-6}$ alkynyl substituted with 0-3 $R^{2a}$, $C_{3-10}$ cycloalkyl substituted with 0-3 $R^{2a}$, $C_{6-10}$ aryl substituted with 0-3 $R^{2a}$, a 5-10 membered heterocyclyl containing 1-4 heteroatoms selected from N, O, and S, substituted with 0-3 $R^{2a}$, a 5-10 membered heteroaryl containing 1-4 heteroatoms selected from N, O, and S, substituted with 0-3 $R^{2a}$;

$R^{2a}$ is hydrogen, =O, F, Cl, Br, OCF$_3$, CN, NO$_2$, —(CH$_2$)$_r$O$R^b$, —(CH$_2$)$_r$S$R^b$, —(CH$_2$)$_r$C(O)$R^b$, —(CH$_2$)$_r$C(O)O$R^b$, —(CH$_2$)$_r$OC(O)$R^b$, —(CH$_2$)$_r$N$R^{11}R^{11}$, —(CH$_2$)$_r$C(O)N$R^{11}R^{11}$, —(CH$_2$)$_r$N$R^b$C(O)$R^c$, —(CH$_2$)$_r$N$R^b$C(O)O$R^c$, —N$R^b$C(O)N$R^{11}R^{11}$, —S(O)$_p$N$R^{11}R^{11}$, —N$R^b$S(O)$_p R^c$, —S(O)$R^c$, —S(O)$_2R^c$, $C_{1-6}$ alkyl substituted with 0-2 $R^a$, $C_{1-6}$ haloalkyl, —(CH$_2$)$_r$-3-14 membered carbocycle substituted with 0-1 $R^a$, or —(CH$_2$)$_r$-5-7 membered heterocycle comprising carbon atoms and 1-4 heteroatoms selected from N, O, and S(O)$_p$ substituted with 0-2 $R^a$;

$R^{11}$ is independently hydrogen or $C_{1-4}$ alkyl substituted with 0-1 $R^f$, CH$_2$-phenyl, or —(CH$_2$)$_r$-5-7 membered heterocycle comprising carbon atoms and 1-4 heteroatoms selected from N, O, and S(O)$_p$;

alternatively, $R^{11}$ along with another $R^{11}$, $R^1$, or $R^2$ on the same nitrogen atom may join to form an optionally substituted azetidinyl, pyrrolidinyl, piperidinyl, morpholinyl, or 4-($C_{1-6}$ alkyl)piperazinyl;

$R^3$ is hydrogen or $C_{1-6}$ alkyl;

$R^a$ is hydrogen, F, Cl, Br, OCF$_3$, CF$_3$, CHF$_2$, CN, NO$_2$, —(CH$_2$)$_r$O$R^b$, —(CH$_2$)$_r$S$R^b$, —(CH$_2$)$_r$C(O)$R^b$, —(CH$_2$)$_r$C(O)O$R^b$, —(CH$_2$)$_r$OC(O)$R^b$, —(CH$_2$)$_r$N$R^{11}R^{11}$, —(CH$_2$)$_r$C(O)N$R^{11}R^{11}$, —(CH$_2$)$_r$N$R^b$C(O)$R^c$, —(CH$_2$)$_r$N$R^b$C(O)O$R^c$, —N$R^b$C(O)N$R^{11}R^{11}$, —S(O)$_p$N$R^{11}R^{11}$, —N$R^b$S(O)$_p R^c$, —S(O)$R^c$, —S(O)$_2R^c$, $C_{1-6}$ alkyl substituted with 0-1 $R^f$, $C_{1-6}$ haloalkyl, —(CH$_2$)$_r$-3-14 membered carbocycle, or —(CH$_2$)$_r$-5-7 membered heterocycle comprising carbon atoms and 1-4 heteroatoms selected from N, O, and S(O)$_p$, alternatively two $R^a$ on adjacent or the same carbon atom form a cyclic acetal of the formula —O—(CH$_2$)$_n$—O—, or —O—CF$_2$—O—, wherein n is selected from 1 or 2;

$R^b$ is hydrogen, $C_{1-6}$ alkyl substituted with 0-2 $R^d$, $C_{1-6}$ haloalkyl, $C_{3-6}$ cycloalkyl substituted with 0-2 $R^d$, or (CH$_2$)$_r$-phenyl substituted with 0-2 $R^d$;

$R^c$ is $C_{1-6}$ alkyl substituted with 0-1 $R^f$, $C_{3-6}$ cycloalkyl, or (CH$_2$)$_r$-phenyl substituted with 0-1 $R^f$;

$R^d$ is hydrogen, F, Cl, Br, OCF$_3$, CF$_3$, CN, NO$_2$, —O$R^e$, —(CH$_2$)$_r$C(O)$R^e$, —N$R^eR^e$, —N$R^e$C(O)O$R^e$, $C_{1-6}$ alkyl, or (CH$_2$)$_r$-phenyl;

$R^e$ is hydrogen, $C_{1-6}$ alkyl, $C_{3-6}$ cycloalkyl, or (CH$_2$)$_r$-phenyl;

$R^f$ is hydrogen, halo, NH$_2$, OH, or OCH$_3$;

r is 0, 1, 2, 3, or 4; and p is 0, 1, or 2.

In another embodiment there are provided compounds of formula (II), wherein $D^1$ and $D^2$ are independently $R^2$, —(CH$_2$)$_r R^2$, —O$R^2$, —C(=O)$R^2$, —C(=O)O$R^2$, —C(=O)N$R^{11}R^2$, —S(=O)$_2$ $R^2$, —S(=O)$R^2$, —S$R^2$, —N$R^{11}$C(=O)$R^2$, —N$R^{11}$C(=O) N$R^{11}R^2$, —N$R^{11}$C(=O)O$R^2$, —N$R^{11}$S(=O)$_2R^2$, or —N$R^{11}R^2$;

$R^2$ is hydrogen, $C_{1-6}$ alkyl substituted with 0-3 $R^{2a}$, $C_{2-6}$ alkenyl substituted with 0-3 $R^{2a}$, $C_{3-10}$ cycloalkyl substituted with 0-3 $R^{2a}$, —$C_{6-10}$ aryl substituted with 0-3 $R^{2a}$, a 5-10 membered heterocyclyl containing 1-4 heteroatoms selected from N, O, and S, substituted with 0-3 $R^{2a}$, a 5-10 membered heteroaryl containing 1-4 heteroatoms selected from N, O, and S, substituted with 0-3 $R^{2a}$;

$R^{2a}$ is hydrogen, =O, F, Cl, Br, OCF$_3$, CF$_3$, CHF$_2$, CN, NO$_2$, O$R^b$, S$R^b$, —C(O)$R^b$, —C(O)O$R^b$, —OC(O)$R^b$, —N$R^{11}R^{11}$, —C(O)N$R^{11}R^{11}$, —N$R^b$C(O)$R^c$, —N$R^b$C(O) O$R^c$, —N$R^b$C(O)N$R^{11}R^{11}$, —S(O)$_p$N$R^{11}R^{11}$, —N$R^b$S(O)$_p$ $R^c$, —S(O)$R^c$, —S(O)$_2R^c$, $C_{1-6}$ alkyl substituted with 0-2 $R^d$, —(CH$_2$)$_r$-3-14 membered carbocycle substituted with 0-1 $R^a$, wherein the carbocycle is cyclopropyl, cyclobutyl, cyclopentyl or cyclohexyl; or —(CH$_2$)$_r$-5-7 membered heterocycle comprising carbon atoms and 1-4 heteroatoms selected from N, O, and S(O)$_p$ substituted with 0-2 $R^a$; and r is 0, 1, or 2.

In another embodiment there are provided compounds of formula (II), wherein

A is $C_{6-10}$ mono- or bicyclic aryl;

$B^1$ is hydrogen, halogen, cyano, nitro, —OH, or $C_{1-6}$ alkyl substituted with 0-3 $R^{1a}$;

$B^2$ is $R^1$, —C(=O)$R^1$, —C(=O)O$R^1$, —C(=O)N$R^{11}R^1$, —S(=O)$_2R^1$, —N$R^{11}$C(=O)$R^1$, —N$R^{11}$C(=O)N$R^{11}R^1$, —N$R^{11}$C(=O)O$R^1$, —N(C(=O)O$R^1$)$_2$, —N$R^{11}$S(=O)$_2$ $R^1$, —N(S(=O)$_2R^1$)$_2$, or —N$R^{11}R^1$;

$R^1$ is hydrogen, $C_{1-6}$ alkyl substituted with 0-3 $R^{1a}$, $C_{1-6}$ haloalkyl, $C_{6-10}$ aryl substituted with 0-3 $R^{1a}$, a 5-10 membered heterocyclyl containing 1-4 heteroatoms selected from N, O, and S, substituted with 0-3 $R^{1a}$, wherein the heterocyclyl is isoquinolin-1(2H)-one, isoindolinyl, isoindoline-1,3-dione, quinolinyl, quinazolinyl quinazolin-4(3H)-one, or

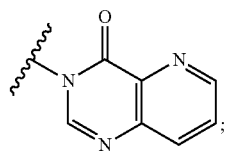 [SMILES: *n1cnc2cccnc2c1=O]

and $R^{1a}$ is hydrogen, =O, F, Cl, Br, $OCF_3$, $CF_3$, $CHF_2$, CN, $NO_2$, $-(CH_2)_rOR^b$.

In another embodiment there are provided compounds of formula (II), wherein $B^1$ is $C_{1-4}$ alkyl or halogen;

$B^2$ is $R^1$, halogen, $C_{1-4}$ alkyl, $-NR^{11}C(=O)R^1$, $-NR^{11}C(O)OR^1$, $-NR^{11}C(=O)NR^{11}R^1$, or $-NR^{11}R^1$;

$R^1$ is hydrogen, $C_{1-4}$ alkyl, indane or phenyl substituted with 0-3 $R^{1a}$, a 5-10 membered heterocyclyl containing 1-4 heteroatoms selected from N, O, and S, substituted with 0-3 $R^{1a}$, a 5-10 membered heteroaryl containing 1-4 heteroatoms selected from N, O, and S, substituted with 0-3 $R^{1a}$, wherein the heterocyclyl or heteroaryl is selected from

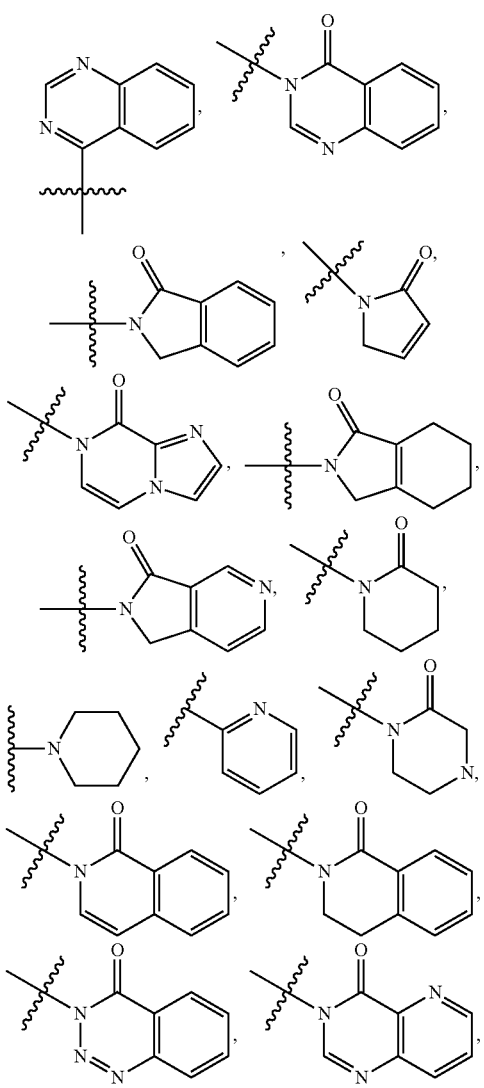

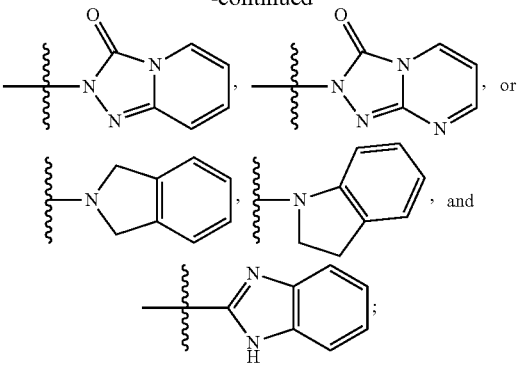

$R^{1a}$ is F, Cl, Br, $-NR^{11}R^{11}$, $-OR^b$, or $C_{1-6}$ alkyl substituted with 0-1 $R^a$;

$D^1$ and $D^2$ are independently $R^2$, halogen, $-OR^2$, $-C(=O)R^2$, $-C(=O)OR^2$, $-C(=O)NR^{11}R^2$, $-NR^{11}C(=O)R^2$, $-NR^{11}S(=O)_2R^2$, $-SR^2$, $S(=O)R^2$, $S(=O)_2R^2$, or $-NR^{11}R^2$; alternatively $D^1$ and $D^2$ join to form $-O-CH_2-O-$;

$R^2$ is hydrogen, $C_{1-6}$ alkyl substituted with 0-3 $R^{2a}$, a 5-10 membered heterocyclyl containing 1-4 heteroatoms selected from N, O, and S, substituted with 0-3 $R^{2a}$, wherein the heterocyclyl is selected from pyrimidinyl, morpholinyl, piperidinyl, pyrrolidinyl, pyridinyl, tetrahydropyranyl, or tetrahydrofuranyl;

$R^{2a}$ is hydrogen, CN, $C_{1-6}$ alkyl, $-N(CH_3)_2$ or $-OR^b$;

$R^{11}$ is independently hydrogen or $C_{1-4}$ alkyl, or $CH_2$-phenyl;

$R^a$ is hydrogen, F, Cl, Br, $OCF_3$, $CF_3$, $CHF_2$, CN, $NO_2$, $-OR^b$, $-SR^b$, $-C(O)R^b$, $-C(O)OR^b$, $-OC(O)R^b$, $-NR^{11}R^{11}$, $-C(O)NR^{11}R^{11}$, $-NR^bC(O)R^c$, $-NR^bC(O)OR^c$, $-NR^bC(O)NR^{11}R^{11}$, $-S(O)_pNR^{11}R^{11}$, $NR^bS(O)_pR^c$, $-S(O)R^c$, $-S(O)_2R^c$, $C_{1-6}$ alkyl substituted with 0-1 $R^f$, $C_{1-6}$ haloalkyl, $-(CH_2)_r$-3-6 membered carbocycle, or $-(CH_2)_r$-5-7 membered heterocycle comprising carbon atoms and 1-4 heteroatoms selected from N, O, and $S(O)_p$, wherein the heterocycle is pyrrolidinyl, pyrrolyl, pyrazolyl, imidazolyl, oxazolyl, isoxazolyl, thiazolyl, isothiazolyl, furyl, thienyl, pyridyl, pyrazinyl, pyrimidinyl, morpholinyl, thiamorpholinyl, triazolyl, indolyl, benzothiazolyl, benzoxazolyl, benzothienyl, quinolinyl, isoquinolinyl, tetrahydroisoquinolinyl, benzimidazolyl, benzopyranyl, benzofuryl, benzisothiazolyl, benzisoxazolyl, benzodiazinyl, or benzofurazanyl;

$R^b$ is hydrogen, $C_{1-4}$ alkyl substituted with 0-2 $R^d$, $C_{1-4}$ haloalkyl, $C_{3-6}$ cycloalkyl substituted with 0-2 $R^d$, or $(CH_2)_r$-phenyl substituted with 0-2 $R^d$;

$R^c$ is $C_{1-4}$ alkyl substituted with 0-1 $R^f$, $C_{3-6}$ cycloalkyl, or $(CH_2)_r$-phenyl substituted with 0-1 $R^f$;

$R^d$ is hydrogen, F, Cl, Br, $OCF_3$, $CF_3$, CN, $NO_2$, $-OR^e$, $-C(O)R^e$, $-NR^eR^e$, $-NR^eC(O)OR^e$, $C_{1-6}$ alkyl, or $(CH_2)_r$-phenyl;

$R^e$ is hydrogen, $C_{1-4}$alkyl, $C_{3-6}$ cycloalkyl, or $(CH_2)_r$-phenyl;

$R^f$ is hydrogen, halo, or $NH_2$; and r is 0 or 1.

In another embodiment there are provided compounds according to formula (IIa), (IIb), or (IIc):

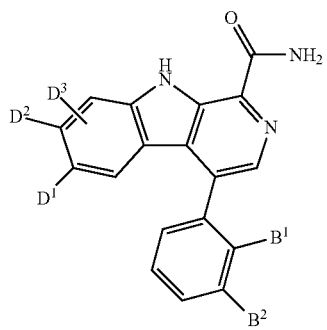
(IIa)

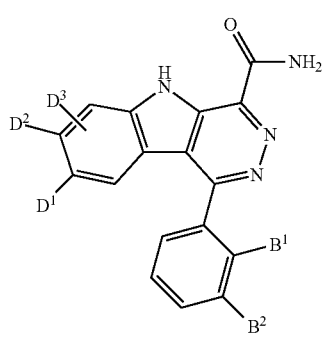
(IIb)

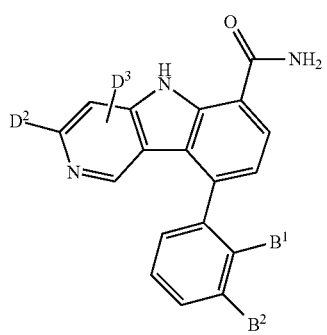
(IIc)

In another embodiment there are provided compounds according to formula (IId) or (IIe):

(IId)

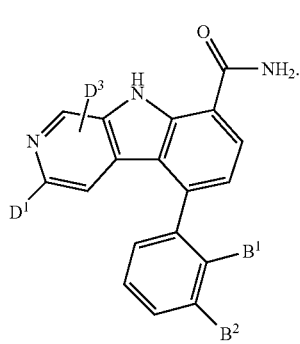
(IIe)

In another embodiment there are provided compounds according to formula (IIf) or (IIg):

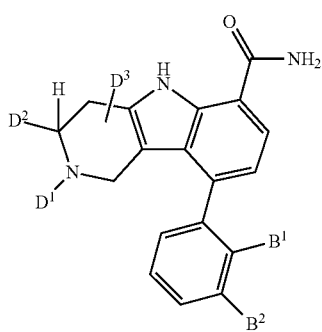
(IIf)

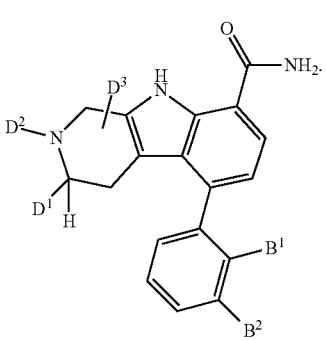
(IIg)

In another embodiment there are provided compounds of formulae (IIa)-(IIg), wherein
B$^1$ is methyl or fluorine;
B$^2$ is hydrogen, R$^{1b}$, —NR$^{11}$C(=O)R$^{1c}$, —NR$^{11}$C(=O)NR$^{11}$R$^{1d}$, or —NR$^{11}$R$^{1e}$;
R$^{1b}$ is,

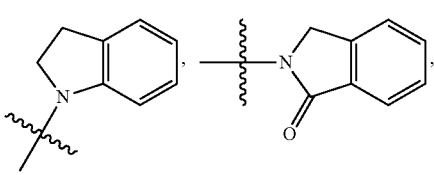

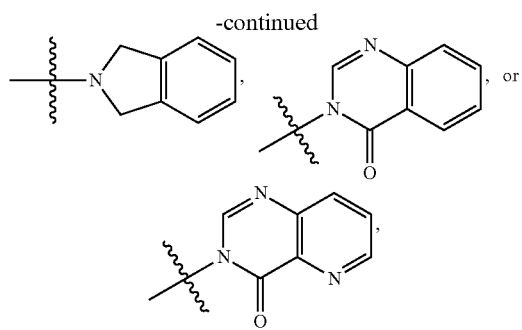

any of which are substituted with 0-3 $R^{1a}$;

$R^{1c}$ is $C_{1-6}$ alkyl,

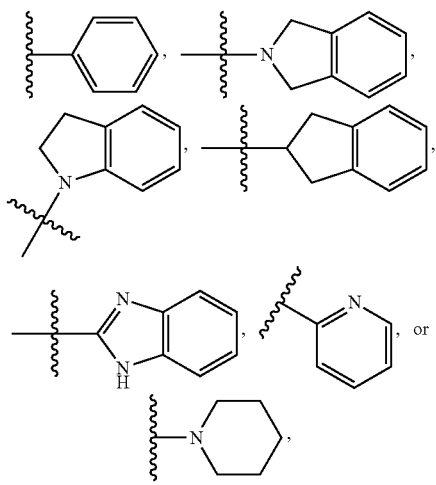

any of which are substituted with 0-2 $R^a$;

$R^{1d}$ is phenyl substituted with 0-1 $R^{1a}$;

$R^{1e}$ is quinazolinyl substituted with 0-1 $R^{1a}$;

$R^{1a}$ is selected from hydrogen, F, Cl, CN, methyl, ethyl, $CF_3$, OH, and O-methyl;

$D^1$ and $D^2$ are independently $R^2$, F, Cl, Br, —$OR^2$, —C(=O)$R^2$, —C(=O)$OR^2$, —C(=O)$NR^{11}R^2$, —S(=O)$_2$ $R^2$, —S(=O)$R^2$, —$SR^2$, —$NR^{11}$C(=O)$R^2$, —$NR^{11}$S(=O)$_2R^2$, and —$NR^{11}R^2$;

$R^2$ is hydrogen, $C_{1-6}$ alkyl substituted with 0-3 $R^{2a}$, piperazinyl, pyrrolidinyl, tetrahydrofuranyl, tetrahydropyranyl, morpholinyl, piperidinyl, pyridinyl, imidazolyl, pyrazinyl, or pyrimidinyl, any of which are substituted with 0-3 $R^{2a}$;

$R^{2a}$ is hydrogen, CN, —$OR^b$, or morpholinyl;

$R^{11}$ is hydrogen or $C_{1-4}$ alkyl;

$R^a$ is hydrogen, F, Cl, $C_{1-4}$ alkyl, —$OR^b$, —$NR^{11}R^{11}$ imidazolyl, or morpholinyl; and $R^b$ is hydrogen or $C_{1-6}$ alkyl.

Where the specification refers to compounds of formula (I), it is intended to include compounds of formulae (Ia)-(Ig), (II), (IIa)-(IIg), either individually or in any combination.

In another embodiment there is provided a compound of formula (I), wherein $D^1$ and $D^2$ are independently $R^2$, halogen, —$OR^2$, —C(=O)$R^2$, —C(=O)$NR^{11}R^2$, —$NR^{11}$C(=O)$R^2$, —$NR^{11}$S(=O)$_2R^2$, or —$NR^{11}R^2$;

$R^2$ is hydrogen, $C_{1-6}$ alkyl substituted with 0-3 $R^{2a}$, a 5-10 membered heterocyclyl containing 1-4 heteroatoms selected from N, O, and S, substituted with 0-3 $R^{2a}$, wherein the heterocyclyl is selected from pyrimidinyl, morpholinyl, pyrrolidinyl, pyridinyl, tetrahydropyranyl, or tetrahydrofuranyl; and $R^{2b}$ is $C_{1-6}$ alkyl substituted with 0-3 $R^{2a}$, a 5-10 membered heterocyclyl containing 1-4 heteroatoms selected from N, O, and S, substituted with 0-3 $R^{2a}$, wherein the heterocyclyl is selected from pyrimidinyl, morpholinyl, pyrrolidinyl, pyridinyl, tetrahydropyranyl, or tetrahydrofuranyl.

In another embodiment there is provided a compound of formula (I), wherein A is $C_{6-10}$ mono- or bicyclic aryl substituted with 0-3 B.

In another embodiment there is provided a compound of formula (I), wherein A is phenyl substituted with 0-2 B.

In another embodiment there is provided a compound of formula (I), wherein B is $R^1$, halogen, cyano, nitro, —$OR^1$, —C(=O)$R^1$, —C(=O)$OR^1$, —C(=O)$NR^{11}R^1$, —S(=O)$_2R^1$, —$NR^{11}$C(=O)$R^1$, —$NR^{11}$C(=O)$NR^{11}R^1$, —$NR^{11}$S(=O)$_2R^1$, —N(S(=O)$_2R^1$)$_2$, or —$NR^{11}R^1$.

In another embodiment there is provided a compound of formula (I), wherein B is $R^1$, halogen, —C(=O)$OR^1$, —S(=O)$_2R^1$, —$NR^{11}$C(=O)$R^1$, —$NR^{11}$C(=O)$NR^{11}R^1$, —$NR^{11}$S(=O)$_2R^1$, N(S(=O)$_2R^1$)$_2$, or —$NR^{11}R^1$.

In another embodiment there is provided a compound of formula (I) or (II), wherein $R^1$ is hydrogen, $C_{1-6}$ alkyl substituted with 0-3 $R^{1a}$, $C_{1-6}$ haloalkyl, $C_{6-10}$ aryl substituted with 0-3 $R^{1a}$, a 5-10 membered heterocyclyl containing 1-4 heteroatoms selected from N, O, and S, substituted with 0-3 $R^{1a}$, a 5-10 membered heteroaryl containing 1-4 heteroatoms selected from N, O, and S, substituted with 0-3 $R^{1a}$.

In another embodiment there is provided a compound of formula (I) or (II), wherein $R^1$ is hydrogen, $C_{1-6}$ alkyl substituted with 0-3 $R^{1a}$, $C_{1-6}$ haloalkyl, $C_{6-10}$ aryl substituted with 0-3 $R^{1a}$, a 5-10 membered heterocyclyl containing 1-4 heteroatoms selected from N, O, and S, substituted with 0-3 $R^{1a}$, wherein the heterocyclyl is isoquinolin-1(2H)-one, isoindolinyl, isoindoline-1,3-dione, quinolinyl, quinazolinyl quinazolin-4(3H)-one or pyrido[3,2-d]pyrimidine.

In another embodiment there is provided a compound of formula (I) or (II), wherein $R^1$ is hydrogen, trifluoromethyl, $C_{1-4}$ alkyl substituted with 0-1 $R^{1a}$, phenyl substituted with 0-3 $R^{1a}$, a 5-10 membered heteroaryl containing 1-4 heteroatoms selected from N, O, and S, substituted with 0-3 $R^{1a}$, wherein the heteroaryl is pyrido[3,2-d]pyrimidine.

In another embodiment there is provided a compound of formula (I) or (II), wherein $R^1$ is hydrogen, methyl, phenyl substituted with 0-3 $R^{1a}$, a 5-10 membered heterocyclyl containing 1-4 heteroatoms selected from N, O, and S, substituted with 0-3 $R^{1a}$, a 5-10 membered heteroaryl containing 1-4 heteroatoms selected from N, O, and S, substituted with 0-3 $R^{1a}$, wherein the heterocycle is selected from pyridinyl, benzimidazolyl,

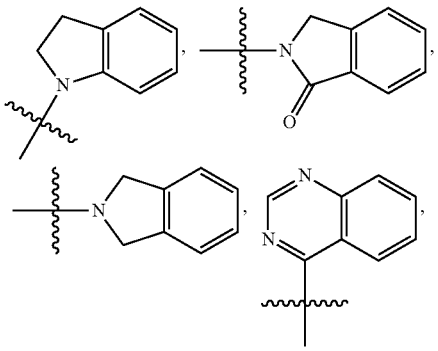

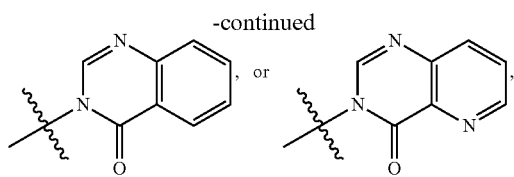

In another embodiment there is provided a compound of formula (I) or (II), wherein $R^{1a}$ is F, Cl, Br, —$NR^{11}R^{11}$, $C_{1-6}$ alkyl substituted with 0-1 $R^a$, or —$OR^b$.

In another embodiment there is provided a compound of formula (I) or (II), wherein $R^2$ is hydrogen, $C_{1-6}$ alkyl substituted with 0-3 $R^{2a}$, $C_{2-6}$ alkenyl substituted with 0-3 $R^{2a}$, $C_{3-10}$ cycloalkyl substituted with 0-3 $R^{2a}$, $C_{6-10}$ aryl substituted with 0-3 $R^{2a}$, a 5-10 membered heterocyclyl containing 1-4 heteroatoms selected from N, O, and S, substituted with 0-3 $R^{2a}$, a 5-10 membered heteroaryl containing 1-4 heteroatoms selected from N, O, and S, substituted with 0-3 $R^{2a}$.

$R^2$ is hydrogen, $C_{1-6}$ alkyl substituted with 0-3 $R^{2a}$, ethenyl, $C_{3-10}$ cycloalkyl substituted with 0-3 $R^{2a}$, $C_{6-10}$ aryl substituted with 0-3 $R^{2a}$, a 5-10 membered heterocyclyl containing 1-4 heteroatoms selected from N, O, and S, substituted with 0-3 $R^{2a}$, wherein the heterocyclyl is pyrrolidinyl, piperidinyl, morpholinyl or piperazinyl, tetrahydrofuranyl, tetrahydropyranyl; a 5-10 membered heteroaryl containing 1-4 heteroatoms selected from N, O, and S, substituted with 0-3 $R^{2a}$, wherein the heteroaryl is pyrimidinyl, imidazolyl, pyrazinyl, thiadiazolyl, pyridinyl, quinolinyl, isoquinolinyl, or thiazolyl.

In another embodiment there is provided a compound of formula (I) or (II), wherein $R^2$ is hydrogen, $C_{1-6}$ alkyl substituted with 0-3 $R^{2a}$, a 5-10 membered heterocyclyl containing 1-4 heteroatoms selected from N, O, and S, substituted with 0-3 $R^{2a}$ where the heterocyclyl is tetrazolyl, pyrrolidinyl, piperidinyl, piperazinyl or morpholinyl;

In another embodiment there is provided a compound of formula (I) or (II), wherein $R^2$ is hydrogen, $C_{1-6}$ alkyl substituted with 0-3 $R^{2a}$, $C_{3-10}$ cyclopropyl substituted with 0-3 $R^{2a}$, a 5-10 membered heterocyclyl containing 1-4 heteroatoms selected from N, O, and S, substituted with 0-3 $R^{2a}$, wherein the heterocyclyl is selected from piperazinyl, pyrrolidinyl, tetrahydrofuranyl, morpholinyl, dioxolanyl, piperidinyl, a 5-10 membered heteroaryl containing 1-4 heteroatoms selected from N, O, and S, substituted with 0-3 $R^{2a}$, wherein the heteroaryl is selected from pyridinyl, imidazolyl, pyrazinyl, pyrimidinyl, tetrazolyl, thiadiazolyl.

In another embodiment there is provided a compound of formula (I), wherein $R^2$ is $C_{1-4}$alkyl substituted with OH, preferably $R^2$ being hydroxypropane.

In another embodiment there is provided a compound of formula (I) or (II), wherein $R^{2a}$ is hydrogen, =O, F, Cl, Br, $OCF_3$, $CF_3$, $CHF_2$, CN, $NO_2$, $OR^b$, $SR^b$, —$C(O)R^b$, —$C(O)OR^b$, —$OC(O)R^b$, —$NR^{11}R^{11}$, —$C(O)NR^{11}R^{11}$, —$NR^bC(O)R^c$, —$NR^bC(O)OR^c$, —$NR^bC(O)NR^{11}R^{11}$, —$S(O)_pNR^{11}R^{11}$, —$NR^bS(O)_pR^c$, —$S(O)R^c$, —$S(O)_2R^c$, $C_{1-6}$ alkyl substituted with 0-2 $R^a$, —$(CH_2)_r$-3-14 membered carbocycle substituted with 0-1 $R^a$, wherein the carbocycle is cyclopropyl, cyclobutyl, cyclopentyl or cyclohexyl; or —$(CH_2)_r$-5-7 membered heterocycle comprising carbon atoms and 1-4 heteroatoms selected from N, O, and $S(O)_p$ substituted with 0-2 $R^a$.

In another embodiment there is provided a compound of formula (I) or (II), wherein $R^{2a}$ is hydrogen, —$(CH_2)_rOR^b$, —$(CH_2)_rOC(O)R^b$, —$(CH_2)_rNR^{11}R^{11}$, —$NR^bC(O)NR^{11}R^{11}$, —$NR^bS(O)_pR^c$, $C_{1-6}$ alkyl substituted with 0-2 $R^a$, or —$(CH_2)_r$-5-7 membered heterocycle comprising carbon atoms and 1-4 heteroatoms selected from N, O, and $S(O)_p$ substituted with 0-2 $R^a$, wherein the heterocycle is selected from pyridinyl, pyrrolidinyl, pyrrolidinonyl, morpholinyl, imidazolyl, piperidinyl.

In another embodiment there is provided a compound of formula (I) or (II), wherein $R^a$ is hydrogen, F, Cl, Br, $OCF_3$, $CF_3$, $CHF_2$, CN, $NO_2$, —$OR^b$, —$SR^b$, —$C(O)R^b$, $C(O)OR^b$, —$OC(O)R^b$, —$NR^{11}R^{11}$, —$C(O)NR^{11}R^{11}$, —$NR^bC(O)R^c$, —$NR^bC(O)OR^c$, —$NR^bC(O)NR^{11}R^{11}$, —$S(O)_pNR^{11}R^{11}$, —$NR^bS(O)_pR^c$, —$S(O)R^c$, —$S(O)_2R^c$, $C_{1-6}$ alkyl substituted with 0-1 $R^f$, $C_{1-6}$ haloalkyl, —$(CH_2)_r$-3-6 membered carbocycle, or —$(CH_2)_r$-5-7 membered heterocycle comprising carbon atoms and 1-4 heteroatoms selected from N, O, and $S(O)_p$, wherein the heterocycle is pyrrolidinyl, pyrrolyl, pyrazolyl, imidazolyl, oxazolyl, isoxazolyl, thiazolyl, isothiazolyl, furyl, thienyl, pyridyl, pyrazinyl, pyrimidinyl, morpholinyl, thiamorpholinyl, triazolyl, indolyl, benzothiazolyl, benzoxazolyl, benzothienyl, quinolinyl, isoquinolinyl, tetrahydroisoquinolinyl, benzimidazolyl, benzopyranyl, benzofuryl, benzisothiazolyl, benzisoxazolyl, benzodiazinyl, or benzofurazanyl.

In another embodiment there is provided a compound of formula (I) or (II), wherein $R^a$ is hydrogen, F, Cl, Br, $OCF_3$, $CF_3$, $CHF_2$, CN, $NO_2$, —$OR^b$, —$SR^b$, —$C(O)R^b$, —$C(O)OR^b$, —$OC(O)R^b$, —$NR^{11}R^{11}$, —$C(O)NR^{11}R^{11}$, —$NR^bC(O)R^c$, —$NR^bC(O)OR^c$, —$NR^bC(O)NR^{11}R^{11}$, —$S(O)_pNR^{11}R^{11}$, —$NR^bS(O)_pR^c$, —$S(O)R^c$, —$S(O)_2R^c$, $C_{1-6}$ alkyl, $C_{1-6}$ haloalkyl, —$(CH_2)_r$-3-6 membered carbocycle phenyl, or —$(CH_2)_r$-5-7 membered heterocycle comprising carbon atoms and 1-4 heteroatoms selected from N, O, and $S(O)_p$, wherein the heterocycle is thiazolyl, pyridinyl, piperidinyl, morpholinyl, piperazinyl, pyrrolidinyl, pyrrolidin-one, In another embodiment there is provided a compound of formula (I) or (II), wherein $R^b$ is hydrogen, $C_{1-6}$ alkyl substituted with 0-2 $R^d$, $C_{1-6}$ haloalkyl, $C_{3-6}$ cycloalkyl substituted with 0-2 $R^d$, or $(CH_2)_r$-phenyl substituted with 0-2 $R^d$.

In another embodiment there is provided a compound of formula (I) or (II), wherein $R^c$ is $C_{1-6}$ alkyl substituted with 0-1 $R^f$, $C_{3-6}$ cycloalkyl, or $(CH_2)_r$-phenyl substituted with 0-1 $R^f$.

In another embodiment there is provided a compound of formula (I) or (II), wherein $R^d$ is hydrogen, F, Cl, Br, $OCF_3$, $CF_3$, CN, $NO_2$, —$OR^c$, —$C(O)R^c$, —$NR^eR^e$, —$NR^eC(O)OR^c$, $C_{1-6}$ alkyl, or $(CH_2)_r$-phenyl.

In another embodiment there is provided a compound of formula (I) or (II), wherein $R^e$ is hydrogen, $C_{1-6}$ alkyl, $C_{3-6}$ cycloalkyl, or $(CH_2)_r$-phenyl.

In another embodiment there is provided a compound of formula (I) or (II), wherein $R^f$ is hydrogen, halo, or $NH_2$.

In another embodiment, there is provided a pharmaceutical composition comprising one or more compounds of formula (I) or (II) and a pharmaceutically acceptable carrier or diluent.

The present invention is also directed to pharmaceutical compositions useful in treating diseases associated with kinase modulation, including modulation (especially inhibition) of Btk and other Tec family kinases such as Itk, comprising compounds of formula (I) or (II), or pharmaceutically-acceptable salts thereof, and pharmaceutically-acceptable carriers or diluents.

The invention further relates to methods of treating diseases associated with the kinase modulation, including the modulation of Btk and other Tec family kinases such as Itk, comprising administering to a patient in need of such treatment a therapeutically-effective amount of a compound according to formula (I) or (II).

The present invention also provides processes and intermediates for making the compounds of the present invention or stereoisomers, tautomers, pharmaceutically acceptable salts, solvates, or prodrugs thereof.

The present invention also provides a method for treating proliferative diseases, allergic diseases, autoimmune diseases and inflammatory diseases, comprising administering to a host in need of such treatment a therapeutically effective amount of at least one of the compounds of the present invention or stereoisomers, tautomers, pharmaceutically acceptable salts, solvates, or prodrugs thereof.

The present invention also provides a method for treating a disease, comprising administering to a patient in need of such treatment a therapeutically-effective amount of a compound of formula (I) or (II), wherein the disease is systemic lupus erythematosus (SLE), rheumatoid arthritis, multiple sclerosis (MS), or transplant rejection.

The present invention also provides a method of treating a condition associated with a proliferative disease, an allergic disease, an autoimmune disease or an inflammatory disease, comprising administering to a patient in need of such treatment a therapeutically-effective amount of a compound of formula (I) or (II).

The present invention also provides a method of treating a condition comprising administering to a patient in need of such treatment a therapeutically-effective amount of a compound of formula (I) or (II), wherein the condition is selected from acute myelogenous leukemia, chronic myelogenous leukemia, metastatic melanoma, Kaposi's sarcoma, multiple myeloma, solid tumors, ocular neovasculization, and infantile haemangiomas, B cell lymphoma, systemic lupus erythematosus (SLE), rheumatoid arthritis, psoriatic arthritis, multiple vasculitides, idiopathic thrombocytopenic purpura (ITP), myasthenia gravis, allergic rhinitis, multiple sclerosis (MS), transplant rejection, Type I diabetes, membranous nephritis, inflammatory bowel disease, autoimmune hemolytic anemia, autoimmune thyroiditis, cold and warm agglutinin diseases, Evan's syndrome, hemolytic uremic syndrome/thrombotic thrombocytopenic purpura (HUS/TTP), sarcoidosis, Sjögren's syndrome, peripheral neuropathies, pemphigus vulgaris and asthma.

The present invention also provides a method for treating rheumatoid arthritis, comprising administering to a patient in need of such treatment a therapeutically-effective amount of a compound of formula (I) or (II).

The present invention also provides a method of treating a B-cell mediated disease, comprising administering to a patient in need of such treatment a therapeutically-effective amount of a compound of formula (I) or (II).

The present invention also provides a method of treating a B-cell mediated disease, comprising administering to a patient in need of such treatment a therapeutically-effective amount of a compound of formula (I) or (II), wherein the B-cell mediated disease is a disease modulated by a kinase selected from Btk, Bmx, Itk, Txk and Tec.

The present invention also provides a method of treating diseases, comprising administering to a patient in need of such treatment a therapeutically-effective amount of a compound of formula (I) or (II), or pharmaceutically acceptable salt thereof, in combination with other therapeutic agents.

The present invention also provides the compounds of the present invention or stereoisomers, tautomers, pharmaceutically acceptable salts, solvates, or prodrugs thereof, for use in therapy.

In another embodiment, compounds of formula (I) or (II), are selected from exemplified examples or combinations of exemplified examples or other embodiments herein.

In another embodiment, the $IC_{50}$ value of compounds of formula (I) or (II) in the Btk assay described below is <10 µM.

In another embodiment, the $IC_{50}$ value of compounds of formula (I) or (II) in the Btk assay described below is <1 µM.

In another embodiment, the $IC_{50}$ value of compounds of formula (I) or (II) in the Btk assay described below is <0.01 µM.

The present invention also provides the use of the compounds of the present invention or stereoisomers, tautomers, pharmaceutically acceptable salts, solvates, or prodrugs thereof, for the manufacture of a medicament for the treatment of cancers, an allergic disease, an autoimmune disease or an inflammatory disease.

The present invention may be embodied in other specific forms without departing from the spirit or essential attributes thereof. This invention encompasses all combinations of preferred aspects and/or embodiments of the invention noted herein. It is understood that any and all embodiments of the present invention may be taken in conjunction with any other embodiment or embodiments to describe additional embodiments. It is also to be understood that each individual element of the embodiments is its own independent embodiment. Furthermore, any element of an embodiment is meant to be combined with any and all other elements from any embodiment to describe an additional embodiment.

DETAILED DESCRIPTION OF THE INVENTION

The following are definitions of terms used in this specification and appended claims. The initial definition provided for a group or term herein applies to that group or term throughout the specification and claims, individually or as part of another group, unless otherwise indicated.

When any variable (e.g., $R^3$) occurs more than one time in any constituent or formula for a compound, its definition at each occurrence is independent of its definition at every other occurrence. Thus, for example, if a group is shown to be substituted with 0-2 $R^3$, then said group may optionally be substituted with up to two $R^3$ groups and $R^3$ at each occurrence is selected independently from the definition of $R^3$. Also, combinations of substituents and/or variables are permissible only if such combinations result in stable compounds.

When a bond to a substituent is shown to cross a bond connecting two atoms in a ring, then such substituent may be bonded to any atom on the ring. When a substituent is listed without indicating the atom via which such substituent is bonded to the rest of the compound of a given formula, then such substituent may be bonded via any atom in such substituent. Combinations of substituents and/or variables are permissible only if such combinations result in stable compounds.

In cases wherein there are nitrogen atoms (e.g., amines) on compounds of the present invention, these can be converted to N-oxides by treatment with an oxidizing agent (e.g., MCPBA and/or hydrogen peroxides) to afford other compounds of this invention. Thus, all shown and claimed nitrogen atoms are considered to cover both the shown nitrogen and its N-oxide (N→O) derivative.

In accordance with a convention used in the art,

is used in structural formulas herein to depict the bond that is the point of attachment of the moiety or substituent to the core or backbone structure.

A dash "-" that is not between two letters or symbols is used to indicate a point of attachment for a substituent. For example, —$CONH_2$ is attached through the carbon atom.

The term "optionally substituted" in reference to a particular moiety of the compound of Formula (I) (e.g., an optionally substituted heteroaryl group) refers to a moiety having 0, 1, 2, or more substituents. For example, "optionally substituted alkyl" encompasses both "alkyl" and "substituted alkyl" as defined below. It will be understood by those skilled in the art, with respect to any group containing one or more substituents, that such groups are not intended to introduce any substitution or substitution patterns that are sterically impractical, synthetically non-feasible and/or inherently unstable.

As used herein, the term "at least one chemical entity" is interchangeable with the term "a compound."

As used herein, the term "alkyl" or "alkylene" is intended to include both branched and straight-chain saturated aliphatic hydrocarbon groups having the specified number of carbon atoms. For example, "$C_{1-10}$ alkyl" (or alkylene), is intended to include $C_1$, $C_2$, $C_3$, $C_4$, $C_5$, $C_6$, $C_7$, $C_8$, $C_9$, and $C_{10}$ alkyl groups. Additionally, for example, "$C_1$-$C_6$ alkyl" denotes alkyl having 1 to 6 carbon atoms. Alkyl groups can be unsubstituted or substituted so that one or more of its hydrogens are replaced by another chemical group. Example alkyl groups include, but are not limited to, methyl (Me), ethyl (Et), propyl (e.g., n-propyl and isopropyl), butyl (e.g., n-butyl, isobutyl, t-butyl), pentyl (e.g., n-pentyl, isopentyl, neopentyl), and the like.

Alkenyl" or "alkenylene" is intended to include hydrocarbon chains of either straight or branched configuration and having one or more double carbon-carbon bonds that may occur in any stable point along the chain. For example, "$C_{2-6}$ alkenyl" (or alkenylene), is intended to include $C_2$, $C_3$, $C_4$, $C_5$, and $C_6$ alkenyl groups. Examples of alkenyl include, but are not limited to, ethenyl, 1-propenyl, 2-propenyl, 2-butenyl, 3-butenyl, 2-pentenyl, 3-pentenyl, 4-pentenyl, 2-hexenyl, 3-hexenyl, 4-hexenyl, 5-hexenyl, 2-methyl-2-propenyl, 4-methyl-3-pentenyl, and the like.

"Alkynyl" or "alkynylene" is intended to include hydrocarbon chains of either straight or branched configuration and having one or more triple carbon-carbon bonds that may occur in any stable point along the chain. For example, "$C_{2-6}$ alkynyl" (or alkynylene), is intended to include $C_2$, $C_3$, $C_4$, $C_5$, and $C_6$ alkynyl groups; such as ethynyl, propynyl, butynyl, pentynyl, hexynyl and the like.

One skilled in the field will understand that, when the designation "$CO_2$" is used herein, this is intended to refer to the group

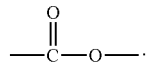

When the term "alkyl" is used together with another group, such as in "arylalkyl", this conjunction defines with more specificity at least one of the substituents that the substituted alkyl will contain. For example, "arylalkyl" refers to a substituted alkyl group as defined above where at least one of the substituents is an aryl, such as benzyl. Thus, the term aryl ($C_{0-4}$)alkyl includes a substituted lower alkyl having at least one aryl substituent and also includes an aryl directly bonded to another group, i.e., aryl($C_0$)alkyl. The term "heteroarylalkyl" refers to a substituted alkyl group as defined above where at least one of the substituents is a heteroaryl.

When reference is made to a substituted alkenyl, alkynyl, alkylene, alkenylene, or alkynylene group, these groups are substituted with one to three substituents as defined above for substituted alkyl groups.

The term "alkoxy" refers to an oxygen atom substituted by alkyl or substituted alkyl, as defined herein. For example, the term "alkoxy" includes the group —O—$C_{1-6}$alkyl such as methoxy, ethoxy, propoxy, isopropoxy, n-butoxy, sec-butoxy, tert-butoxy, pentoxy, 2-pentyloxy, isopentoxy, neopentoxy, hexoxy, 2-hexoxy, 3-hexoxy, 3-methylpentoxy, and the like. "Lower alkoxy" refers to alkoxy groups having one to four carbons.

It should be understood that the selections for all groups, including for example, alkoxy, thioalkyl, and aminoalkyl, will be made by one skilled in the field to provide stable compounds.

The term "substituted", as used herein, means that any one or more hydrogens on the designated atom or group is replaced with a selection from the indicated group, provided that the designated atom's normal valence is not exceeded. When a substituent is oxo, or keto, (i.e., =O) then 2 hydrogens on the atom are replaced. Keto substituents are not present on aromatic moieties. Unless otherwise specified, substituents are named into the core structure. For example, it is to be understood that when (cycloalkyl)alkyl is listed as a possible substituent, the point of attachment of this substituent to the core structure is in the alkyl portion. Ring double bonds, as used herein, are double bonds that are formed between two adjacent ring atoms (e.g., C=C, C=N, or N=N).

Combinations of substituents and/or variables are permissible only if such combinations result in stable compounds or useful synthetic intermediates. A stable compound or stable structure is meant to imply a compound that is sufficiently robust to survive isolation from a reaction mixture to a useful degree of purity, and subsequent formulation into an efficacious therapeutic agent. It is preferred that the presently recited compounds do not contain a N-halo, $S(O)_2H$, or $S(O)H$ group.

The term "cycloalkyl" refers to cyclized alkyl groups, including mono-, bi- or poly-cyclic ring systems. $C_{3-7}$ cycloalkyl is intended to include $C_3$, $C_4$, $C_5$, $C_6$, and $C_7$ cycloalkyl groups. Example cycloalkyl groups include, but are not limited to, cyclopropyl, cyclobutyl, cyclopentyl, cyclohexyl, norbornyl, and the like. As used herein, "carbocycle" or "carbocyclic residue" is intended to mean any stable 3-, 4-, 5-, 6-, or 7-membered monocyclic or bicyclic or 7-, 8-, 9-, 10-, 11-, 12-, or 13-membered bicyclic or tricyclic ring, any of which may be saturated, partially unsaturated, unsaturated or aromatic. Examples of such carbocycles include, but are not limited to, cyclopropyl, cyclobutyl, cyclobutenyl, cyclopentyl, cyclopentenyl, cyclohexyl, cycloheptenyl, cycloheptyl, cycloheptenyl, adamantyl, cyclooctyl, cyclooctenyl, cyclooctadienyl, [3.3.0]bicyclooctane, [4.3.0] bicyclononane, [4.4.0]bicyclodecane, [2.2.2]bicyclooctane, fluorenyl, phenyl, naphthyl, indanyl, adamantyl, anthracenyl, and tetrahydronaphthyl (tetralin). As shown above, bridged rings are also included in the definition of carbocycle (e.g.,

[2.2.2]bicyclooctane). Preferred carbocycles, unless otherwise specified, are cyclopropyl, cyclobutyl, cyclopentyl, cyclohexyl, and phenyl. When the term "carbocycle" is used, it is intended to include "aryl". A bridged ring occurs when one or more carbon atoms link two non-adjacent carbon atoms. Preferred bridges are one or two carbon atoms. It is noted that a bridge always converts a monocyclic ring into a bicyclic ring. When a ring is bridged, the substituents recited for the ring may also be present on the bridge.

The term "aryl" refers to monocyclic or bicyclic aromatic hydrocarbon groups having 6 to 12 carbon atoms in the ring portion, such as phenyl, and naphthyl groups, each of which may be substituted.

Accordingly, in compounds of formula (I), the term "cycloalkyl" includes cyclopropyl, cyclobutyl, cyclopentyl, cyclohexyl, cycloheptyl, bicyclooctyl, etc., as well as the following ring systems,

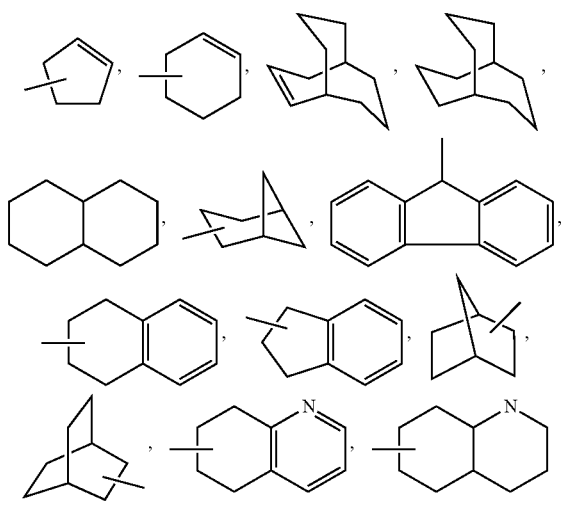

and the like, which optionally may be substituted at any available atoms of the ring(s). Preferred cycloalkyl groups include cyclopropyl, cyclopentyl, cyclohexyl, and

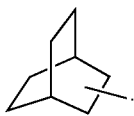

The term "halo" or "halogen" refers to chloro, bromo, fluoro and iodo.

The term "haloalkyl" means a substituted alkyl having one or more halo substituents. For example, "haloalkyl" includes mono, bi, and trifluoromethyl.

The term "haloalkoxy" means an alkoxy group having one or more halo substituents. For example, "haloalkoxy" includes OCF$_3$.

Thus, examples of aryl groups include:

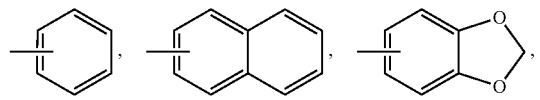

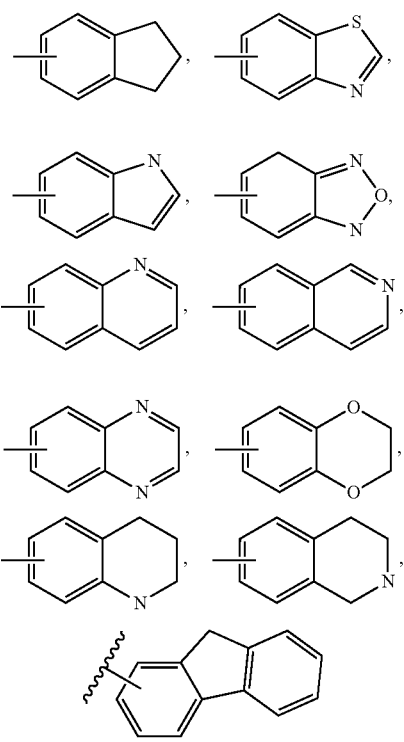

(fluorenyl) and the like, which optionally may be substituted at any available carbon or nitrogen atom. A preferred aryl group is optionally-substituted phenyl.

The terms "heterocycloalkyl", "heterocyclo", "heterocyclic", or "heterocyclyl" may be used interchangeably and refer to substituted and unsubstituted non-aromatic 3- to 7-membered monocyclic groups, 7- to 11-membered bicyclic groups, and 10- to 15-membered tricyclic groups, in which at least one of the rings has at least one heteroatom (O, S or N), said heteroatom containing ring preferably having 1, 2, or 3 heteroatoms selected from O, S, and N. Each ring of such a group containing a heteroatom can contain one or two oxygen or sulfur atoms and/or from one to four nitrogen atoms provided that the total number of heteroatoms in each ring is four or less, and further provided that the ring contains at least one carbon atom. The nitrogen and sulfur atoms may optionally be oxidized and the nitrogen atoms may optionally be quaternized. The fused rings completing the bicyclic and tricyclic groups may contain only carbon atoms and may be saturated, partially saturated, or unsaturated. The heterocyclo group may be attached at any available nitrogen or carbon atom. The term "heterocycle" includes "heteroaryl" groups. As valence allows, if said further ring is cycloalkyl or heterocyclo it is additionally optionally substituted with =O (oxo).

Exemplary monocyclic heterocyclyl groups include azetidinyl, pyrrolidinyl, oxetanyl, imidazolinyl, oxazolidinyl, isoxazolinyl, thiazolidinyl, isothiazolidinyl, tetrahydrofuranyl, piperidyl, piperazinyl, 2-oxopiperazinyl, 2-oxopiperidyl, 2-oxopyrrolodinyl, 2-oxoazepinyl, azepinyl, 1-pyridonyl, 4-piperidonyl, tetrahydropyranyl, morpholinyl, thiamorpholinyl, thiamorpholinyl sulfoxide, thiamorpholinyl sulfone, 1,3-dioxolane and tetrahydro-1,1-dioxothienyl and the like. Exemplary bicyclic heterocyclo groups include quinuclidinyl. Additional heterocyclyl groups include

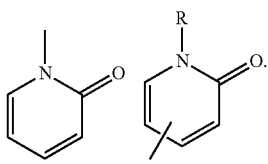 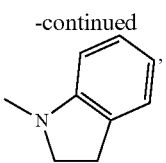

The term "heteroaryl" refers to substituted and unsubstituted aromatic 5- or 6-membered monocyclic groups, 9- or 10-membered bicyclic groups, and 11- to 14-membered tricyclic groups which have at least one heteroatom (O, S or N) in at least one of the rings, said heteroatom-containing ring preferably having 1, 2, or 3 heteroatoms selected from O, S, and N. Each ring of the heteroaryl group containing a heteroatom can contain one or two oxygen or sulfur atoms and/or from one to four nitrogen atoms provided that the total number of heteroatoms in each ring is four or less and each ring has at least one carbon atom. The fused rings completing the bicyclic and tricyclic groups may contain only carbon atoms and may be saturated, partially saturated, or unsaturated. The nitrogen and sulfur atoms may optionally be oxidized and the nitrogen atoms may optionally be quaternized. Heteroaryl groups which are bicyclic or tricyclic must include at least one fully aromatic ring but the other fused ring or rings may be aromatic or non-aromatic. The heteroaryl group may be attached at any available nitrogen or carbon atom of any ring. As valence allows, if said further ring is cycloalkyl or heterocyclo it is additionally optionally substituted with =O (oxo).

Exemplary monocyclic heteroaryl groups include pyrrolyl, pyrazolyl, pyrazolinyl, imidazolyl, oxazolyl, isoxazolyl, thiazolyl, thiadiazolyl, isothiazolyl, furanyl, thienyl, oxadiazolyl, pyridyl, pyrazinyl, pyrimidinyl, pyridazinyl, triazinyl and the like.

Exemplary bicyclic heteroaryl groups include indolyl, benzothiazolyl, benzodioxolyl, benzoxazolyl, benzothienyl, quinolinyl, tetrahydroisoquinolinyl, isoquinolinyl, benzimidazolyl, benzopyranyl, indolizinyl, benzofuranyl, chromonyl, coumarinyl, benzopyranyl, cinnolinyl, quinoxalinyl, indazolyl, pyrrolopyridyl, furopyridyl, dihydroisoindolyl, tetrahydroquinolinyl, and the like.

Exemplary tricyclic heteroaryl groups include carbazolyl, benzindolyl, phenanthrollinyl, acridinyl, phenanthridinyl, xanthenyl and the like.

In compounds of formula (I), preferred heteroaryl groups include

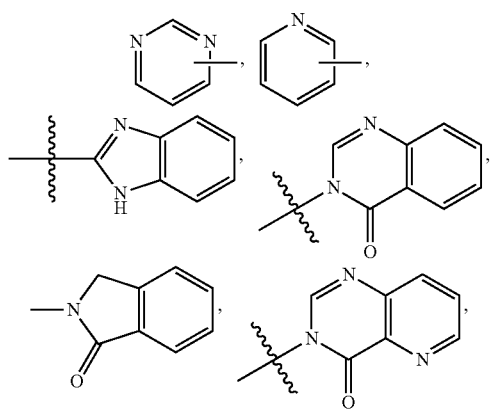

and the like, which optionally may be substituted at any available carbon or nitrogen atom.

Unless otherwise indicated, when reference is made to a specifically-named aryl (e.g., phenyl), cycloalkyl (e.g., cyclohexyl), heterocyclo (e.g., pyrrolidinyl, piperidinyl, and morpholinyl) or heteroaryl (e.g., tetrazolyl, imidazolyl, pyrazolyl, triazolyl, thiazolyl, and furyl) the reference is intended to include rings having 0 to 3, preferably 0-2, substituents selected from those recited above for the aryl, cycloalkyl, heterocyclo and/or heteroaryl groups, as appropriate.

The term "carbocyclyl" or "carbocyclic" refers to a saturated or unsaturated monocyclic or bicyclic ring in which all atoms of all rings are carbon. Thus, the term includes cycloalkyl and aryl rings. Monocyclic carbocycles have 3 to 6 ring atoms, still more typically 5 or 6 ring atoms. Bicyclic carbocycles have 7 to 12 ring atoms, e.g., arranged as a bicyclo [4,5], [5,5], [5,6] or [6,6] system, or 9 or 10 ring atoms arranged as a bicyclo [5,6] or [6,6] system. Examples of mono- and bicyclic carbocycles include cyclopropyl, cyclobutyl, cyclopentyl, 1-cyclopent-1-enyl, 1-cyclopent-2-enyl, 1-cyclopent-3-enyl, cyclohexyl, 1-cyclohex-1-enyl, 1-cyclohex-2-enyl, 1-cyclohex-3-enyl, phenyl and naphthyl. The carbocyclic ring may be substituted in which case the substituents are selected from those recited above for cycloalkyl and aryl groups.

The term "heteroatoms" shall include oxygen, sulfur and nitrogen.

When the term "unsaturated" is used herein to refer to a ring or group, the ring or group may be fully unsaturated or partially unsaturated.

Throughout the specification, groups and substituents thereof may be chosen by one skilled in the field to provide stable moieties and compounds and compounds useful as pharmaceutically-acceptable compounds and/or intermediate compounds useful in making pharmaceutically-acceptable compounds.

The compounds of formula (I) may exist in a free form (with no ionization) or can form salts which are also within the scope of this invention. Unless otherwise indicated, reference to an inventive compound is understood to include reference to the free form and to salts thereof. The term "salt(s)" denotes acidic and/or basic salts formed with inorganic and/or organic acids and bases. In addition, the term "salt(s) may include zwitterions (inner salts), e.g., when a compound of formula (I), contains both a basic moiety, such as an amine or a pyridine or imidazole ring, and an acidic moiety, such as a carboxylic acid. Pharmaceutically acceptable (i.e., non-toxic, physiologically acceptable) salts are preferred, such as, for example, acceptable metal and amine salts in which the cation does not contribute significantly to the toxicity or biological activity of the salt. However, other salts may be useful, e.g., in isolation or purification steps which may be employed during preparation, and thus, are contemplated within the scope of the invention. Salts of the compounds of the formula (I) may be formed, for example, by reacting a compound of the formula (I) with an amount of acid or base, such as an equivalent amount, in a medium such as one in which the salt precipitates or in an aqueous medium followed by lyophilization.

Exemplary acid addition salts include acetates (such as those formed with acetic acid or trihaloacetic acid, for example, trifluoroacetic acid), adipates, alginates, ascorbates, aspartates, benzoates, benzenesulfonates, bisulfates, borates, butyrates, citrates, camphorates, camphorsulfonates, cyclopentanepropionates, digluconates, dodecylsulfates, ethanesulfonates, fumarates, glucoheptanoates, glycerophosphates, hemisulfates, heptanoates, hexanoates, hydrochlorides (formed with hydrochloric acid), hydrobromides (formed with hydrogen bromide), hydroiodides, 2-hydroxyethanesulfonates, lactates, maleates (formed with maleic acid), methanesulfonates (formed with methanesulfonic acid), 2-naphthalenesulfonates, nicotinates, nitrates, oxalates, pectinates, persulfates, 3-phenylpropionates, phosphates, picrates, pivalates, propionates, salicylates, succinates, sulfates (such as those formed with sulfuric acid), sulfonates (such as those mentioned herein), tartrates, thiocyanates, toluenesulfonates such as tosylates, undecanoates, and the like.

Exemplary basic salts include ammonium salts, alkali metal salts such as sodium, lithium, and potassium salts; alkaline earth metal salts such as calcium and magnesium salts; barium, zinc, and aluminum salts; salts with organic bases (for example, organic amines) such as trialkylamines such as triethylamine, procaine, dibenzylamine, N-benzyl-β-phenethylamine, 1-ephenamine, N,N'-dibenzylethylene-diamine, dehydroabietylamine, N-ethylpiperidine, benzylamine, dicyclohexylamine or similar pharmaceutically acceptable amines and salts with amino acids such as arginine, lysine and the like. Basic nitrogen-containing groups may be quaternized with agents such as lower alkyl halides (e.g., methyl, ethyl, propyl, and butyl chlorides, bromides and iodides), dialkyl sulfates (e.g., dimethyl, diethyl, dibutyl, and diamyl sulfates), long chain halides (e.g., decyl, lauryl, myristyl and stearyl chlorides, bromides and iodides), aralkyl halides (e.g., benzyl and phenethyl bromides), and others. Preferred salts include monohydrochloride, hydrogensulfate, methanesulfonate, phosphate or nitrate salts.

The phrase "pharmaceutically acceptable" is employed herein to refer to those compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

As used herein, "pharmaceutically acceptable salts" refer to derivatives of the disclosed compounds wherein the parent compound is modified by making acid or base salts thereof. Examples of pharmaceutically acceptable salts include, but are not limited to, mineral or organic acid salts of basic groups such as amines; and alkali or organic salts of acidic groups such as carboxylic acids. The pharmaceutically acceptable salts include the conventional non-toxic salts or the quaternary ammonium salts of the parent compound formed, for example, from non-toxic inorganic or organic acids. For example, such conventional non-toxic salts include those derived from inorganic acids such as hydrochloric, hydrobromic, sulfuric, sulfamic, phosphoric, and nitric; and the salts prepared from organic acids such as acetic, propionic, succinic, glycolic, stearic, lactic, malic, tartaric, citric, ascorbic, pamoic, maleic, hydroxymaleic, phenylacetic, glutamic, benzoic, salicylic, sulfanilic, 2-acetoxybenzoic, fumaric, toluenesulfonic, methanesulfonic, ethane disulfonic, oxalic, and isethionic, and the like.

The pharmaceutically acceptable salts of the present invention can be synthesized from the parent compound which contains a basic or acidic moiety by conventional chemical methods. Generally, such salts can be prepared by reacting the free acid or base forms of these compounds with a stoichiometric amount of the appropriate base or acid in water or in an organic solvent, or in a mixture of the two; generally, nonaqueous media like ether, ethyl acetate, ethanol, isopropanol, or acetonitrile are preferred. Lists of suitable salts are found in *Remington's Pharmaceutical Sciences,* 18th Edition, Mack Publishing Company, Easton, Pa. (1990), the disclosure of which is hereby incorporated by reference.

All stereoisomers of the compounds of the instant invention are contemplated, either in admixture or in pure or substantially pure form. Stereoisomers may include compounds which are optical isomers through possession of one or more chiral atoms, as well as compounds which are optical isomers by virtue of limited rotation about one or more bonds (atropisomers). The definition of compounds according to the invention embraces all the possible stereoisomers and their mixtures. It very particularly embraces the racemic forms and the isolated optical isomers having the specified activity. The racemic forms can be resolved by physical methods, such as, for example, fractional crystallization, separation or crystallization of diastereomeric derivatives or separation by chiral column chromatography. The individual optical isomers can be obtained from the racemates from the conventional methods, such as, for example, salt formation with an optically active acid followed by crystallization.

The present invention is intended to include all isotopes of atoms occurring in the present compounds. Isotopes include those atoms having the same atomic number but different mass numbers. By way of general example and without limitation, isotopes of hydrogen include deuterium and tritium. Isotopes of carbon include $^{13}C$ and $^{14}C$. Isotopically-labeled compounds of the invention can generally be prepared by conventional techniques known to those skilled in the art or by processes analogous to those described herein, using an appropriate isotopically-labeled reagent in place of the non-labeled reagent otherwise employed.

Prodrugs and solvates of the inventive compounds are also contemplated. The term "prodrug" denotes a compound which, upon administration to a subject, undergoes chemical conversion by metabolic or chemical processes to yield a compound of the formula (I), and/or a salt and/or solvate thereof. Any compound that will be converted in vivo to provide the bioactive agent (i.e., the compound for formula (I)) is a prodrug within the scope and spirit of the invention. For example, compounds containing a carboxy group can form physiologically hydrolyzable esters which serve as prodrugs by being hydrolyzed in the body to yield formula (I) compounds per se. Such prodrugs are preferably administered orally since hydrolysis in many instances occurs principally under the influence of the digestive enzymes. Parenteral administration may be used where the ester per se is active, or in those instances where hydrolysis occurs in the blood. Examples of physiologically hydrolyzable esters of compounds of formula (I) include $C_{1-6}$alkylbenzyl, 4-methoxybenzyl, indanyl, phthalyl, methoxymethyl, $C_{1-6}$alkanoyloxy-$C_{1-6}$alkyl, e.g., acetoxymethyl, pivaloyloxymethyl or propionyloxymethyl, $C_{1-6}$alkoxycarbonyloxy-$C_{1-6}$alkyl, e.g., methoxycarbonyl-oxymethyl or ethoxycarbonyloxymethyl, glycyloxymethyl, phenylglycyloxymethyl, (5-methyl-2-oxo-1,3-dioxolen-4-yl)-methyl and other well known physiologically hydrolyzable esters used, for example, in the penicillin and cephalosporin arts. Such esters may be prepared by conventional techniques known in the art.

Various forms of prodrugs are well known in the art. For examples of such prodrug derivatives, see:

a) *Design of Prodrugs*, Bundgaard, H., ed. (Elsevier, 1985) and *Methods in Enzymology*, Vol. 112, pp. 309-396, K. Widder, K. et al., eds. (Academic Press, 1985);

b) *A Textbook of Drug Design and Development*, Krosgaard-Larsen et al., eds., and Bundgaard, H., Chapter 5, "Design and Application of Prodrugs", pp. 113-191 (1991); and c) Bundgaard, H., *Advanced Drug Delivery Reviews*, Vol. 8, pp. 1-38 (1992), each of which is incorporated herein by reference.

Compounds of the formula (I) and salts thereof may exist in their tautomeric form, in which hydrogen atoms are transposed to other parts of the molecules and the chemical bonds between the atoms of the molecules are consequently rearranged. It should be understood that the all tautomeric forms, insofar as they may exist, are included within the invention.

Compounds of this invention may have one or more asymmetric centers. Unless otherwise indicated, all chiral (enantiomeric and diastereomeric) and racemic forms of compounds of the present invention are included in the present invention. Many geometric isomers of olefins, C=N double bonds, and the like can also be present in the compounds, and all such stable isomers are contemplated in the present invention. Cis and trans geometric isomers of the compounds of the present invention are described and may be isolated as a mixture of isomers or as separated isomeric forms. The present compounds can be isolated in optically active or racemic forms. It is well known in the art how to prepare optically active forms, such as by resolution of racemic forms or by synthesis from optically active starting materials. All chiral, (enantiomeric and diastereomeric) and racemic forms and all geometric isomeric forms of a structure are intended, unless the specific stereochemistry or isomer form is specifically indicated. All geometric isomers, tautomers, atropisomers, hydrates, solvates, polymorphs, and isotopically labeled forms of the compounds referred to herein, and mixtures thereof, are considered within the scope of the present invention. Methods of solvation are generally known in the art.

Utility

The compounds of the invention modulate kinase activity, including the modulation of Btk. Other types of kinase activity that may be modulated by the compounds of the instant invention include, but are not limited to, the Tec family of compounds, such as Bmx, Btk, Itk, Txk and Tec, and mutants thereof.

Accordingly, compounds of formula (I) have utility in treating conditions associated with the modulation of kinase activity, and particularly the selective inhibition of Btk activity or the inhibition of Btk and other Tec family kinases such as Itk. Such conditions include B-cell mediated diseases in which cytokine levels are modulated as a consequence of intracellular signaling. In another embodiment, compounds of formula (I) have advantageous selectivity for Btk activity and other Tec family kinases such as Tec over Lck activity, preferably from at least 20 fold to over 1,000 fold more selective.

As used herein, the terms "treating" or "treatment" encompass the treatment of a disease state in a mammal, particularly in a human, and include: (a) preventing or delaying the occurrence of the disease state in a mammal, in particular, when such mammal is predisposed to the disease state but has not yet been diagnosed as having it; (b) inhibiting the disease state, i.e., arresting its development; and/or (c) achieving a full or partial reduction of the symptoms or disease state, and/or alleviating, ameliorating, lessening, or curing the disease or disorder and/or its symptoms.

In view of their activity as selective inhibitors of Btk or Btk and other Tec family kinase such as Itk, compounds of Formula (I) are useful in treating cytokine-associated conditions including, but not limited to, inflammatory diseases such as Crohn's and ulcerative colitis, asthma, graft versus host disease, chronic obstructive pulmonary disease; autoimmune diseases such as Graves' disease, rheumatoid arthritis, systemic lupus erythematosis, psoriasis; destructive bone disorders such as bone resorption disease, osteoarthritis, osteoporosis, multiple myeloma-related bone disorder; proliferative disorders such as acute myelogenous leukemia, chronic myelogenous leukemia; angiogenic disorders such as angiogenic disorders including solid tumors, ocular neovasculization, and infantile haemangiomas; infectious diseases such as sepsis, septic shock, and Shigellosis; neurodegenerative diseases such as Alzheimer's disease, Parkinson's disease, cerebral ischemias or neurodegenerative disease caused by traumatic injury, oncologic and viral diseases such as metastatic melanoma, Kaposi's sarcoma, multiple myeloma, and HIV infection and CMV retinitis, AIDS, respectively.

More particularly, the specific conditions or diseases that may be treated with the inventive compounds include, without limitation, pancreatitis (acute or chronic), asthma, allergies, adult respiratory distress syndrome, chronic obstructive pulmonary disease, glomerulonephritis, rheumatoid arthritis, systemic lupus erythematosis, scleroderma, chronic thyroiditis, Graves' disease, autoimmune gastritis, diabetes, autoimmune hemolytic anemia, autoimmune neutropenia, thrombocytopenia, atopic dermatitis, chronic active hepatitis, myasthenia gravis, multiple sclerosis, inflammatory bowel disease, ulcerative colitis, Crohn's disease, psoriasis, graft vs. host disease, inflammatory reaction induced by endotoxin, tuberculosis, atherosclerosis, muscle degeneration, cachexia, psoriatic arthritis, Reiter's syndrome, gout, traumatic arthritis, rubella arthritis, acute synovitis, pancreatic β-cell disease; diseases characterized by massive neutrophil infiltration; rheumatoid spondylitis, gouty arthritis and other arthritic conditions, cerebral malaria, chronic pulmonary inflammatory disease, silicosis, pulmonary sarcoisosis, bone resorption disease, allograft rejections, fever and myalgias due to infection, cachexia secondary to infection, meloid formation, scar tissue formation, ulcerative colitis, pyresis, influenza, osteoporosis, osteoarthritis, acute myelogenous leukemia, chronic myelogenous leukemia, metastatic melanoma, Kaposi's sarcoma, multiple myeloma, sepsis, septic shock, and Shigellosis; Alzheimer's disease, Parkinson's disease, cerebral ischemias or neurodegenerative disease caused by traumatic injury; angiogenic disorders including solid tumors, ocular neovasculization, and infantile haemangiomas; viral diseases including acute hepatitis infection (including hepatitis A, hepatitis B and hepatitis C), HIV infection and CMV retinitis, AIDS, ARC or malignancy, and herpes; stroke, myocardial ischemia, ischemia in stroke heart attacks, organ hyposia, vascular hyperplasia, cardiac and renal reperfusion injury, thrombosis, cardiac hypertrophy, thrombin-induced platelet aggregation, endotoxemia and/or toxic shock syndrome, conditions associated with prostaglandin endoperoxidase syndase-2, and pemphigus vulgaris. Preferred methods of treatment are those wherein the condition is selected from Crohn's and ulcerative colitis, allograft rejection, rheumatoid arthritis, psoriasis, ankylosing spondylitis, psoriatic arthritis, and pemphigus vulgaris. Alternatively preferred methods of treatment are those wherein the condition is selected from ischemia reperfusion injury, including cerebral ischemia reperfusions injury arising from stroke and cardiac ischemia reperfusion injury arising from myocardial infarction. Another preferred method of treatment is one in which the condition is multiple myeloma.

In addition, the kinase inhibitors of the present invention inhibit the expression of inducible pro-inflammatory proteins such as prostaglandin endoperoxide synthase-2 (PGHS-2), also referred to as cyclooxygenase-2 (COX-2). Accordingly, additional Btk-associated conditions include edema, analgesia, fever and pain, such as neuromuscular pain, headache, pain caused by cancer, dental pain and arthritis pain. The inventive compounds also may be used to treat veterinary viral infections, such as lentivirus infections, including, but not limited to equine infectious anemia virus; or retro virus infections, including feline immunodeficiency virus, bovine immunodeficiency virus, and canine immunodeficiency virus.

When the terms "Btk-associated condition" or "Btk-associated disease or disorder" are used herein, each is intended to encompass all of the conditions identified above as if repeated at length, as well as any other condition that is affected by Btk kinase activity.

The present invention thus provides methods for treating such conditions, comprising administering to a subject in need thereof a therapeutically-effective amount of at least one compound of Formula (I) or a salt thereof "Therapeutically effective amount" is intended to include an amount of a compound of the present invention that is effective when administered alone or in combination to inhibit Btk and other Tec family kinases and/or treat diseases.

The methods of treating Btk kinase-associated conditions may comprise administering compounds of Formula (I) alone or in combination with each other and/or other suitable therapeutic agents useful in treating such conditions. Accordingly, "therapeutically effective amount" is also intended to include an amount of the combination of compounds claimed that is effective to inhibit Btk and/or treat diseases associated with Btk.

Exemplary of such other therapeutic agents include corticosteroids, rolipram, calphostin, cytokine-suppressive anti-inflammatory drugs (CSAIDs), Interleukin-10, glucocorticoids, salicylates, nitric oxide, and other immunosuppressants; nuclear translocation inhibitors, such as deoxyspergualin (DSG); non-steroidal antiinflammatory drugs (NSAIDs) such as ibuprofen, celecoxib and rofecoxib; steroids such as prednisone or dexamethasone; antiviral agents such as abacavir; antiproliferative agents such as methotrexate, leflunomide, FK506 (tacrolimus, PROGRAF®); cytotoxic drugs such as azathiprine and cyclophosphamide; TNF-α inhibitors such as tenidap, anti-TNF antibodies or soluble TNF receptor, and rapamycin (sirolimus or RAPAMUNE®) or derivatives thereof.

The above other therapeutic agents, when employed in combination with the compounds of the present invention, may be used, for example, in those amounts indicated in the *Physicians' Desk Reference* (PDR) or as otherwise determined by one of ordinary skill in the art. In the methods of the present invention, such other therapeutic agent(s) may be administered prior to, simultaneously with, or following the administration of the inventive compounds. The present invention also provides pharmaceutical compositions capable of treating Btk kinase-associated conditions, including IL-1, IL-6, IL-8, IFNγ and TNF-α-mediated conditions, as described above.

The inventive compositions may contain other therapeutic agents as described above and may be formulated, for example, by employing conventional solid or liquid vehicles or diluents, as well as pharmaceutical additives of a type appropriate to the mode of desired administration (e.g., excipients, binders, preservatives, stabilizers, flavors, etc.) according to techniques such as those well known in the art of pharmaceutical formulation.

Accordingly, the present invention further includes compositions comprising one or more compounds of Formula (I) and a pharmaceutically acceptable carrier.

A "pharmaceutically acceptable carrier" refers to media generally accepted in the art for the delivery of biologically active agents to animals, in particular, mammals. Pharmaceutically acceptable carriers are formulated according to a number of factors well within the purview of those of ordinary skill in the art. These include without limitation the type and nature of the active agent being formulated; the subject to which the agent-containing composition is to be administered; the intended route of administration of the composition; and, the therapeutic indication being targeted. Pharmaceutically acceptable carriers include both aqueous and non-aqueous liquid media, as well as a variety of solid and semi-solid dosage forms. Such carriers can include a number of different ingredients and additives in addition to the active agent, such additional ingredients being included in the formulation for a variety of reasons, e.g., stabilization of the active agent, binders, etc., well known to those of ordinary skill in the art. Descriptions of suitable pharmaceutically acceptable carriers, and factors involved in their selection, are found in a variety of readily available sources such as, for example, *Remington's Pharmaceutical Sciences,* 17th Edition (1985), which is incorporated herein by reference in its entirety.

The compounds of Formula (I) may be administered by any means suitable for the condition to be treated, which may depend on the need for site-specific treatment or quantity of drug to be delivered. Topical administration is generally preferred for skin-related diseases, and systematic treatment preferred for cancerous or pre-cancerous conditions, although other modes of delivery are contemplated. For example, the compounds may be delivered orally, such as in the form of tablets, capsules, granules, powders, or liquid formulations including syrups; topically, such as in the form of solutions, suspensions, gels or ointments; sublingually; bucally; parenterally, such as by subcutaneous, intravenous, intramuscular or intrasternal injection or infusion techniques (e.g., as sterile injectable aq. or non-aq. solutions or suspensions); nasally such as by inhalation spray; topically, such as in the form of a cream or ointment; rectally such as in the form of suppositories; or liposomally. Dosage unit formulations containing non-toxic, pharmaceutically acceptable vehicles or diluents may be administered. The compounds may be administered in a form suitable for immediate release or extended release. Immediate release or extended release may be achieved with suitable pharmaceutical compositions or, particularly in the case of extended release, with devices such as subcutaneous implants or osmotic pumps.

Exemplary compositions for topical administration include a topical carrier such as PLASTIBASE® (mineral oil gelled with polyethylene).

Exemplary compositions for oral administration include suspensions which may contain, for example, microcrystalline cellulose for imparting bulk, alginic acid or sodium alginate as a suspending agent, methylcellulose as a viscosity enhancer, and sweeteners or flavoring agents such as those known in the art; and immediate release tablets which may contain, for example, microcrystalline cellulose, dicalcium phosphate, starch, magnesium stearate and/or lactose and/or other excipients, binders, extenders, disintegrants, diluents and lubricants such as those known in the art. The inventive compounds may also be orally delivered by sublingual and/or buccal administration, e.g., with molded, compressed, or freeze-dried tablets. Exemplary compositions may include fast-dissolving diluents such as mannitol, lactose, sucrose, and/or cyclodextrins. Also included in such formulations may be high molecular weight excipients such as celluloses (AVICEL®) or polyethylene glycols (PEG); an excipient to aid mucosal adhesion such as hydroxypropyl cellulose (HPC), hydroxypropyl methyl cellulose (HPMC), sodium carboxymethyl cellulose (SCMC), and/or maleic anhydride copolymer (e.g., GANTREZ®); and agents to control release such as polyacrylic copolymer (e.g., CARBOPOL 934®). Lubricants, glidants, flavors, coloring agents and stabilizers may also be added for ease of fabrication and use.

Exemplary compositions for nasal aerosol or inhalation administration include solutions which may contain, for example, benzyl alcohol or other suitable preservatives, absorption promoters to enhance absorption and/or bioavailability, and/or other solubilizing or dispersing agents such as those known in the art.

Exemplary compositions for parenteral administration include injectable solutions or suspensions which may contain, for example, suitable non-toxic, parenterally acceptable diluents or solvents, such as mannitol, 1,3-butanediol, water, Ringer's solution, an isotonic sodium chloride solution, or other suitable dispersing or wetting and suspending agents, including synthetic mono- or diglycerides, and fatty acids, including oleic acid.

Exemplary compositions for rectal administration include suppositories which may contain, for example, suitable non-irritating excipients, such as cocoa butter, synthetic glyceride esters or polyethylene glycols, which are solid at ordinary temperatures but liquefy and/or dissolve in the rectal cavity to release the drug.

The therapeutically-effective amount of a compound of the present invention may be determined by one of ordinary skill in the art, and includes exemplary dosage amounts for a mammal of from about 0.05 to 1000 mg/kg; 1-1000 mg/kg; 1-50 mg/kg; 5-250 mg/kg; 250-1000 mg/kg of body weight of active compound per day, which may be administered in a single dose or in the form of individual divided doses, such as from 1 to 4 times per day. It will be understood that the specific dose level and frequency of dosage for any particular subject may be varied and will depend upon a variety of factors, including the activity of the specific compound employed, the metabolic stability and length of action of that compound, the species, age, body weight, general health, sex and diet of the subject, the mode and time of administration, rate of excretion, drug combination, and severity of the particular condition. Preferred subjects for treatment include animals, most preferably mammalian species such as humans, and domestic animals such as dogs, cats, horses, and the like. Thus, when the term "patient" is used herein, this term is intended to include all subjects, most preferably mammalian species, that are affected by mediation of Btk enzyme levels.

Biological Assays

Human Recombinant Btk Enzyme Assay

To V-bottom 384-well plates were added test compounds, human recombinant Btk (1 nM, Invitrogen Corporation), fluoresceinated peptide (1.5 µM), ATP (20 µM), and assay buffer (20 mM HEPES pH 7.4, 10 mM MgCl$_2$, 0.015% Brij35 and 4 mM DTT in 1.6% DMSO), with a final volume of 30 µL. After incubating at room temperature for 60 min, the reaction was terminated by adding 45 µl of 35 mM EDTA to each sample. The reaction mixture was analyzed on the Caliper LABCHIP® 3000 (Caliper, Hopkinton, Mass.) by electrophoretic separation of the fluorescent substrate and phosphorylated product. Inhibition data were calculated by comparison to no enzyme control reactions for 100% inhibition and no inhibitor controls for 0% inhibition. Dose response curves were generated to determine the concentration required inhibiting 50% of kinase activity (IC$_{50}$). Compounds were dissolved at 10 mM in dimethylsulfoxide (DMSO) and evaluated at eleven concentrations.

Using this assay, the IC$_{50}$ values of the following compounds were determined. See Table 1.

TABLE 1

| Example | IC$_{50}$ for Inhibition of Btk, nM |
|---------|-------------------------------------|
| 9       | 2                                   |
| 11      | 3                                   |
| 30      | 3                                   |
| 32      | 7                                   |
| 34      | 7                                   |
| 35      | 57                                  |
| 36      | 3                                   |
| 37      | 14                                  |
| 41      | 6                                   |
| 42      | 521                                 |
| 54      | 65                                  |
| 55      | 43                                  |
| 56      | 32                                  |
| 60      | 85                                  |
| 64      | 8                                   |
| 71      | 3                                   |
| 87      | 7                                   |
| 99      | 8                                   |
| 110     | 14                                  |
| 117     | 23                                  |

Mouse Splenic B Cell Proliferation Assay

Spleens from Balb/c mice (<12 weeks old) were mashed through screens and red blood cells were removed from splenocytes with RBC lysing buffer (Sigma-Aldrich Chemical Co, St. Louis, Mo.). T cells were depleted by incubation on nylon wool columns (Wako, Richmond, Va.). Resulting splenic B cells prepared this way were routinely >90% CD19$^+$ as measured by FACS analysis. B cells (1×10$^5$ cells per well) were added to serial dilutions of compounds in triplicate in 96-well flat-bottom plates in RPMI 1640 (Invitrogen, Grand Island, N.Y.), supplemented with 10% heat-inactivated fetal calf serum (FCS, Summit Biotechnology, Fort Collins, Colo.), containing 1% L-glutamine (Invitrogen), 50 µg/ml gentamicin (Invitrogen) and 5×10$^{-5}$M β-mercaptoethanol (Sigma-Aldrich). Cells were stimulated with 10 µg/ml of Affinipure F(ab')$_2$ fragment goat anti-mouse IgG IgM (Jackson Immunoresearch, West Grove, Pa.). Cultures were incubated for 72 hours, and pulsed for the last 6 hours with one µCi/well of $^3$[H]-thymidine (PerkinElmer, Boston, Mass.) prior to harvest on a Packard cell harvester (PerkinElmer), and counted by liquid scintillation on a Packard TOPCOUNT® NXT (PerkinElmer). The most potent analogs were found to be active below 1 µM.

Human Tonsillar B Cell Proliferation Assay

Tonsils were excised from patients undergoing routine tonsillectomy. Tonsil tissue was minced, mashed through screens and mononuclear cells were isolated on ficoll density gradients (Lymphocyte Separation Media; Mediatech Inc., Herndon, Va.). T cells were depleted from mononuclear cells by rosetting with sheep red blood cells (SRBC, Colorado Serum Company; Denver, Colo.). Tonsillar B cells prepared by this method were routinely >95% CD19$^+$ as measured by FACS analysis. B cells (1×10⁵ cells per well) were added to serial dilutions of compounds in triplicate in 96-well flat-bottom plates in RPMI 1640, (Invitrogen, Grand Island, N.Y.), supplemented with 10% heat-inactivated fetal calf serum (FCS, Summit Biotechnology, Fort Collins, Colo.), and containing antibiotic/antimycotic (Invitrogen, 1:100 dilution) and gentamicin (Invitrogen, 5 μg/ml). Cells were stimulated with 40 μg/ml AffinPure F(ab')2 Fragment Goat anti Human IgG+IgM (Jackson Immunoresearch, West Grove, Pa.) in a total volume of 0.2 ml. Cultures were incubated for 72 hours, and pulsed for the last 6 hours with one μCi/well of $^3$[H]-thymidine (PerkinElmer, Boston, Mass.) prior to harvest on a Packard cell harvester (PerkinElmer), and counted by liquid scintillation on a Packard TOPCOUNT® NXT (PerkinElmer).

Btk Phosphorylation Assay

Ramos cells (~6×10⁶ cells/ml) were incubated in the presence of Btk inhibitors for 1 hr at 37° C. before being stimulated with anti-human IgM+IgG (F(ab')2 fragment, Jackson ImmunoResearch, catalog #109-006-127) at 50 μg/mL for exactly 2 min at 37° C. Cells were immediately fixed by adding an equal volume of pre-warmed BD Phosflow Fix Buffer I (BD Biosciences, catalog number 557870) to the cell suspension. After incubating at 37° C. for 10 minutes, the cells were washed once with 3 mL FACS washing buffer (1% FBS/PBS) and permeabilized by adding 0.5 mL of cold BD Phosflow Perm Buffer III (BD Biosciences, catalog number 558050) and incubating for 30 minutes on ice. The cells were washed an additional two times with 3 mL BD FACS washing buffer, re-suspended in 100 μL FACS washing buffer, stained with 20 μL Alexa647 anti-Btk (pY551) (BD Biosciences, catalog number 558134), incubated at room temperature for 30 minutes in the dark, and washed once with 3 ml of FACS washing buffer. The cells were re-suspended in 400 μl FACS wash buffer and analyzed using FACSCalibur (BD Biosciences). Median fluorescent intensity (MFI) on Alexa 647 (FL-4) data were collected and used for calculations of inhibition.

Ramos FLIPR® Assay

Ramos RA1 B cells (ATCC CRL-1596) at a density of 2×10⁶ cells/ml in RPMI minus phenol red (Invitrogen 11835-030) and 50 mM HEPES (Invitrogen 15630-130) containing 0.1% BSA (Sigma A8577) were added to one half volume of calcium loading buffer (BD bulk kit for probenecid sensitive assays, #640177) and incubated at room temperature in the dark for 1 hour. Dye-loaded cells were pelleted (Beckmann GS-CKR, 1200 rpm, RT, 5 minutes) and resuspended in RT RPMI minus phenol red with 50 mM HEPES and 10% FBS to a density of 1×10⁶ cells/ml. 150 μl aliquots (150,000/well) were plated into 96 well poly-D-lysine coated assay plates (BD 35 4640) and briefly centrifuged (Beckmann GS-CKR 800 rpm, 5 minutes, without brake). 50 μl compound dilutions in 0.4% DMSO/RPMI minus phenol red+50 mM HEPES+10% FBS were added to the wells and the plate was incubated at RT in the dark for 1 hour. Assay plate was briefly centrifuged as above prior to measuring calcium levels.

Using the FLIPR1 (Molecular devices), cells were stimulated by adding goat anti-human IgM (Invitrogen AHI0601) to 2.5 μg/mL. Changes in intracellular calcium concentrations were measured for 180 seconds and percent inhibition was determined relative to peak calcium levels seen in the presence of stimulation only. Biological activity of certain compounds as assessed using this assay is shown in Table 2.

TABLE 2

| Example | IC50 for Inhibition of Ramos FLIPR® assay, nM |
|---|---|
| 25 | 62 |
| 30 | 16 |
| 31 | 71 |
| 35 | 1,382 |
| 37 | 190 |
| 41 | >500 |
| 42 | >1000 |
| 71 | 71 |
| 73 | 1,031 |
| 77 | 81 |
| 79 | 856 |
| 82 | 1,078 |
| 85 | 1,417 |
| 87 | 63 |
| 90 | 84 |
| 92 | 56 |
| 97 | 15 |
| 100 | 19 |
| 110 | 96 |
| 117 | 294 |

NFAT-bla RA1 Reporter Assay

Ramos B cells containing a stable integration of a beta-lactamase reporter gene under the control of an NFAT response element (NFAT-bla RA1, Invitrogen, K1434) at a density of 100×103 cells/well were incubated with test compounds at 37° C. for 30 min prior to stimulation with F(ab')2 anti-human IgM (Jackson ImmunoResearch, 109-006-129) at 2.5 μg/ml for 4.5 hrs at 37° C. After stimulation, Live-BLAzer-FRET B/G Substrate (CCF2/AM, or CCF4/AM, Invitrogen) was added to each well and incubated for 90 min at room temperature in the dark. Assay plates were read on an LJL Analyst, with raw emission values subtracted from a media-only blank containing substrate in assay media (no cells). The ratios of 460 nm/530 nm emission (405 nm excitation) were used to calculate the amount of stimulation.

KLH Antigen Challenge and Antibody Measurement

Female BALB/c mice (6-8 weeks old) were immunized intraperitoneally (IP) with 250 μg keyhole limit hemocyanin (KLH) (Pierce, Rockford, Ill.) in phosphate-buffered saline (PBS). Mice in appropriate groups were dosed as indicated. Blood was collected 14 days post-immunization, serum was separated and analyzed for anti-KLH IgG titers by ELISA. Briefly, 96 well plates were coated with KLH in PBS, blocked, and serial dilutions of test serum samples were added. Captured anti-KLH antibodies were detected using horseradish peroxidase-conjugated antibody specific for mouse IgG (Southern Biotechnology Associates, Birmingham, Ala.) and the TMB peroxidase substrate system (Kirkegaard and Perry Laboratories, Gaithersburg, Md.). Optical densities of developed plates were quantitated in a SPECTRAMAX® Plus ELISA plate reader (Molecular Devices, Sunnyvale, Calif.). When administered twice daily, the compound of Example 76-15 inhibited the anti-KLH IgG response by 29% and 56% at 10 mg/kg and 30 mg/kg, respectively.

Methods of Preparation

Compounds of Formula (I), and intermediates used in the preparation of compounds of Formula (I), can be prepared using procedures shown in the following examples and related procedures. The methods and conditions used in these examples, and the actual compounds prepared in these examples, are not meant to be limiting, but are meant to demonstrate how the compounds of Formula (I) can be prepared. Starting materials and reagents used in these examples, when not prepared by a procedure described herein, are generally either commercially available, or are reported in the chemical literature, or may be prepared by using procedures described in the chemical literature.

In the examples given, the phrase "dried and concentrated" generally refers to drying of a solution in an organic solvent over either sodium sulfate or magnesium sulfate, followed by filtration and removal of the solvent from the filtrate (generally under reduced pressure and at a temperature suitable to the stability of the material being prepared). Column chromatography was performed with pre-packed silica gel cartridges using an ISCO medium pressure chromatography apparatus (Teledyne Corporation), eluting with the solvent or solvent mixture indicated. Preparative high performance liquid chromatography (HPLC) was performed using a reverse phase column (Waters Sunfire $C_{18}$, Waters Xbridge $C_{18}$, PHENOMENEX® Axia $C_{18}$, YMC S5 ODS or the like) of a size appropriate to the quantity of material being separated, generally eluting with a gradient of increasing concentration of methanol or acetonitrile in water, also containing 0.05% or 0.1% trifluoroacetic acid or 10 mM ammonium acetate, at a rate of elution suitable to the column size and separation to be achieved. Chemical names were determined using ChemDraw Ultra, version 9.0.5 (CambridgeSoft). The following abbreviations are used:

$NaHCO_3$ (aq)—saturated aqueous sodium bicarbonate
brine—saturated aqueous sodium chloride
DCM—dichloromethane
DIEA—N,N-diisopropylethylamine
DMAP—4-(N,N-dimethylamino)pyridine
DMF—N,N-dimethylformamide
DMSO—dimethyl sulfoxide
EDC—N-(3-dimethylaminopropyl)-N'-ethylcarbodiimide hydrochloride
EtOAc—ethyl acetate
HOAT—1-hydroxy-7-azabenzotriazole
HOBT—1-hydroxybenzotriazole hydrate
rt—ambient room temperature (generally about 20-25° C.).
TEA—triethylamine
TFA—trifluoroacetic acid
THF—tetrahydrofuran Schemes The compounds of Formula (I) may be prepared according to the following schemes and the knowledge of one skilled in the art.

Scheme 1

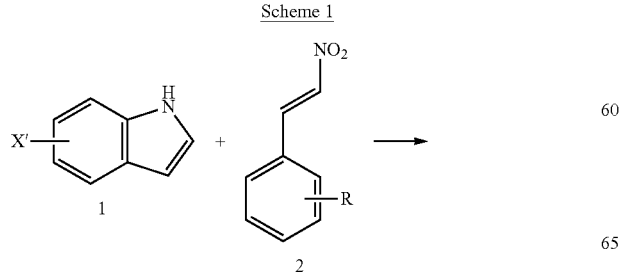

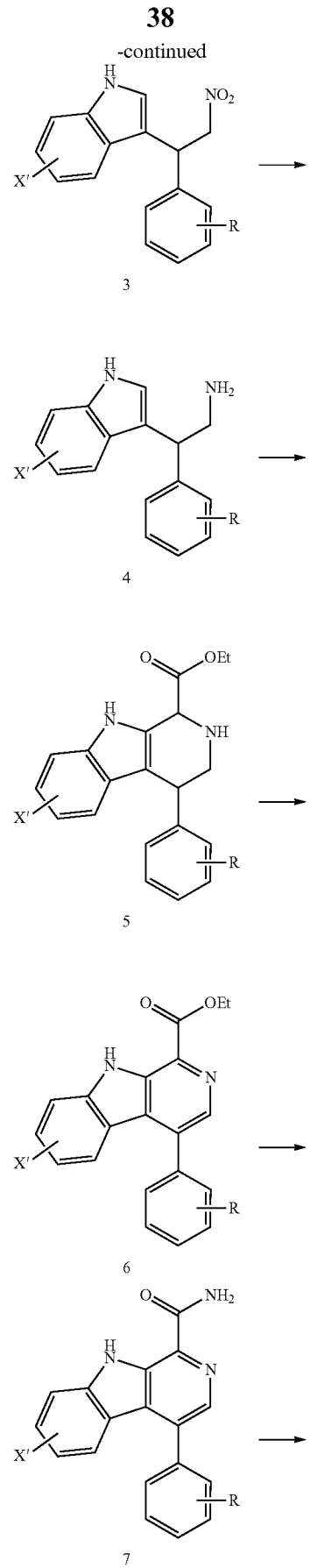

-continued

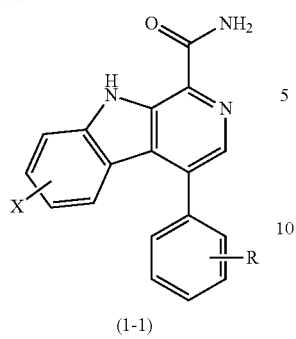

(1-1)

The compounds of Formula (1-1) can be prepared according to Scheme 1. Michael addition of indole 1 to nitro olefin 2 at melting conditions provides nitro intermediate 3. In some cases, the addition can also be effected in solution with or without a catalyst such as tris(trifluoromethylsulfonyloxy) ytterbium and indium (III) bromide. Reduction of 3 by hydrogenation with Raney Ni affords amine 4. This conversion can also be realized with zinc dust and ammonium chloride. Treatment of 4 with ethyl 2-oxoacetate in the presence of hydrogen chloride gives 5, which is aromatized with Pd/C to form β-carboline system 6. Hydrolysis of 6 and subsequent primary amide formation supplies target or target precursor 7. When necessary, compound 7 is further elaborated to (1-1) by methods known to those skilled in the art.

Scheme 2

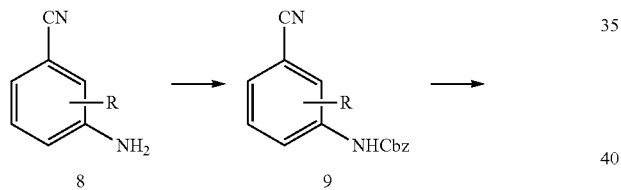

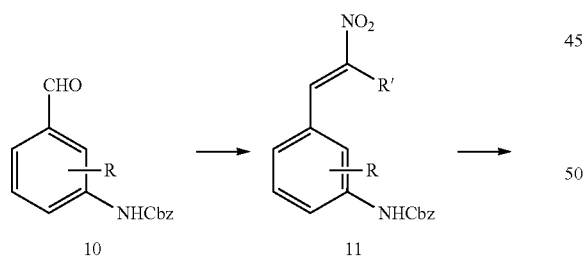

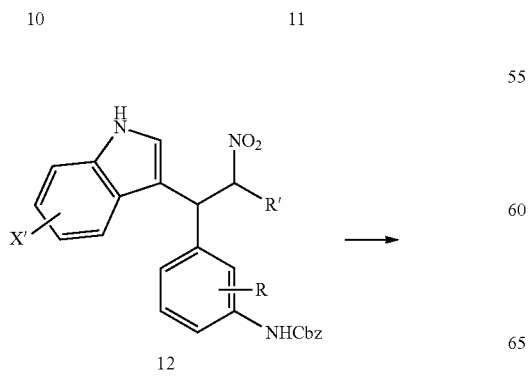

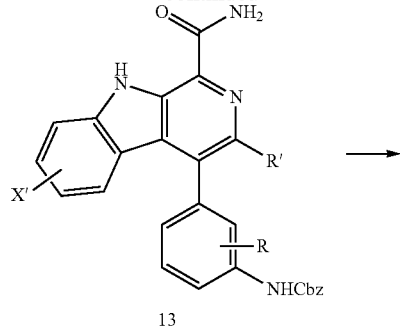

13

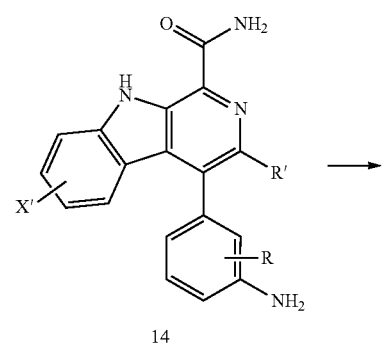

14

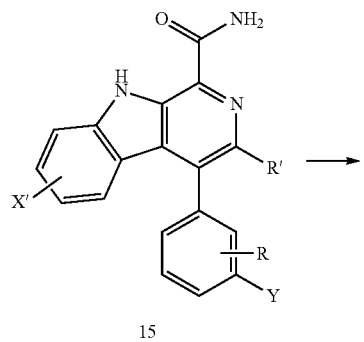

15

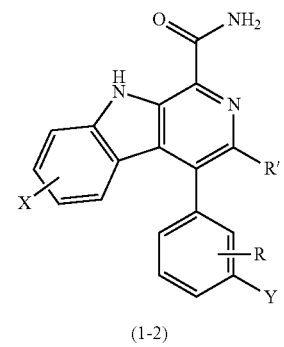

(1-2)

-continued

—Y = 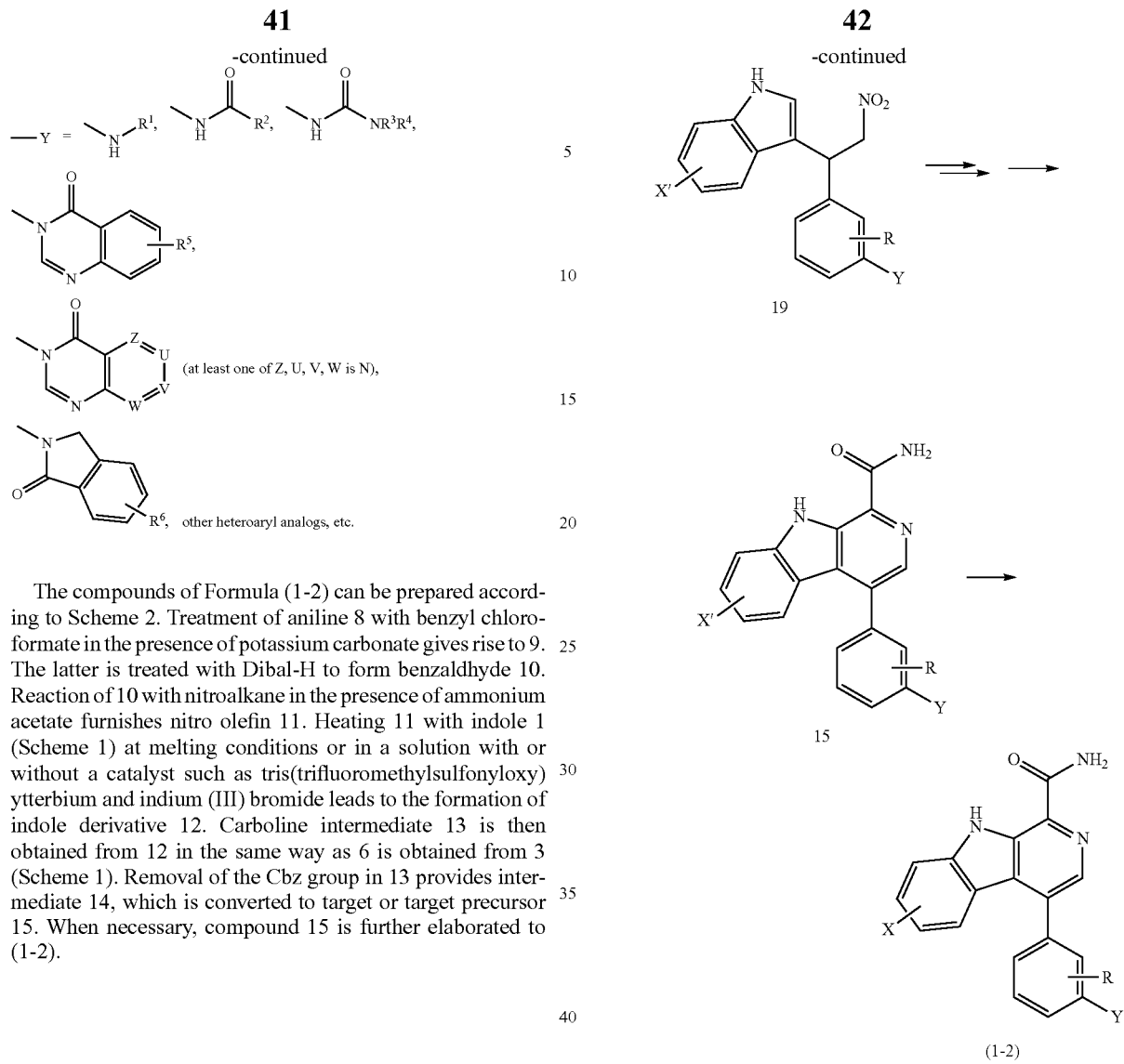

other heteroaryl analogs, etc.

The compounds of Formula (1-2) can be prepared according to Scheme 2. Treatment of aniline 8 with benzyl chloroformate in the presence of potassium carbonate gives rise to 9. The latter is treated with Dibal-H to form benzaldhyde 10. Reaction of 10 with nitroalkane in the presence of ammonium acetate furnishes nitro olefin 11. Heating 11 with indole 1 (Scheme 1) at melting conditions or in a solution with or without a catalyst such as tris(trifluoromethylsulfonyloxy) ytterbium and indium (III) bromide leads to the formation of indole derivative 12. Carboline intermediate 13 is then obtained from 12 in the same way as 6 is obtained from 3 (Scheme 1). Removal of the Cbz group in 13 provides intermediate 14, which is converted to target or target precursor 15. When necessary, compound 15 is further elaborated to (1-2).

Y is same as in Scheme 2

The compounds of Formula (1-2) can also be prepared according to Scheme 3. Aniline 8 can be converted to 16 in the same way as 14 is converted to 15 (Scheme 2). Treatment of 16 with Dibal-H produces benzaldhyde 17, which is converted to nitro olefin 18 with nitromethane in the presence of ammonium acetate. Heating 18 with indole 1 (Scheme 1) at melting conditions or in a solution with or without a catalyst such as tris(trifluoromethylsulfonyloxy)ytterbium and indium (III) bromide generates indole derivative 19. Target or target precursor 15 can be derived from 19 in the same way as compound 6 is derived from 3 (Scheme 1). When necessary, compound 15 is further elaborated to (1-2).

Scheme 3

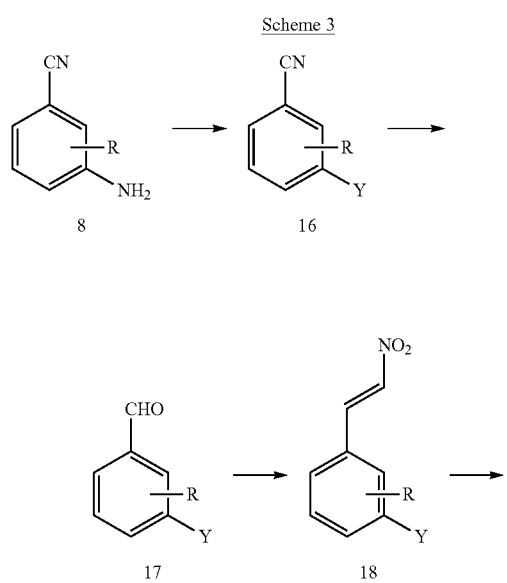

Scheme 4

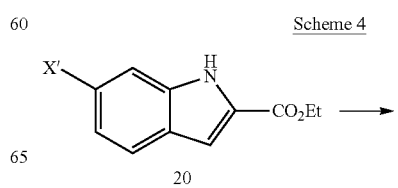

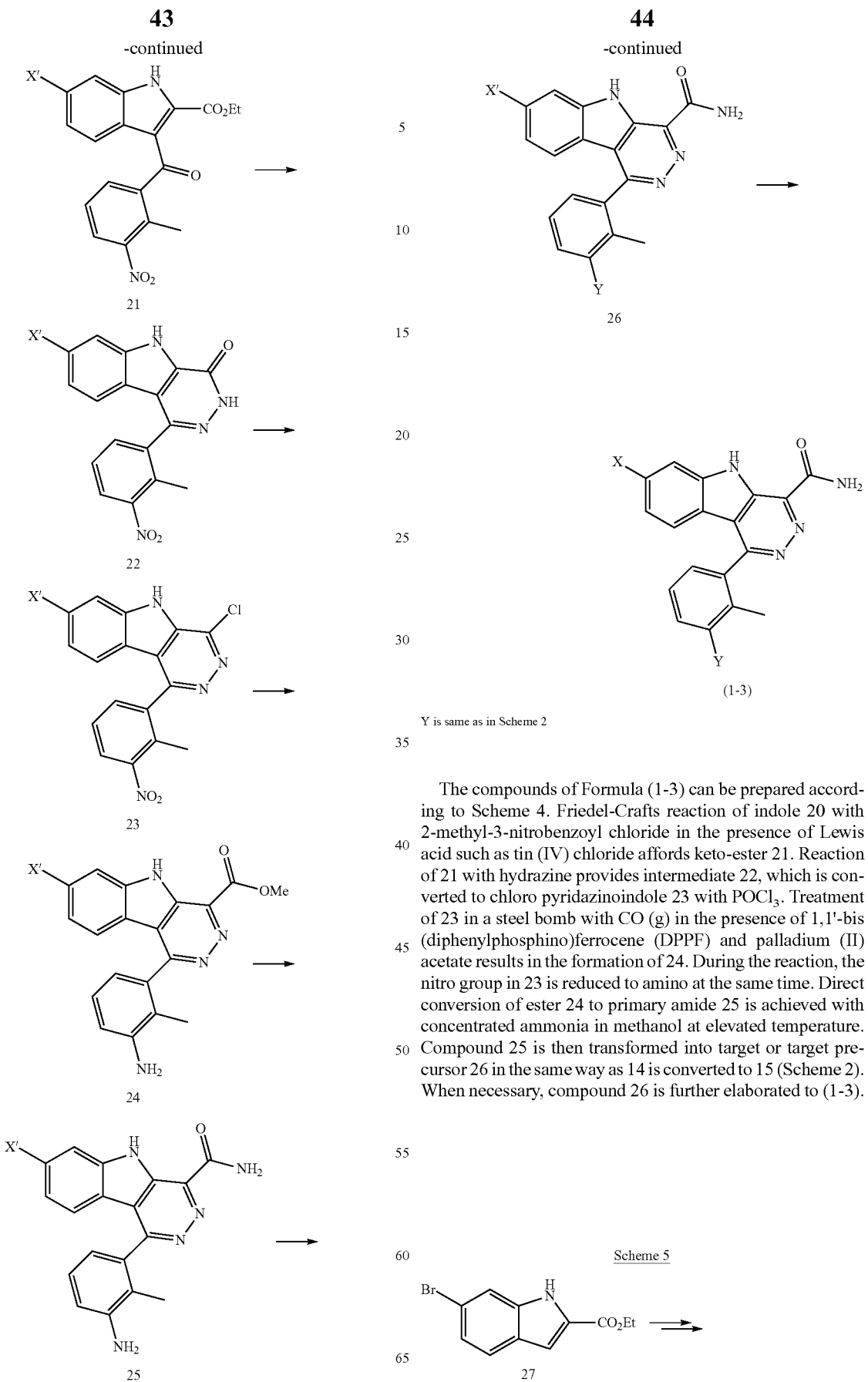

Y is same as in Scheme 2

The compounds of Formula (1-3) can be prepared according to Scheme 4. Friedel-Crafts reaction of indole 20 with 2-methyl-3-nitrobenzoyl chloride in the presence of Lewis acid such as tin (IV) chloride affords keto-ester 21. Reaction of 21 with hydrazine provides intermediate 22, which is converted to chloro pyridazinoindole 23 with $POCl_3$. Treatment of 23 in a steel bomb with CO (g) in the presence of 1,1'-bis(diphenylphosphino)ferrocene (DPPF) and palladium (II) acetate results in the formation of 24. During the reaction, the nitro group in 23 is reduced to amino at the same time. Direct conversion of ester 24 to primary amide 25 is achieved with concentrated ammonia in methanol at elevated temperature. Compound 25 is then transformed into target or target precursor 26 in the same way as 14 is converted to 15 (Scheme 2). When necessary, compound 26 is further elaborated to (1-3).

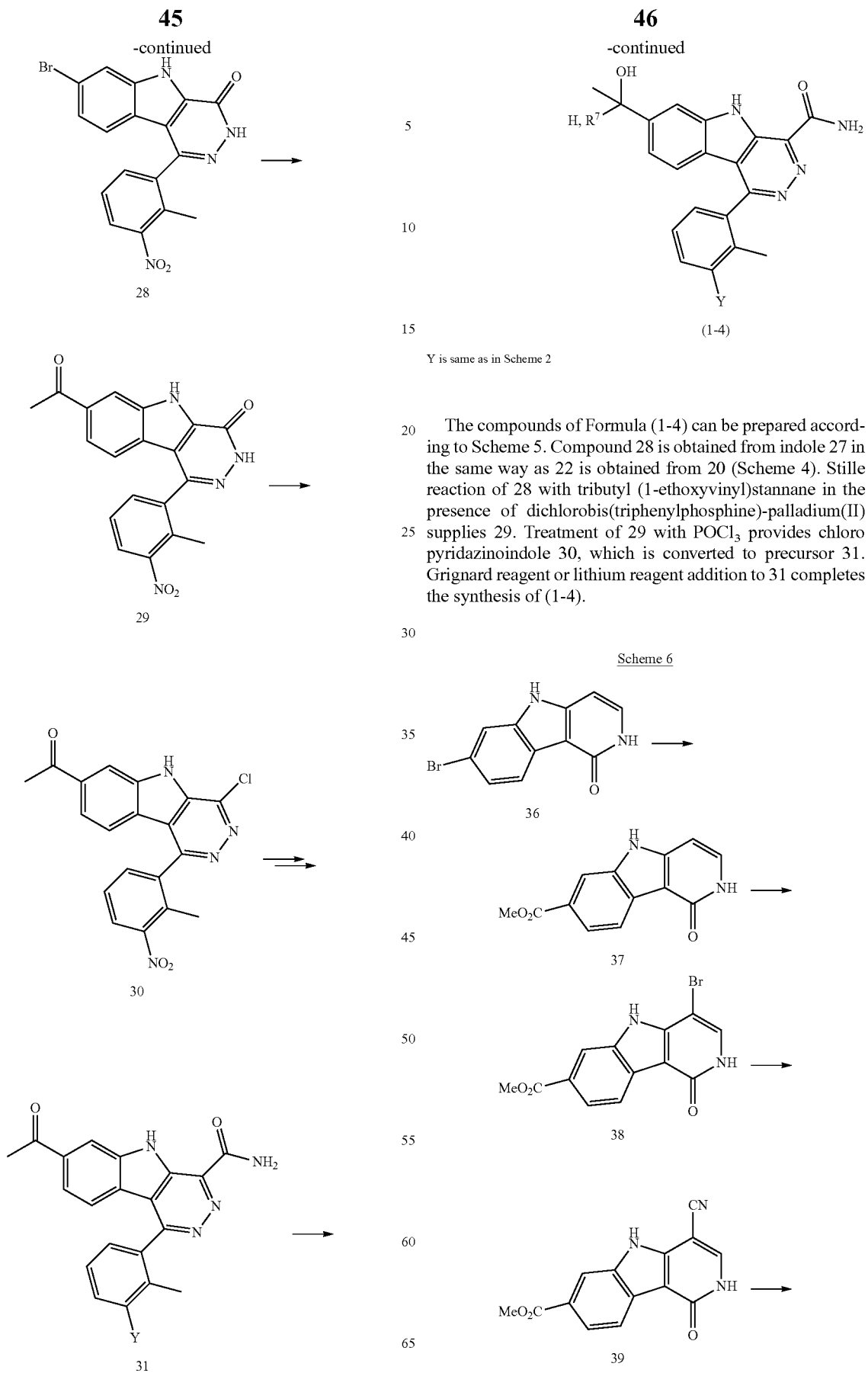

The compounds of Formula (1-4) can be prepared according to Scheme 5. Compound 28 is obtained from indole 27 in the same way as 22 is obtained from 20 (Scheme 4). Stille reaction of 28 with tributyl (1-ethoxyvinyl)stannane in the presence of dichlorobis(triphenylphosphine)-palladium(II) supplies 29. Treatment of 29 with POCl₃ provides chloro pyridazinoindole 30, which is converted to precursor 31. Grignard reagent or lithium reagent addition to 31 completes the synthesis of (1-4).

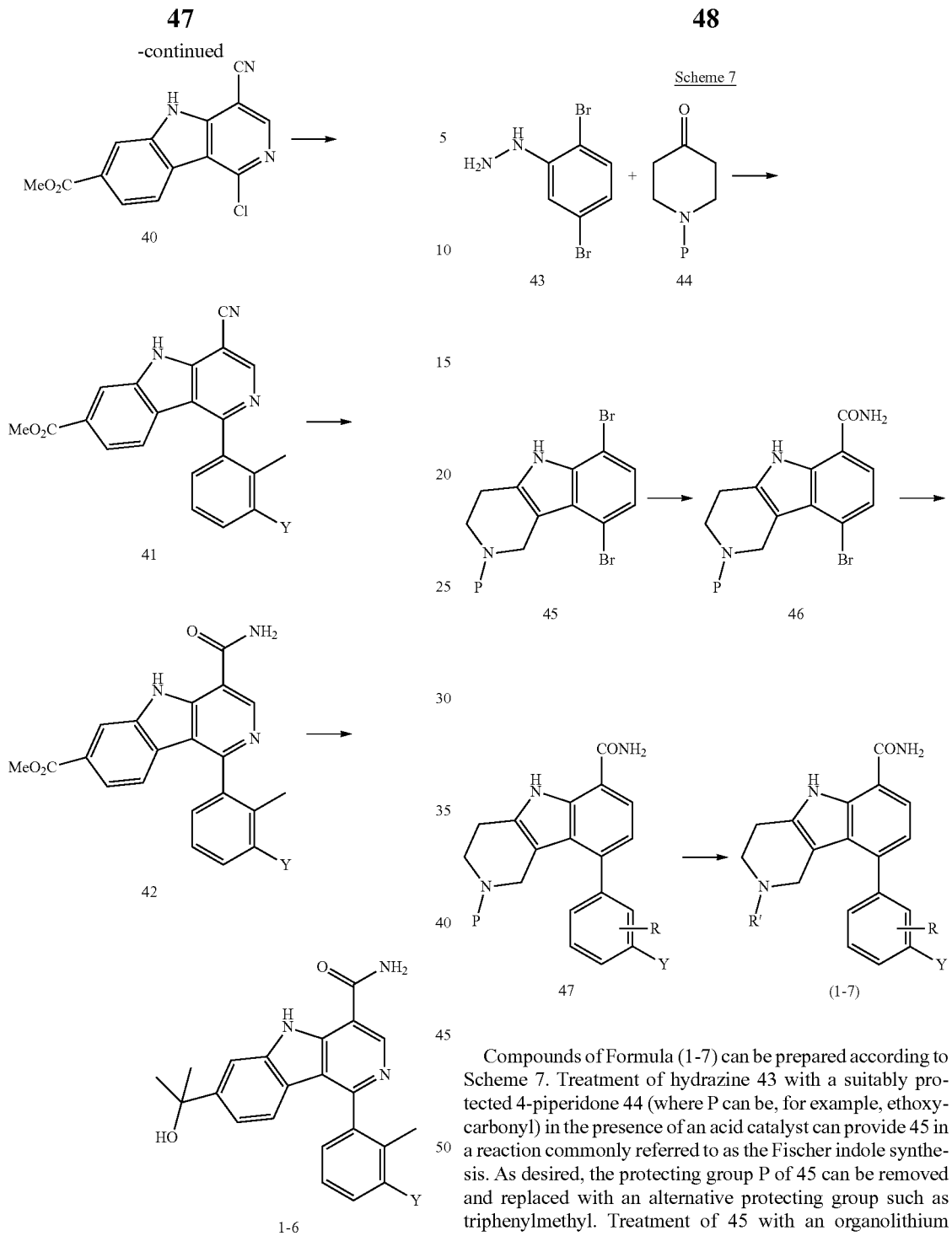

The compounds of Formula (1-6) can be prepared according to Scheme 6. The preparation of 36 is described in the literature. Intermediate 36 is carbonylated under pressure to give 37, which is brominated to give 38. Treatment of 38 with copper cyanide at high temperature gives 39 which on treatment with phosphorous oxychloride gave 40. 40 is coupled under Suzuki conditions with the requisite boronic acid to give 41, the cyano-group of which is later hydrolyzed under acidic conditions to give 42. The ester functionality of 42 on treatment with methyl lithium can be further elaborated to (1-6).

Compounds of Formula (1-7) can be prepared according to Scheme 7. Treatment of hydrazine 43 with a suitably protected 4-piperidone 44 (where P can be, for example, ethoxycarbonyl) in the presence of an acid catalyst can provide 45 in a reaction commonly referred to as the Fischer indole synthesis. As desired, the protecting group P of 45 can be removed and replaced with an alternative protecting group such as triphenylmethyl. Treatment of 45 with an organolithium reagent such as tert-butyl lithium, followed by treatment with trimethylsilyl isocyanate, can provide the amide 46. Coupling of 46 with a suitable boronic acid or boronic acid ester, using an appropriate base and an appropriate palladium-containing catalyst (commonly known as the Suzuki reaction), can provide 47. Removal of the protecting group P under suitable conditions can provide compounds of Formula (1-7) where R' is H. Treatment of compounds of Formula (1-7) where R' is H with a suitable reagent such as a carboxylic acid anhydride, carboxylic acid chloride, sulfonyl chloride, carbamoyl chloride or chloroformate can provide compounds of Formula (1-7) where R' is an acyl, sulfonyl, carbamoyl or alkoxycarbonyl group, respectively.

Scheme 8

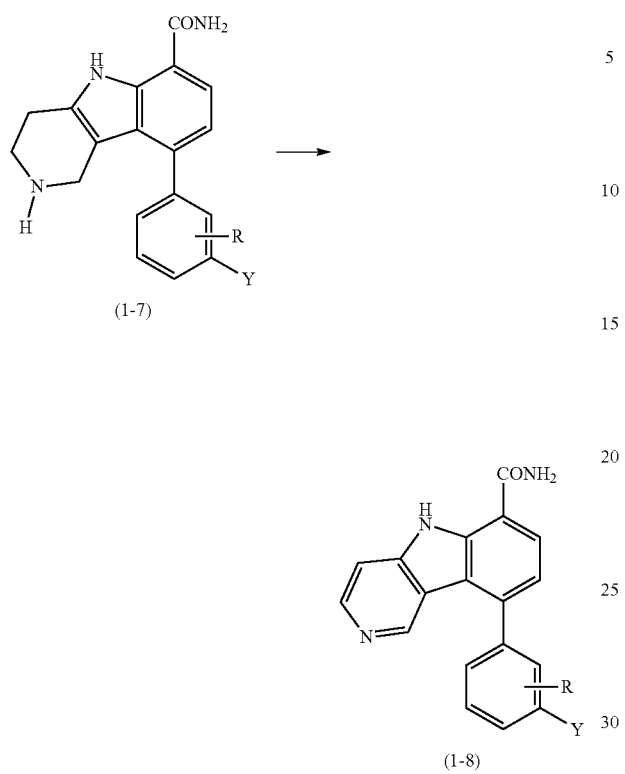

Compounds of Formula (1-8) can be prepared according to Scheme 8. Compounds of Formula (1-7) where R' is H can be treated with an appropriate oxidizing agent such as, for example, manganese dioxide or 2,3-dichloro-5,6-dicyano-1,4-benzoquinone (DDQ) to provide Compounds of Formula (1-8).

Scheme 9

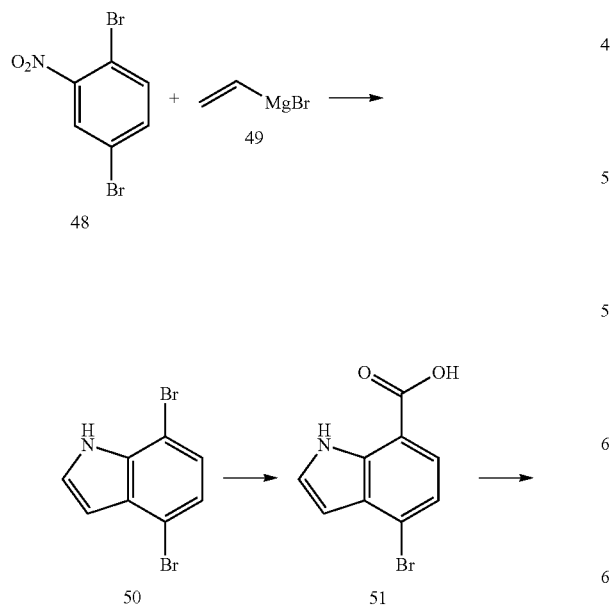

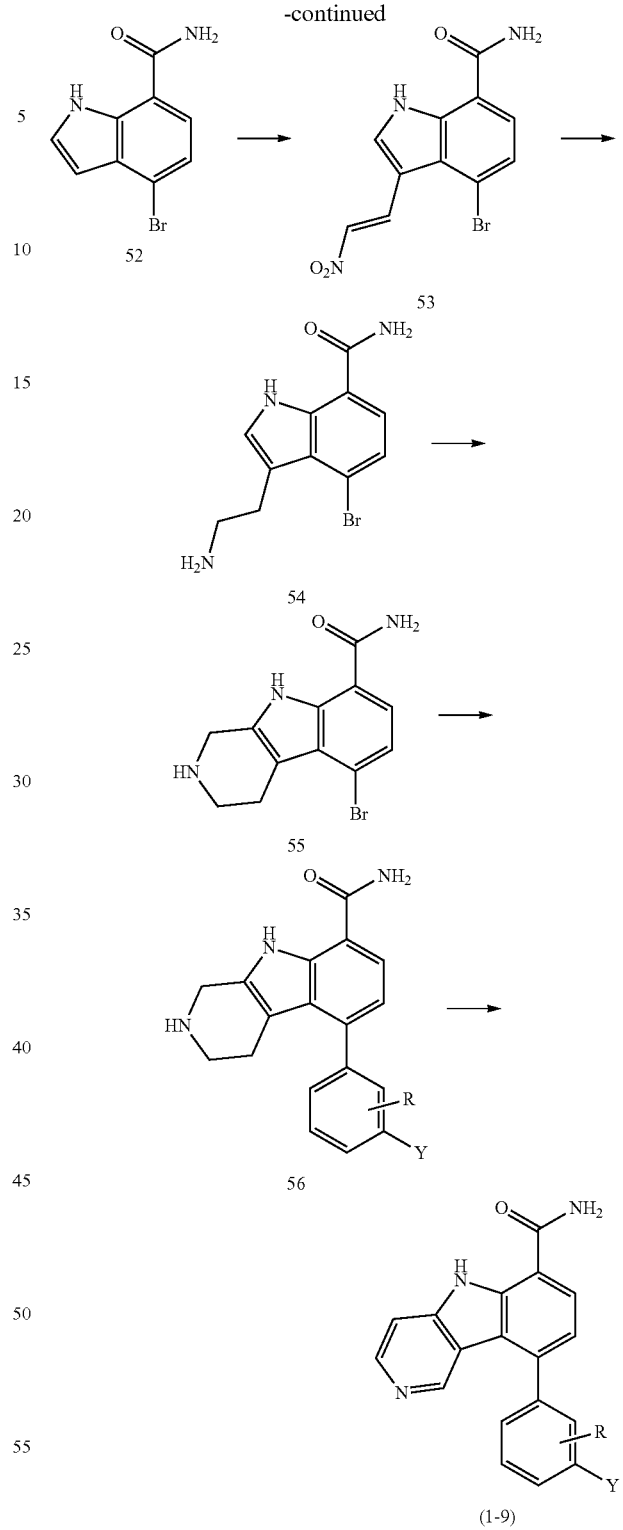

Compounds of Formula (1-9) can be prepared according to Scheme 9. Treatment of 1,4-dibromo-2-nitrobenzene 48 with vinylmagnesium bromide 49 can provide 50 in a reaction commonly referred to as the Bartoli indole synthesis. Treatment of 50 with an organolithium reagent such as butyllithium, followed by treatment with carbon dioxide, can provide the carboxylic acid 51. Treatment of 51 with ammonium hydroxide, EDC, and HOBT can provide amide 52. Treatment of 52 with N,N-dimethyl-2-nitroethenamine can provide 53, which can be reduced with lithium aluminum hydride to provide 54. Treatment of 54 with formaldehyde in the presence of aqueous HCl can provide 55. Compounds 56 can be prepared similarly to the preparation of compound 47 in Scheme 7. Compounds of Formula (1-9) can be prepared from 56 using the procedure shown in Scheme 8.

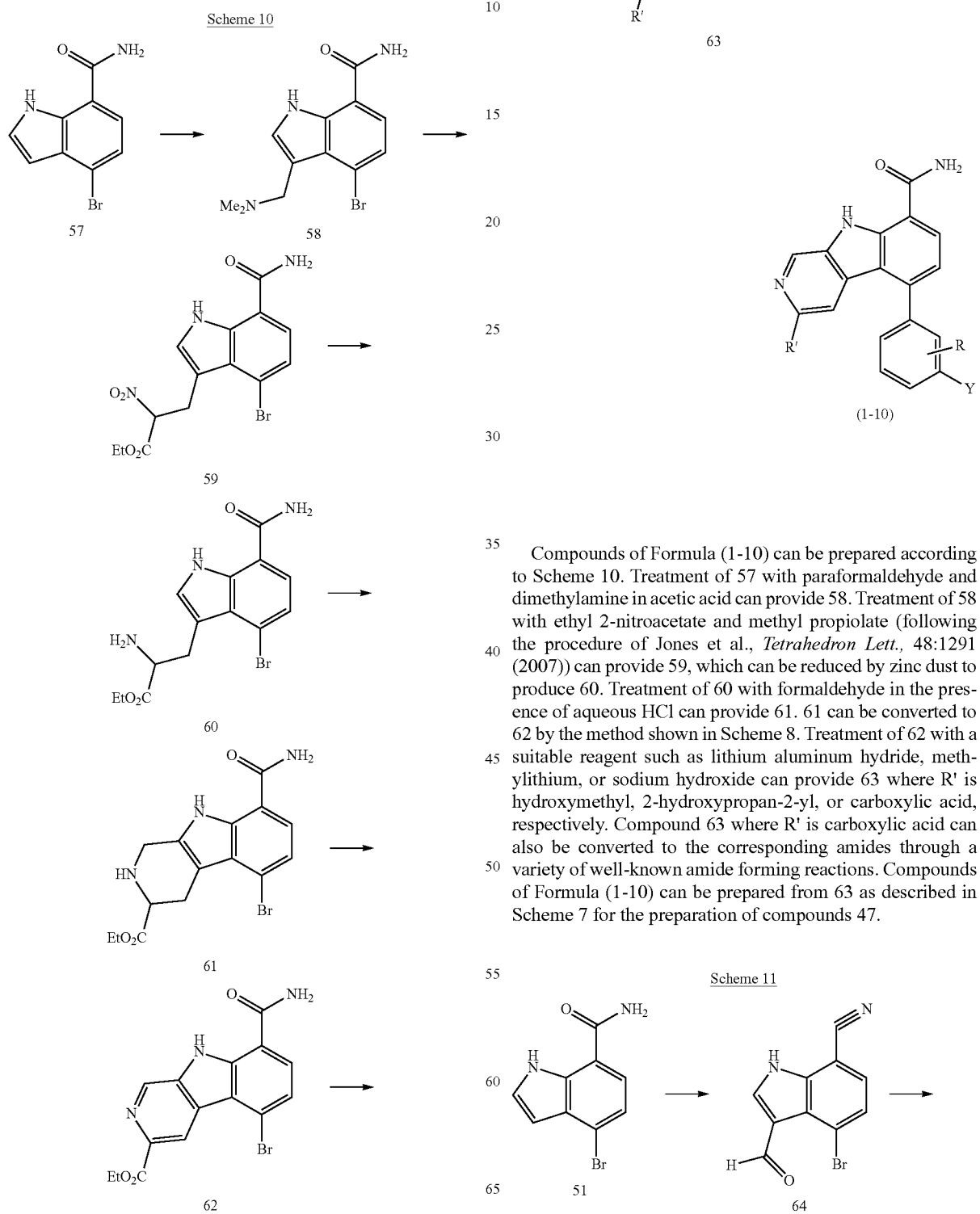

Compounds of Formula (1-10) can be prepared according to Scheme 10. Treatment of 57 with paraformaldehyde and dimethylamine in acetic acid can provide 58. Treatment of 58 with ethyl 2-nitroacetate and methyl propiolate (following the procedure of Jones et al., *Tetrahedron Lett.*, 48:1291 (2007)) can provide 59, which can be reduced by zinc dust to produce 60. Treatment of 60 with formaldehyde in the presence of aqueous HCl can provide 61. 61 can be converted to 62 by the method shown in Scheme 8. Treatment of 62 with a suitable reagent such as lithium aluminum hydride, methyllithium, or sodium hydroxide can provide 63 where R' is hydroxymethyl, 2-hydroxypropan-2-yl, or carboxylic acid, respectively. Compound 63 where R' is carboxylic acid can also be converted to the corresponding amides through a variety of well-known amide forming reactions. Compounds of Formula (1-10) can be prepared from 63 as described in Scheme 7 for the preparation of compounds 47.

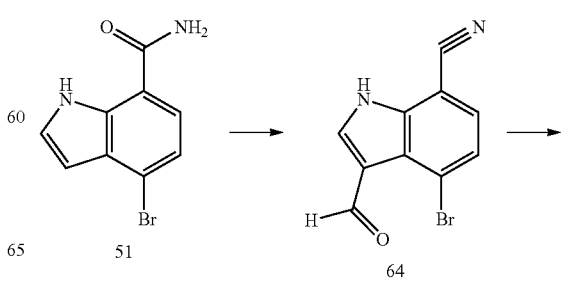

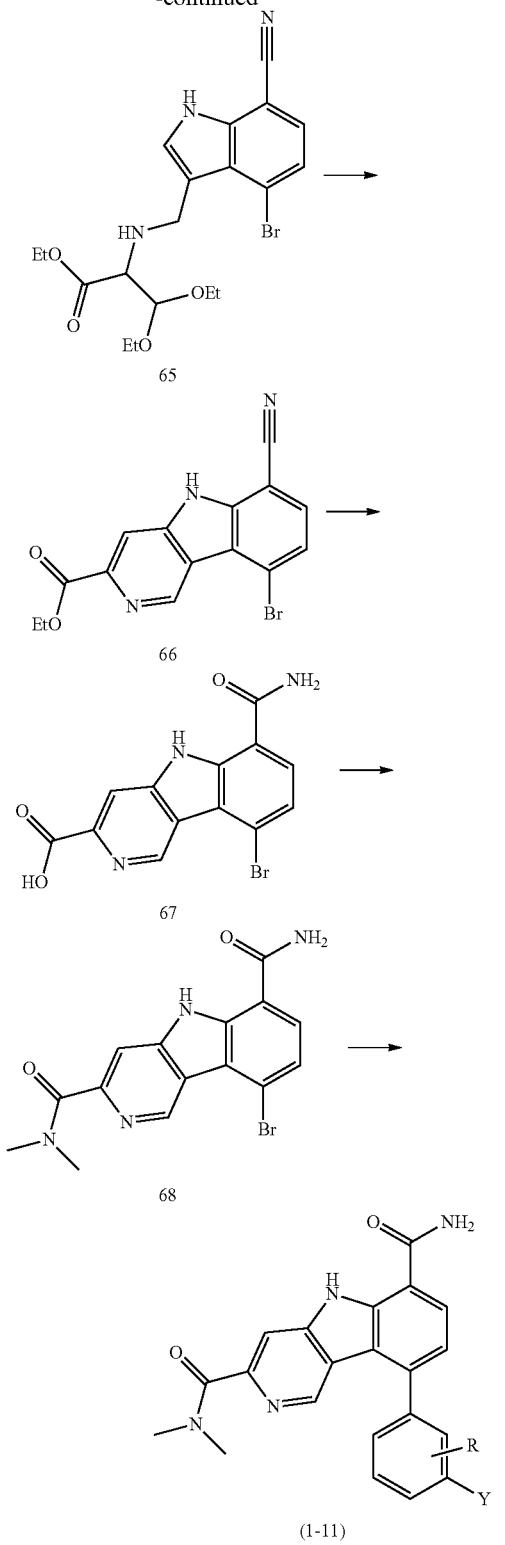

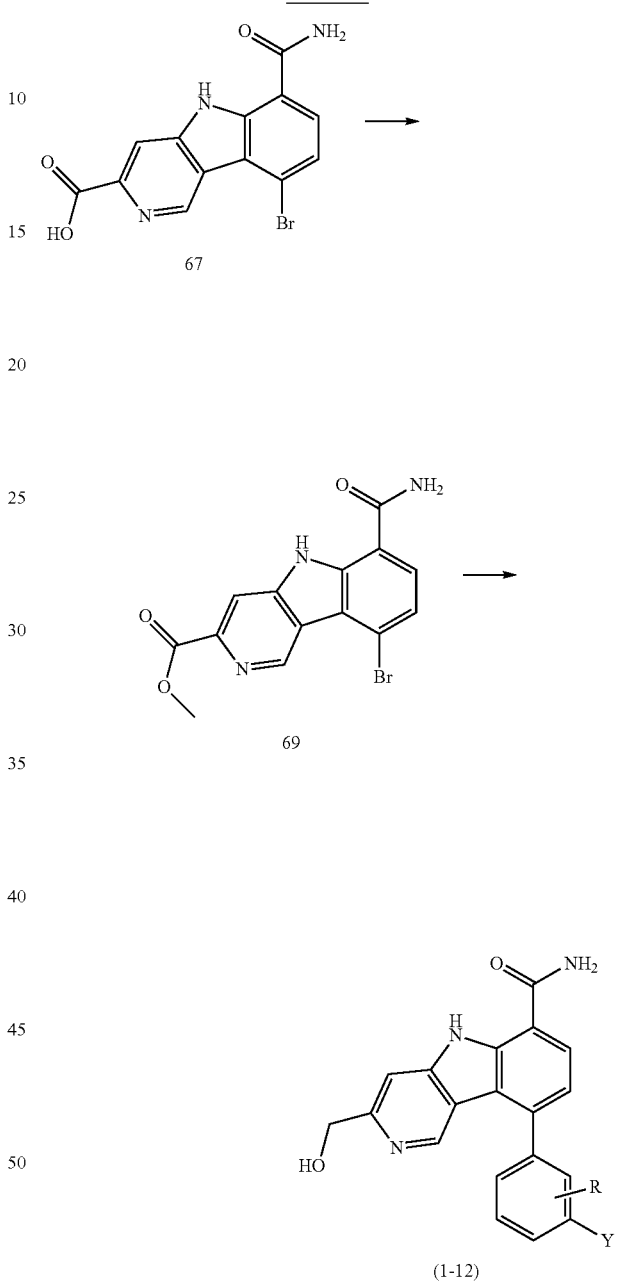

Compounds of Formula (1-11) can be prepared according to Scheme 11. Treatment of 51 with DMF and phosphorus oxychloride can provide 64. Treatment of 64 with ethyl 2-amino-3,3-diethoxypropanoate in the presence of sodium triacetoxyborohydride can provide 65. Treatment of 65 with titanium tetrachloride can provide 66, which can be converted to 67 by using sodium perborate tetrahydrate. Coupling of 67 with dimethylamine in the presence of EDC and HOAt can provide 68, which can be converted to compounds of Formula (1-11) as described for the preparation of 47 in Scheme 7.

Compounds of Formula (1-12) can be prepared according to Scheme 12. Treatment of 67 with methanol in the presence of EDC and HOAt can provide 69. Intermediate 69 can be reduced by lithium aluminum hydride, and the intermediate can then be reacted with a suitable boronic acid or boronic acid ester as describe in preparation of compound 47 in Scheme 7 to provide compounds of Formula (1-12).

EXAMPLES 1 and 2

4-(2-Fluorophenyl)-7-morpholino-9H-pyrido[3,4-b]indole-1-carboxamide, and 8-Chloro-4-(2-fluorophenyl)-7-morpholino-9H-pyrido[3,4-b]indole-1-carboxamide

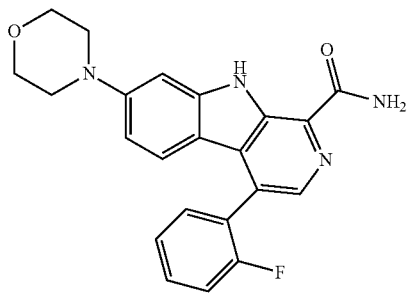

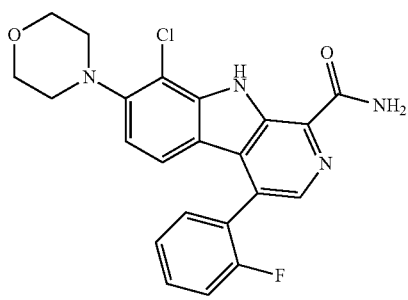

1. 4-(1H-indol-6-yl)morpholine

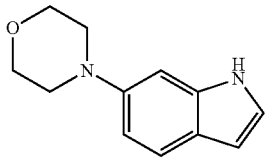 [SMILES: c1cc2ccc(N3CCOCC3)cc2[nH]1]

mixture of 1H-indol-6-amine (3.14 g, 23.76 mmol), 1-chloro-2-(2-chloroethoxy)ethane (4.18 mL, 35.6 mmol), and sodium carbonate (10.07 g, 95 mmol) in t-BuOH (90 mL) was heated at 100° C. in a pressure tube for 3.5 days. On cooling to room temperature, the mixture was diluted with ethyl acetate and filtered through CELITE®. The filtrate was concentrated under vacuum to dryness. To the residue was added water (50 mL). The mixture was adjusted to pH 11 with saturated NaHCO₃ solution and extracted with CH₂Cl₂ (4×80 mL). The combined extract was washed with brine (50 mL) and dried over anhydrous MgSO₄. The desired product (3.96 g, 19.58 mmol, 82% yield) was isolated as a beige solid with ISCO (300 g silica gel, solid loading, 20-50% ethyl acetate/hexane).

2. 4-(3-(1-(2-Fluorophenyl)-2-nitroethyl)-1H-indol-6-yl)morpholine

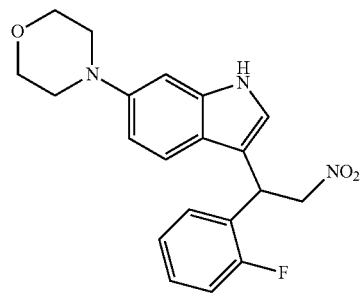 [SMILES: O=[N+]([O-])CC(c1ccccc1F)c1c[nH]c2cc(N3CCOCC3)ccc12]

A mixture of 4-(1H-indol-6-yl)morpholine (0.300 g, 1.483 mmol) and (E)-1-fluoro-2-(2-nitrovinyl)benzene (0.372 g, 2.225 mmol) in toluene (8 mL) was heated in a pressure tube at 150° C. for 2 days. The solvent was removed under vacuum, and the residue was subjected to ISCO (80 g silica gel, solid loading, 30-60% ethyl acetate/hexane) to provide the desired product (0.239 g, 0.647 mmol, 43.6% yield) as a tan solid.

3. 2-(2-Fluorophenyl)-2-(6-morpholino-1H-indol-3-yl)ethanamine

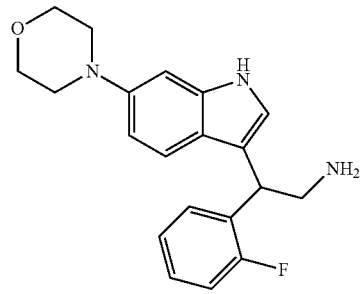 [SMILES: NCC(c1ccccc1F)c1c[nH]c2cc(N3CCOCC3)ccc12]

A mixture of 4-(3-(1-(2-fluorophenyl)-2-nitroethyl)-1H-indol-6-yl)morpholine (0.235 g, 0.636 mmol) and Raney Ni (a small spatula) in MeOH (30 mL) was treated with hydrogen at 55 psi in a Parr shaker apparatus for 3 hr. The catalyst was removed by suction filtration. The filtrate was concentrated under vacuum, diluted with CH₂Cl₂ (100 mL), washed with brine (25 mL) and dried over anhydrous MgSO₄. Removal of solvent under vacuum provided the desired product (0.181 g, 0.533 mmol, 84% yield) as an off-white solid.

4. Ethyl 4-(2-fluorophenyl)-7-morpholino-9H-pyrido[3,4-b]indole-1-carboxylate

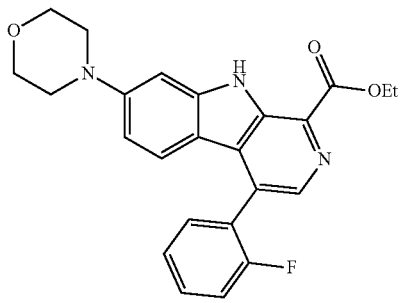 [SMILES: CCOC(=O)c1ncc(-c2ccccc2F)c2c1[nH]c1cc(N3CCOCC3)ccc12]

To a solution of 2-(2-fluorophenyl)-2-(6-morpholino-1H-indol-3-yl)ethanamine (0.181 g, 0.533 mmol) and ethyl 2-oxoacetate in toluene (50%) (0.233 mL, 1.173 mmol) in 1,4-dioxane (18 mL) at room temperature was added hydrogen chloride (4 N in 1,4-dioxane) (0.267 mL, 1.067 mmol). The solution turned heterogeneous and it was stirred at room temperature for 16 hr. The volatiles were removed under vacuum. The residue was diluted with water (20 mL), basified with saturated $NaHCO_3$ solution to pH 10, and extracted with ethyl acetate (3×30 mL). The combined extract was washed with brine (25 ml), dried over anhydrous $MgSO_4$, and concentrated to dryness under vacuum. To the residue were added toluene (10 mL) and 10% Pd/C (0.3 g), and the mixture was heated at 140° C. under an ambient atmosphere for 4.5 hr. The solid phase was removed by suction filtration. The filtrate was diluted with ethyl acetate (100 ml), washed with brine (25 ml), and dried over anhydrous $MgSO_4$. The desired product (94 mg, 0.222 mmol, 41.6% yield) was isolated with ISCO (24 g silica gel, 30-60% ethyl acetate/hexane) as a tan solid.

5. 4-(2-Fluorophenyl)-7-morpholino-9H-pyrido[3,4-b]indole-1-carboxylic acid

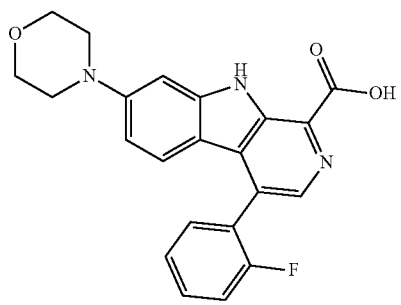 [SMILES: O=C(O)c1ncc(-c2ccccc2F)c2c1[nH]c1cc(N3CCOCC3)ccc12]

To a solution of ethyl 4-(2-fluorophenyl)-7-morpholino-9H-pyrido[3,4-b]indole-1-carboxylate (94 mg, 0.224 mmol) in MeOH (5 mL) at room temperature was added 1N sodium hydroxide solution (1.121 mL, 1.121 mmol). The mixture was heated at reflux for 1 hr and then concentrated under vacuum. To the residue was added water (20 mL), and the resulting mixture was neutralized with 1 N HCl solution to pH 5. The precipitating product (68 mg, 0.172 mmol, 77% yield) was collected as a tan solid by suction filtration and dried at 50° C. under vacuum.

6. 4-(2-Fluorophenyl)-7-morpholino-9H-pyrido[3,4-b]indole-1-carboxamide and 8-chloro-4-(2-fluorophenyl)-7-morpholino-9H-pyrido[3,4-b]indole-1-carboxamide To 4-(2-fluorophenyl)-7-morpholino-9H-pyrido[3,4-b]indole-1-carboxylic acid (63 mg, 0.161 mmol) at 0° C. was added sulfurous dichloride (19.15 mg, 0.161 mmol). The mixture was stirred at room temperature for 1 hr, at which point a mixture of the following components were identified in the reaction mixture with HPLC and LCMS.

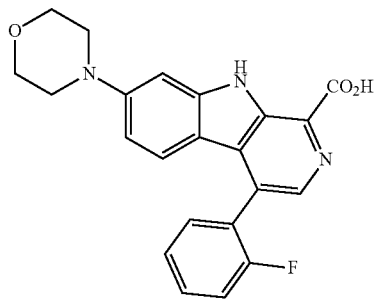

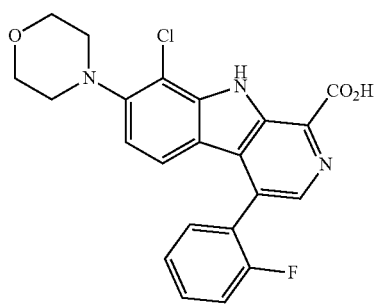

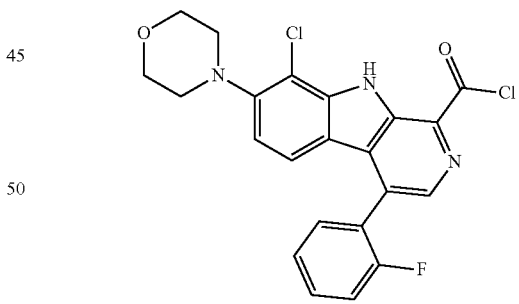

The reaction was stopped by removing thionyl chloride under vacuum. To the residue was added toluene, and the volatiles were removed again under vacuum. Then, to the residue was added ammonium chloride (34.4 mg, 0.644 mmol), N,N-diisopropylamine (0.169 mL, 0.966 mmol), BOP (107 mg, 0.241 mmol), and DMF (3 mL). The mixture was stirred at room temperature for 1.5 hr, diluted with ethyl acetate (60 mL), washed with water (3×15 mL), and brine (15 mL). The organic solution was concentrated under vacuum, and the residue was subjected to prep. HPLC. The corresponding fractions were concentrated under vacuum, basified with saturated NaHCO₃ solution. The precipitating products, 4-(2-fluorophenyl)-7-morpholino-9H-pyrido[3,4-b]indole-1-carboxamide (3.97 mg, 9.97 μmol, 6.19% yield) and 8-chloro-4-(2-fluorophenyl)-7-morpholino-9H-pyrido[3,4-b]indole-1-carboxamide (11.7 mg, 0.027 mmol, 16.94% yield), were collected as a tan solid and a beige solid, respectively, by suction filtration and dried at 55° C. under vacuum.

Analytical data for 4-(2-fluorophenyl)-7-morpholino-9H-pyrido[3,4-b]indole-1-carboxamide: LCMS (M+H)⁺= 391.10. Analytical data for 8-chloro-4-(2-fluorophenyl)-7-morpholino-9H-pyrido[3,4-b]indole-1-carboxamide: LCMS (M+H)⁺=425.05. $^1$H NMR (500 MHz, DMSO-$d_6$/$D_2$O) δ: 8.31 (s, 1H), 7.67-7.60 (m, 2H), 7.48-7.43 (m, 2H), 7.22 (dd, J1=8.4 Hz, J2=1.8 Hz, 1H), 6.98 (d, J=8.4 Hz, 1H), 3.76-3.73 (m, 4H), 3.06-3.02 (m, 4H).

EXAMPLE 3

4-(2-Fluorophenyl)-7-(morpholine-4-carbonyl)-9H-pyrido[3,4-b]indole-1-carboxamide

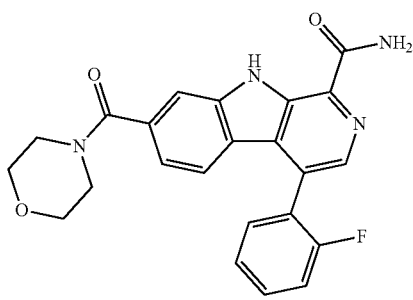 [SMILES: NC(=O)c1ncc(-c2ccccc2F)c2c1[nH]c1cc(C(=O)N3CCOCC3)ccc12]

1. (1H-Indol-6-yl)(morpholino)methanone

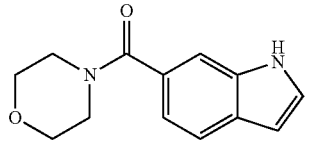 [SMILES: O=C(c1ccc2cc[nH]c2c1)N1CCOCC1]

A solution of morpholine (1.320 mL, 15.14 mmol), 1H-indole-6-carboxylic acid (2.0332 g, 12.62 mmol), 1-(3-dimethylaminopropyl)-3-ethylcarbodiimide hydrochloride (EDC) (3.63 g, 18.92 mmol), 1-hydroxybenzotriazole (HOBt) (2.90 g, 18.92 mmol) and diisopropylethylamine (DIPEA) (6.61 mL, 37.8 mmol) in DMF (31.5 mL) was stirred overnight. The reaction was poured into a 1:1 water:brine solution and extracted with EtOAc (2×). The organic layers were combined and washed with 0.25 M aqueous KHSO₄, water, brine and 10% aqueous LiCl; dried over Na₂SO₄, filtered and concentrated in vacuo. Trituration with Et₂O provided the desired product (2.20 g, 9.58 mmol, 76% yield) as a light tan solid.

2. (3-(1-(2-Fluorophenyl)-2-nitroethyl)-1H-indol-6-yl)(morpholino)methanone

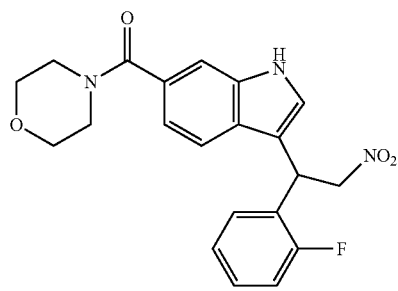 [SMILES: O=C(c1ccc2c(C(C[N+](=O)[O-])c3ccccc3F)c[nH]c2c1)N1CCOCC1]

A sealed tube containing (1H-indol-6-yl)(morpholino)methanone (0.6323 g, 2.75 mmol) and (E)-1-fluoro-2-(2-nitrovinyl)benzene (0.551 g, 3.30 mmol) in toluene (14 mL) was stirred at 150° C. for 4 days. The reaction was cooled and concentrated in vacuo to give a residue which was purified by flash chromatography using an ISCO 80 g column eluting with 0-100% EtOAc/hexanes. Appropriate fractions (100% elution) were collected and concentrated in vacuo to give the desired product (0.222 g, 0.508 mmol, 18.5% yield).

3. (3-(2-Amino-1-(2-fluorophenyl)ethyl)-1H-indol-6-yl)(morpholino)methanone

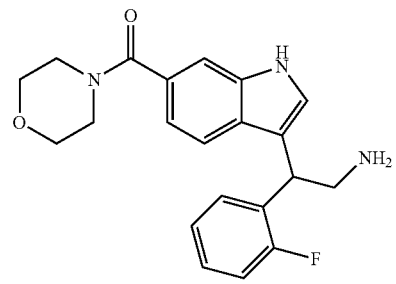 [SMILES: NCC(c1ccccc1F)c1c[nH]c2cc(C(=O)N3CCOCC3)ccc12]

To a spatula full of Raney-Ni in a Parr tube was added a solution of (3-(1-(2-fluorophenyl)-2-nitroethyl)-1H-indol-6-yl)(morpholino)methanone (0.3659 g, 0.921 mmol) in MeOH (30.7 mL). The reaction was shaken under hydrogenation at 53 psi for 3 hr. After flushing with nitrogen, the mixture was filtered through a pad of CELITE® and rinsed with MeOH. The filtrate was concentrated in vacuo to give the desired product (0.270 g, 0.596 mmol, 64.7% yield).

4. Ethyl 4-(2-fluorophenyl)-7-(morpholine-4-carbonyl)-9H-pyrido[3,4-b]indole-1-carboxylate

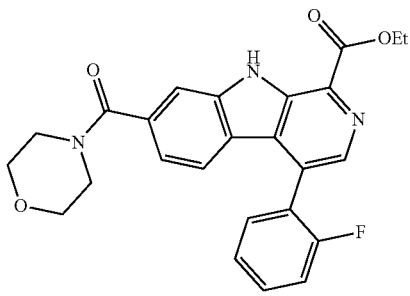 [SMILES: CCOC(=O)c1ncc(-c2ccccc2F)c2c1[nH]c1cc(C(=O)N3CCOCC3)ccc12]

To a yellow, homogeneous solution of (3-(2-amino-1-(2-fluorophenyl)ethyl)-1H-indol-6-yl)(morpholino)methanone (0.270 g, 0.736 mmol) and 50% ethyl 2-oxoacetate/toluene (0.321 mL, 1.619 mmol) in 1,4-dioxane (30 mL) was added 4 N HCl/dioxane (0.368 mL, 1.472 mmol) under nitrogen, and the reaction was stirred overnight. The reaction was concentrated in vacuo, diluted with water and basified to pH ~10 (by litmus paper) with NaHCO₃. This was extracted with EtOAc (3×), and the organic layers were combined and washed with brine, dried over MgSO₄, filtered and concentrated in vacuo to give crude product which was used in the subsequent step. This was combined with 10% Pd/C (0.710 g, 0.668 mmol) in toluene (10 mL), and the solution was refluxed. After 45 min, the reaction was cooled to room temperature and filtered through a pad of CELITE®, rinsing with EtOAc. The filtrate was washed with brine, dried over MgSO₄, filtered and concentrated in vacuo to give a residue which was purified by flash chromatography using an ISCO 24 g column eluting with 0-100% EtOAc/hexanes. Appropriate fractions were collected and concentrated in vacuo to give the desired product (0.0592 g, 0.132 mmol, 19.8% yield) as an off-white solid.

5. 4-(2-Fluorophenyl)-7-(morpholine-4-carbonyl)-9H-pyrido[3,4-b]indole-1-carboxylic acid

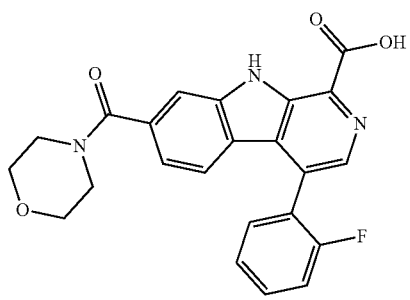 [SMILES: O=C(O)c1ncc(-c2ccccc2F)c2c1[nH]c1cc(C(=O)N3CCOCC3)ccc12]

To a yellow, homogeneous solution of ethyl 4-(2-fluorophenyl)-7-(morpholine-4-carbonyl)-9H-pyrido[3,4-b]indole-1-carboxylate (0.0592 g, 0.132 mmol) in THF (2.84 mL) and MeOH (0.945 mL) was added LiOH (0.022 g, 0.529 mmol) in water (0.5 mL). After 2 hr, the reaction mixture was concentrated in vacuo, and the residue was diluted with water and acidified with 1N aq. HCl to pH ~4 by litmus paper. The mixture was extracted with EtOAc (3×), and the organic layers were combined, dried over Na₂SO₄, and concentrated in vacuo to give the desired product (0.0382 g, 0.091 mmol, 68.8% yield) as a yellow solid.

6. 4-(2-Fluorophenyl)-7-(morpholine-4-carbonyl)-9H-pyrido[3,4-b]indole-1-carboxamide

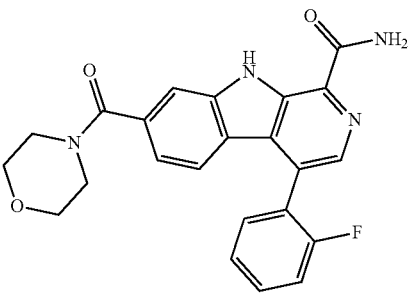 [SMILES: NC(=O)c1ncc(-c2ccccc2F)c2c1[nH]c1cc(C(=O)N3CCOCC3)ccc12]

To a yellow, heterogeneous solution of 4-(2-fluorophenyl)-7-(morpholine-4-carbonyl)-9H-pyrido[3,4-b]indole-1-carboxylic acid (0.0381 g, 0.091 mmol), ammonium chloride (9.72 mg, 0.182 mmol), HOAt (0.025 g, 0.182 mmol) and EDC (0.035 g, 0.182 mmol) in DMF (1.0 mL) was added DIPEA (0.063 mL, 0.364 mmol). The reaction was stirred overnight. EtOAc and water were added, and the layers were separated. The organic layer was washed with brine and 10% aq. LiCl successively, dried over Na₂SO₄, filtered and concentrated in vacuo to give a residue which was diluted with MeOH (1 mL) and subjected to autoprep reverse phase HPLC purification. The appropriate fractions were combined, basified with NaHCO₃ (solid), and concentrated in vacuo. It was extracted with CH₂Cl₂ (3×). The organic layers were combined, dried over Na₂SO₄, and concentrated in vacuo to give the desired product (0.0124 g, 0.030 mmol, 32.6% yield) as a white solid. LC/MS (M+H)=419.08; $^1$H NMR (500 MHz, DMSO-d₆) δ ppm 12.03 (s, 1H), 8.38 (br. S, 1H), 8.32 (s, 1H), 7.89 (s, 1H), 7.86 (br. S, 1H), 7.63-7.75 (m, 2H), 7.44-7.58 (m, 2H), 7.34 (d, J=8.2 Hz, 1H), 7.13 (d, J=8.2 Hz, 1H), 3.42-3.83 (m, 8H).

EXAMPLE 4

4-(2-Fluorophenyl)-7-methyl-6-(pyrimidin-5-yloxy)-9H-pyrido[3,4-b]indole-1-carboxamide

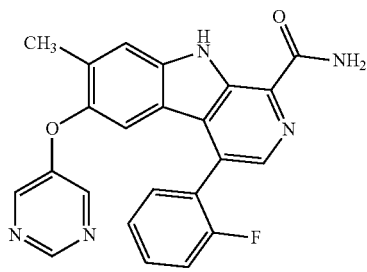 [SMILES: Cc1cc2[nH]c3c(C(N)=O)ncc(-c4ccccc4F)c3c2cc1Oc1cncnc1]

1. 1-Bromo-2,5-dimethyl-4-nitrobenzene

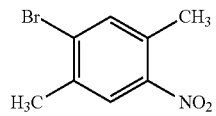

To a slurry of 2-bromo-1,4-dimethylbenzene (10.13 g, 54.7 mmol) in acetic acid (44 mL) at 8° C. (inner temperature) was added a solution of nitric acid (6 mL, 134 mmol) in sulfuric acid (22 mL, 413 mmol) over 45 min; temperature rose to 10° C. After 1 hr, the reaction mixture was poured into ice and stirred, filtered and washed with water to give a light yellow solid. This was triturated with EtOH (10 mL) to give the desired product (4.550 g, 19.78 mmol, 36.1% yield) as an off-white solid.

2. 5-(2,5-Dimethyl-4-nitrophenoxy)pyrimidine

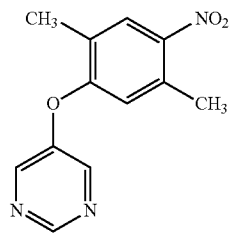 [SMILES: Cc1cc([N+](=O)[O-])c(C)cc1Oc1cncnc1]

A solution of 1-bromo-2,5-dimethyl-4-nitrobenzene (3.53 g, 15.34 mmol), pyrimidin-5-ol (1.474 g, 15.34 mmol), 2,2,6,6-tetramethylheptane-3,5-dione (0.141 g, 0.767 mmol), cesium carbonate (5.15 g, 15.80 mmol) and copper(I) chloride (0.410 g, 4.14 mmol) in N-methyl-2-pyrrolidinone (15.34 mL) was heated in a sealed pressure tube at 130° C. and stirred overnight. The reaction was cooled to room temperature, diluted with EtOAc and washed with water (2×) and brine, successively, dried over Na$_2$SO$_4$, filtered and concentrated in vacuo. This was triturated with diethyl ether to give the first crop of the desired product (1.682 g) as a light tan solid. The filtrate was concentrated in vacuo, and the residue was purified by flash chromatography using an ISCO 80 g column eluting with 0-50% EtOAc/hexanes. Appropriate fractions were collected and concentrated in vacuo to give the second crop of the desired product (0.3973 g) as an off-white solid.

3. (E)-5-(2-Methyl-4-nitro-5-(2-(pyrrolidin-1-yl)vinyl)phenoxy)pyrimidine

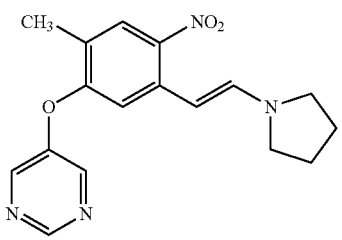 [SMILES: Cc1cc([N+](=O)[O-])c(/C=C/N2CCCC2)cc1Oc1cncnc1]

A solution of 5-(2,5-dimethyl-4-nitrophenoxy)pyrimidine (0.7243 g, 2.95 mmol), pyrrolidine (0.345 mL, 4.13 mmol) and DMF-DMA (0.551 mL, 4.13 mmol) in DMF (3.0 mL) under nitrogen was heated at 115° C. After 45 min, the reaction was cooled to room temperature and concentrated in vacuo, followed by a short-path distillation. The crude residue was used in the subsequent step.

4. 6-Methyl-5-(pyrimidin-5-yloxy)-1H-indole

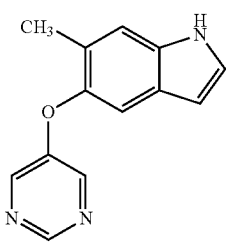 [SMILES: Cc1cc2[nH]ccc2cc1Oc1cncnc1]

A red, heterogeneous solution of (E)-5-(2-methyl-4-nitro-5-(2-(pyrrolidin-1-yl)vinyl)phenoxy)pyrimidine (0.963 g, 2.95 mmol) and 10% Pd/C (0.314 g, 0.295 mmol) in methanol (49.2 mL) was hydrogenated overnight. The reaction was flushed with nitrogen, filtered through a pad of CELITE®, and rinsed with MeOH. The filtrate was concentrated in vacuo to give a residue which was purified by flash chromatography using an ISCO 40 g column eluting with 0-5% MeOH/CH$_2$Cl$_2$. Appropriate fractions were collected and concentrated in vacuo to the desired product (0.3082 g, 1.37 mmol, 46.4%) as a light yellow solid.

5. 3-(1-(2-Fluorophenyl)-2-nitroethyl)-6-methyl-5-(pyrimidin-5-yloxy)-1H-indole

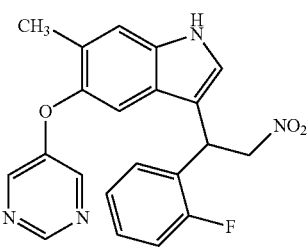

6-Methyl-5-(pyrimidin-5-yloxy)-1H-indole (0.1783 g, 0.792 mmol) and (E)-1-fluoro-2-(2-nitrovinyl)benzene (0.159 g, 0.950 mmol) were dissolved in CH$_2$Cl$_2$, and the solution was concentrated in vacuo. The residue was heated at 130° C. for 4 hr, and the crude product was purified by flash chromatography using an ISCO 40 g column eluting with 0-5% MeOH/CH$_2$Cl$_2$. Appropriate fractions were collected and concentrated in vacuo to give the desired product (0.1644 g, 0.419 mmol, 52.9% yield) as a tan foam.

6. 2-(2-Fluorophenyl)-2-(6-methyl-5-(pyrimidin-5-yloxy)-1H-indol-3-yl)ethanamine

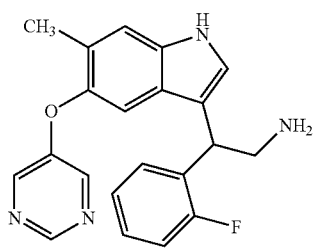 [SMILES: Cc1cc2[nH]cc(C(C[N+](=O)[O-])c3ccccc3F)c2cc1Oc1cncnc1]

To a spatula of Raney-Ni in a hydrogenation flask was added 3-(1-(2-fluorophenyl)-2-nitroethyl)-6-methyl-5-(pyrimidin-5-yloxy)-1H-indole (0.284 g, 0.724 mmol) in methanol (12.06 mL). The reaction was hydrogenated at 53 psi. After 3 hr, the vessel was evacuated and flushed with nitrogen. The solution was filtered through a pad of CELITE® and rinsed with MeOH. The filtrate was concentrated in vacuo, dissolved in $CH_2Cl_2$, dried over $Na_2SO_4$, filtered and concentrated in vacuo to give the desired product (0.2405 g, 0.664 mmol, 92% yield).

7. Ethyl 4-(2-fluorophenyl)-7-methyl-6-(pyrimidin-5-yloxy)-9H-pyrido[3,4-b]indole-1-carboxylate

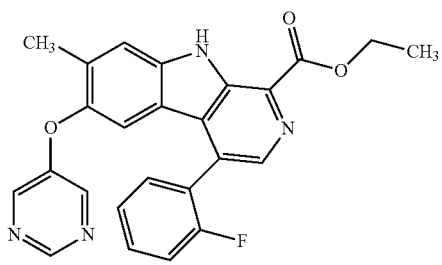 [SMILES: CCOC(=O)c1ncc(-c2ccccc2F)c2c1[nH]c1cc(C)c(Oc3cncnc3)cc12]

To a solution of 2-(2-fluorophenyl)-2-(6-methyl-5-(pyrimidin-5-yloxy)-1H-indol-3-yl)ethanamine (0.262 g, 0.724 mmol) and 50% ethyl 2-oxoacetate in toluene (0.316 mL, 1.593 mmol) in 1,4-dioxane (18.10 mL) under nitrogen was added 4 N HCl/1,4-dioxane (0.543 mL, 2.172 mmol). After stirring overnight, the reaction was concentrated in vacuo and dissolved in water. Saturated aqueous $NaHCO_3$ was added until pH ~12 by litmus paper. The solution was extracted with EtOAc (2×). After separation of the layers, the organic layer was dried over $Na_2SO_4$, filtered and concentrated in vacuo to give crude product which was used in subsequent step. This was added to 10% Pd/C (0.770 g, 0.724 mmol) in toluene (10.34 mL), and the reaction was refluxed for 45 min. After cooling to room temperature, the reaction was filtered through a pad of CELITE® and rinsed with EtOAc. The filtrate was concentrated in vacuo to give a residue which was purified by flash chromatography using an ISCO 40 g column eluting with 0-2% MeOH/$CH_2Cl_2$. Appropriate fractions were collected and concentrated in vacuo to give the desired product (0.0716 g, 0.162 mmol, 22.4% yield) as a tan solid.

8. 4-(2-Fluorophenyl)-7-methyl-6-(pyrimidin-5-yloxy)-9H-pyrido[3,4-b]indole-1-carboxylic acid

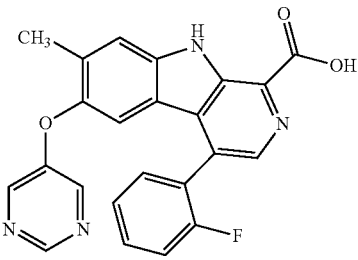 [SMILES: Cc1cc2[nH]c3c(C(=O)O)ncc(-c4ccccc4F)c3c2cc1Oc1cncnc1]

A solution of ethyl 4-(2-fluorophenyl)-7-methyl-6-(pyrimidin-5-yloxy)-9H-pyrido[3,4-b]indole-1-carboxylate (0.08 g, 0.181 mmol) and 1N aqueous NaOH (0.814 mL, 0.814 mmol) in methanol (3.01 mL) was refluxed. After 1 hr, the reaction was cooled to room temperature and concentrated in vacuo. Water was added, and the solution was acidified to pH ~4 by litmus paper. The precipitate was filtered, washed with water, and dried over Drierite to give the desired product (0.0456 g, 0.110 mmol, 60.9% yield) as a yellow solid.

9. 4-(2-Fluorophenyl)-7-methyl-6-(pyrimidin-5-yloxy)-9H-pyrido[3,4-b]indole-1-carboxamide A sealed vial containing 4-(2-fluorophenyl)-7-methyl-6-(pyrimidin-5-yloxy)-9H-pyrido[3,4-b]indole-1-carboxylic acid (0.0456 g, 0.110 mmol), ammonium chloride (0.024 g, 0.440 mmol), benzotriazole-1-yloxytris(dimethylamino) phosphonium hexafluorophosphate (BOP) (0.063 g, 0.143 mmol), DIPEA (0.092 mL, 0.528 mmol) and N-methylmorpholine (0.047 mL, 0.429 mmol) in DMF (0.8 mL) was stirred. After 1 hr, the reaction was diluted with MeOH (1 mL) and subjected to autoprep reverse phase HPLC purification. The appropriate fractions were combined, basified with $NaHCO_3$ (solid), and concentrated in vacuo. It was extracted with $CH_2Cl_2$ (3×). The organic layers were combined, dried over $Na_2SO_4$, and concentrated in vacuo to give the desired product (0.0137 g, 0.033 mmol, 30.1% yield) as a light tan solid, LC/MS (M+H)=414.10; $^1$H NMR (500 MHz, DMSO-$d_6$) δ ppm 11.87 (br. S, 1 H), 8.98 (s, 1H), 8.47 (s, 2H), 8.33 (br. S, 1H), 8.26 (s, 1H), 7.81 (s, 2H), 7.59 (dd, J1=7.49, J2=1.39 Hz, 1H), 7.48-7.54 (m, 1H), 7.22-7.33 (m, 2H), 6.72 (s, 1H), 2.35 (s, 3 H).

EXAMPLE 5

7-Amino-4-(2-fluorophenyl)-9H-pyrido[3,4-b]indole-1-carboxamide

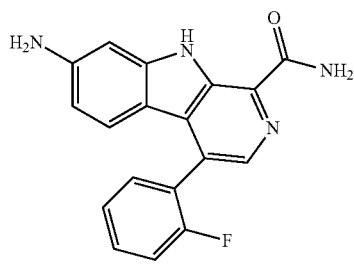 [SMILES: NC(=O)c1ncc(-c2ccccc2F)c2c1[nH]c1cc(N)ccc12]

1. Benzyl 1H-indol-6-ylcarbamate

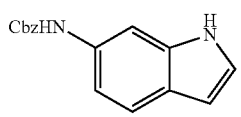

A mixture of 1H-indol-6-amine (1.0 g, 7.57 mmol), benzyl carbonochloridate (1.421 mL, 9.46 mmol), and potassium carbonate (1.307 g, 9.46 mmol) in tetrahydrofuran (50 mL) was stirred at room temperature for 16 hr. The mixture was diluted with ethyl acetate (150 mL) and insoluble material was removed by filtration. The filtrate was washed sequentially with saturated NaHCO$_3$ solution (50 mL) and brine (50 mL). The organic solution was dried over anhydrous MgSO$_4$. The desired product (1.05 g, 3.94 mmol, 52.1% yield) was isolated as a white solid by ISCO (120 g silica gel, solid loading, 5-30% ethyl acetate/hexane).

2. Benzyl 3-(1-(2-fluorophenyl)-2-nitroethyl)-1H-indol-6-ylcarbamate

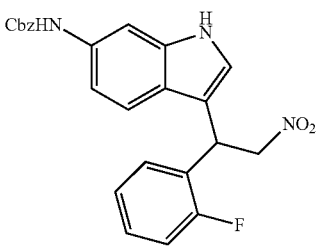 [SMILES: O=C(Nc1ccc2c(C(C[N+](=O)[O-])c3ccccc3F)c[nH]c2c1)OCc1ccccc1]

Benzyl 1H-indol-6-ylcarbamate (0.981 g, 3.68 mmol) and (E)-1-fluoro-2-(2-nitrovinyl)benzene (0.770 g, 4.60 mmol) were suspended and well mixed in dichloromethane (15 mL). The suspension was concentrated under vacuum to dryness. The solid mixture was then heated at 105° C. under nitrogen for 7 hr. The mixture was subjected to ISCO (120 g silica gel, solid loading, 20-45% ethyl acetate) to afford the desired product (1.287 g, 2.97 mmol, 81% yield) as a white solid.

3. Benzyl 3-(2-amino-1-(2-fluorophenyl)ethyl)-1H-indol-6-ylcarbamate

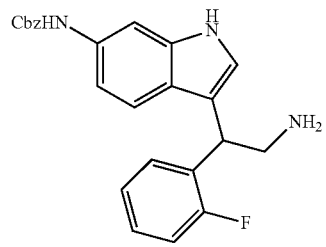 [SMILES: NCC(c1ccccc1F)c1c[nH]c2cc(NC(=O)OCc3ccccc3)ccc12]

A mixture of benzyl 3-(1-(2-fluorophenyl)-2-nitroethyl)-1H-indol-6-ylcarbamate (0.600 g, 1.384 mmol), zinc (1.358 g, 20.76 mmol), and ammonium chloride (1.111 g, 20.76 mmol) in tetrahydrofuran (30 mL) and methanol (30.0 mL) was stirred at room temperature for 2 hr. The insoluble material was removed by suction filtration through CELITE®. The filtrate was concentrated under vacuum. The residue was diluted with ethyl acetate (100 mL), washed with 10% NaHCO$_3$ solution (25 mL) and brine (25 mL), and dried over anhydrous MgSO$_4$. Removal of solvent under vacuum provided the desired product (0.586 g, 1.322 mmol, 95% yield) as a pale white solid.

4. Ethyl 7-(benzyloxycarbonylamino)-4-(2-fluorophenyl)-9H-pyrido[3,4-b]indole-1-carboxylate

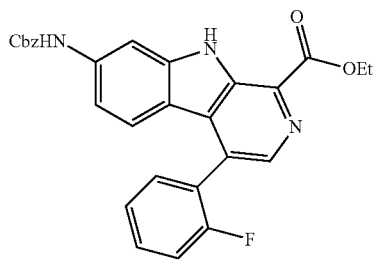 [SMILES: CCOC(=O)c1ncc(-c2ccccc2F)c2c1[nH]c1cc(NC(=O)OCc3ccccc3)ccc12]

To a solution of benzyl 3-(2-amino-1-(2-fluorophenyl)ethyl)-1H-indol-6-ylcarbamate (0.586 g, 1.452 mmol) and ethyl 2-oxoacetate in toluene (50%) (0.576 mL, 2.90 mmol) in 1,4-dioxane (15 mL) at room temperature was added hydrogen chloride in 1,4-dioxane (0.436 mL, 1.743 mmol). The mixture was stirred room temperature for 16 hr. The volatiles were removed under vacuum. The residue was diluted with water (30 mL), basified with NaHCO$_3$ solution to pH 10, and extracted with ethyl acetate (3×30 mL). The combined extract was washed with brine (30 ml), dried over anhydrous MgSO$_4$, and concentrated to dryness under vacuum. To the residue were added toluene (15 mL) and 10% Pd/C (0.2 g), and the mixture was heated at 110° C. under an ambient atmosphere for 3.5 hr. The solid phase was removed by suction filtration. The filtrate was diluted with ethyl acetate (100 ml), washed with brine (25 ml), and dried over anhydrous MgSO$_4$. The desired product (0.238 g, 0.492 mmol, 33.9% yield) was isolated as a beige solid by ISCO (40 g silica gel, solid loading, 20-40% ethyl acetate/hexane).

5. 7-(Benzyloxycarbonylamino)-4-(2-fluorophenyl)-9H-pyrido[3,4-b]indole-1-carboxylic acid

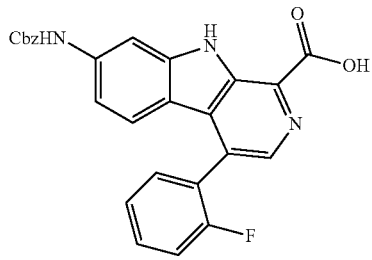 [SMILES: O=C(Nc1ccc2c(c1)[nH]c1c(C(=O)O)ncc(-c3ccccc3F)c12)OCc1ccccc1]

To a solution of ethyl 7-(benzyloxycarbonylamino)-4-(2-fluorophenyl)-9H-pyrido[3,4-b]indole-1-carboxylate (0.238 g, 0.492 mmol) in tetrahydrofuran (12 mL) and methanol (4 mL) at room temperature was added a solution of lithium hydroxide hydrate (0.083 g, 1.969 mmol) in water (1.8 mL). The mixture was stirred at room temperature for 1 hr, and then concentrated under vacuum. To the residue was added water (5 ml), and the mixture was acidified to pH 5 with 1 N HCl. The precipitating product (0.214 g, 0.470 mmol, 95% yield) was collected by suction filtration and dried over Drierite under vacuum.

6. 4-(2-Fluorophenyl)-7-(isonicotinamido)-9H-pyrido[3,4-b]indole-1-carboxamide

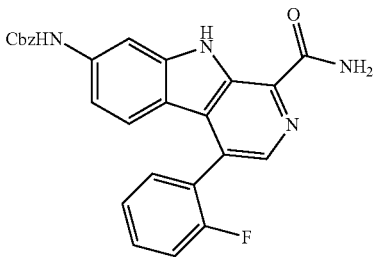 [SMILES: NC(=O)c1ncc(-c2ccccc2F)c2c1[nH]c1cc(NC(=O)OCc3ccccc3)ccc12]

A mixture of 7-(benzyloxycarbonylamino)-4-(2-fluorophenyl)-9H-pyrido[3,4-b]indole-1-carboxylic acid (214 mg, 0.470 mmol), ammonium chloride (101 mg, 1.880 mmol), N,N-diisopropylamine (0.394 mL, 2.255 mmol), BOP (270 mg, 0.611 mmol), N-methylmorpholine (0.201 mL, 1.833 mmol) in DMF (2 mL) was stirred at rt for 1 hr. To the reaction solution was added water (20 mL), and the precipitating product (213 mg, 0.422 mmol, 90% yield) was collected as a beige solid by suction filtration and dried over Drierite under vacuum.

7. 7-Amino-4-(2-fluorophenyl)-9H-pyrido[3,4-b]indole-1-carboxamide

A mixture of benzyl 1-carbamoyl-4-(2-fluorophenyl)-9H-pyrido[3,4-b]indol-7-ylcarbamate (210 mg, 0.416 mmol) and 10% Pd/C (45 mg, 0.042 mmol) in tetrahydrofuran (5 mL) and methanol (15 mL) was stirred under $H_2$, provided with a $H_2$ balloon, at rt for 1 hr. The catalyst was removed by suction filtration through CELITE®. The filtrate was concentrated under vacuum. The residue was diluted with $CH_2Cl_2$ (100 mL), washed with brine (30 mL), and dried over anhydrous $MgSO_4$. Removal of solvent under vacuum provided the desired product, 7-amino-4-(2-fluorophenyl)-9H-pyrido[3,4-b]indole-1-carboxamide (132 mg, 0.375 mmol, 90% yield), as a tan solid. LCMS (M+H)$^+$=321.10.

EXAMPLE 6

4-(2-Fluorophenyl)-7-(isonicotinamido)-9H-pyrido[3,4-b]indole-1-carboxamide

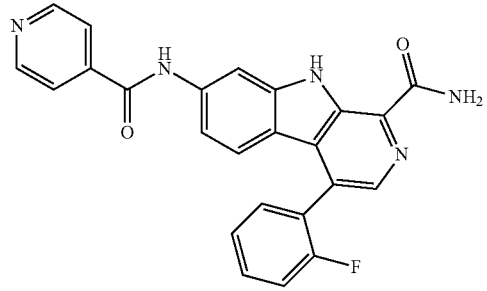 [SMILES: NC(=O)c1ncc(-c2ccccc2F)c2c1[nH]c1cc(NC(=O)c3ccncc3)ccc12]

A mixture of 7-amino-4-(2-fluorophenyl)-9H-pyrido[3,4-b]indole-1-carboxamide (25 mg, 0.078 mmol), isonicotinic acid (11.53 mg, 0.094 mmol), BOP (49.7 mg, 0.112 mmol), and N-methylmorpholine (0.037 mL, 0.337 mmol) in DMF (0.25 mL) was stirred at room temperature for 1.5 hr. The mixture was diluted with MeOH (1.5 mL) and subjected to prep LC. reverse phase HPLC purification. The correct fraction was concentrated under vacuum, basified with saturated $NaHCO_3$ solution to pH 9. The precipitating product (10.8 mg, 0.025 mmol, 32.5% yield) was collected as a pale solid by suction filtration. LCMS (M+H)$^+$=426.14. $^1$H NMR (500 MHz, DMSO-$d_6$) δ: 11.95 (s, 1H), 10.96 (s, 1H), 6.80 (m, 2H), 8.44 (s, 1H), 8.33 (s, 1H), 8.27 (s, 1H), 7.89 (m, 2H), 7.79 (s, 1H), 7.71-7.67 (m, 2H), 7.54-7.48 (m, 2H), 7.42 (dd, J1=8.6 Hz, J2=1.9 Hz, 1H), 7.28 (d, J=8.6 Hz, 1H).

EXAMPLE 7

4-(2-Fluorophenyl)-7-(tetrahydro-2H-pyran-4-ylamino)-9H-pyrido[3,4-b]indole-1-carboxamide

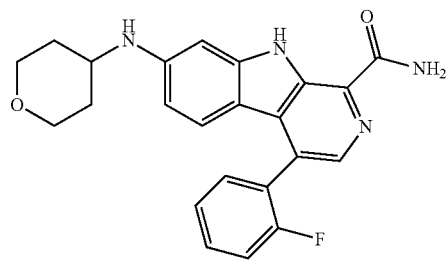 [SMILES: NC(=O)c1ncc(-c2ccccc2F)c2c1[nH]c1cc(NC3CCOCC3)ccc12]

A mixture of 7-amino-4-(2-fluorophenyl)-9H-pyrido[3,4-b]indole-1-carboxamide (30.0 mg, 0.094 mmol), dihydro-2H-pyran-4(3H)-one (10.37 µL, 0.112 mmol), and sodium triacetoxyborohydride (39.7 mg, 0.187 mmol) in tetrahydrofuran (1 mL) and dichloromethane (1 mL) was stirred at rt for 16 hr. Additional dihydro-2H-pyran-4(3H)-one (10.37 μL, 0.112 mmol) and sodium triacetoxyborohydride (39.7 mg, 0.187 mmol) were added, and the mixture was stirred at room temperature for another 8 hr. To the reaction mixture was added water (2 mL), and the resulting mixture was stirred at room temperature for 20 min. It was diluted with ethyl acetate (50 mL), washed with saturated NaHCO$_3$ solution (15 mL) and brine (15 mL), and dried over anhydrous MgSO$_4$. Solvent was removed under vacuum, and the residue was subjected to prep. reverse phase HPLC purification. The correct fraction was concentrated under vacuum and basified with saturated NaHCO$_3$ solution. The precipitating product (11.8 mg, 0.029 mmol, 30.8% yield) was collected as a yellow solid by suction filtration and dried at 50° C. under vacuum. LCMS (M+H)$^+$ =405.17. $^1$H NMR (500 MHz, DMSO-d$_6$) δ: 11.30 (s, 1H), 8.23 (s, 1H), 8.11 (s, 1H), 7.70 (s, 1H), 7.65-7.61 (m, 2H), 7.49-7.42 (m, 2H), 6.98 (d, J=8.0 Hz, 1H), 6.94 (s, 1H), 6.46 (dd, J1=8.7 Hz, J2=1.5 Hz, 1H), 6.19 (br. s, 1H), 3.90 (m, 2H), 3.47 (m, 1H), 3.43 (m, 2H), 1.94 (m, 2H), 1.44 (m, 2H).

EXAMPLE 8

4-(2-Fluorophenyl)-7-(methylsulfonamido)-9H-pyrido[3,4-b]indole-1-carboxamide

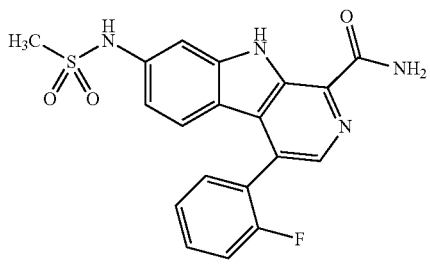 [SMILES: CS(=O)(=O)Nc1ccc2c(c1)[nH]c1c(C(N)=O)ncc(-c3ccccc3F)c12]

To a solution of 7-amino-4-(2-fluorophenyl)-9H-pyrido[3,4-b]indole-1-carboxamide (25 mg, 0.078 mmol) in dichloromethane (2 mL) at rt was sequentially added methanesulfonyl chloride (22.35 mg, 0.195 mmol) and pyridine (0.016 mL, 0.195 mmol). The mixture was stirred at room temperature for 1 hr and then at 50° C. in a closed vial for 30 min. The mixture was concentrated. The residue was diluted with MeOH (1.5 mL) and subjected to prep. reverse phase HPLC purification. The correct fraction was concentrated under vacuum, basified with saturated NaHCO$_3$ solution to pH 9, and extracted with ethyl acetate (3×30 mL). The combined extracts were washed with brine (25 mL) and dried over anhydrous MgSO$_4$. Removal of solvent under vacuum provided the desired product (4.81 mg, 0.012 mmol, 15.00% yield) as a pale solid. LCMS (M+H)$^+$=399.03. $^1$H NMR (500 MHz, DMSO-d$_6$) δ: 11.85 (s, 1H), 10.03 (s, 1H), 8.30 (s, 1H), 8.23 (s, 1H), 7.77 (s, 1H), 7.75 (s, 1H), 7.67-7.63 (m, 2H), 7.50-7.43 (m, 2H), 7.19 (d, J=7.7 Hz, 1H), 6.92 (dd, J1=8.8 Hz, J2=2.2 Hz, 1H), 3.02 (s, 3H).

EXAMPLE 9

4-(3-(6-Chloro-1-oxoisoindolin-2-yl)-2-methylphenyl)-7-(2-methoxyethoxy)-9H-pyrido[3,4-b]indole-1-carboxamide

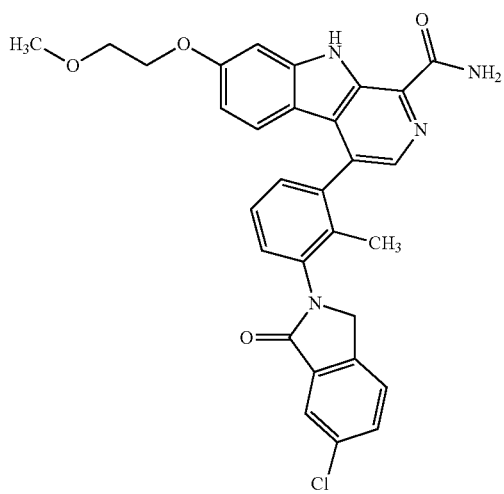 [SMILES: COCCOc1ccc2c(c1)[nH]c1c(C(N)=O)ncc(-c3cccc(N4Cc5ccc(Cl)cc5C4=O)c3C)c12]

1. 6-(2-Methoxyethoxy)-1H-indole

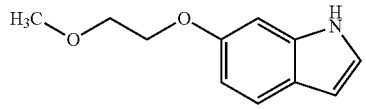

A mixture of 1H-indol-6-ol (4.0 g, 30.0 mmol), 1-bromo-2-methoxyethane (3.53 mL, 37.6 mmol), and cesium carbonate (11.75 g, 36.1 mmol) in DMF (50 mL) was heated at 75° C. for 16 hr. DMF was removed under vacuum with a oil pump. The residue was diluted with ethyl acetate (200 mL), washed sequentially with 1 N NaOH solution (50 mL), water (2×50 mL), and brine (50 mL). The organic solution was dried over anhydrous MgSO$_4$ and concentrated under vacuum. The desired product (4.68 g, 21.54 mmol, 71.7% yield) was isolated as a white solid by ISCO (300 g silica gel, solid loading, 10-50% ethyl acetate/hexane).

2. 3-Amino-2-methylbenzonitrile

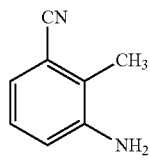

To a mixture of 2-methyl-3-nitrobenzonitrile (5.50 g, 33.9 mmol) and ammonium chloride (25.4 g, 475 mmol) in tetrahydrofuran (100 mL) and methanol (100 mL) at 0° C. was added zinc dust (31.1 g, 475 mmol) in portions. The mixture was stirred at room temperature for 2 hr. The insoluble material was removed by suction filtration through CELITE®, and the filtrate was concentrated under vacuum. The residue was diluted with water (50 mL) and extracted with $CH_2Cl_2$ (4×100 mL). The combined extract was dried over anhydrous $MgSO_4$. Removal of solvent under vacuum provided the desired product (4.19 g, 31.7 mmol, 93% yield) as a white solid.

3. Benzyl 3-cyano-2-methylphenylcarbamate

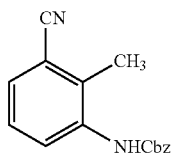 [SMILES: Cc1c(C#N)cccc1NC(=O)OCc1ccccc1]

A mixture of 3-amino-2-methylbenzonitrile (4.32 g, 32.7 mmol), benzyl carbonochloridate (7.26 mL, 49.0 mmol), and potassium carbonate (6.78 g, 79.0 mmol) in tetrahydrofuran (280 mL) was stirred at room temperature for 3 days. The insoluble material was removed by filtration, and the filtrate was concentrated under vacuum. The residue was diluted with ethyl acetate (250 mL), washed with 1N HCl solution (60 mL), water (60 mL), and brine (60 mL). The organic solution was dried over anhydrous $MgSO_4$, and the solution was concentrated under vacuum to dryness. The residue was stirred with hexane (100 mL) at room temperature for 1 hr. The insoluble product (6.41 g, 24.07 mmol, 73.6% yield) was collected as a white solid by suction filtration.

4. Benzyl 3-formyl-2-methylphenylcarbamate

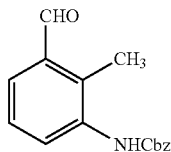

To a solution of benzyl 3-cyano-2-methylphenylcarbamate (6.41 g, 24.07 mmol) in tetrahydrofuran (250 mL) at −78° C. was added DIBAL-H in dichloromethane (96 mL, 96 mmol) over 1 hr. The mixture was stirred at −78° C. for 45 min and then at room temperature for 5 hr. It was poured into ice cold water (300 mL) and the resulting mixture was stirred at room temperature for 30 min. The mixture was filtered through CELITE®, and the filtrate was concentrated to remove most of the THF. The remaining aqueous solution was extracted with ethyl acetate (4×150 mL). The combined extract was dried over anhydrous $MgSO_4$. Removal of solvent under vacuum provided the desired product (5.65 g, 20.98 mmol, 87% yield) as a pale yellow solid.

5. (E)-Benzyl 2-methyl-3-(2-nitrovinyl)phenylcarbamate

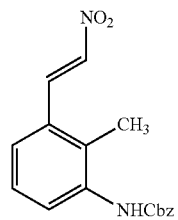 [SMILES: Cc1c(/C=C/[N+](=O)[O-])cccc1NC(=O)OCc1ccccc1]

A mixture of benzyl 3-formyl-2-methylphenylcarbamate (4.968 g, 18.45 mmol), nitromethane (2.478 mL, 46.1 mmol), and ammonium acetate (3.56 g, 46.1 mmol) in acetic acid (70 mL, 1223 mmol) was heated at 90° C. for 4.5 hr. The acetic acid was removed under vacuum. To the residue was added water (100 mL), and the mixture was stirred at room temperature for 30 min. The insoluble material was collected with suction filtration. The filter cake was mixed with water (100 mL) and the aqueous mixture was adjusted to pH 9 with saturated $NaHCO_3$ solution and stirred at room temperature for 30 min. The insoluble product (4.13 g, 88% purity, 13.22 mmol, 71.7% yield) was collected as a yellow solid with suction filtration and dried over Drierite under vacuum.

6. Benzyl 3-(1-(6-(2-methoxyethoxy)-1H-indol-3-yl)-2-nitroethyl)-2-methylphenylcarbamate

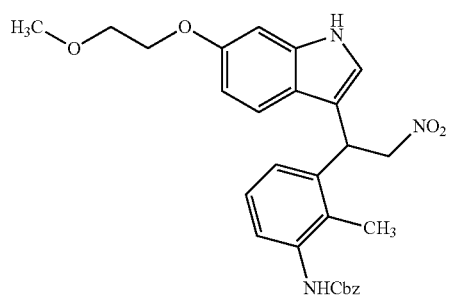 [SMILES: COCCOc1ccc2c(C(C[N+](=O)[O-])c3cccc(NC(=O)OCc4ccccc4)c3C)c[nH]c2c1]

6-(2-Methoxyethoxy)-1H-indole (1.461 g, 88% purity, 6.72 mmol) and (E)-benzyl 2-methyl-3-(2-nitrovinyl)phenylcarbamate (1.75 g, 5.60 mmol) were dissolved in THF (50 mL). The solution was then concentrated under vacuum to dryness. The solid mixture was melted at 125° C. and heated at this temperature for 16 hr. The mixture was subjected to ISCO (220 g silica gel, solid loading, 25-65% ethyl acetate/hexane) to afford the desired product (1.75 g, 3.48 mmol, 62% yield) as a beige solid.

7. Benzyl 3-(2-amino-1-(6-(2-methoxyethoxy)-1H-indol-3-yl)ethyl)-2-methylphenylcarbamate

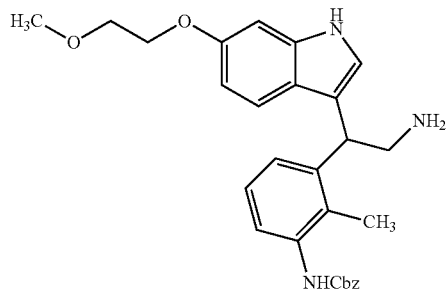 [SMILES: COCCOc1ccc2c(C(CN)c3cccc(NC(=O)OCc4ccccc4)c3C)c[nH]c2c1]

A mixture of benzyl 3-(1-(6-(2-methoxyethoxy)-1H-indol-3-yl)-2-nitroethyl)-2-methylphenylcarbamate (1.75 g, 3.48 mmol), ammonium chloride (2.79 g, 52.1 mmol), and zinc dust (3.41 g, 52.1 mmol) in tetrahydrofuran (35 mL) and methanol (35 mL) was stirred at room temperature for 4.5 hr. The mixture was diluted with ethyl acetate (40 mL) and filtered through CELITE®. The filtrate was concentrated under vacuum, and the residue was diluted with water (40 mL), basified with saturated NaHCO$_3$ solution, and extracted with ethyl acetate (4×40 mL). The combined extract was washed with brine (40 mL) and dried over anhydrous MgSO$_4$. Removal of solvent under vacuum provided the desired product (1.65 g, 3.48 mmol, 100% yield) as beige solid.

8. Ethyl 4-(3-(benzyloxycarbonylamino)-2-methylphenyl)-7-(2-methoxyethoxy)-9H-pyrido[3,4-b]indole-1-carboxylate

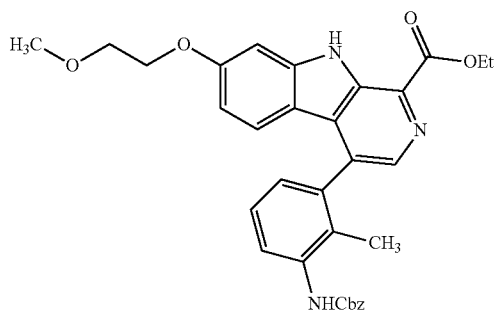 [SMILES: CCOC(=O)c1ncc(-c2cccc(NC(=O)OCc3ccccc3)c2C)c2c1[nH]c1cc(OCCOC)ccc12]

To a solution of benzyl 3-(2-amino-1-(6-(2-methoxyethoxy)-1H-indol-3-yl)ethyl)-2-methylphenylcarbamate (0.780 g, 1.647 mmol) and ethyl 2-oxoacetate in toluene (50%) (0.653 mL, 3.29 mmol) at room temperature was added hydrogen chloride in 1,4-dioxane (4.0 M) (0.494 mL, 1.977 mmol). The mixture was stirred room temperature for 16 hr. The volatiles were removed under vacuum. The residue was diluted with water (50 mL), basified with NaHCO$_3$ solution to pH 10, and extracted with ethyl acetate (4×50 mL). The combined extract was washed with brine (40 ml), dried over anhydrous MgSO$_4$, and concentrated to dryness under vacuum. To the residue were added p-xylene (60 mL) and 10% Pd/C (0.46 g), and the mixture was heated at 125° C. under an ambient atmosphere for 4.5 hr. The solid phase was removed by suction filtration. The filtrate was diluted with ethyl acetate (120 ml), washed with brine (40 ml), and dried over anhydrous MgSO$_4$. The desired product (0.399 g, 0.721 mmol, 43.8% yield) was isolated by ISCO (40 g silica gel, solid loading, 15-35% ethyl acetate/CH$_2$Cl$_2$).

9. 4-(3-(Benzyloxycarbonylamino)-2-methylphenyl)-7-(2-methoxyethoxy)-9H-pyrido[3,4-b]indole-1-carboxylic acid

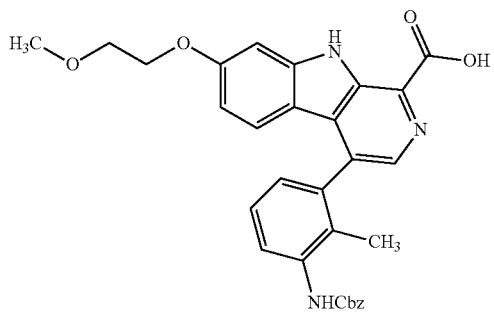 [SMILES: COCCOc1ccc2c(c1)[nH]c1c(C(=O)O)ncc(-c3cccc(NC(=O)OCc4ccccc4)c3C)c12]

To a solution of ethyl 4-(3-(benzyloxycarbonylamino)-2-methylphenyl)-7-(2-methoxyethoxy)-9H-pyrido[3,4-b]indole-1-carboxylate (0.299 g, 0.540 mmol) in tetrahydrofuran (15 mL) and methanol (5 mL) at room temperature was added a solution of lithium hydroxide hydrate (0.091 g, 2.160 mmol) in water (2 mL). The resulting mixture was stirred at room temperature for 1.5 hr, and then concentrated under vacuum to almost dryness. To the residue was added water (8 mL), and the mixture was neutralized with 1N HCl to pH 4-5. The insoluble product (0.237 g, 0.451 mmol, 83% yield) was collected as a beige solid by suction filtration and dried over Drierite under vacuum.

10. Benzyl 3-(1-carbamoyl-7-(2-methoxyethoxy)-9H-pyrido[3,4-b]indol-4-yl)-2-methylphenylcarbamate

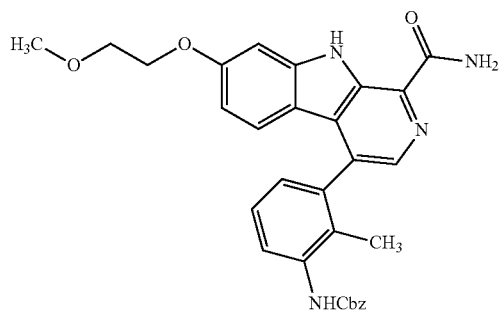 [SMILES: COCCOc1ccc2c(c1)[nH]c1c(C(N)=O)ncc(-c3cccc(NC(=O)OCc4ccccc4)c3C)c12]

A mixture of 4-(3-(benzyloxycarbonylamino)-2-methylphenyl)-7-(2-methoxyethoxy)-9H-pyrido[3,4-b]indole-1-carboxylic acid (0.237 g, 0.451 mmol), ammonium chloride (0.096 g, 1.804 mmol), N,N-diisopropylamine (0.378 mL, 2.165 mmol), BOP (0.259 g, 0.586 mmol), and N-methylmorpholine (0.193 mL, 1.759 mmol) in N,N-dimethylformamide (3 mL) was stirred at room temperature for 1.5 hr. To the reaction mixture was added water (30 mL), and the resulting mixture was stirred at room temperature for 30 min. The insoluble product (0.226 g, 0.431 mmol, 96% yield) was collected as a beige solid by suction filtration and dried over Drierite under vacuum.

11. 4-(3-Amino-2-methylphenyl)-7-(2-methoxyethoxy)-9H-pyrido[3,4-b]indole-1-carboxamide

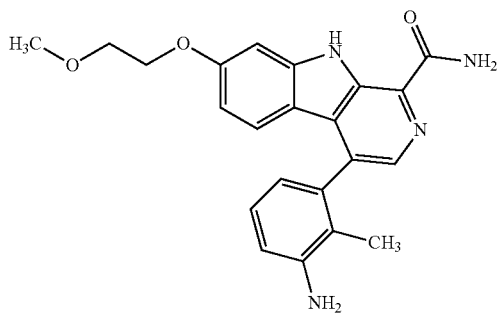 [SMILES: COCCOc1ccc2c(c1)[nH]c1c(C(N)=O)ncc(-c3cccc(N)c3C)c12]

A mixture of benzyl 3-(1-carbamoyl-7-(2-methoxyethoxy)-9H-pyrido[3,4-b]indol-4-yl)-2-methylphenylcarbamate (0.226 g, 0.431 mmol) and Pd/C (60 mg, 0.056 mmol) in tetrahydrofuran (12 mL) and methanol (18 mL) was stirred at room temperature under $H_2$, provided with a $H_2$ balloon, for 1.5 hr. The catalyst was removed by suction filtration, and the filtrate was concentrated under vacuum. The residue was dissolved in ethyl acetate (80 mL) and dried over anhydrous $MgSO_4$. Removal of the solvent under vacuum provided the desired product (0.172 g, 0.441 mmol, 102% yield) as a beige solid.

12. 2-((3-(1-Carbamoyl-7-(2-methoxyethoxy)-9H-pyrido[3,4-b]indol-4-yl)-2-methylphenylamino)methyl)-5-chlorobenzoic acid

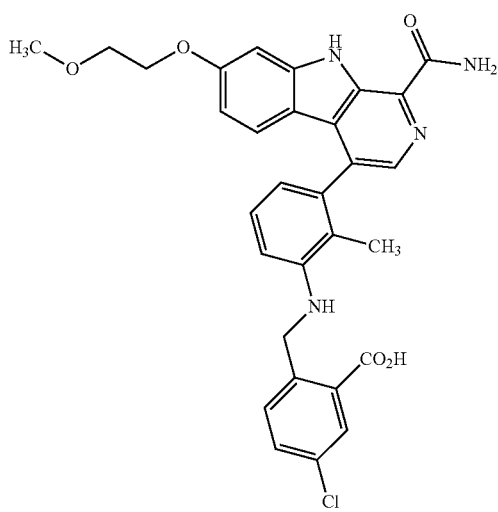 [SMILES: COCCOc1ccc2c(c1)[nH]c1c(C(N)=O)ncc(-c3cccc(NCc4ccc(Cl)cc4C(=O)O)c3C)c12]

A mixture of 4-(3-amino-2-methylphenyl)-7-(2-methoxyethoxy)-9H-pyrido[3,4-b]indole-1-carboxamide (60.0 mg, 0.154 mmol), 5-chloro-2-formylbenzoic acid (70.9 mg, 0.384 mmol), sodium triacetoxyborohydride (98 mg, 0.461 mmol), and acetic acid (0.018 mL, 0.307 mmol) in dichloroethane (3 mL) and tetrahydrofuran (2 mL) was stirred at room temperature for 16 hr and then quenched with water (3 mL). The resulting mixture was diluted with ethyl acetate (50 mL) and washed with water (25 mL). The aqueous solution was extracted with ethyl acetate (2×30 mL). The combined extract was washed with brine (25 mL) and dried over anhydrous $MgSO_4$. The organic solution was concentrated under vacuum to dryness. The residue was dissolved with minimum amount of DMF, diluted with MeOH (3 mL), divided into 2 portions, and purified by prep. reverse phase HPLC. The correct fractions were combined, concentrated under vacuum, and lyophilized to afford the desired product (TFA salt) (38 mg, 0.056 mmol, 36.7% yield) as a white powder.

13. 4-(3-(6-Chloro-1-oxoisoindolin-2-yl)-2-methylphenyl)-7-(2-methoxyethoxy)-9H-pyrido[3,4-b]indole-1-carboxamide A mixture of 2-((3-(1-carbamoyl-7-(2-methoxyethoxy)-9H-pyrido[3,4-b]indol-4-yl)-2-methylphenylamino)methyl)-5-chlorobenzoic acid, TFA (38 mg, 0.056 mmol), N,N-diisopropylamine (0.015 mL, 0.085 mmol), BOP (32.5 mg, 0.073 mmol), and N-methylmorpholine (0.024 mL, 0.220 mmol) in DMF (4 mL) was heated at 45° C. for 1 hr. The mixture was diluted with ethyl acetate (60 mL), washed sequentially with water (3×25 mL) and brine (25 mL), and dried over anhydrous $MgSO_4$. After the solvent was removed under vacuum, the residue was purified by prep. Reverse phase HPLC. The correct fraction was concentrated under vacuum, basified with saturated $NaHCO_3$ solution, and extracted with $CH_2Cl_2$ (3×30 mL). The combined extract was washed with brine (30 mL) and dried over anhydrous $MgSO_4$. Removal of solvent under vacuum provided the desired product (21.7 mg, 0.039 mmol, 68.2% yield) as a yellow solid. LCMS $(M+H)^+$=541.33. $^1$H NMR (500 MHz, DMSO-$d_6$) δ: 11.66 (s, 1H), 8.30 (s, 1H), 8.20 (s, 1H), 7.82 (s, 1H), 7.77-7.73 (m, 3H), 7.67 (m, 1H), 7.54 (m, 1H), 7.45 (m, 1H), 7.36 (d, J=2.2 Hz, 1H), 7.14 (d, J=8.9 Hz, 1H), 6.71 (dd, J1=8.7 Hz, J2=2.4 Hz, 1H), 5.04 (d, J=17.5 Hz, 1H), 4.95 (d, J=17.5 Hz, 1H), 4.16 (m, 2H), 3.72 (m, 2H), 3.34 (s, 3H), 1.87 (s, 3H).

EXAMPLE 10

7-(2-Methoxyethoxy)-4-(2-methyl-3-(4-oxoquinazolin-3(4H)-yl)phenyl)-9H-pyrido[3,4-b]indole-1-carboxamide

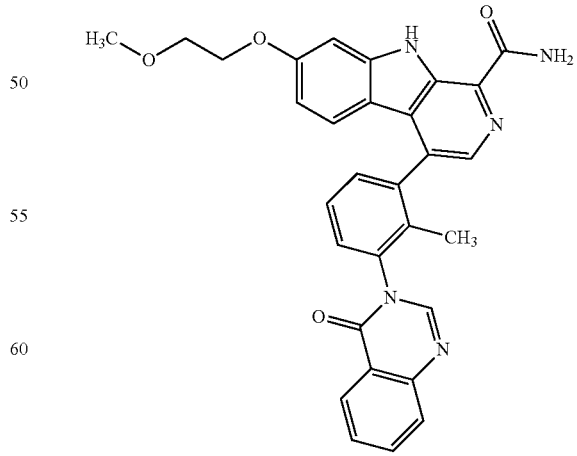

A mixture of 4-(3-amino-2-methylphenyl)-7-(2-methoxyethoxy)-9H-pyrido[3,4-b]indole-1-carboxamide (330 mg, 0.845 mmol), 1H-benzo[d][1,3]oxazine-2,4-dione (345 mg, 2.113 mmol), trimethoxymethane (0.926 mL, 8.45 mmol), and tris(nitrooxy)lanthanum, 6H$_2$O (110 mg, 0.254 mmol) in tetrahydrofuran (Volume: 2 mL) was heated at 95° C. in a sealed vial for 20 hr. The mixture was diluted with ethyl acetate (100 mL), washed with water (30 mL), 1 N NaOH solution (30 mL), and brine (30 mL). The organic solution was dried over anhydrous MgSO$_4$ and concentrated under vacuum. The residue was subjected to prep. reverse phase HPLC purification. The correct fractions were concentrated under vacuum, basified with saturated NaHCO$_3$ solution, and extracted with ethyl acetate (3×35 mL). The combined extract was washed with brine (30 mL) and dried over anhydrous MgSO$_4$. Removal of solvent under vacuum provided the desired product (188 mg, 0.362 mmol, 42.8% yield) as a yellow solid. The product is mixture of two atropisomers at rt. LCMS (M+H)$^+$=520.29. $^1$H NMR (500 MHz, DMSO-d$_6$) (recognizable peaks for the major atropisomer) δ: 11.68 (s, 1H), 8.44 (s, 1H), 8.21 (s, 1H), 7.36 (s, 1H), 7.25 (d, J=8.9 Hz), 4.17 (m, 2H), 3.73 (m, 2H), 3.35 (s, 3H), 1.81 (s, 3H).

concentrated under vacuum, basified with saturated NaHCO$_3$ solution, and extracted with ethyl acetate (3×30 mL). The combined extract was washed with brine (30 mL) and dried over anhydrous MgSO$_4$. Removal of solvent under vacuum provided the desired product (44.0 mg, 0.084 mmol, 43.3% yield) as a yellow solid. The product is mixture of two atropisomers at rt. LCMS (M+H)$^+$=506.23. $^1$H NMR (500 MHz, DMSO-d$_6$) (recognizable peaks for the major atropisomer) δ: 11.67 (s, 1H), 8.44 (s, 1H), 8.21 (s, 1H), 7.37 (s, 1H), 4.07 (m, 2H), 3.78 (m, 2H), 1.81 (s, 3H).

EXAMPLE 12

7-Hydroxy-4-(2-methyl-3-(4-oxoquinazolin-3(4H)-yl)phenyl)-9H-pyrido[3,4-b]indole-1-carboxamide

EXAMPLE 11

7-(2-Hydroxyethoxy)-4-(2-methyl-3-(4-oxoquinazolin-3(4H)-yl)phenyl)-9H-pyrido[3,4-b]indole-1-carboxamide

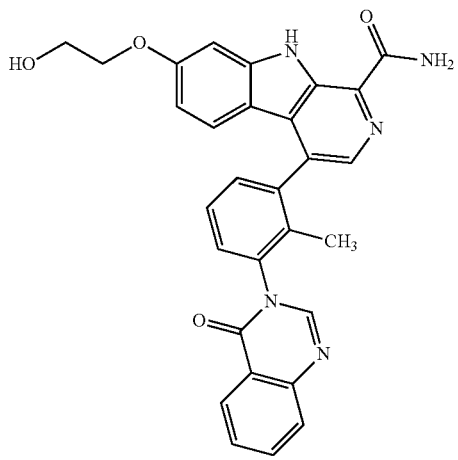

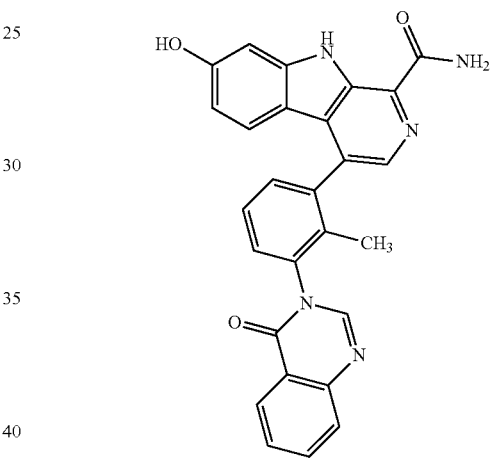 [SMILES: COCCOc1ccc2c(c1)[nH]c1c(C(N)=O)ncc(-c3cccc(-n4cnc5ccccc5c4=O)c3C)c12]

To a solution of 7-(2-methoxyethoxy)-4-(2-methyl-3-(4-oxoquinazolin-3(4H)-yl)phenyl)-9H-pyrido[3,4-b]indole-1-carboxamide (101 mg, 0.194 mmol) in dichloromethane (5 mL) at 0° C. was added tribromoborane in dichloromethane (0.622 mL, 0.622 mmol) over 5 min. The resulting heterogeneous mixture was stirred at room temperature for 1.5 hr. The reaction was quenched with ice water (15 mL). The mixture was basified with 1 N NaOH solution to pH 10 and extracted with ethyl acetate (3×40 mL). The combined extract was washed with brine (30 mL) and dried over anhydrous MgSO$_4$. After the solvent was removed under vacuum, the residue was purified by reverse phase HPLC. The correct fraction was A mixture of 7-(2-methoxyethoxy)-4-(2-methyl-3-(4-oxoquinazolin-3(4H)-yl)phenyl)-9H-pyrido[3,4-b]indole-1-carboxamide (70 mg, 0.135 mmol) and aluminum triiodide (137 mg, 0.337 mmol) in acetonitrile (6 mL) was heated at reflux for 4 hr. Upon cooling to room temperature, the reaction was quenched with ice water (20 mL). The mixture was extracted with ethyl acetate (3×30 mL). The combined extract was with brine (25 mL) and dried over anhydrous MgSO$_4$. After the solvent was removed under vacuum, the residue was purified by reverse phase HPLC. The correct fractions were concentrated under vacuum, basified with saturated NaHCO$_3$ solution, and extracted with ethyl acetate (3×30 mL). The combined extract was washed with brine (30 mL) and dried over anhydrous MgSO$_4$. Removal of solvent under vacuum provided the desired product (12.9 mg, 0.026 mmol, 19.54% yield) as a yellow solid. LCMS (M+H)$^+$=462.23. $^1$H NMR (500 MHz, DMSO-d$_6$) (recognizable peaks for the major atropisomer) δ: 11.56 (s, 1H), 9.84 (s, 1H), 8.16 (s, 1H), 7.19 (s, 1H), 7.16 (d, J=8.6 Hz, 1H), 1.81 (s, 3H).

EXAMPLE 13

7-(2-Methoxyethoxy)-4-(2-methyl-3-(4-oxopyrido[3,2-d]pyrimidin-3(4H)-yl)phenyl)-9H-pyrido[3,4-b]indole-1-carboxamide

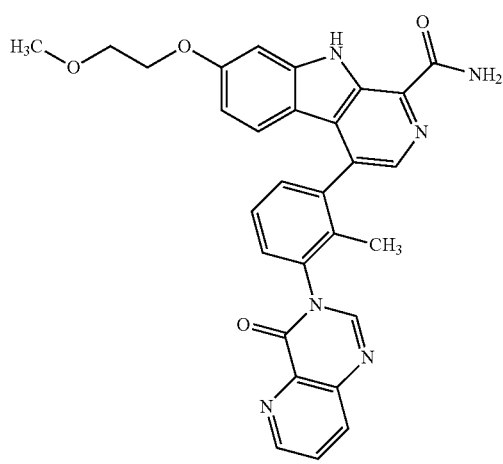 [SMILES: COCCOc1ccc2c(c1)[nH]c1c(C(N)=O)ncc(-c3cccc(-n4cnc5cccnc5c4=O)c3C)c12]

A mixture of 4-(3-amino-2-methylphenyl)-7-(2-methoxyethoxy)-9H-pyrido[3,4-b]indole-1-carboxamide (60 mg, 0.154 mmol), 3-aminopicolinic acid (53.1 mg, 0.384 mmol), trimethoxymethane (0.151 mL, 1.383 mmol), and tris(nitrooxy)lanthanum, 6H₂O (19.96 mg, 0.046 mmol) in tetrahydrofuran (0.2 mL) was heated at 95° C. in a sealed vial for 16 hr. The mixture remained heterogeneous and very little (<5%) of the desired product was formed. DMF (0.5 mL) was added to the reaction mixture. Also added were additional 3-aminopicolinic acid (26.5 mg, 0.192 mmol) and tris(nitrooxy) lanthanum, 6H₂O (10 mg, 0.023 mmol). The mixture was heated at 90° C. for two days. It was diluted with ethyl acetate (100 mL) and washed sequentially with water (25 mL), 1 N NaOH solution (25 mL), water (25 ml), and brine (25 mL). The organic solution was dried over anhydrous MgSO₄ and concentrated under vacuum. The residue was purified by reverse phase HPLC. The correct fractions were concentrated under vacuum, basified with saturated NaHCO₃ solution, and extracted with ethyl acetate (3×30 mL). The combined extract was washed with brine (30 mL) and dried over anhydrous MgSO₄. Removal of solvent under vacuum provided the desired product (7.1 mg, 0.013 mmol, 8.51% yield) as a yellow solid. LCMS (M+H)⁺=521.03. ¹H NMR (500 MHz, DMSO-d₆) (recognizable peaks for the major atropisomer) δ: 11.68 (s, 1H), 8.89 (s, 1H), 8.53 (s, 1H), 8.29 (s, 1H), 8.21 (s, 1H), 7.91 (m, 1H), 7.37 (s, 1H), 4.18 (m, 2H), 3.73 (m, 2H), 3.35 (s, 3H), 1.84 (s, 3H).

EXAMPLE 14

7-(2-Hydroxypropoxy)-4-(2-methyl-3-(4-oxoquinazolin-3(4H)-yl)phenyl)-9H-pyrido[3,4-b]indole-1-carboxamide

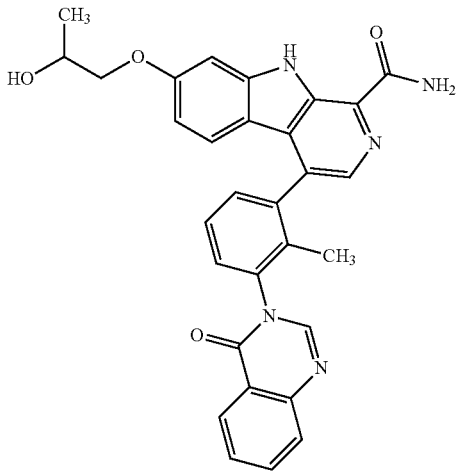 [SMILES: Cc1c(-c2cnc(C(N)=O)c3[nH]c4cc(OCC(C)O)ccc4c23)cccc1-n1cnc2ccccc2c1=O]

1. 4-(2-Methyl-3-(4-oxoquinazolin-3(4H)-yl)phenyl)-7-(2-oxoethoxy)-9H-pyrido[3,4-b]indole-1-carboxamide

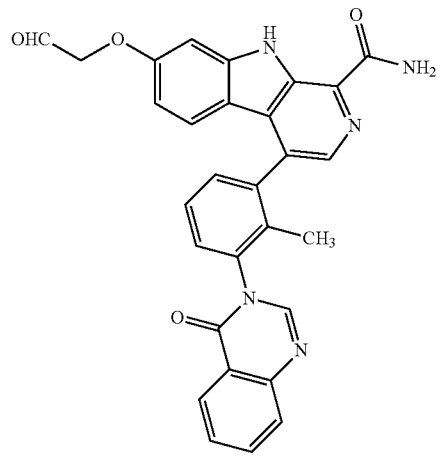 [SMILES: Cc1c(-c2cnc(C(N)=O)c3[nH]c4cc(OCC=O)ccc4c23)cccc1-n1cnc2ccccc2c1=O]

To a solution of 7-(2-hydroxyethoxy)-4-(2-methyl-3-(4-oxoquinazolin-3(4H)-yl)phenyl)-9H-pyrido[3,4-b]indole-1-carboxamide (152 mg, 0.301 mmol) in dichloromethane (10 mL) and tetrahydrofuran (10.00 mL) at room temperature was added Dess-Martin periodinane (191 mg, 0.451 mmol) in one portion. The mixture was stirred at room temperature for 16 hr. To the mixture was added saturated NaHCO₃ solution (10 mL) and water (10 mL). The mixture was stirred at room temperature for 20 min and extracted with ethyl acetate (3×40 mL). The combined extract was washed with brine (30 mL)

and dried over anhydrous MgSO₄. Removal of solvent under vacuum provided the desired product (178 mg, 0.354 mmol, 118% yield) as a beige solid.

2. 7-(2-Hydroxypropoxy)-4-(2-methyl-3-(4-oxo-quinazolin-3(4H)-yl)phenyl)-9H-pyrido[3,4-b]indole-1-carboxamide To a solution of 4-(2-methyl-3-(4-oxoquinazolin-3(4H)-yl)phenyl)-7-(2-oxoethoxy)-9H-pyrido[3,4-b]indole-1-carboxamide (178 mg, 85% purity, 0.300 mmol) in tetrahydrofuran (10 mL) at 0° C. was added methylmagnesium bromide (0.707 mL, 2.121 mmol). The mixture was stirred at rt for 20 min. Additional methylmagnesium bromide (0.50 mL, 1.50 mmol) was added. The mixture was stirred at room temperature for another 20 min and then the reaction was quenched with water (20 mL). The resulting mixture was extracted with ethyl acetate (3×40 mL). The combined extract was washed with brine (30 mL) and dried over anhydrous MgSO₄. After solvent was removed under vacuum, the residue was purified by reverse phase HPLC. The correct fractions were combined and concentrated under vacuum, basified with saturated NaHCO₃ solution, and extracted with ethyl acetate (3×35 mL). The combined extract was washed with brine (30 mL) and dried over anhydrous MgSO₄. Removal of solvent under vacuum provided the desired product (7.6 mg, 0.014 mmol, 4.9% yield) as a yellow solid. LCMS (M+H)⁺=520.21. ¹H NMR (500 MHz, DMSO-d₆) (recognizable peaks for the major atropisomer) δ: 11.68 (s, 1H), 8.44 (s, 1H), 8.21 (s, 1H), 7.36 (s, 1H), 4.01 (m, 1H), 3.92-3.84 (m, 2H), 1.81 (s, 3H).

EXAMPLE 15

4-(3-(6-Fluoro-1-oxoisoindolin-2-yl)-2-methylphenyl)-7-(2-methoxyethoxy)-9H-pyrido[3,4-b]indole-1-carboxamide

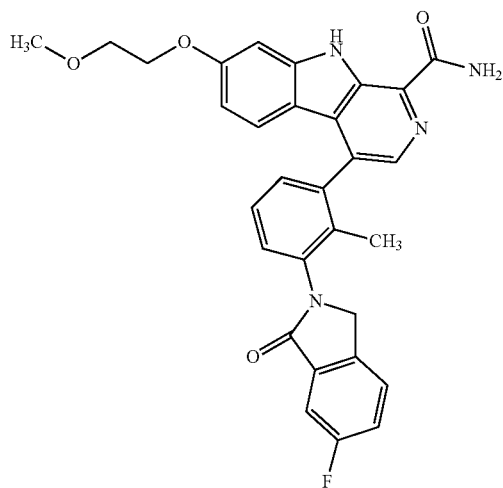 [SMILES: COCCOc1ccc2c(c1)[nH]c1c(C(N)=O)ncc(-c3cccc(N4Cc5ccc(F)cc5C4=O)c3C)c12]

1. 6-Fluoroisobenzofuran-1(3H)-one

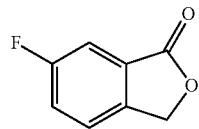 [SMILES: O=C1OCc2ccc(F)cc21]

A mixture of methyl 2-(bromomethyl)-5-fluorobenzoate (0.750 g, 3.04 mmol) and calcium carbonate (1.823 g, 18.21 mmol) in 1,4-dioxane (30 mL) and water (30.0 mL) was heated at reflux for 2.5 hr. The insoluble material was removed by filtration. The filtrate was concentrated under vacuum and then extracted with CH₂Cl₂ (4×30 mL). The combined extract was dried over anhydrous MgSO₄. Removal of solvent under vacuum provided the desired product (0.423 g, 2.78 mmol, 92% yield) as a white solid.

2. 5-Fluoro-2-(hydroxymethyl)benzoic acid

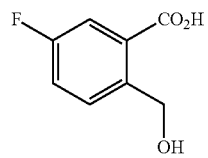

To a solution of 6-fluoroisobenzofuran-1(3H)-one (0.549 g, 3.61 mmol) in methanol (12 mL) and water (3 mL) at room temperature was added potassium hydroxide (0.350 g, 6.24 mmol). The mixture was heated at reflux for 1.5 hr. The mixture was concentrated under vacuum to a volume of about 3 mL. The residue was acidified with 1 M KHSO₄ solution to pH 3-4. The insoluble material (inorganic salt) was removed by suction filtration and the filtrate was extracted with ethyl acetate (5×30 mL). The combined extract was dried over anhydrous MgSO₄. Removal of solvent under vacuum provided the desired product (0.479 g, 2.82 mmol, 78% yield) as a white solid.

3. 5-Fluoro-2-formylbenzoic acid

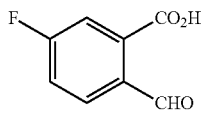

A mixture of 5-fluoro-2-(hydroxymethyl)benzoic acid (0.518 g, 3.04 mmol) and manganese(IV) oxide (3.71 g, 42.6 mmol) in tetrahydrofuran (25 mL) was stirred at room temperature for 16 hr. The insoluble material was removed by filtration through CELITE®. The filtrate was concentrated under vacuum to dryness. The residue was dissolved in CH₂Cl₂ (100 mL) and dried over anhydrous MgSO₄.

Removal of solvent under vacuum provided the desired product (0.211 g, 1.255 mmol, 41.2% yield) as a white solid.

4. 2-((3-(1-Carbamoyl-7-(2-methoxyethoxy)-9H-pyrido[3,4-b]indol-4-yl)-2-methylphenylamino)methyl)-5-fluorobenzoic acid

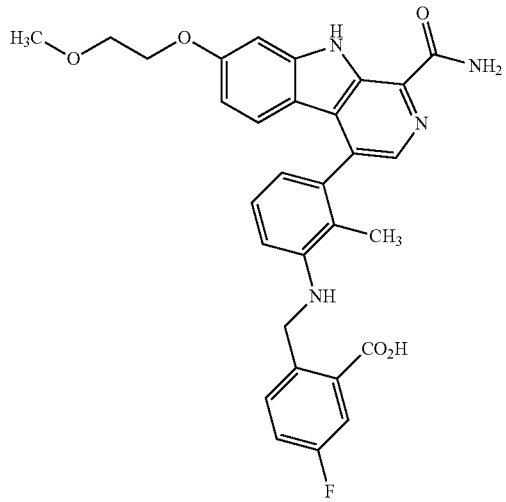 [SMILES: COCCOc1ccc2c(c1)[nH]c1c(C(N)=O)ncc(-c3cccc(NCc4ccc(F)cc4C(=O)O)c3C)c12]

A mixture of 4-(3-amino-2-methylphenyl)-7-(2-methoxyethoxy)-9H-pyrido[3,4-b]indole-1-carboxamide (60.0 mg, 0.154 mmol), 5-fluoro-2-formylbenzoic acid (64.6 mg, 0.384 mmol), sodium triacetoxyborohydride (98 mg, 0.461 mmol), and acetic acid (0.022 mL, 0.384 mmol) in dichloroethane (3 mL) and tetrahydrofuran (2 mL) was stirred at room temperature for 16 hr and then quenched with water (3 mL). The resulting mixture was diluted with ethyl acetate (50 mL) and washed with water (25 mL). The aqueous solution was extracted with ethyl acetate (2×30 mL). The combined extract was washed with brine (25 mL) and dried over anhydrous MgSO$_4$. The organic solution was concentrated under vacuum to dryness. The residue was dissolved with minimum amount of DMF, diluted with MeOH (3 mL), divided into 2 portions, and purified by reverse phase HPLC. The correct fractions were combined, concentrated under vacuum, and lyophilized to afford the desired product (TFA salt) (31.6 mg, 0.048 mmol, 31.3% yield) as a white powder.

5. 4-(3-(6-Fluoro-1-oxoisoindolin-2-yl)-2-methylphenyl)-7-(2-methoxyethoxy)-9H-pyrido[3,4-b]indole-1-carboxamide A mixture of 2-((3-(1-carbamoyl-7-(2-methoxyethoxy)-9H-pyrido[3,4-b]indol-4-yl)-2-methylphenylamino)methyl)-5-fluorobenzoic acid, TFA (31.6 mg, 0.048 mmol), N,N-diisopropylamine (0.013 mL, 0.072 mmol), BOP (27.7 mg, 0.063 mmol), and N-methylmorpholine (0.021 mL, 0.188 mmol) in DMF (4 mL) was heated at 45° C. for 1 hr. The mixture was diluted with ethyl acetate (60 mL), washed sequentially with water (3×25 mL) and brine (25 mL), and dried over anhydrous MgSO$_4$. After the solvent was removed under vacuum, the residue was purified by reverse phase HPLC. The correct fraction was concentrated under vacuum, basified with saturated NaHCO$_3$ solution, and extracted with ethyl acetate (3×30 mL). The combined extract was washed with brine (30 mL) and dried over anhydrous MgSO$_4$. Removal of solvent under vacuum provided the desired product (13.3 mg, 0.025 mmol, 51.0% yield) as a yellow solid. LCMS (M+H)$^+$=525.09. $^1$H NMR (500 MHz, DMSO-d$_6$) δ: 11.72 (s, 1H), 8.37 (s, 1H), 8.25 (s, 1H), 7.82-7.79 (m, 2H), 7.72 (d, J=7.8 Hz, 1H), 7.65 (m, 1H), 7.63-7.58 (m, 2H), 7.50 (d, J=6.9 Hz, 1H), 7.41 (d, J=2.2 Hz, 1H), 7.20 (d, J=8.6 Hz, 1H), 6.76 (dd, J1=8.9 Hz, J2=2.2 Hz, 1H), 5.08 (d, J=17.2 Hz, 1H), 4.98 (d, J=17.2 Hz, 1H), 4.21 (m, 2H), 3.77 (m, 2H), 3.40 (s, 3H), 1.92 (s, 3H).

EXAMPLE 16

7-(2-Methoxyethoxy)-4-(2-methyl-3-(quinazolin-4-ylamino)phenyl)-9H-pyrido[3,4-b]indole-1-carboxamide

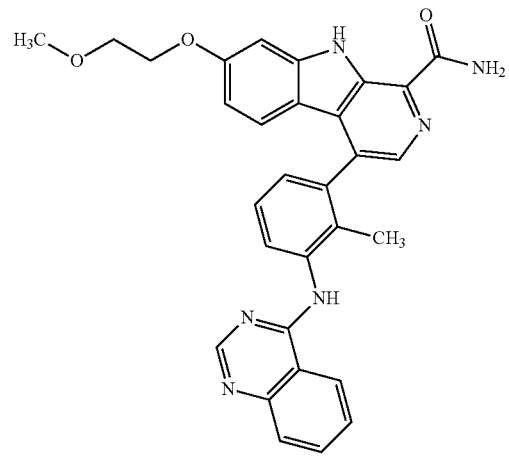 [SMILES: COCCOc1ccc2c(c1)[nH]c1c(C(N)=O)ncc(-c3cccc(Nc4ncnc5ccccc45)c3C)c12]

A mixture of 4-(3-amino-2-methylphenyl)-7-(2-methoxyethoxy)-9H-pyrido[3,4-b]indole-1-carboxamide (51 mg, 0.131 mmol), and 4-chloroquinazoline (47.3 mg, 0.287 mmol) in 2-Propanol (5 mL) was heated at 115° C. under microwave for 30 min. The mixture was diluted with ethyl acetate (80 mL), washed with saturated NaHCO$_3$ solution (20 mL) and brine (20 mL), and dried over anhydrous MgSO$_4$. The solvent was removed under vacuum, and the residue was purified by reverse phase HPLC. The correct fractions were concentrated under vacuum, basified with saturated NaHCO$_3$ solution, and extracted with ethyl acetate (3×30 mL). The combined extract was washed with brine (30 mL) and dried over anhydrous MgSO$_4$. Removal of solvent under vacuum provided the desired product (18.0 mg, 0.033 mmol, 25.5% yield) as a yellow solid. LCMS (M+H)$^+$=519.30. $^1$H NMR (500 MHz, DMSO-d$_6$) δ: 11.65 (s, 1H), 10.17 (s, 1H), 8.61 (s, 1H), 8.55 (d, J=8.0 Hz, 1H), 8.29 (s, 1H), 8.19 (s, 1H), 7.89 (m, 1H), 7.80 (d, J=8.3 Hz, 1H), 7.75 (s, 1H), 7.66 (m, 1H), 7.55-7.49 (m, 2H), 7.38-7.36 (m, 2H), 7.33 (d, J=8.9 Hz, 1H), 6.80 (dd, J1=8.7 Hz, J2=2.4 Hz, 1H), 4.17 (m, 2H), 3.73 (m, 2H), 3.34 (s, 3H), 1.87 (s, 3H).

EXAMPLE 17

4-(2-Methyl-3-(4-oxoquinazolin-3(4H)-yl)phenyl)-7-morpholino-9H-pyrido[3,4-b]indole-1-carboxamide

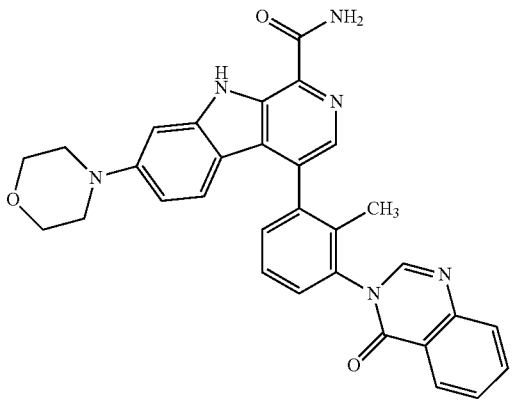 [SMILES: Cc1c(-c2cnc(C(N)=O)c3[nH]c4cc(N5CCOCC5)ccc4c23)cccc1-n1cnc2ccccc2c1=O]

1. Benzyl 2-methyl-3-(1-(6-morpholino-1H-indol-3-yl)-2-nitroethyl)phenylcarbamate

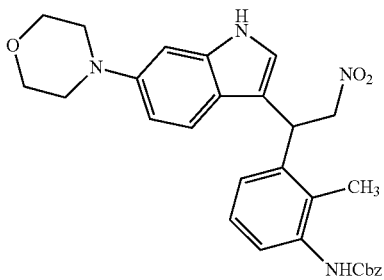

A solution of 4-(1H-indol-6-yl)morpholine (1.1132 g, 5.50 mmol) and (E)-benzyl 2-methyl-3-(2-nitrovinyl)phenylcarbamate (2.58 g, 8.26 mmol) in THF (50 mL) was concentrated in vacuo. The residue was melted at 137° C. and stirred overnight. After cooling to room temperature, the crude product was purified by flash chromatography using an ISCO 330 g column (solid loading) eluting with 40-80% EtOAc/hexanes to give the desired product (0.9544 g, 1.855 mmol, 33.7% yield) as a light brown solid.

2. Benzyl 3-(2-amino-1-(6-morpholino-1H-indol-3-yl)ethyl)-2-methylphenylcarbamate

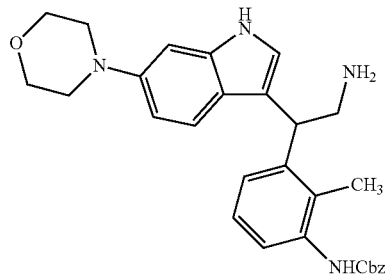 [SMILES: Cc1c(NC(=O)OCc2ccccc2)cccc1C(C[N+](=O)[O-])c1c[nH]c2cc(N3CCOCC3)ccc12]

A heterogeneous solution of benzyl 2-methyl-3-(1-(6-morpholino-1H-indol-3-yl)-2-nitroethyl)phenylcarbamate (1.8743 g, 3.64 mmol), ammonium chloride (2.92 g, 54.6 mmol) and zinc (3.57 g, 54.6 mmol) in THF (Ratio: 1.000, Volume: 79 ml) and methanol (Ratio: 1.000, Volume: 79 ml) was stirred under nitrogen for 2.5 hr. EtOAc (60 mL) was added, and the solution was filtered through a pad of CELITE®. The filtrate was concentrated in vacuo; the residue was dissolved in water (50 mL) and EtOAc (75 mL). After separation of the layers, the aqueous layer was extracted with EtOAc (2×75 mL). The organic layers were combined, dried over MgSO₄, and concentrated in vacuo to give the desired product (1.4934 g, 3.08 mmol, 85% yield) as a tan solid.

3. Ethyl 4-(3-(benzyloxycarbonylamino)-2-methylphenyl)-7-morpholino-9H-pyrido[3,4-b]indole-1-carboxylate

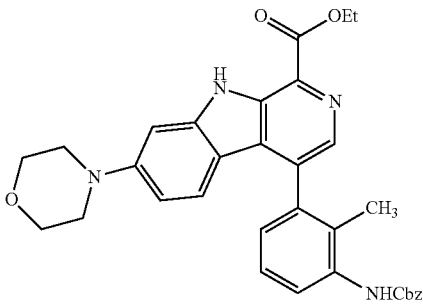 [SMILES: Cc1c(NC(=O)OCc2ccccc2)cccc1-c1cnc(C(=O)O)c2[nH]c3cc(N4CCOCC4)ccc3c12]

To a homogeneous solution of benzyl 3-(2-amino-1-(6-morpholino-1H-indol-3-yl)ethyl)-2-methylphenylcarbamate (1.4934 g, 3.08 mmol) in dioxane (154 ml) were added 50% ethyl 2-oxoacetate/toluene (1.222 ml, 6.16 mmol) and 4N HCl/dioxane (1.541 ml, 6.16 mmol) under nitrogen. The reaction was stirred overnight. More 50% ethyl 2-oxoacetate/toluene (1.222 ml, 6.16 mmol) was added, and the reaction was stirred overnight. The reaction was concentrated in vacuo, dissolved in EtOAc (100 mL) and washed with water (25 mL) and brine (25 mL) successively, dried over MgSO₄, and concentrated in vacuo to give a crude product, which was used in the subsequent step. To this crude were added 10% Pd/C (0.819 g, 0.770 mmol) and toluene (77 ml), and the mixture was refluxed overnight. The reaction was cooled to room temperature, diluted with EtOAc (200 mL), and filtered through a pad of CELITE®. The filtrate was washed with water (75 mL) and brine (75 mL), dried over MgSO$_4$, and concentrated in vacuo. The residue was purified by flash chromatography using an ISCO 120 g column eluting with 15-70% EtOAc/CH$_2$Cl$_2$ to give the desired product (0.354 g, 0.627 mmol, 20.4% yield) as a tan solid.

4. 4-(3-(Benzyloxycarbonylamino)-2-methylphenyl)-7-morpholino-9H-pyrido[3,4-b]indole-1-carboxylic acid

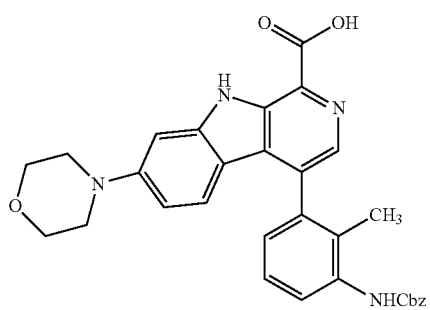

To a solution of ethyl 4-(3-(benzyloxycarbonylamino)-2-methylphenyl)-7-morpholino-9H-pyrido[3,4-b]indole-1-carboxylate (0.3539 g, 0.627 mmol) in THF (17.4 mL) and MeOH (5.8 mL) was added a solution of lithium hydroxide hydrate (0.105 g, 2.507 mmol) in water (3 mL). After 1 hr, the reaction was concentrated in vacuo. Water (12 mL) was added, and the solution was acidified with aqueous 1N HCl to pH 5-6 by litmus paper. The precipitate was filtered, washed with water, dried over Drierite to give the desired product (0.286 g, 0.533 mmol, 85% yield) as an orange solid.

5. Benzyl 3-(1-carbamoyl-7-morpholino-9H-pyrido[3,4-b]indol-4-yl)-2-methylphenylcarbamate

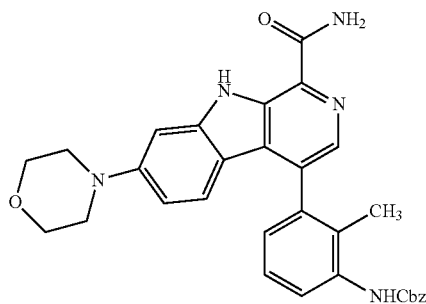 [SMILES: Cc1c(NC(=O)OCc2ccccc2)cccc1-c1cnc(C(N)=O)c2[nH]c3cc(N4CCOCC4)ccc3c12]

A homogeneous, burgundy solution of 4-(3-(benzyloxycarbonylamino)-2-methylphenyl)-7-morpholino-9H-pyrido[3,4-b] indole-1-carboxylic acid (0.2860 g, 0.533 mmol), ammonium chloride (0.114 g, 2.132 mmol), BOP (0.306 g, 0.693 mmol), DIPEA (0.447 ml, 2.56 mmol) and N-methylmorpholine (0.229 ml, 2.079 mmol) in DMF (Volume: 3.33 ml) was stirred. After 1 hr, water (35 mL) was added and the mixture was stirred at room temperature for 30 min. The precipitate was filtered, washed with water, dried over Drierite to give the desired product (0.274 g, 0.511 mmol, 96% yield) as a tan solid.

6. 4-(3-Amino-2-methylphenyl)-7-morpholino-9H-pyrido[3,4-b]indole-1-carboxamide

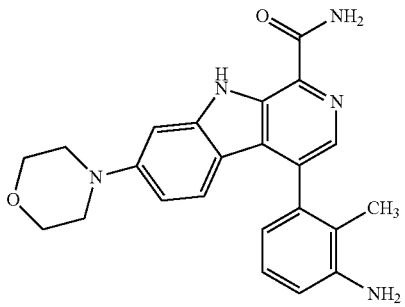 [SMILES: Cc1c(N)cccc1-c1cnc(C(N)=O)c2[nH]c3cc(N4CCOCC4)ccc3c12]

A solution of benzyl 3-(1-carbamoyl-7-morpholino-9H-pyrido[3,4-b]indol-4-yl)-2-methylphenylcarbamate (0.2735 g, 0.511 mmol) and 10% Pd/C (0.109 g, 0.102 mmol) in THF (12.8 mL) and MeOH (19.2 mL) was hydrogenated. After 1.5 hr, the reaction was flushed with nitrogen and filtered through a wad of CELITE®. The filtrate was concentrated in vacuo, dissolved in CH$_2$Cl$_2$, dried over MgSO$_4$, and concentrated in vacuo to give the desired product (0.196 g, 0.450 mmol, 88% yield) as a tan solid.

7. 4-(2-Methyl-3-(4-oxoquinazolin-3(4H)-yl)phenyl)-7-morpholino-9H-pyrido[3,4-b]indole-1-carboxamide A burgundy solution of 4-(3-amino-2-methylphenyl)-7-morpholino-9H-pyrido[3,4-b]indole-1-carboxamide (0.0612 g, 0.140 mmol), 1H-benzo[d][1,3]oxazine-2,4-dione (0.057 g, 0.351 mmol), trimethoxymethane (0.154 ml, 1.402 mmol) and lanthanum nitrate hexahydrate (0.018 g, 0.042 mmol) in THF (0.334 mL) in a sealed vial was stirred overnight at 95° C. The reaction was cooled to room temperature and concentrated in vacuo. The residue was dissolved in DMSO (0.2 mL) and MeOH (1.6 mL), and subjected to autoprep reverse phase HPLC. The appropriate fractions were collected, basified with NaHCO$_3$ (solid), and concentrated in vacuo. The residue was extracted with CH$_2$Cl$_2$ (3×). The combine extract was dried over Na$_2$SO$_4$ and concentrated in vacuo to give the desired product (0.0135 g, 0.024 mmol, 17.1% yield) as a tan solid. LC/MS (M+H)=531.29; $^1$H NMR (500 MHz, DMSO-d$_6$) (recognizable peaks for major atropoisomer) δ ppm 11.48 (1 H, s), 8.42 (1 H, s), 8.21-8.28 (2 H, m), 8.15 (1 H, s), 7.88-7.94 (1 H, m), 7.76-7.81 (1 H, m), 7.69-7.74 (1 H, m), 7.53-7.69 (4 H, m), 7.27 (1 H, d, J=2.22 Hz), 6.79-6.86 (1 H, m), 3.74-3.81 (4 H, m), 3.16-3.23 (4 H, m), 1.81 (3 H, s).

EXAMPLE 18

4-(3-(5-Fluoroisoindoline-2-carboxamido)-2-methylphenyl)-7-(tetrahydrofuran-3-yloxy)-9H-pyrido[3,4-b]indole-1-carboxamide

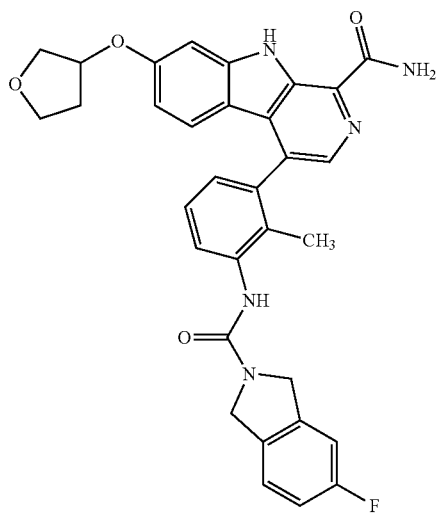 [SMILES: Cc1c(NC(=O)N2Cc3ccc(F)cc3C2)cccc1-c1cnc(C(N)=O)c2[nH]c3cc(OC4CCOC4)ccc3c12]

1. 6-(Tetrahydrofuran-3-yloxy)-1H-indole

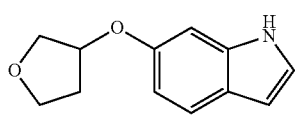 [SMILES: c1cc2ccc(OC3CCOC3)cc2[nH]1]

To a mixture of 1H-indol-6-ol (2.00 g, 15.02 mmol), tetrahydrofuran-3-ol (1.46 mL, 18.0 mmol), and triphenylphosphine (4.33 g, 16.52 mmol) in dichloromethane (80 mL) at 0° C. was added diisopropyl diazene-1,2-dicarboxylate (3.49 mL, 18.03 mmol) over 10 min. The mixture was stirred at room temperature for 16 hr. The starting indole and desired product were detected in a ratio of 3:2. The dark mixture was diluted with CH$_2$Cl$_2$ (80 mL), washed with 1N NaOH (50 mL), water (50 mL), and brine (50 mL). The organic solution was dried over anhydrous MgSO$_4$. The desired product (0.642 g, 3.16 mmol, 21.03% yield) was isolated as viscous oil by ISCO (300 g silica gel, solid loading, 10-50% ethyl acetate/hexane).

2. Benzyl 2-methyl-3-(2-nitro-1-(6-(tetrahydrofuran-3-yloxy)-1H-indol-3-yl)ethyl)phenylcarbamate

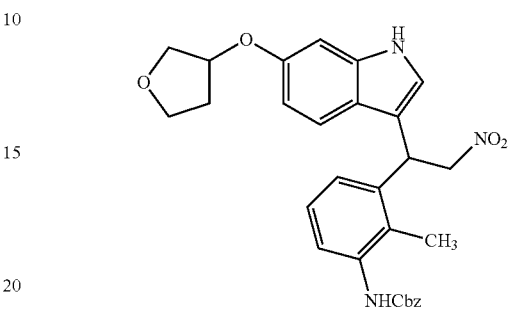

6-(Tetrahydrofuran-3-yloxy)-1H-indole (0.632 g, 3.11 mmol) and (E)-benzyl 2-methyl-3-(2-nitrovinyl)phenylcarbamate (0.800 g, 2.56 mmol) were dissolved in THF (50 mL). The solution was then concentrated under vacuum to dryness. The solid mixture was melted at 130° C. and heated at this temperature for 6 hr. The mixture was subjected to ISCO (120 g silica gel, solid loading, 25-65% ethyl acetate/hexane) to afford the desired product (0.612 g, 1.187 mmol, 46.3% yield) as a beige solid.

3. Benzyl 3-(2-amino-1-(6-(tetrahydrofuran-3-yloxy)-1H-indol-3-yl)ethyl)-2-methylphenylcarbamate

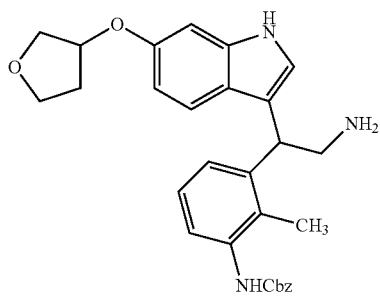 [SMILES: Cc1c(NC(=O)OCc2ccccc2)cccc1C(C[N+](=O)[O-])c1c[nH]c2cc(OC3CCOC3)ccc12]

A mixture of benzyl 2-methyl-3-(2-nitro-1-(6-(tetrahydrofuran-3-yloxy)-1H-indol-3-yl)ethyl)phenylcarbamate (0.720 g, 1.397 mmol), ammonium chloride (1.121 g, 20.95 mmol), and zinc dust (1.370 g, 20.95 mmol) in tetrahydrofuran (35 mL) and methanol (35 mL) was stirred at room temperature for 4.5 hr. The mixture was diluted with ethyl acetate (40 mL) and filtered through CELITE®. The filtrate was concentrated under vacuum, and the residue was diluted with water (40 mL), basified with saturated NaHCO$_3$ solution, and extracted with ethyl acetate (4×40 mL). The combined extract was washed with brine (40 mL) and dried over anhydrous MgSO$_4$.

4. Ethyl 4-(3-(benzyloxycarbonylamino)-2-methylphenyl)-7-(tetrahydrofuran-3-yloxy)-9H-pyrido[3,4-b]indole-1-carboxylate

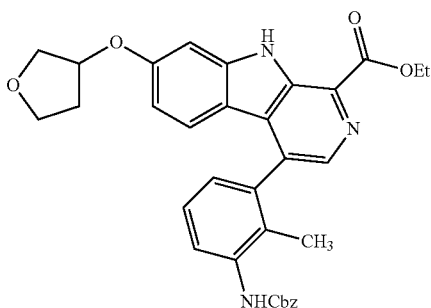 [SMILES: CCOC(=O)c1ncc(-c2cccc(NC(=O)OCc3ccccc3)c2C)c2c1[nH]c1cc(OC3CCOC3)ccc12]

To a solution of benzyl 3-(2-amino-1-(6-(tetrahydrofuran-3-yloxy)-1H-indol-3-yl)ethyl)-2-methylphenylcarbamate (0.678 g, 1.396 mmol) and ethyl 2-oxoacetate in toluene (50%) (0.554 mL, 2.79 mmol) at room temperature was added hydrogen chloride in 1,4-dioxane (4.0 M) (0.419 mL, 1.676 mmol). The mixture was stirred room temperature for 16 hr. The volatiles were removed under vacuum. The residue was diluted with water (50 mL), basified with NaHCO₃ solution to pH 10, and extracted with ethyl acetate (4×50 mL). The combined extract was washed with brine (40 ml), dried over anhydrous MgSO₄, and concentrated to dryness under vacuum. To the residue were added p-xylene (60 mL) and 10% Pd/C (0.46 g), and the mixture was heated at 125° C. under an ambient atmosphere for 4.5 hr. The solid phase was removed by suction filtration. The filtrate was diluted with ethyl acetate (120 ml), washed with brine (40 ml), and dried over anhydrous MgSO₄. The desired product (0.240 g, 0.424 mmol, 30.4% yield) was isolated by ISCO (40 g silica gel, solid loading, 15-35% ethyl acetate/CH₂Cl₂).

5. 4-(3-(Benzyloxycarbonylamino)-2-methylphenyl)-7-(tetrahydrofuran-3-yloxy)-9H-pyrido[3,4-b]indole-1-carboxylic acid

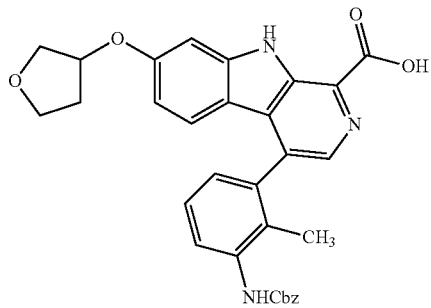 [SMILES: Cc1c(NC(=O)OCc2ccccc2)cccc1-c1cnc(C(=O)O)c2[nH]c3cc(OC4CCOC4)ccc3c12]

To a solution of ethyl 4-(3-(benzyloxycarbonylamino)-2-methylphenyl)-7-(tetrahydrofuran-3-yloxy)-9H-pyrido[3,4-b]indole-1-carboxylate (0.240 g, 0.424 mmol) in tetrahydrofuran (12 mL) and methanol (4 mL) at room temperature was added a solution of lithium hydroxide hydrate (0.071 g, 1.696 mmol) in water (2 mL). The resulting mixture was stirred at room temperature for 1.5 hr, and then concentrated under vacuum to almost dryness. To the residue was added water (8 mL), and the mixture was neutralized with 1N HCl to pH 4-5. The insoluble product (0.195 g, 0.363 mmol, 86% yield) was collected as a beige solid by suction filtration and dried over Drierite under vacuum.

6. Benzyl 3-(1-carbamoyl-7-(tetrahydrofuran-3-yloxy)-9H-pyrido[3,4-b]indol-4-yl)-2-methylphenylcarbamate

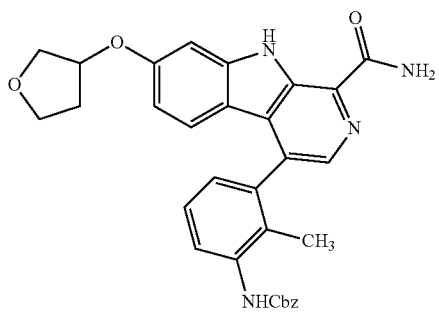 [SMILES: Cc1c(NC(=O)OCc2ccccc2)cccc1-c1cnc(C(N)=O)c2[nH]c3cc(OC4CCOC4)ccc3c12]

A mixture of 4-(3-(benzyloxycarbonylamino)-2-methylphenyl)-7-(tetrahydrofuran-3-yloxy)-9H-pyrido[3,4-b]indole-1-carboxylic acid (0.195 g, 0.363 mmol), ammonium chloride (0.078 g, 1.451 mmol), N,N-diisopropylethylamine (0.304 mL, 1.741 mmol), BOP (0.209 g, 0.472 mmol), and N-methylmorpholine (0.156 mL, 1.415 mmol) in N,N-dimethylformamide (3 mL) was stirred at room temperature for 1.5 hr. To the reaction mixture was added water (30 mL), and the resulting mixture was stirred at room temperature for 30 min. The insoluble product (0.189 g, 0.352 mmol, 97% yield) was collected as a beige solid by suction filtration and dried over Drierite under vacuum.

7. 4-(3-Amino-2-methylphenyl)-7-(tetrahydrofuran-3-yloxy)-9H-pyrido[3,4b]indole-1-carboxamide

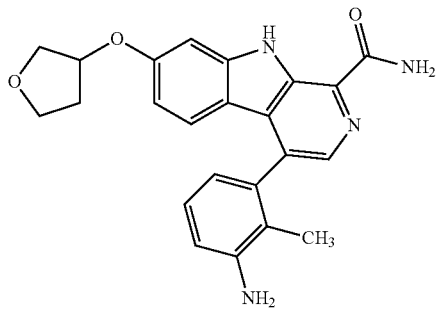 [SMILES: Cc1c(N)cccc1-c1cnc(C(N)=O)c2[nH]c3cc(OC4CCOC4)ccc3c12]

A mixture of benzyl 3-(1-carbamoyl-7-(tetrahydrofuran-3-yloxy)-9H-pyrido[3,4-b]indol-4-yl)-2-methylphenylcarbamate (189 mg, 0.352 mmol) and Pd/C (50 mg, 0.047 mmol) in tetrahydrofuran (10 mL) and methanol (15 mL) was stirred at room temperature under H₂, provided with H₂ balloon, for 1.5 hr. The catalyst was removed by suction filtration, and the filtrate was concentrated under vacuum to dryness to afford the desired product (164 mg, 0.350 mmol, 99% yield) as a beige solid.

8. 4-(3-(5-Fluoroisoindoline-2-carboxamido)-2-methylphenyl)-7-(tetrahydrofuran-3-yloxy)-9H-pyrido[3,4-b]indole-1-carboxamide To a heterogeneous mixture of 4-(3-amino-2-methylphenyl)-7-(tetrahydrofuran-3-yloxy)-9H-pyrido[3,4-b]indole-1-carboxamide (38 mg, 0.081 mmol) and 4-nitrophenyl carbonochloridate (19.64 mg, 0.097 mmol) in dichloromethane (2 mL) at room temperature was added pyridine (0.013 mL, 0.162 mmol). The resulting homogeneous mixture was stirred at room temperature for 1 hr before 5-fluoroisoindoline hydrocloride (35.2 mg, 0.203 mmol) and N,N-diisopropylethylamine (0.053 mL, 0.305 mmol) was added. The mixture was heated at 50° C. for 1 hr. It was concentrated under vacuum, diluted with MeOH (1.8 mL), and was purified by reverse phase HPLC. The correct fraction was concentrated under vacuum, basified with saturated NaHCO$_3$ solution, and extracted with CH$_2$Cl$_2$ (3×30 mL). The combined extract was washed with brine (30 mL) and dried over anhydrous MgSO$_4$. Removal of solvent under vacuum provided the desired product (26.4 mg, 0.045 mmol, 54.9% yield) as a yellow solid. LCMS (M+H)$^+$=566.34. $^1$H NMR (500 MHz, DMSO-d$_6$) δ: 11.67 (s, 1H), 8.36 (m, 1H), 8.18 (s, 1H), 8.12 (s, 1H), 7.79 (s, 1H), 7.64 (d, J=6.9 Hz, 1H), 7.46-7.39 (m, 3H), 7.29 (dd, J1=9.0 Hz, J2=2.4 Hz, 1H), 7.23-7.17 (m, 2H), 7.08 (d, J=8.6 Hz, 1H), 6.70 (dd, J1=8.7 Hz, J2=2.4 Hz, 1H), 5.10 (m, 1H), 4.85 (s, 2H), 4.82 (s, 2H), 3.99 (dd, J1=10.5 Hz, J2=4.2 Hz, 1H), 3.92-3.83 (m, 2H), 3.84 (m, 1H), 2.32 (m, 1H), 2.09 (m, 1H), 2.01 (s, 3H).

EXAMPLE 19

7-(Cyanomethyl)-4-(3-(6-methoxy-1-oxoisoindolin-2-yl)-2-methylphenyl)-9H-pyrido[3,4-b]indole-1-carboxamide

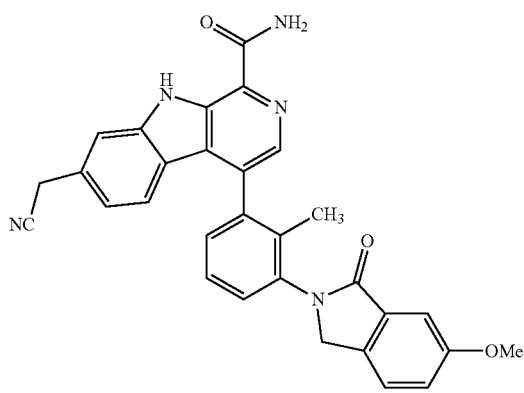 [SMILES: COc1ccc2c(c1)C(=O)N(c1cccc(-c3cnc(C(N)=O)c4[nH]c5cc(CC#N)ccc5c34)c1C)C2]

1. Benzyl 3-(1-(6-cyanomethyl)-1H-indol-3-yl)-2-nitroethyl)-2-methylphenylcarbamate

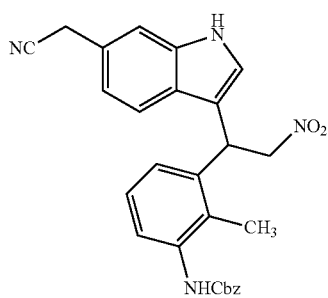 [SMILES: Cc1c(NC(=O)OCc2ccccc2)cccc1C(C[N+](=O)[O-])c1c[nH]c2cc(CC#N)ccc12]

A mixture of (E)-benzyl-2-methyl-3-(2-nitrovinyl)phenylcarbamate (1.0 g, 3.2 mmol) and 2-(1H-indol-6-yl)acetonitrile (0.55 g, 3.52 mmol) in water (50 mL) was heated at 105° C. for 24 hr. The reaction mixture was cooled to RT, diluted with water (50 mL) and extracted with EtOAc (2×200 mL). The combined extracts were washed with water, brine, dried over Na$_2$SO$_4$ and concentrated. The residue was purified by silica gel column chromatography, eluting with 35% EtOAc in hexane to give the desired product (0.70 g, 1.49 mmol, 46.7%) as pale yellow sticky solid.

2. Benzyl 3-(2-amino-6-(cyanomethyl)-1H-indol-3-yl)ethyl)-2-methylphenylcarbamate

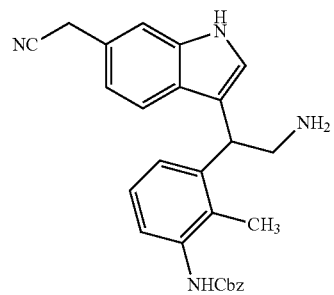

To a solution of benzyl 3-(1-(6-(cyanomethyl)-1H-indol-3-yl)-2-nitroethyl-2-methylphenylcarbamate (1.4 g, 2.99 mmol) in MeOH (60 mL) and THF (60 mL) was added zinc powder (2.93 g, 45 mmol) and ammonium chloride (2.4 g, 45 mmol) and the mixture was stirred at RT for 5 h. Then the reaction mixture was diluted with EtOAc (25 mL), filtered over CELITE® and the filtrate was concentrated under vacuum to give the desired product (1.30 g, 2.96 mmol, 99% yield) as pale brown sticky solid.

3. Ethyl 4-(3-(benzyloxycarbonylamino)-2-methylphenyl)-7-cyanomethyl)-9H-pyrido[3,4-b]indole-1-carboxylate

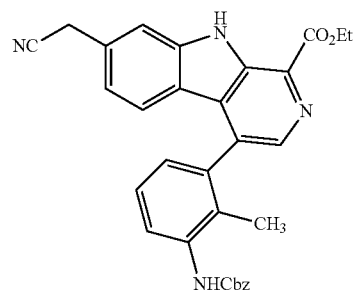 [SMILES: CCOC(=O)c1ncc(-c2cccc(NC(=O)OCc3ccccc3)c2C)c2c1[nH]c1cc(CC#N)ccc12]

To a solution of benzyl 3-(2-amino-1-(6-cyanomethyl)-1H-indol-3-yl)ethyl)-2-methyl phenylcarbamate (1.30 g, 2.96 mmol) and ethyl glyoxylate (1.83 mL, 8.88 mmol) in toluene (80 mL) and THF (30 mL) was added HCl in dioxane (4M solution, 1.48 mL, 5.92 mmol). The reaction mixture was stirred at RT for 48 hr. The solvents were removed under vacuum. The residue was diluted with water (50 mL), basified with 10% NaHCO$_3$ solution and extracted with EtOAc (2×200 mL). The combined extract was washed with water, brine, dried over Na$_2$SO$_4$ and concentrated to give a crude cyclic intermediate. To the intermediate was added xylene (120 mL) and 10% Pd/C (1 g), and the mixture was heated at 125° C. for 10 h under inert atmosphere. Reaction mixture was cooled to room temperature, diluted with EtOAc and filtered over CELITE®. Filtrate was concentrated under reduced pressure to get crude product which was purified by silica gel column chromatography. Elution of the column with 40% EtOAc in hexane gave the desired product (300 mg, 0.58 mmol, 19.6%) as yellow solid.

4. Benzyl 3-(1-aminoxycarbonyl)-7-cyanomethyl)-9H-pyrido[3,4-b]indole-4-yl)-2-methylphenylcarbamate

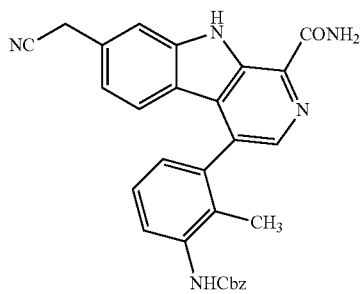 [SMILES: Cc1c(NC(=O)OCc2ccccc2)cccc1-c1cnc(C(N)=O)c2[nH]c3cc(CC#N)ccc3c12]

Ethyl 4-(3-(benzyloxycarbonylamino)-2-methylphenyl)-7-cyanomethyl)-9H-pyrido[3,4-b]indole-1-carboxylate (300 mg, 0.58 mmol) was taken in mathanolic ammonia (25 mL, ≈15% solution) in pressure tube and heated at 100° C. for 2 h. Solvent was evaporated under vacuum and the residue was purified by silica gel column chromatography. Elution of the column with 30% EtOAc in hexane gave the desired product (170 mg, 0.35 mmol, 60%) as a yellow solid.

5. 3-(1-Aminoxycarbonyl)-7-cyanomethyl)-9H-pyrido[3,4-b]indole-4-yl)-2-methylaniline

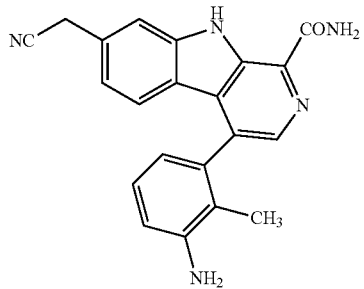 [SMILES: Cc1c(N)cccc1-c1cnc(C(N)=O)c2[nH]c3cc(CC#N)ccc3c12]

A mixture of benzyl 3-(1-aminoxycarbonyl)-7-cyanomethyl)-9H-pyrido[3,4-b]indole-4-yl)-2-methylphenylcarbamate (170 mg, 0.35 mmol) and Pd/C (50 mg) in THF (10 mL) and MeOH (15 mL) was stirred at room temperature under hydrogen atmosphere for 1.5 hr. After that the reaction mixture was filtered over CELITE® pad and the filtrate was concentrated to give the desired product (120 mg, 0.33 mmol, 97% yield) as pale yellow sticky solid.

6. 2-(3-(1-Carbamoyl-7-(cyanomethyl)-9H-pyrido-[3,4-b]indole-1-4-yl)-2-methylphenylamino)methyl)-5-methoxybenzoic acid

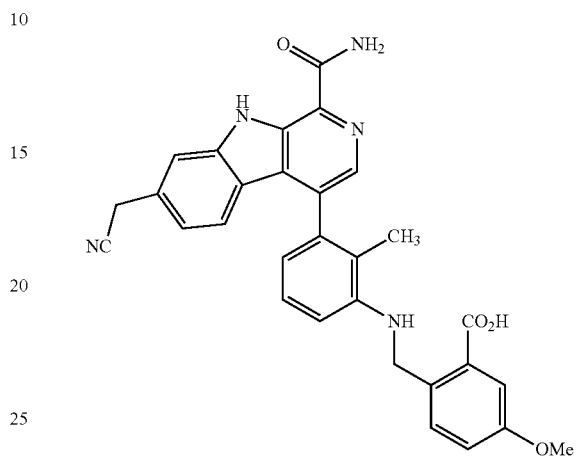

To a mixture of 3-(1-aminoxycarbonyl)-7-cyanomethyl)-9H-pyrido[3,4-b]indole-4-yl-2-methylaniline (20 mg, 0.056 mmol), 2-formyl-5-methoxybenzoic aid (25.3 mg, 0.14 mmol) in 1,2 dichloroethane (1.6 mL) and THF (1 mL) were added sodium triacetoxyborohydride (35.6 mg, 0.168 mmol) and acetic acid (0.0085 mL, 0.14 mmol) and stirred at room temperature for 24 h. Then the reaction mixture was diluted with water (10 mL) and extracted with EtOAc (2×20 mL). Organic extracts were washed with water, brine, dried over $Na_2SO_4$ and concentrated to give crude product, which was purified by silica gel column chromatography. Elution of the column with 10% MeOH in chloroform gave desired product (25 mg, 50% pure product by LC-MS), which was used in the next step without further purification.

7. 7-(Cyanomethyl)-4-(3-(6-methoxy-1-oxoisoindolin-2-yl)-2-methylphenyl)-9H-pyrido[3,4-b]indole-1-carboxamide To a solution of 2-(3-(1-carbamoyl-7-(cyanomethyl)-9H-pyrido-[3,4-b]indole-1-4-yl)-2-methylphenylamino)methyl)-5-methoxybenzoic acid (25 mg, 0.048 mmol) in DMF (1.5 mL) were added BOP reagent (42.6 mg, 0.096 mmol) and N-methylmorpholine (0.021 mL, 0.192 mmol) and stirred at 45° C. for 1 hr. Then the reaction mixture was cooled to room temperature, diluted with water (15 mL) and extracted with EtOAc (2×25 mL). Combined organic extracts were washed with water, brine, dried over $Na_2SO_4$ and concentrated. The crude product obtained was purified by column chromatography, eluting with 4% MeOH in $CHCl_3$ followed by recrystallization with hexane/EtOAc to give 7-(cyanomethyl)-4-(3-(6-methoxy-1-oxoisoindolin-2-yl)-2-methylphenyl)-9H-pyrido[3,4-b]indole-1-carboxamide (3.5 mg, 0.007 mmol, 15% yield) as a pale yellow solid. LCMS (M+H)=502.2. $^1$H NMR (400 MHz, $CDCl_3$) δ: 10.44 (bs, 1H), 8.33 (s, 1H), 8.00

(bs, 1H), 7.56 (s, 1H), 7.52-7.40 (m, 6H), 7.20-7.13 (m, 2H), 5.67 (bs, 1H), 4.86-4.72 9 (m, 2H), 3.92 (s, 2H), 3.89 (s, 3H), 1.97 (s, 3H).

EXAMPLE 20

4-(3-(6-Chloro-1-oxoisoindolin-2-yl)-2-methylphenyl)-7-(cyanomethyl)-9H-pyrido[3,4-b]indole-1-carboxamide

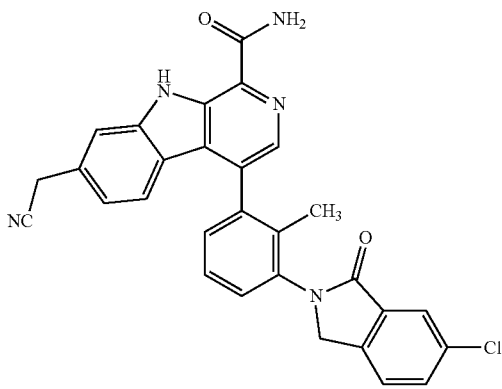 [SMILES: Cc1c(-c2cnc(C(N)=O)c3[nH]c4cc(CC#N)ccc4c23)cccc1N1Cc2ccc(Cl)cc2C1=O]

1. 2-(3-(1-Carbamoyl-7-(cyanomethyl)-9H-pyrido-[3,4-b]indole-1-4-yl)-2-methylphenylamino)methyl)-5-chlorobenzoic acid

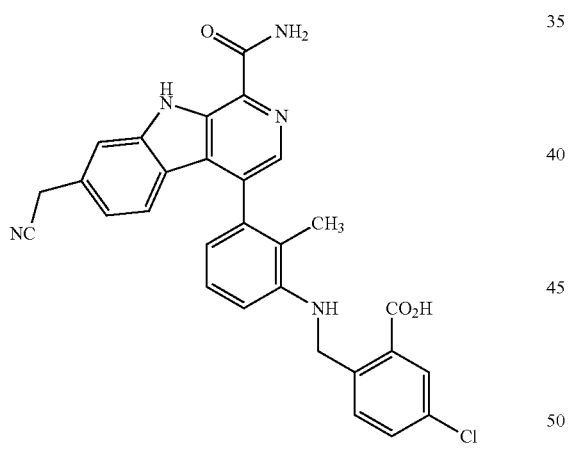

A mixture of 3-(1-aminoxycarbonyl)-7-cyanomethyl)-9H-pyrido[3,4-b]indole-4-yl-2-methylaniline 7 (40 mg, 0.112 mmol), 5-chloro-2-formylbenzoic acid (51.6 mg, 0.28 mmol) and 4 angstrom molecular sieves (0.5 g) in methanol (15 mL) was stirred at RT for 24 h. After that the mixture was cooled to −20° C. and sodium borohydride (29.6 mg, 0.78 mmol) was added and the reaction mixture was allowed to warm up to 10° C. The solvent was removed under reduced pressure, quenched with saturated NH$_4$Cl solution (5 ml) and extracted with EtOAc (2×10 ml). Combined organic extracts were washed with water, brine, dried over Na$_2$SO$_4$ and concentrated. The crude product obtained was purified by silica gel column chromatography eluting with 5% MeOH in CHCl$_3$ to give the desired product (10 mg, 0.019 mmol, 17% yield) as a yellow sticky solid.

2. 4-(3-(6-chloro-1-oxoisoindolin-2-yl)-2-methylphenyl)-7-(cyanomethyl)-9H-pyrido[3,4-b]indole-1-carboxamide To a solution of 2-(3-(1-carbamoyl-7-(cyanomethyl)-9H-pyrido-[3,4-b]indole-1-4-yl)-2-methylphenylamino)methyl)-5-chlorobenzoic acid (10 mg, 0.019 mmol) in DMF (0.6 mL) were added BOP reagent (16.9 mg, 0.038 mmol) and N-methylmorpholine (0.0084 mL, 0.076 mmol) and the mixture was stirred at 45° C. for 1 hr. Then the reaction mixture was cooled to RT, diluted with water (10 mL) and extracted with EtOAc (2×10 mL). Combined organic extracts were washed with water, brine, dried over Na$_2$SO$_4$ and concentrated. The crude product obtained was purified by silica gel column chromatography. Elution of the column with 3% MeOH in chloroform gave desired 4-(3-(6-chloro-1-oxoisoindolin-2-yl)-2-methylphenyl)-7-(cyanomethyl)-9H-pyrido[3,4-b]indole-1-carboxamide (4.5 mg, 0.0089 mmol, 46% yield) as a pale yellow solid. $^1$H NMR (400 MHz, DMSO-d$_6$) δ: 11.93 (bs, 1H), 8.32 (s, 1H), 8.24 (s, 1H), 7.83-7.66 (m, 5H), 7.55-7.51 (t, J=8.0 Hz, 1H), 7.44-7.42 (d, 1H), 7.28-7.26 (d, J=8.0 HZ, 1H), 7.03-7.01 (d, J=8.0 Hz, 1H), 5.07-4.90 (m, 2H), 4.19 (s, 3H), 1.84 (s, 3H); LCMS (M−H)=504.0.

EXAMPLE 21

4-(3-(6-Chloro-1-oxoisoindolin-2-yl)-2-methylphenyl)-7-hydroxy-9H-pyrido[3,4-b]indole-1-carboxamide

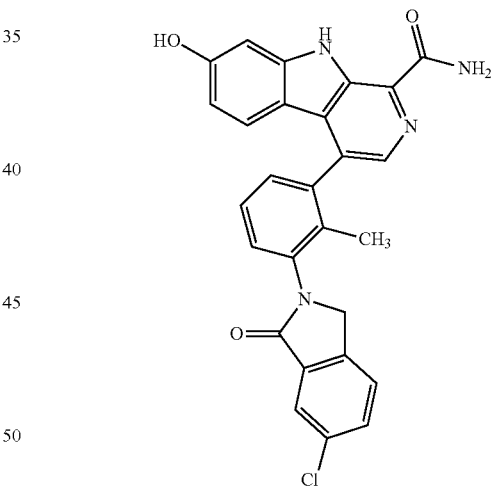

To a heterogeneous mixture of 4-(3-(6-chloro-1-oxoisoindolin-2-yl)-2-methylphenyl)-7-methoxy-9H-pyrido[3,4-b]indole-1-carboxamide (prepared in the same manner as Example 15) (0.277 g, 0.557 mmol) in dichloromethane (20 mL) at 0° C. was added tribromoborane in dichloromethane (2.79 mL, 2.79 mmol) over 5 min. The heterogeneous mixture was stirred at room temperature for 3 hr and then poured into ice cold water (20 mL). The resulting mixture was basified with saturated NaHCO$_3$ solution to pH 8 and extracted with ethyl acetate (3×40 mL). The combined extract was washed with brine (30 mL) and dried over anhydrous MgSO$_4$. Removal of solvent under vacuum provided the desired product (0.217 g, 85% purity, 0.382 mmol, 68.5% yield) as a yellow solid. A pure sample was obtained through prep.

reverse phase HPLC purification. LCMS (M+H)+=483.15. ¹H NMR (500 MHz, DMSO-d₆) δ: 11.61 (s, 1H), 9.89 (s, 1H), 8.34 (s, 1H), 8.20 (s, 1H), 7.88 (s, 1H), 7.81-7.77 (m, 3H), 7.72 (dd, J1=7.8 Hz, J2=1.2 Hz, 1H), 7.58 (m, 1H), 7.48 (dd, J1=7.5 Hz, J2=1.2 Hz, 1H), 7.23 (d, J=2.0 Hz, 1H), 7.12 (d, J=8.6 Hz, 1H), 6.60 (dd, J1=8.7 Hz, J2=2.3 Hz, 1H), 5.10 (d, J=17.6 Hz, 1H), 4.99 (d, J=17.6 Hz, 1H), 1.92 (s, 3H).

EXAMPLE 22

4-(3-(6-Chloro-1-oxoisoindolin-2-yl)-2-methylphenyl)-7-(3-hydroxypropoxy)-9H-pyrido[3,4-b]indole-1-carboxamide

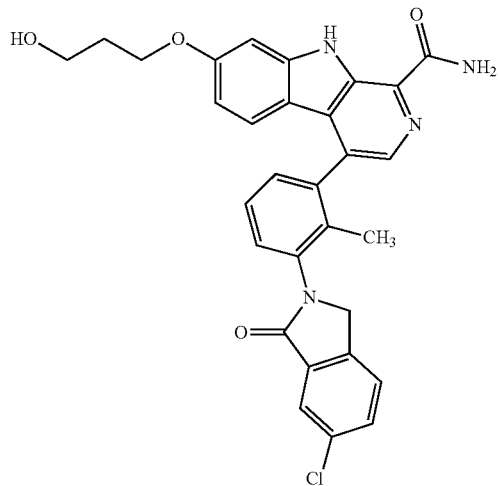 [SMILES: Cc1c(-c2cnc(C(N)=O)c3[nH]c4cc(OCCCO)ccc4c23)cccc1N1Cc2ccc(Cl)cc2C1=O]

A mixture of 4-(3-(6-chloro-1-oxoisoindolin-2-yl)-2-methylphenyl)-7-hydroxy-9H-pyrido[3,4-b]indole-1-carboxamide (32 mg, 0.066 mmol) and cesium carbonate (25.9 mg, 0.080 mmol) in DMF (3 mL) was heated at 75° C. for 4 hr. The mixture was diluted with ethyl acetate (60 mL), washed with water (2×20 mL) and brine (20 mL), and dried over anhydrous MgSO₄. The organic solution was concentrated under vacuum and the residue was purified by reverse phase HPLC. The correct fraction was concentrated under vacuum, basified with saturated NaHCO₃ solution, and extracted with ethyl acetate (3×30 mL). The combined extract was washed with brine (30 mL) and dried over anhydrous MgSO₄. Removal of solvent under vacuum provided the desired product (6.2 mg, 0.011 mmol, 16.6% yield) as a yellow solid. LCMS (M+H)+= 541.28. ¹H NMR (500 MHz, DMSO-d₆) δ: 11.70 (s, 1H), 8.35 (s, 1H), 8.24 (s, 1H), 7.87 (s, 1H), 7.80-7.78 (m, 3H), 7.72 (m, 1H), 7.59 (m, 1H), 7.50 (m, 1H), 7.41 (d, J=2.2 Hz, 1H), 7.19 (d, J=8.9 Hz, 1H), 6.74 (dd, J1=8.9 Hz, J2=2.4 Hz, 1H), 5.09 (d, J=17.5 Hz, 1H), 5.00 (d, J=17.5 Hz, 1H), 4.17 (m, 2H), 3.65 (m, 2H), 1.97 (m, 2H), 1.92 (s, 3H).

EXAMPLE 23

4-(3-(6-Chloro-1-oxoisoindolin-2-yl)-2-methylphenyl)-7-(2-morpholinoethoxy)-9H-pyrido[3,4-b]indole-1-carboxamide

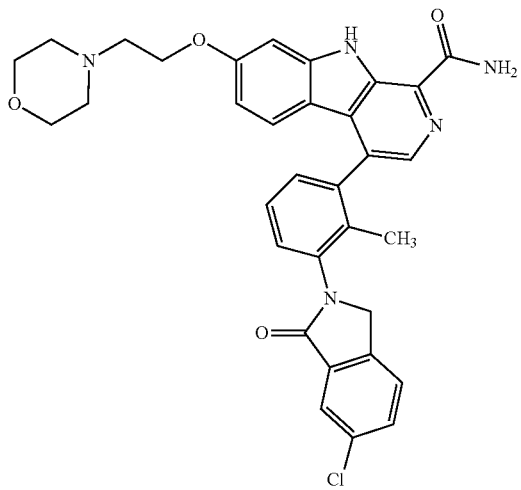 [SMILES: Cc1c(-c2cnc(C(N)=O)c3[nH]c4cc(OCCN5CCOCC5)ccc4c23)cccc1N1Cc2ccc(Cl)cc2C1=O]

A mixture of 4-(3-(6-chloro-1-oxoisoindolin-2-yl)-2-methylphenyl)-7-hydroxy-9H-pyrido[3,4-b]indole-1-carboxamide (50 mg, 0.104 mmol), 4-(2-chloroethyl)morpholine, HCl (67.4 mg, 0.362 mmol), and cesium carbonate (202 mg, 0.621 mmol) in DMF (6 mL) was heated at 100° C. for 3 hr. The mixture was diluted with ethyl acetate (100 mL) and filtered through CELITE®. The filtrate was washed with water (2×30 mL) and brine (30 mL), and dried over anhydrous MgSO₄. After the solvent was removed under vacuum, the residue was purified by reverse phase HPLC. The correct fractions were concentrated under vacuum, basified with saturated NaHCO₃ solution, and extracted with ethyl acetate (3×30 mL). The combined extract was washed with brine (30 mL) and dried over anhydrous MgSO₄. Removal of solvent under vacuum provided the purified product (7.1 mg, 0.011 mmol, 10.9% yield) as a pale yellow sold. LCMS (M+H)+= 596.29. ¹H NMR (500 z, DMSO-d₆) δ: 11.72 (s, 1H), 8.36 (s, 1H), 8.25 (s, 1H), 7.86 (s, 1H), 7.82-7.78 (m, 3H), 7.72 (d, J=6.9 Hz, 1H), 7.59 (m, 1H), 7.50 (m, 1H), 7.43 (s, 1H), 7.22 (br. S, 1H), 6.79 (br. S, 1H), 5.10 (d, J=17.6 Hz, 1H), 5.00 (d, J=17.6 Hz, 1H), 4.23 (m, 2H), 3.81-3.53 (m, 8H), 2.81 (m, 2H), 1.92 (s, 3H).

EXAMPLE 24

4-(3-(6-Chloro-1-oxoisoindolin-2-yl)-2-methylphenyl)-7-(3-hydroxypyrrolidin-1-yl)-9H-pyrido[3,4-b]indole-1-carboxamide

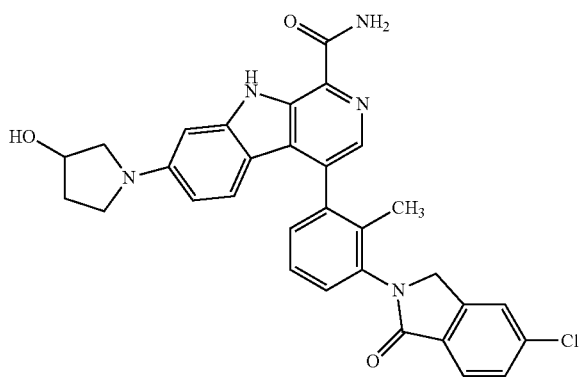 [SMILES: Cc1c(-c2cnc(C(N)=O)c3[nH]c4cc(N5CCC(O)C5)ccc4c23)cccc1N1Cc2cc(Cl)ccc2C1=O]

1. 1-(1H-Indol-6-yl)pyrrolidin-3-ol

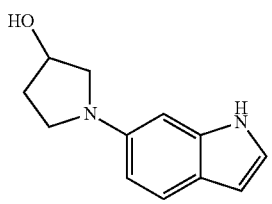 [SMILES: OC1CCN(c2ccc3cc[nH]c3c2)C1]

To a pressure tube containing a light orange, homogeneous solution of 6-bromo-1H-indole (1.01 g, 5.15 mmol) in DMSO (8.58 mL) purged with nitrogen were added pyrrolidin-3-ol (4.49 g, 51.5 mmol), cesium carbonate (3.36 g, 10.30 mmol), copper(I) iodide (0.098 g, 0.515 mmol) and (S)-pyrrolidine-2-carboxylic acid (0.652 g, 5.67 mmol). The pressure tube was sealed and stirred at 95° C. for 5.5 hr. The reaction was cooled to room temperature and immersed in an ice-water bath. Ice water (20 mL) was added, and the mixture was stirred for 10 min. It was extracted with EtOAc (4×75 mL), and the organic layers were combined, dried over MgSO$_4$, and concentrated in vacuo to give a residue which was purified by flash chromatography using an ISCO 120 g column eluting with 20-100% EtOAc/hexanes. Appropriate fractions were collected and concentrated in vacuo to give the desired product (0.5215 g, 2.58 mmol, 50.1% yield) as an off-white solid.

2. 6-(3-(tert-Butyldimethylsilyloxy)pyrrolidin-1-yl)-1H-indole

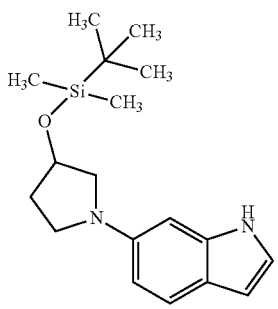 [SMILES: CC(C)(C)[Si](C)(C)OC1CCN(c2ccc3cc[nH]c3c2)C1]

A homogeneous, colorless solution of 1-(1H-indol-6-yl)pyrrolidin-3-ol (0.1036 g, 0.512 mmol), tert-butylchlorodimethylsilane (0.093 g, 0.615 mmol) and imidazole (0.087 g, 1.281 mmol) in DMF (2.56 mL) was stirred overnight. The mixture was diluted with EtOAc (75 mL), washed with water (4×25 mL) and brine (25 mL) successively, dried over MgSO$_4$, and concentrated in vacuo. The residue was triturated with hexanes to give the desired product (0.1600 g, 0.470 mmol, 92%).

3. Benzyl 3-(1-(6-(3-(tert-butyldimethylsilyloxy)pyrrolidin-1-yl)-1H-indol-3-yl)-2-nitroethyl)-2-methylphenylcarbamate

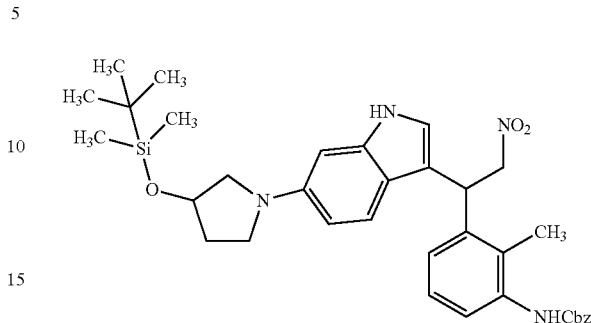

6-(3-(tert-Butyldimethylsilyloxy)pyrrolidin-1-yl)-1H-indole (1.867 g, 5.90 mmol) and (E)-benzyl 2-methyl-3-(2-nitrovinyl)phenylcarbamate (1.5354 g, 4.92 mmol) were dissolved in THF (40 mL), concentrated in vacuo, and the mixture was heated at 110° C. for 1 hr. The reaction mixture was cooled to room temperature and purified by flash chromatography using an ISCO 220 g column eluting with 25-100% EtOAc/hexanes to give the desired product (1.0324 g, 1.642 mmol, 33.4% yield) as a tan solid.

4. Benzyl 3-(2-amino-1-(6-(3-(tert-butyldimethylsilyloxy)pyrrolidin-1-yl)-1H-indol-3-yl)ethyl)-2-methylphenylcarbamate

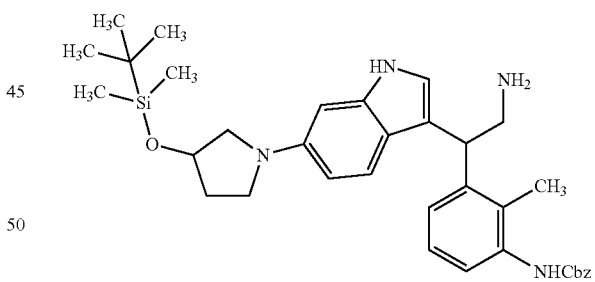

To a solution of benzyl 3-(1-(6-(3-(tert-butyldimethylsilyloxy)pyrrolidin-1-yl)-1H-indol-3-yl)-2-nitroethyl)-2-methylphenylcarbamate (1.0324 g, 1.642 mmol) and ammonium chloride (1.317 g, 24.63 mmol) in methanol (32.8 mL) and tetrahydrofuran (32.8 mL) under nitrogen was added zinc (1.610 g, 24.63 mmol), and the reaction was stirred overnight. The solution was filtered through a pad of CELITE® and rinsed with MeOH and THF. The filtrate was concentrated in vacuo, dissolved in EtOAc (100 mL) and water (40 mL). After separation of the layers, the aqueous layer was extracted with EtOAc (2×100 mL). The organic layers were combined, dried over MgSO₄, filtered and concentrated in vacuo to give the desired product (1.007 g, 1.682 mmol, 102% yield) as a dark solid.

5. Ethyl 4-(3-(benzyloxycarbonylamino)-2-methylphenyl)-7-(3-(tert-butyldimethylsilyloxy)pyrrolidin-1-yl)-9H-pyrido[3,4-b]indole-1-carboxylate

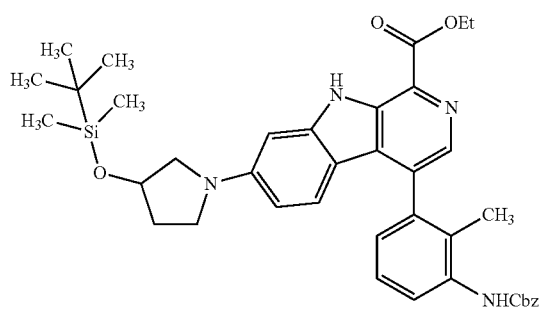

To a solution of benzyl 3-(2-amino-1-(6-(3-(tert-butyldimethylsilyloxy)pyrrolidin-1-yl)-1H-indol-3-yl)ethyl)-2-methylphenylcarbamate (0.1010 g, 0.169 mmol) in 1,4-dioxane (4.82 mL) was added 50% ethyl 2-oxoacetate/toluene (0.067 mL, 0.337 mmol) at 10° C. The cold bath was removed, and the reaction was stirred to room temperature for 3 h. The reaction was concentrated in vacuo to give crude ethyl 4-(3-(benzyloxycarbonylamino)-2-methylphenyl)-7-(3-(tert-butyldimethylsilyloxy)pyrrolidin-1-yl)-2,3,4,9-tetrahydro-1H-pyrido[3,4-b]indole-1-carboxylate which was used in the subsequent step. This was added to p-xylene (41.6 mL) and 10% Pd/C (0.310 g, 0.291 mmol). The reaction was heated to 125° C. for 4.5 hr and cooled to room temperature. The solution was filtered through a pad of CELITE® and rinsed with EtOAc (150 mL). The filtrate was washed with water (40 mL), dried over MgSO₄, filtered and concentrated in vacuo to give a residue which was purified by flash chromatography using an ISCO 120 g column eluting with 0-30% EtOAc/CH₂Cl₂. Appropriate fractions (20% elution) were combined, concentrated in vacuo to give the desired product (0.1487 g, 0.219 mmol, 15.0% yield) as a tan solid.

6. Ethyl 4-(3-(benzyloxycarbonylamino)-2-methylphenyl)-7-(3-(tert-butyldimethylsilyloxy)pyrrolidin-1-yl)-9H-pyrido[3,4-b]indole-1-carboxylate

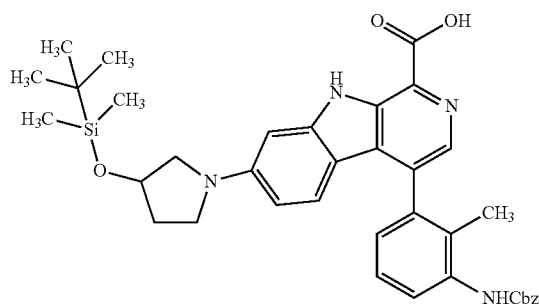 [SMILES: Cc1c(NC(=O)OCc2ccccc2)cccc1-c1cnc(C(=O)O)c2[nH]c3cc(N4CCC(O[Si](C)(C)C(C)(C)C)C4)ccc3c12]

To a burgundy, homogeneous solution of ethyl 4-(3-(benzyloxycarbonylamino)-2-methylphenyl)-7-(3-(tert-butyldimethylsilyloxy)pyrrolidin-1-yl)-9H-pyrido[3,4-b]indole-1-carboxylate (0.1487 g, 0.219 mmol) in tetrahydrofuran (7.47 mL) and methanol (2.489 mL) was added a solution of LiOH hydrate (0.037 g, 0.876 mmol) in water (2 mL). After 2.5 h, the reaction was concentrated in vacuo not to dryness, and the solution was dissolved in water (8 mL). 1 N aqueous HCl was added until pH 5-6 by litmus paper. The precipitate was filtered and dried over Drierite to give the desired product (0.1323 g, 0.203 mmol, 93% yield) as a brown solid.

7. Benzyl 3-(7-(3-(tert-butyldimethylsilyloxy)pyrrolidin-1-yl)-1-carbamoyl-9H-pyrido[3,4-b]indol-4-yl)-2-methylphenylcarbamate

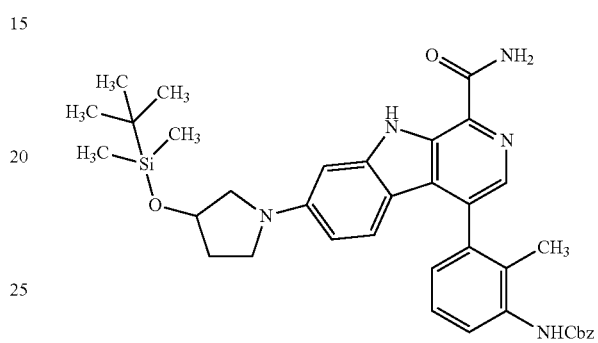

A burgundy, homogeneous solution of 4-(3-(benzyloxycarbonylamino)-2-methylphenyl)-7-(3-(tert-butyldimethylsilyloxy)pyrrolidin-1-yl)-9H-pyrido[3,4-b]indole-1-carboxylic acid (0.1323 g, 0.203 mmol), ammonium chloride (0.043 g, 0.813 mmol), BOP (0.117 g, 0.264 mmol), DIPEA (0.170 mL, 0.976 mmol) and N-methylmorpholine (0.087 mL, 0.793 mmol) in DMF (1.694 mL) was stirred for 1 h. Water (20 mL) was added, and the precipitate was filtered and dried over Drierite to give benzyl the desired product (0.1164 g, 0.179 mmol, 88% yield) as a brown solid.

8. 4-(3-Amino-2-methylphenyl)-7-(3-(tert-butyldimethylsilyloxy)pyrrolidin-1-yl)-9H-pyrido[3,4-b]indole-1-carboxamide

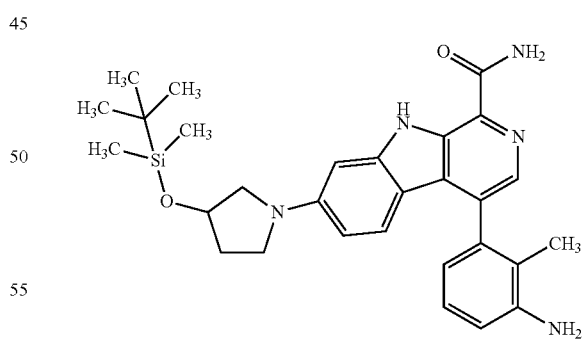

A solution of benzyl 3-(7-(3-(tert-butyldimethylsilyloxy)pyrrolidin-1-yl)-1-carbamoyl-9H-pyrido[3,4-b]indol-4-yl)-2-methylphenylcarbamate (0.1164 g, 0.179 mmol) and 10% Pd/C (0.019 g, 0.018 mmol) in methanol (6.7 mL) and tetrahydrofuran (2.2 mL) under hydrogen was stirred for 45 min. After purging with nitrogen, the reaction was filtered through a pad of CELITE® and rinsed with MeOH. The filtrate was concentrated in vacuo, dissolved in CH₂Cl₂ (75 mL) and washed with brine (25 mL). The organic layer was dried over MgSO₄ and concentrated in vacuo to give the desired product (0.0782 g, 0.152 mmol, 85% yield) as a brick-red solid.

9. 2-((3-(7-(3-(tert-Butyldimethylsilyloxy)pyrrolidin-1-yl)-1-carbamoyl-9H-pyrido[3,4-b]indol-4-yl)-2-methylphenylamino)methyl)-5-chlorobenzoic acid

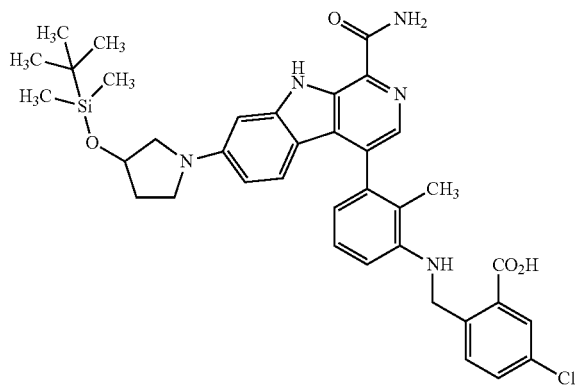 [SMILES: Cc1c(NCc2ccc(Cl)cc2C(=O)O)cccc1-c1cnc(C(N)=O)c2[nH]c3cc(N4CCC(O[Si](C)(C)C(C)(C)C)C4)ccc3c12]

To a homogeneous, light orange solution of 4-(3-amino-2-methylphenyl)-7-(3-(tert-butyldimethylsilyloxy)pyrrolidin-1-yl)-9H-pyrido[3,4-b]indole-1-carboxamide (0.0782 g, 0.152 mmol), 5-chloro-2-formylbenzoic acid (0.070 g, 0.379 mmol), and acetic acid (0.022 mL, 0.379 mmol) in dichloromethane (3.03 mL) and tetrahydrofuran (2.022 mL) under nitrogen was added sodium triacetoxyborohydride (0.096 g, 0.455 mmol), and the mixture was stirred overnight. Water (3 mL) was added, and the reaction was stirred at rt for 10 min. EtOAc (50 mL) and water (20 mL) were added, and the layers were separated. The organic layer was washed with water (6×20 mL) and brine (20 mL), dried over MgSO₄, and concentrated in vacuo to give a crude product which was used in the subsequent step.

10. 7-(3-(tert-Butyldimethylsilyloxy)pyrrolidin-1-yl)-4-(3-(6-chloro-1-oxoisoindolin-2-yl)-2-methylphenyl)-9H-pyrido[3,4-b]indole-1-carboxamide

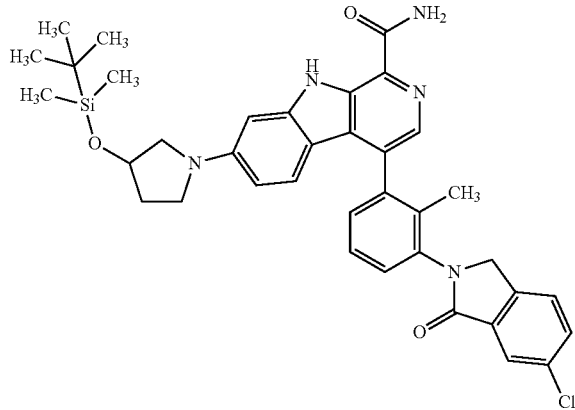 [SMILES: Cc1c(-c2cnc(C(N)=O)c3[nH]c4cc(N5CCC(O[Si](C)(C)C(C)(C)C)C5)ccc4c23)cccc1N1Cc2ccc(Cl)cc2C1=O]

A solution of 2-((3-(7-(3-(tert-butyldimethylsilyloxy)pyrrolidin-1-yl)-1-carbamoyl-9H-pyrido[3,4-b]indol-4-yl)-2-methylphenylamino)methyl)-5-chlorobenzoic acid (0.104 g, 0.152 mmol), DIPEA (0.080 mL, 0.456 mmol), N-methyl-morpholine (0.134 mL, 1.216 mmol) and BOP (0.175 g, 0.395 mmol) in DMF (1.520 mL) under nitrogen was heated at 45° C. for 1 h. The reaction was cooled to room temperature, dissolved in EtOAc (100 mL) and washed with water (3×25 mL) and brine (25 mL), dried over MgSO₄, filtered and concentrated in vacuo to give a residue which was purified by flash chromatography using an ISCO 12 g column eluting with 0-20 EtOAc/hexanes. Appropriate fractions were collected and concentrated in vacuo to give the desired product (0.0456 g, 0.068 mmol, 45.0% yield) as a light orange solid.

11. 4-(3-(6-Chloro-1-oxoisoindolin-2-yl)-2-methylphenyl)-7-(3-hydroxypyrrolidin-1-yl)-9H-pyrido[3,4-b]indole-1-carboxamide To a homogeneous, orange solution of 7-(3-(tert-butyldimethylsilyloxy)pyrrolidin-1-yl)-4-(3-(6-chloro-1-oxoisoindolin-2-yl)-2-methylphenyl)-9H-pyrido[3,4-b]indole-1-carboxamide (0.0456 g, 0.068 mmol) in tetrahydrofuran (0.684 mL) under nitrogen was added 1 M TBAF/THF (0.103 mL, 0.103 mmol). The reaction was stirred for 75 min and concentrated in vacuo. The residue was dissolved in DMSO (0.2 mL) and MeOH, and subjected to autoprep HPLC. The appropriate fractions were collected, basified with NaHCO₃ (solid), and concentrated in vacuo. The residue was extracted with CH₂Cl₂ (3×). The combined extract was dried over Na₂SO₄ and concentrated in vacuo to give the desired product (0.0112 g, 0.020 mmol, 29.7% yield) as a light yellow solid. LC/MS (M+H)=552.11; $^1$H NMR (500 MHz, DMSO-d₆) (recognizable peaks for major atropoisomer) δ ppm 11.26 (s, 1H), 8.21 (d, J=2.8 Hz, 1H), 8.08 (s, 1H), 7.81 (s, 1H), 7.74 (d, J=1.94 Hz, 2H), 7.63-0.65 (m, 2H), 7.45-7.58 (m, 1H), 7.42 (d, J=1.11 Hz, 1H), 7.03 (d, J=8.60 Hz, 1H), 6.83 (d, J=1.66 Hz, 1H), 6.38 (dd, J1=9.0 Hz, J2=2.1 Hz, 1H), 5.02 (d, J=17.76 Hz, 1H), 4.95-4.98 (m, 1H), 4.94 (d, J=17.76 Hz, 1H), 4.43 (br. S, 1H), 3.47 (ddd, J1=10.2 Hz, J2=4.8 Hz, J3=2.2 Hz, 1H), 3.37-3.44 (m, 1H), 3.31-3.37 (m, 1H), 3.15 (d, J=10.0 Hz, 1H), 2.07 (dd, J=8.25, 4.30 Hz, 1H), 1.90-1.96 (m, 1H), 1.88 (s, 3H).

EXAMPLE 25

4-(3-(6-Chloro-1-oxoisoindolin-2-yl)-2-methylphenyl)-7-(tetrahydrofuran-3-ylamino)-9H-pyrido[3,4-b]indole-1-carboxamide

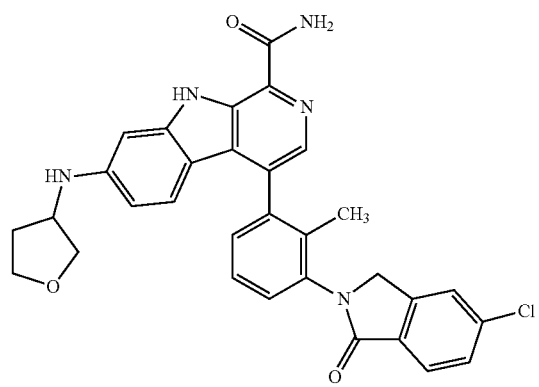 [SMILES: Cc1c(-c2cnc(C(N)=O)c3[nH]c4cc(NC5CCOC5)ccc4c23)cccc1N1Cc2cc(Cl)ccc2C1=O]

1. 2-(Trimethylsilyl)ethyl 1H-indol-6-ylcarbamate

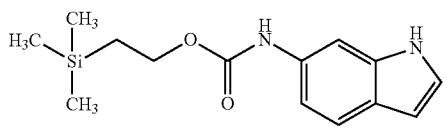 [SMILES: C[Si](C)(C)CCOC(=O)Nc1ccc2cc[nH]c2c1]

To a yellow, homogeneous solution of 1H-indol-6-amine (1.3007 g, 9.84 mmol) and DIPEA (2.58 mL, 14.76 mmol) in 1,4-dioxane (19.68 mL) under nitrogen was added 2,5-dioxopyrrolidin-1-yl 2-(trimethylsilyl)ethyl carbonate (2.81 g, 10.83 mmol) The reaction was stirred overnight, diluted with EtOAc (1500 mL), washed with water (3×50 mL) and brine (50 mL), dried over MgSO₄, filtered and concentrated in vacuo to give the desired product (2.666 g, 9.65 mmol, 98% yield) as a light tan solid.

2. 2-(Trimethylsilyl)ethyl 3-(1-(2-methyl-3-(benzyloxycarbonylamino)-2-nitroethyl)-1H-indol-6-ylcarbamate

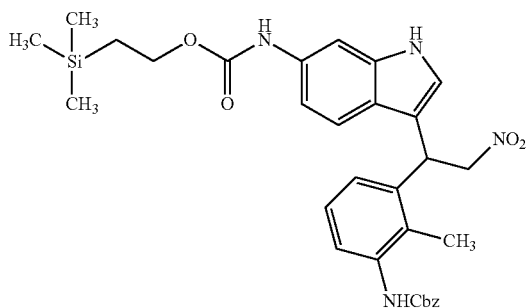 [SMILES: Cc1c(NC(=O)OCc2ccccc2)cccc1C(CN)c1c[nH]c2cc(NC(=O)OCC[Si](C)(C)C)ccc12]

2-(Trimethylsilyl)ethyl 1H-indol-6-ylcarbamate (2.666 g, 9.65 mmol) and (E)-benzyl 2-methyl-3-(2-nitrovinyl)phenylcarbamate (3.62 g, 11.58 mmol) were dissolved in THF (50 mL), concentrated in vacuo, and the mixture was melted at 115° C. for 6.5 h. The reaction was cooled to room temperature and purified by flash chromatography using an ISCO 330 g column eluting with 30-75% EtOAc/hexanes to give the desired product (2.184 g, 3.71 mmol, 38.5% yield) as a light brown solid.

3. 2-(Trimethylsilyl)ethyl 3-(1-(2-methyl-3-(benzyloxycarbonylamino)-2-aminoethyl)-1H-indol-6-ylcarbamate

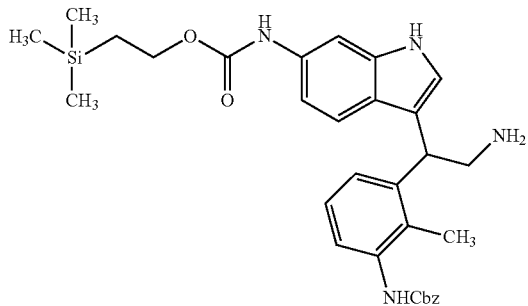

To a light brown, homogeneous solution of 2-(trimethylsilyl)ethyl 3-(1-(2-methyl-3-(benzyloxycarbonylamino)-2-nitroethyl)-1H-indol-6-ylcarbamate (2.1655 g, 3.68 mmol) in tetrahydrofuran (73.6 mL) and methanol (73.6 mL) under nitrogen were added ammonium chloride (2.95 g, 55.2 mmol) and zinc (3.61 g, 55.2 mmol). After 5.25 h, the solution was filtered through a pad of CELITE®, rinsed with MeOH, and the filtrate was concentrated in vacuo. The residue was dissolved in CH₂Cl₂ (100 mL) and washed with water (2×30 mL) and brine (30 mL) successively. The organic solution was dried over MgSO₄ and concentrated in vacuo to give the desired product (2.1981 g, 3.93 mmol, 107% yield) as a light violet foam.

4. Ethyl 4-(3-(benzyloxycarbonylamino)-2-methylphenyl)-7-((2-(trimethylsilyl)ethoxy)carbonylamino)-9H-pyrido[3,4-b]indole-1-carboxylate

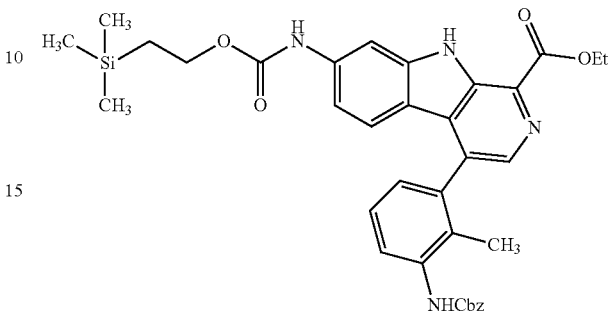

To a light orange, homogeneous solution of 2-(trimethylsilyl)ethyl 3-(1-(2-methyl-3-(benzyloxycarbonylamino)-2-aminoethyl)-1H-indol-6-ylcarbamate (1.111 g, 1.988 mmol) in 1,4-dioxane (56.8 mL) and 50% ethyl 2-oxoacetate/toluene (0.985 mL, 4.97 mmol) under nitrogen was added 4N hydrochloric acid/dioxane (1.243 mL, 4.97 mmol). The reaction was stirred overnight. More 50% ethyl 2-oxoacetate/toluene (0.985 mL, 4.97 mmol) and 4 N HCl/dioxane (0.5 mL) were added. The reaction was stirred overnight. This was combined with another similar reaction mixture (1.919 mmol scale), concentrated in vacuo, dissolved in EtOAc (75 mL) and washed with water (30 mL) and brine (30 mL), successively. The organic solution was dried over MgSO₄, filtered and concentrated in vacuo to give a crude product as a burgundy foam which was used in the subsequent step. This was added to p-xylene (112 mL) and 10% Pd/C (0.832 g, 0.781 mmol). The reaction was heated to 115° C. After 6.5 hr, the solution was cooled to room temperature and filtered through a pad of CELITE® and rinsed with EtOAc (150 mL). The filtrate was washed with water (40 mL), dried over MgSO₄, and concentrated in vacuo. Xylene was removed via short-path distillation to give a residue which was purified by flash chromatography using an ISCO 220 g column eluting with 40-100% EtOAc/hexane. Appropriate fractions (45-55% elution) were combined, concentrated in vacuo to give the desired product (0.5133 g, 0.804 mmol, 20.57% yield) as a tan solid.

5. 4-(3-(Benzyloxycarbonylamino)-2-methylphenyl)-7-((2-(trimethylsilyl)ethoxy)carbonylamino)-9H-pyrido[3,4-b]indole-1-carboxylic acid

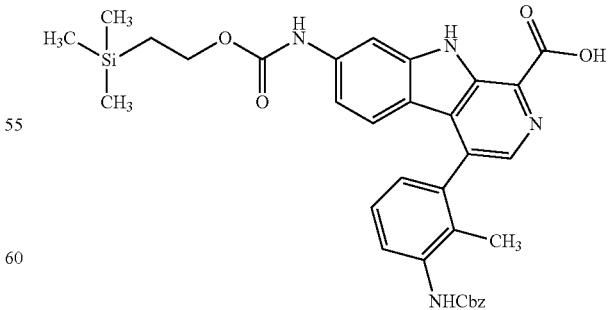

To a homogeneous, burgundy solution of ethyl 4-(3-(benzyloxycarbonylamino)-2-methylphenyl)-7-((2-(trimethylsilyl)ethoxy)carbonylamino)-9H-pyrido[3,4-b]indole-1-carboxylate (0.565 g, 0.884 mmol) in tetrahydrofuran (30.2 mL)

and methanol (10.05 mL) was added a solution of lithium hydroxide hydrate (0.148 g, 3.54 mmol) in water (4 mL). After 1 hr, the reaction was concentrated in vacuo, acidified with 1 N aqueous HCl to pH ~5 by litmus paper. The precipitate was filtered, dried over Drierite to give the desired product (0.419 g, 0.686 mmol, 78% yield) as a light brown solid.

6. 4-(3-(Benzyloxycarbonylamino)-2-methylphenyl)-7-((2-(trimethylsilyl)ethoxy)carbonylamino)-9H-pyrido[3,4-b]indole-1-carboxamide

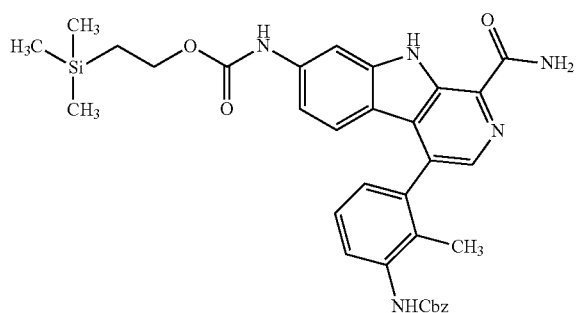 [SMILES: Cc1c(NC(=O)OCc2ccccc2)cccc1-c1cnc(C(N)=O)c2[nH]c3cc(NC(=O)OCC[Si](C)(C)C)ccc3c12]

To a dark, homogeneous solution of 4-(3-(benzyloxycarbonylamino)-2-methylphenyl)-7-((2-(trimethylsilyl)ethoxy)carbonylamino)-9H-pyrido[3,4-b]indole-1-carboxylic acid (0.4181 g, 0.685 mmol) in DMF (2.74 mL) were added ammonium chloride (0.146 g, 2.74 mmol), BOP (0.394 g, 0.890 mmol), DIPEA (0.574 mL, 3.29 mmol) and N-methylmorpholine (0.294 mL, 2.67 mmol). After 2.5 hr, water was added, and the precipitate was collected and dried over Drierite to give the desired product (0.365 g, 0.599 mmol, 87% yield) as a light brown solid.

7. 2-(Trimethylsilyl)ethyl 4-(3-amino-2-methylphenyl)-1-carbamoyl-9H-pyrido[3,4-b]indol-7-ylcarbamate

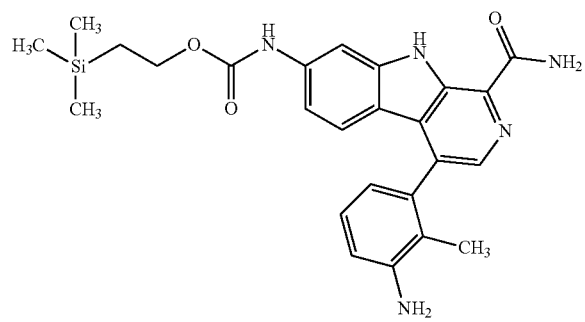 [SMILES: Cc1c(N)cccc1-c1cnc(C(N)=O)c2[nH]c3cc(NC(=O)OCC[Si](C)(C)C)ccc3c12]

A solution of 4-(3-(benzyloxycarbonylamino)-2-methylphenyl)-7-((2-(trimethylsilyl)ethoxy)carbonylamino)-9H-pyrido[3,4-b]indole-1-carboxylic acid (0.2535 g, 0.533 mmol, 89% yield) and 10% Pd/C (0.064 g, 0.060 mmol) in methanol (22.39 mL) and tetrahydrofuran (7.46 mL) was hydrogenated for 1 hr. The reaction mixture was filtered through a pad of CELITE® and rinsed with MeOH. The filtrate was concentrated in vacuo, dissolved in $CH_2Cl_2$ (75 mL) and washed with brine (25 mL). The organic layer was dried over $MgSO_4$ and concentrated in vacuo to give the desired product (0.254 g, 0.533 mmol, 89% yield) as a light brown solid.

8. 2-((3-(1-Carbamoyl-7-((2-(trimethylsilyl)ethoxy)carbonylamino)-9H-pyrido[3,4-b]indol-4-yl)-2-methylphenylamino)methyl)-5-chlorobenzoic acid

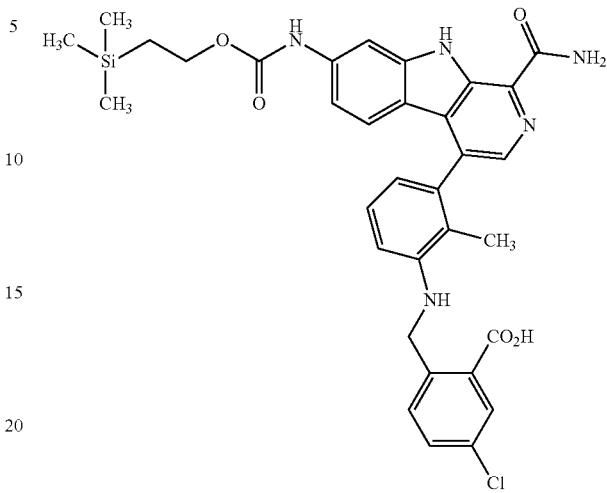

To a homogeneous, light burgundy solution of 2-(trimethylsilyl)ethyl 4-(3-amino-2-methylphenyl)-1-carbamoyl-9H-pyrido[3,4-b]indol-7-ylcarbamate (0.2535 g, 0.533 mmol), 5-chloro-2-formylbenzoic acid (0.246 g, 1.332 mmol), and acetic acid (0.076 mL, 1.332 mmol) in dichloromethane (10.66 mL) and tetrahydrofuran (7.11 mL) under nitrogen was added sodium triacetoxyborohydride (0.339 g, 1.599 mmol). The reaction was stirred overnight. Water (5 mL) was added, and the reaction was stirred for 10 min. EtOAc (50 mL) and water (20 mL) were added, and the layers were separated. The organic layer was washed with water (6×20 mL) and brine (20 mL), dried over $MgSO_4$, and concentrated in vacuo to give a crude product that was used in the subsequent step.

9. 2-(Trimethylsilyl)ethyl 1-carbamoyl-4-(3-(6-chloro-1-oxoisoindolin-2-yl)-2-methylphenyl)-9H-pyrido[3,4-b]indol-7-ylcarbamate

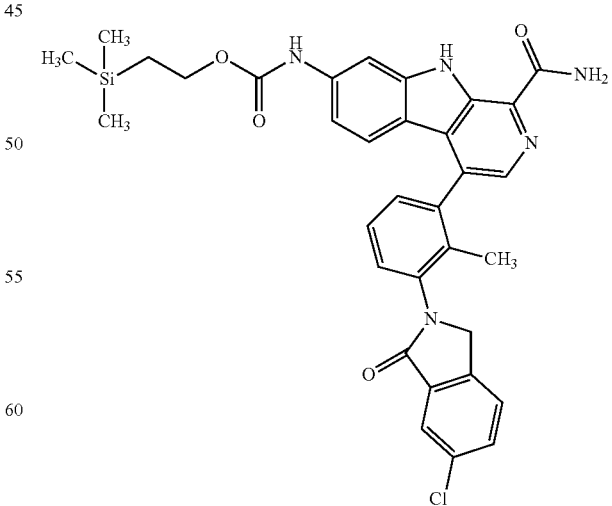

A solution of 2-((3-(1-carbamoyl-7-((2-(trimethylsilyl)ethoxy)carbonylamino)-9H-pyrido[3,4-b]indol-4-yl)-2-methylphenylamino)methyl)-5-chlorobenzoic acid (0.343 g, 0.533 mmol), DIPEA (0.279 mL, 1.599 mmol), N-methylmorpholine (0.469 mL, 4.26 mmol) and BOP (0.613 g, 1.386 mmol) in DMF (5.33 mL) under nitrogen was heated at 45° C. for 45 min. The reaction was cooled to room temperature, dissolved in EtOAc (100 mL) and washed with water (3×25 mL) and brine (25 mL), dried over MgSO$_4$, and concentrated in vacuo to give a residue which was purified by flash chromatography using an ISCO 40 g column eluting with 30-75% EtOAc/hexanes. Appropriate fractions were collected and concentrated in vacuo to give the desired product (0.140 g, 0.224 mmol, 41.9% yield) as a light orange solid.

10. 7-Amino-4-(3-(6-chloro-1-oxoisoindolin-2-yl)-2-methylphenyl)-9H-pyrido[3,4-b]indole-1-carboxamide

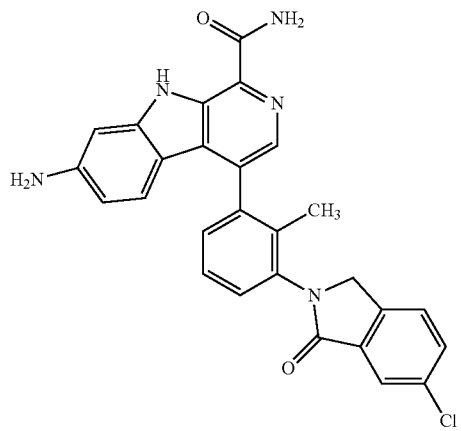 [SMILES: Cc1c(-c2cnc(C(N)=O)c3[nH]c4cc(N)ccc4c23)cccc1N1Cc2ccc(Cl)cc2C1=O]

To a burgundy, homogeneous solution of 2-(trimethylsilyl)ethyl 1-carbamoyl-4-(3-(6-chloro-1-oxoisoindolin-2-yl)-2-methylphenyl)-9H-pyrido[3,4-b]indol-7-ylcarbamate (0.126 g, 0.201 mmol) in tetrahydrofuran (0.2 mL) was added 1M TBAF/THF (0.402 mL, 0.402 mmol). After 4 hr, EtOAc (80 mL) was added, and the layer was washed with water (20 mL) and brine (20 mL), successively. The organic solution was dried over MgSO$_4$ and concentrated in vacuo to give a crude product as a light brown solid, which was used in the subsequent step.

11. 4-(3-(6-Chloro-1-oxoisoindolin-2-yl)-2-methylphenyl)-7-(tetrahydrofuran-3-ylamino)-9H-pyrido[3,4-b]indole-1-carboxamide To a light burgundy, homogeneous solution of 7-amino-4-(3-(6-chloro-1-oxoisoindolin-2-yl)-2-methylphenyl)-9H-pyrido[3,4-b]indole-1-carboxamide (0.0695 g, 0.144 mmol), dihydrofuran-3(2H)-one (0.050 g, 0.577 mmol) and acetic acid (0.041 mL, 0.721 mmol) in dichloromethane (1.602 mL) and THF (1.602 mL) was added sodium triacetoxyborohydride (0.122 g, 0.577 mmol). The reaction was stirred overnight. Water (2 mL) was added, and the solution was stirred at room temperature for 10 min. EtOAc (50 mL) and water (20 mL) were added. After separation of layers, the organic layer was washed with sat. aq. NaHCO$_3$, brine (20 mL), dried over MgSO$_4$, and concentrated in vacuo to give a residue which was diluted with DMSO (0.2 mL) and MeOH (0.8 mL) and purified by reverse phase HPLC. The appropriate fractions were collected, basified with NaHCO$_3$ (solid), and concentrated in vacuo. The residue was extracted with CH$_2$Cl$_2$ (3×). The combined extract was dried over Na$_2$SO$_4$ and concentrated in vacuo to give the desired product (0.00234 g, 4.03 µmol, 2.79% yield) as a tan solid. LC/MS (M+H)=552.24.

EXAMPLE 26

4-(2-Fluoro-3-(6-methyl-1-oxoisoindolin-2-yl)phenyl)-7-(2-methoxyethoxy)-9H-pyrido[3,4-b]indole-1-carboxamide

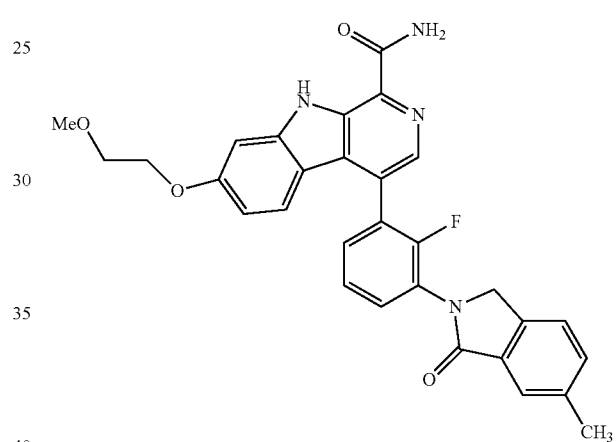

1. Benzyl 3-cyano-2-fluorophenylcarbamate

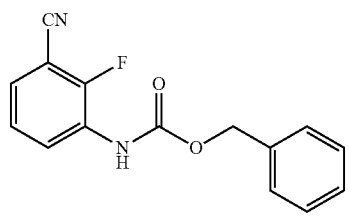 [SMILES: N#Cc1cccc(NC(=O)OCc2ccccc2)c1F]

To a light brown solution of 3-amino-2-fluorobenzonitrile (2.7141 g, 19.94 mmol) and potassium carbonate (4.13 g, 29.9 mmol) in THF (166 mL) was syringed benzyl carbonochloridate (4.49 mL, 29.9 mmol) under nitrogen, and the reaction was stirred overnight. The insoluble material was filtered, and the filtrate was concentrated in vacuo. The residue was dissolved in EtOAc (200 mL) and washed with 1 N aqueous HCl (50 mL), water (50 mL) and brine (50 mL), successively. The organic solution was dried over MgSO$_4$ and concentrated in vacuo to give crude product which was stirred in hexanes (75 mL) for 1 hr. The insoluble material was filtered and washed with hexanes to give the desired product (4.4541 g, 16.48 mmol, 83% yield) as a light tan solid.

2. Benzyl 2-fluoro-3-formylphenylcarbamate

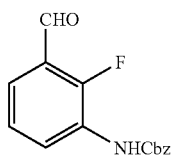

To a slightly tan, homogeneous solution of benzyl 3-cyano-2-fluorophenylcarbamate (4.45 g, 16.47 mmol) in THF (211 mL) in a −78° C. bath under nitrogen was syringed DIBAL-H (65.9 mL, 65.9 mmol)/CH$_2$Cl$_2$ dropwise over 75 min. The reaction was stirred for 30 min. The cold bath was removed, and the reaction was stirred to room temperature. After 4 hr, the solution was added to ice-cold water (300 mL) over 50 minutes; heavy emulsion ensued. After stirring for another 30 min, the organic layer was separated, and the aqueous layer/emulsion was filtered, and the insoluble materials were rinsed with CH$_2$Cl$_2$ (200 mL). The organic layers were combined and concentrated in vacuo. The residue was dissolved in CH$_2$Cl$_2$ (300 mL) and washed with brine (75 mL), dried over MgSO$_4$, and concentrated in vacuo to give the desired product (4.0253 g, 11.78 mmol, 71.6% yield) as a tan solid.

3. (E)-Benzyl 2-fluoro-3-(2-nitrovinyl)phenylcarbamate

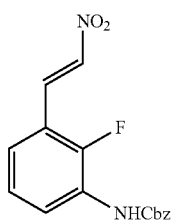 [SMILES: O=C(Nc1cccc(/C=C/[N+](=O)[O-])c1F)OCc1ccccc1]

A solution of benzyl 2-fluoro-3-formylphenylcarbamate (4.0253 g, 14.73 mmol), nitromethane (1.98 mL, 36.8 mmol) and nitromethane (1.979 mL, 36.8 mmol) in acetic acid (49.1 mL) under nitrogen was heated at 90° C. After 2 hr, the reaction was cooled to room temperature and concentrated in vacuo. The residue was dissolved in CH$_2$Cl$_2$ (75 mL) and water (75 mL), and Na$_2$CO$_3$ (s) was added until pH basic by litmus paper. After separation of layers, the aqueous layer was extracted with CH$_2$Cl$_2$ (3×75 mL). The organic layers were combined and washed with brine (50 mL), dried over MgSO$_4$, and concentrated in vacuo to give the desired product (4.251 g, 10.08 mmol, 68.4% yield) as a burgundy oil.

4. Methyl 2,5-dimethylbenzoate

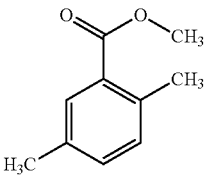

A colorless, homogeneous solution of 2,5-dimethylbenzoic acid (6.3264 g, 42.1 mmol) and 4 N HCl/1,4-dioxane (11.58 mL, 46.3 mmol) was refluxed under nitrogen. After 2.5 hr, the reaction was cooled to room temperature and concentrated in vacuo. The residue was dissolved in EtOAc (100 mL) and washed with water (40 mL), 1N aq. NaOH (40 mL), water (40 mL) and brine (40 mL), successively. The organic solution was dried over MgSO$_4$ and concentrated in vacuo to give the desired product (5.934 g, 34.7 mmol, 82% yield) as a colorless oil.

5. Methyl 2-(bromomethyl)-5-methylbenzoate

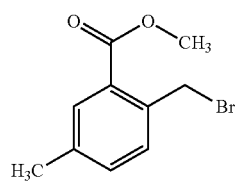

A light yellow, homogeneous solution of methyl 2,5-dimethylbenzoate (4.467 g, 27.2 mmol), 1-bromopyrrolidine-2,5-dione (4.84 g, 27.2 mmol) and benzoic peroxyanhydride (0.659 g, 2.72 mmol) in benzene (136 mL) under nitrogen was refluxed. After 8.5 hr, the reaction was cooled to room temperature. The succinimide was filtered, rinsed with benzene and the filtrate was concentrated in vacuo. The residue was dissolved in EtOAc (100 mL) and washed with water (50 mL) and brine (50 mL), dried over MgSO$_4$, and concentrated in vacuo to give crude product that was a mixture of the desired product and its regioisomer. This crude product was used in the next step without further purification.

6. 6-Methylisobenzofuran-1(3H)-one

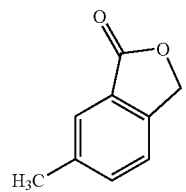

A heterogeneous, colorless solution of methyl 2-(bromomethyl)-5-methylbenzoate and regioisomer (27.2 mmol) and calcium carbonate (16.33 g, 163 mmol) in 1,4-dioxane (194 mL) and water (194 mL) was refluxed. After 5 hr, the reaction was cooled to room temperature. The insolubles were filtered, and the filtrate was concentrated in vacuo. The residue was extracted with CH₂Cl₂ (2×200 mL). The organic layers were combined, dried over MgSO₄, and concentrated in vacuo to give an oil which was purified by flash chromatography using an ISCO 220 g column eluting with 10-50% EtOAc/hexanes. Appropriate fractions were collected and concentrated in vacuo to give the desired product (1.205 g, 8.13 mmol, 29.9% yield) as a white solid.

7. 2-(Hydroxymethyl)-5-methylbenzoic acid

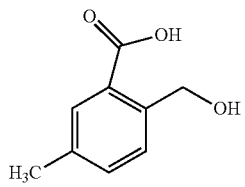

A colorless, homogeneous solution of 6-methylisobenzofuran-1(3H)-one (0.95 g, 6.41 mmol), KOH (0.576 g, 10.26 mmol) in methanol (20.52 mL) and water (5.13 mL) was refluxed. After two hr, the reaction was cooled to room temperature, concentrated in vacuo, and acidified with 1 M aqueous KHSO₄ to pH ~3. The mixture was extracted with EtOAc (4×50 mL). The combined extract was dried over MgSO₄ and concentrated in vacuo to give the desired product (0.632 g, 3.81 mmol, 59.4% yield) as a white solid.

8. 2-Formyl-5-methylbenzoic acid

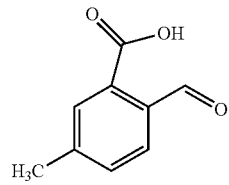

To a homogeneous, colorless solution of 2-(hydroxymethyl)-5-methylbenzoic acid (0.6325 g, 3.81 mmol) in THF (35 mL) under nitrogen was added MnO₂ (4.96 g, 57.1 mmol), and the reaction was stirred overnight. Additional MnO₂ (~3 g) was added, and the reaction was stirred overnight. The mixture was filtered through a pad of CELITE® and rinsed with THF. The filtrate was concentrated in vacuo to give the desired product (0.3302 g, 2.011 mmol, 52.8% yield) as an off-white solid.

9. Benzyl 2-fluoro-3-(1-(6-(2-methoxyethoxy)-1H-indol-3-yl)-2-nitroethyl)phenylcarbamate

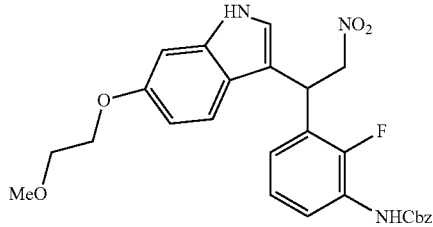

6-(2-Methoxyethoxy)-1H-indole (1.198 g, 6.26 mmol) and (E)-benzyl 2-fluoro-3-(2-nitrovinyl)phenylcarbamate (1.651 g, 5.22 mmol) were dissolved in THF (50 mL) and concentrated in vacuo, and the mixture was heated at 125° C. overnight. The reaction was cooled to room temperature, and the crude product was purified by flash chromatography (solid loading) using an ISCO 220 g column eluting with 15-75% EtOAc/hexanes to give the desired product (1.888 g, 3.61 mmol, 69.2% yield) as a light orange foam.

10. Benzyl 3-(2-amino-1-(6-(2-methoxyethoxy)-1H-indol-3-yl)ethyl)-2-fluorophenylcarbamate

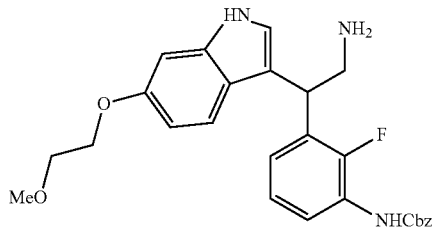 [SMILES: COCCOc1ccc2c(C(C[N+](=O)[O-])c3cccc(NC(=O)OCc4ccccc4)c3F)c[nH]c2c1]

To a solution of benzyl 2-fluoro-3-(1-(6-(2-methoxyethoxy)-1H-indol-3-yl)-2-nitroethyl)phenylcarbamate (3.75 g, 7.39 mmol) and ammonium chloride (5.93 g, 111 mmol) in methanol (148 mL) and tetrahydrofuran (148 mL) under nitrogen was added zinc (7.25 g, 111 mmol). After 3 hr, the reaction was filtered through a pad of CELITE®, rinsed with EtOAc and MeOH. The filtrate was concentrated in vacuo. Water (40 mL) was added followed by saturated aq. NaHCO₃ (to pH ~11 by litmus paper) and extracted with EtOAc (4×50 mL). The organic layers were combined, washed with brine (40 mL), dried over MgSO₄, and concentrated in vacuo to give the desired product (3.523 g, 6.35 mmol, 86% yield) as a light tan solid.

11. Ethyl 4-(3-(benzyloxycarbonylamino)-2-fluorophenyl)-7-(2-methoxyethoxy)-9H-pyrido[3,4-b]indole-1-carboxylate

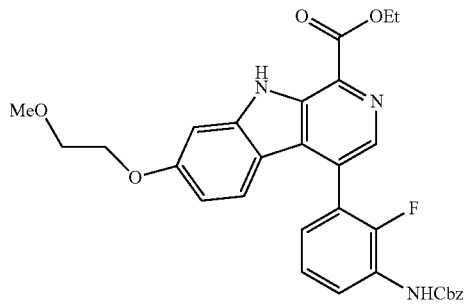 [SMILES: COCCOc1ccc2c(c1)[nH]c1c(C(=O)O)ncc(-c3cccc(NC(=O)OCc4ccccc4)c3F)c12]

To a light homogeneous, orange solution of benzyl 3-(2-amino-1-(6-(2-methoxyethoxy)-1H-indol-3-yl)ethyl)-2- fluorophenylcarbamate (3.5215 g, 7.37 mmol) and ethyl 2-oxoacetate (2.92 mL, 14.75 mmol) (50% in toluene) under nitrogen was added 4N HCl/1,4-dioxane (2.212 mL, 8.85 mmol); reaction turned dark burgundy. The reaction was stirred overnight, concentrated in vacuo, dissolved in EtOAc (50 mL) and saturated aqueous NaHCO$_3$ (20 mL). After separation of the layers, the aqueous layer was extracted with EtOAc (3×50 mL). The organic layers were combined, washed with brine (30 mL), dried over MgSO$_4$, and concentrated in vacuo to give crude product which was used in subsequent step. This was added to 10% Pd/C (1.569 g, 1.474 mmol) in p-xylene (211 mL), and the solution was heated at 125° C. After 3.5 hr, the reaction was cooled to room temperature, filtered through a pad of CELITE®, and the insolubles were rinsed with EtOAc (250 mL). The filtrate was washed with brine (75 mL), and the layers were separated. The organic layer was dried over MgSO$_4$, filtered and concentrated in vacuo to give a residue which was purified by flash chromatography using an ISCO 220 g column eluting with 5-40% EtOAc/CH$_2$Cl$_2$. Appropriate fractions (20-25% elution) were collected and concentrated in vacuo to give the desired product (0.811 g, 1.381 mmol, 18.7% yield) as a light orange solid.

12. 4-(3-(Benzyloxycarbonylamino)-2-fluorophenyl)-7-(2-methoxyethoxy)-9H-pyrido[3,4-b]indole-1-carboxylic acid

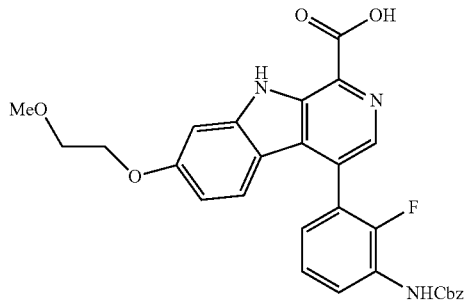

To a light orange, homogeneous solution of ethyl 4-(3-(benzyloxycarbonylamino)-2-fluorophenyl)-7-(2-methoxyethoxy)-9H-pyrido[3,4-b]indole-1-carboxylate (0.8002 g, 1.435 mmol) in THF (30.8 mL) and MeOH (10.25 mL) was added a solution of LiOH hydrate (0.241 g, 5.74 mmol) in water (2 mL). After 1.5 hr. the reaction was concentrated in vacuo. Water (10 mL) was added followed by 1 N aqueous HCl to pH 4-5 by litmus paper. The precipitate was filtered and washed with water, dried over Drierite under vacuum to give the desired product (0.705 g, 1.331 mmol, 93% yield) as a tan solid.

13. Benzyl 3-(1-carbamoyl-7-(2-methoxyethoxy)-9H-pyrido[3,4-b]indol-4-yl)-2-fluorophenylcarbamate

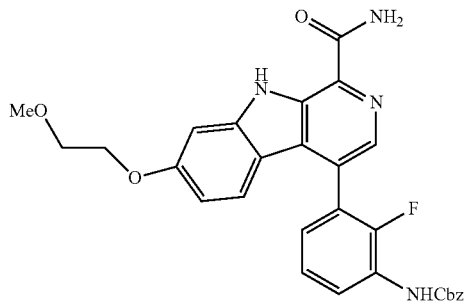 [SMILES: COCCOc1ccc2c(c1)[nH]c1c(C(N)=O)ncc(-c3cccc(NC(=O)OCc4ccccc4)c3F)c12]

A burgundy, homogeneous solution of 4-(3-(benzyloxycarbonylamino)-2-fluorophenyl)-7-(2-methoxyethoxy)-9H-pyrido[3,4-b]indole-1-carboxylic acid (0.7 g, 1.322 mmol), ammonium chloride (0.283 g, 5.29 mmol), BOP (0.760 g, 1.719 mmol), DIPEA (1.108 mL, 6.35 mmol) and N-methylmorpholine (0.567 mL, 5.16 mmol) in DMF (8 mL) under nitrogen was stirred. After 2 hr, water (20 mL) was added, and the reaction was stirred at room temperature for 45 min. The precipitate was collected, rinsed with water and dried over Drierite under vacuum to give the desired product (0.6318 g, 1.195 mmol, 90% yield) as a tan solid.

14. 4-(3-Amino-2-fluorophenyl)-7-(2-methoxyethoxy)-9H-pyrido[3,4-b]indole-1-carboxamide

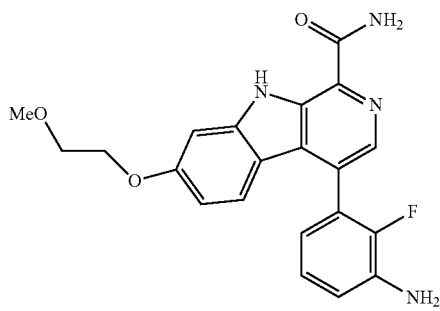 [SMILES: COCCOc1ccc2c(c1)[nH]c1c(C(N)=O)ncc(-c3cccc(N)c3F)c12]

A solution of benzyl 3-(1-carbamoyl-7-(2-methoxyethoxy)-9H-pyrido[3,4-b]indol-4-yl)-2-fluorophenylcarbamate (0.6318 g, 1.195 mmol) and 10% Pd/C (0.191 g, 0.179 mmol) in THF (31.9 mL) and MeOH (47.8 mL) was hydrogenated. After 2 hr, the reaction was filtered through a wad of CELITE® and rinsed with THF and MeOH. The filtrate was concentrated in vacuo, dissolved in EtOAc (100 mL) and brine (25 mL). The layers were separated, and the aqueous layer was extracted with EtOAc (50 mL). The organic layers were combined, dried over MgSO$_4$, and concentrated in vacuo to give the desired product (0.4462 g, 1.007 mmol, 84% yield) as a tan solid.

15. 2-((3-(1-Carbamoyl-7-(2-methoxyethoxy)-9H-pyrido[3,4-b]indol-4-yl)-2-fluorophenylamino)methyl)-5-methylbenzoic acid

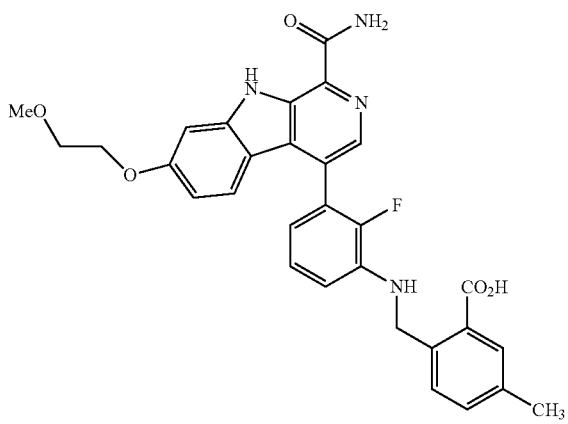 [SMILES: COCCOc1ccc2c(c1)[nH]c1c(C(N)=O)ncc(-c3cccc(NCc4ccc(C)cc4C(=O)O)c3F)c12]

To a light orange, homogeneous solution of 4-(3-amino-2-fluorophenyl)-7-(2-methoxyethoxy)-9H-pyrido[3,4-b]indole-1-carboxamide (0.0767 g, 0.194 mmol), 2-formyl-5-methylbenzoic acid (0.096 g, 0.583 mmol) and acetic acid (0.033 mL, 0.583 mmol) in dichloromethane (3.89 mL) and THF (2.59 mL) under nitrogen was added sodium triacetoxyborohydride (0.206 g, 0.972 mmol). The reaction was stirred overnight. More sodium triacetoxyborohydride (0.206 g, 0.972 mmol) and acetic acid (0.033 mL, 0.583 mmol) were added. After 4.5 hr, water (3 mL) was added, and the reaction was stirred for 10 min. EtOAc (50 mL) and water (20 mL) were added, and the layers were separated. The organic layer was washed with water (6×20 mL) and brine (20 mL), dried over MgSO$_4$, and concentrated in vacuo to give a crude product used in subsequent step.

16. 4-(2-Fluoro-3-(6-methyl-1-oxoisoindolin-2-yl) phenyl)-7-(2-methoxyethoxy)-9H-pyrido[3,4-b]indole-1-carboxamide A homogeneous, orange solution of 2-((3-(1-carbamoyl-7-(2-methoxyethoxy)-9H-pyrido[3,4-b]indol-4-yl)-2-fluorophenylamino)methyl)-5-methylbenzoic acid (0.105 g, 0.194 mmol), BOP (0.257 g, 0.582 mmol), DIPEA (0.119 mL, 0.679 mmol) and N-methylmorpholine (0.192 mL, 1.746 mmol) in DMF (1.940 mL) under nitrogen was heated at 45° C. After 45 min, the reaction was cooled to room temperature, dissolved in EtOAc (75 mL) and washed with water (4×30 mL) and brine (30 mL), successively. The organic solution was dried over MgSO$_4$ and concentrated in vacuo. It was diluted with DMF (0.3 mL) and MeOH (2 mL) and purified by reverse phase HPLC. The appropriate fractions were combined, basified with NaHCO$_3$ (solid), and concentrated in vacuo. The residue was extracted with CH$_2$Cl$_2$ (3×). The combined extract was dried over MgSO$_4$, and concentrated in vacuo to give the desired product (0.00758 g, 0.0144 mmol, 7.4%) as a light tan solid. LC/MS (M+H)=525.30; $^1$H NMR (500 MHz, DMSO-d$_6$) δ ppm 11.69 (s, 1H), 8.31 (d, J=2.2 Hz, 1H), 7.89 (dd, J1=7.6, J2=1.7 Hz, 1H), 7.76 (d, J=2.2 Hz, 1H), 7.61-7.66 (m, 2H), 7.54-7.59 (m, 2H), 7.50-7.54 (m, 2H), 7.47 (dd, J1=8.7 Hz, J2=1.8 Hz, 1H), 7.37 (d, J=2.2 Hz, 1H), 6.77 (dd, J1=8.9 Hz, J2=2.2 Hz, 1 H), 5.03 (d, J=16.1 Hz, 1H), 4.95 (d, J=16.6 Hz, 1H), 4.15-4.19 (m, 2H), 3.69-3.74 (m, 2H), 3.33 (s, 3H), 2.44 (s, 3 H).

EXAMPLE 27

4-(2-Methyl-3-(4-methylbenzamido)phenyl)-6-morpholino-9H-pyrido[3,4-b]indole-1-carboxamide

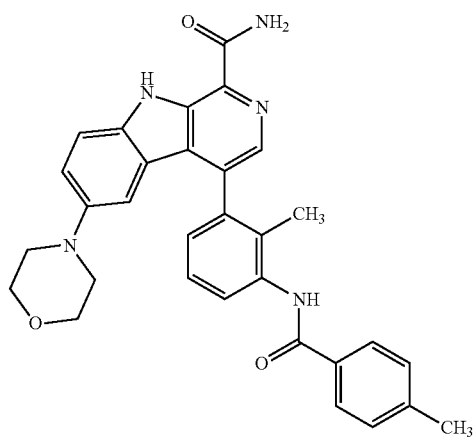 [SMILES: Cc1ccc(C(=O)Nc2cccc(-c3cnc(C(N)=O)c4[nH]c5ccc(N6CCOCC6)cc5c34)c2C)cc1]

1. 4-(1H-Indol-5-yl)morpholine

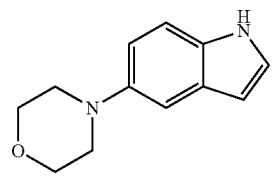 [SMILES: c1cc2cc(N3CCOCC3)ccc2[nH]1]

A heterogeneous, tan solution of 1H-indol-5-amine (4.5547 g, 34.5 mmol), 1-chloro-2-(2-chloroethoxy)ethane (6.06 mL, 51.7 mmol) and Na$_2$CO$_3$ (14.61 g, 138 mmol) in t-BuOH (90 mL) in a sealed pressure tube was heated to 100° C. for 2 days. The reaction was cooled to room temperature, diluted with EtOAc and filtered through a pad of CELITE®, and the filtrate was concentrated in vacuo. Water (50 mL) was added to the residue and basified to pH ~11 with saturated aqueous NaHCO$_3$; this was extracted with CH$_2$Cl$_2$ (4×75 mL). The organic layers were combined and washed with brine, dried over MgSO$_4$, filtered and concentrated in vacuo to give crude product. This was triturated with Et$_2$O to give the first crop of desired product (3.7495 g) as a tan solid. The filtrate was concentrated in vacuo, and the residue was purified by flash chromatography using an ISCO 120 g column eluting with 20-50% EtOAc/hexanes to give the second crop of the desired product (1.9458 g).

2. Benzyl 2-methyl-3-(1-(5-morpholino-1H-indol-3-yl)-2-nitroethyl)phenylcarbamate

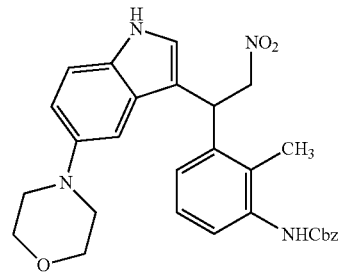 [SMILES: Cc1c(NC(=O)OCc2ccccc2)cccc1C(C[N+](=O)[O-])c1c[nH]c2ccc(N3CCOCC3)cc12]

4-(1H-Indol-5-yl)morpholine (1.102 g, 5.45 mmol) and (E)-benzyl 2-methyl-3-(2-nitrovinyl)phenylcarbamate (1.2154 g, 3.89 mmol) were dissolved in THF and concentrated in vacuo to dryness. The mixture was then melted at 140° C. After 5 h, the reaction was cooled to room temperature and purified by flash chromatography using an ISCO 120 g column eluting with 0-60% EtOAc/hexanes to give the desired product (0.8047 g, 1.454 mmol, 37.4% yield) as a tan foam.

3. Benzyl 3-(2-amino-1-(5-morpholino-1H-indol-3-yl)ethyl)-2-methylphenylcarbamate

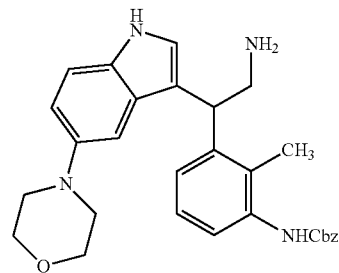 [SMILES: Cc1c(NC(=O)OCc2ccccc2)cccc1C(CN)c1c[nH]c2ccc(N3CCOCC3)cc12]

A solution of benzyl 2-methyl-3-(1-(5-morpholino-1H-indol-3-yl)-2-nitroethyl)phenylcarbamate (0.8011 g, 1.557 mmol), ammonium chloride (1.249 g, 23.35 mmol) and zinc (1.527 g, 23.35 mmol) in methanol (32.4 mL) and tetrahydrofuran (32.4 mL) was stirred for 2 hr. The reaction was filtered through a pad of CELITE® and rinsed with methanol. The filtrate was concentrated in vacuo, dissolved in EtOAc and water. The layers were separated, and the aqueous layer was extracted with EtOAc (6×). The aqueous layer was basified by NaHCO$_3$ (s) and extracted with EtOAc (3×). The organic layers were combined, dried over MgSO$_4$, and concentrated in vacuo to give the desired product (0.7121 g, 1.337 mmol, 86% yield) as a tan solid.

5. 4-(3-(Benzyloxycarbonylamino)-2-methylphenyl)-6-morpholino-9H-pyrido[3,4-b]indole-1-carboxylic acid

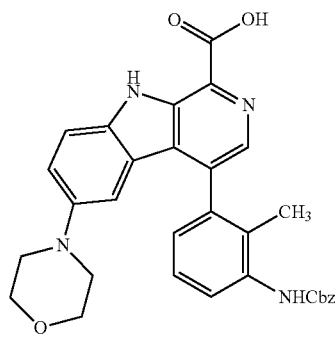

To a light orange, homogeneous solution of ethyl 4-(3-(benzyloxycarbonylamino)-2-methylphenyl)-6-morpholino-9H-pyrido[3,4-b]indole-1-carboxylate (0.1705 g, 0.302 mmol) in methanol (3.59 mL) and THF (10.78 mL) was added LiOH (0.029 g, 1.208 mmol) in water (5.44 µL, 0.302 mmol). After 1.5 hr, the reaction was concentrated in vacuo. Water was added to the residue and acidified to pH ~6 with 1 N aqueous HCl. The insoluble material was filtered and dried over Drierite to give the desired product (0.14098 g, 0.263 mmol, 87% yield) as an orange solid.

4. Ethyl 4-(3-(benzyloxycarbonylamino)-2-methylphenyl)-6-morpholino-9H-pyrido[3,4-b]indole-1-carboxylate

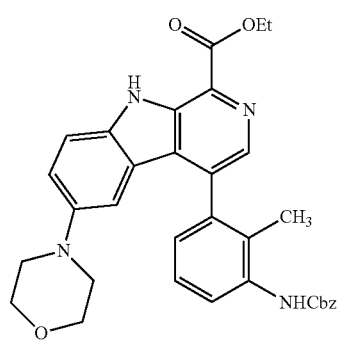 [SMILES: CCOC(=O)c1ncc(-c2cccc(NC(=O)OCc3ccccc3)c2C)c2c1[nH]c1ccc(N3CCOCC3)cc12]

To a solution of benzyl 3-(2-amino-1-(5-morpholino-1H-indol-3-yl)ethyl)-2-methylphenylcarbamate (0.713 g, 1.471 mmol) and 50% ethyl 2-oxoacetate (0.583 mL, 2.94 mmol)/toluene in 1,4-dioxane (61.3 mL) was added 4 N hydrochloric acid/1,4-dioxane (0.736 mL, 2.94 mmol)/dioxane under nitrogen. After stirring overnight, more 50% ethyl 2-oxoacetate (0.583 mL, 2.94 mmol) was added. After 2 hr, the reaction was heated to 40° C. After another 2 hr, the reaction was cooled to room temperature, concentrated in vacuo, and dissolved in water (50 mL) and EtOAc (50 mL). The mixture was basified with saturated NaHCO$_3$ solution to pH ~10. The layers were separated and the aqueous layer was extracted with EtOAc (3×50 mL). The organic layers were combined, washed with brine, dried over MgSO$_4$, and concentrated in vacuo to give crude product used in subsequent step. This was added to 10% Pd/C (0.377 g, 0.354 mmol) in p-xylene (39.4 mL), and the reaction was heated at 125° C. After 9 h, the reaction was cooled to room temperature, filtered through a wad of CELITE®, rinsed with EtOAc, and the filtrate was concentrated in vacuo. The residue was dissolved in EtOAc (100 mL), washed with brine (25 mL), dried over MgSO$_4$, and concentrated in vacuo. The residue was purified by flash chromatography using an ISCO 40 g column eluting with 0-50% EtOAc/CH$_2$Cl$_2$ to give the desired product (0.1558 g, 0.276 mmol, 23.4% yield) as a light orange foam.

6. Benzyl 3-(1-carbamoyl-6-morpholino-9H-pyrido[3,4-b]indol-4-yl)-2-methylphenylcarbamate

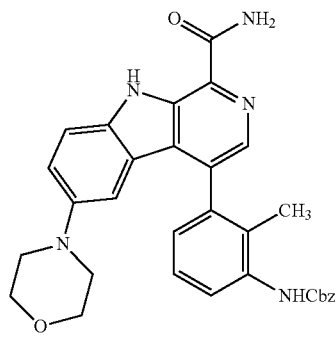 [SMILES: Cc1c(NC(=O)OCc2ccccc2)cccc1-c1cnc(C(N)=O)c2[nH]c3ccc(N4CCOCC4)cc3c12]

A solution of 4-(3-(benzyloxycarbonylamino)-2-methylphenyl)-6-morpholino-9H-pyrido[3,4-b]indole-1-carboxylic acid (0.1408 g, 0.262 mmol), ammonium chloride (0.056 g, 1.050 mmol), BOP (0.151 g, 0.341 mmol), DIPEA (0.220 mL, 1.260 mmol) and N-methylmorpholine (0.113 mL, 1.023 mmol) in DMF (2.187 mL) was stirred for 1 hr. Water (22 mL) was added, and the precipitate was filtered, washed with water, dried over Drierite to give the desired product (0.1277 g, 0.231 mmol, 88% yield) as a light tan solid.

7. 4-(3-Amino-2-methylphenyl)-6-morpholino-9H-pyrido[3,4-b]indole-1-carboxamide

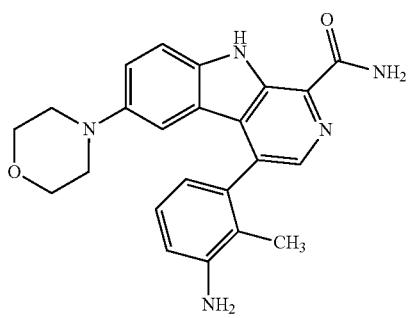 [SMILES: Cc1c(N)cccc1-c1cnc(C(N)=O)c2[nH]c3ccc(N4CCOCC4)cc3c12]

A solution of benzyl 3-(1-carbamoyl-6-morpholino-9H-pyrido[3,4-b]indol-4-yl)-2-methylphenylcarbamate (0.125 g, 0.233 mmol) and 10% Pd/C (0.025 g, 0.023 mmol) in methanol (8.75 mL) and THF (2.92 mL) was stirred under a hydrogen balloon. After 1 hr, the reaction was flushed with nitrogen, filtered through a pad of CELITE®, rinsed with MeOH. The filtrate was concentrated in vacuo, dissolved in CH$_2$Cl$_2$ (100 mL), dried over MgSO$_4$, and concentrated in vacuo to give the desired product (0.0786 g, 0.196 mmol, 84% yield) as a light tan solid.

8. 4-(2-Methyl-3-(4-methylbenzamido)phenyl)-6-morpholino-9H-pyrido[3,4-b]indole-1-carboxamide To a solution of 4-(3-amino-2-methylphenyl)-6-morpholino-9H-pyrido[3,4-b]indole-1-carboxamide (0.0287 g, 0.071 mmol) and 4-methylbenzoyl chloride (0.013 g, 0.086 mmol) in dichloromethane (0.953 mL) under nitrogen was added pyridine (0.012 mL, 0.143 mmol). The vial was sealed and stirred at 40° C. After 15 min, the reaction was cooled to room temperature and concentrated in vacuo. It was diluted with MeOH (1 mL) and purified by reverse phase HPLC. The appropriate fractions were combined, basified with NaHCO$_3$ (solid), and concentrated in vacuo. It was extracted with CH$_2$Cl$_2$ (3×). The organic layers were combined, dried over Na$_2$SO$_4$, and concentrated in vacuo to give the desired product (0.0192 g, 0.037 mmol, 51.7% yield) as a light yellow solid. LC/MS (M+H)=520.25; $^1$H NMR (400 MHz, DMSO-d$_6$) δ ppm 11.56 (s, 1H), 10.00 (s, 1H), 8.31 (d, J=2.2 Hz, 1H), 8.15 (s, 1H), 7.92 (s, 1H), 7.90 (s, 1H), 7.75 (d, J=2.0 Hz, 1H), 7.70 (d, J=8.80 Hz, 1H), 7.55 (d, J=7.0 Hz, 1H), 7.45 (t, J=7.7 Hz, 1H), 7.35 (s, 1H), 7.33 (s, 1H), 7.25-7.32 (m, 1H), 6.53 (d, J=2.2 Hz, 1H), 3.68 (m, 4H), 2.80-2.91 (m, 4H), 2.38 (s, 3H), 1.94 (s, 3H).

EXAMPLE 28

4-(3-(4-(Dimethylamino)benzamido)-2-fluorophenyl)-7-morpholino-9H-pyrido[3,4-b]indole-1-carboxamide

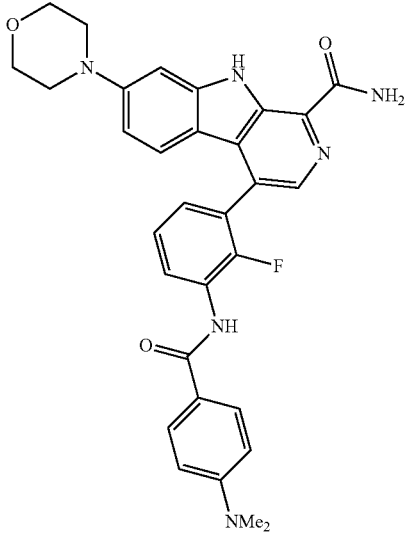 [SMILES: CN(C)c1ccc(C(=O)Nc2cccc(-c3cnc(C(N)=O)c4[nH]c5cc(N6CCOCC6)ccc5c34)c2F)cc1]

1. N-(3-Cyano-2-fluorophenyl)-4-(dimethylamino)benzamide

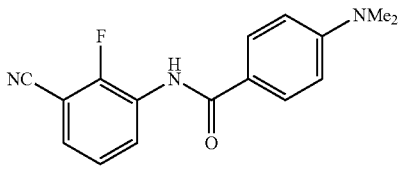 [SMILES: CN(C)c1ccc(C(=O)Nc2cccc(C#N)c2F)cc1]

To a mixture of 3-amino-2-fluorobenzonitrile (2.24 g, 16.46 mmol) and 4-(dimethylamino)benzoyl chloride (3.46 g, 18.84 mmol) in 1,2-dichloroethane (50 mL) at rt was added pyridine (0.891 mL, 11.02 mmol). The resulting mixture was heated at 70° C. for 5 hr. On cooling to room temperature, the mixture was diluted with ethyl acetate (250 mL), washed with water (5×60 mL) and brine (60 mL), and dried over anhydrous MgSO$_4$. The organic solution was concentrated under vacuum, and the residue was subjected to ISCO (2×330 g silica gel, 25-50% ethyl acetate/hexane) to afford the desired product (4.11 g, 14.51 mmol, 88% yield) as a white solid.

2. 4-(Dimethylamino)-N-(2-fluoro-3-formylphenyl)benzamide

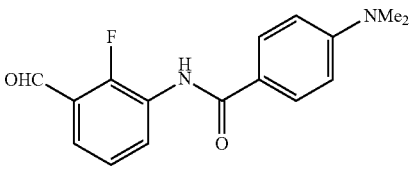 [SMILES: CN(C)c1ccc(C(=O)Nc2cccc(C=O)c2F)cc1]

To a solution of N-(3-cyano-2-fluorophenyl)-4-(dimethylamino)benzamide (2.18 g, 7.70 mmol) in tetrahydrofuran (150 mL) at −78° C. was added DIBAL-H (23.09 mL, 23.09 mmol) over 20 min. The mixture was stirred at −78° C. for 1 h before it was allowed to warm to room temperature and stirred at room temperature for 4 hr. The mixture was poured into ice/water (600 mL) and stirred at room temperature for 30 min. The mixture was extracted with CH₂Cl₂ (4×100 mL). The combined extract was filtered through CELITE®, washed with brine (80 mL), and dried over anhydrous MgSO₄. Evaporation of the solvent under vacuum provided a crude product (1.83 g) as a pale yellow solid. This product was used in the next step without further purification.

3. (E)-4-(Dimethylamino)-N-(2-fluoro-3-(2-nitrovinyl)phenyl)benzamide

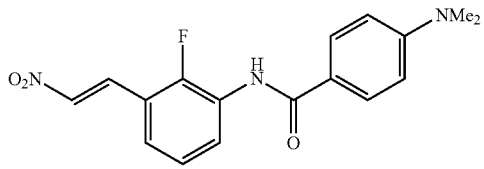 [SMILES: CN(C)c1ccc(C(=O)Nc2cccc(/C=C/[N+](=O)[O-])c2F)cc1]

A mixture of 4-(dimethylamino)-N-(2-fluoro-3-formylphenyl)benzamide (1.83 g, the crude product from previous step), nitromethane (0.859 mL, 15.98 mmol), and ammonium acetate (1.232 g, 15.98 mmol) in acetic acid (25 mL, 52.4 mmol) was heated at 100° C. for 2 hr. Acetic acid was removed under vacuum. To the residue was added CH₂Cl₂ (60 mL) and water (60 mL) and the mixture was basified with solid Na₂CO₃ to pH 9. The organic layer was separated, and the aqueous layer was extracted with CH₂Cl₂ (3×50 mL). The combined organic phase was washed with saturated NaHCO₃ solution (40 mL) and brine (40 mL), and dried over anhydrous MgSO₄. The desired product (0.786 g, 31% over 2 steps) was isolated by ISCO (120 g silica gel, 0-5% ethyl acetate/CH₂Cl₂) as a red solid.

4. 4-(Dimethylamino)-N-(2-fluoro-3-(1-(6-morpholino-1H-indol-3-yl)-2-nitroethyl)phenyl)benzamide

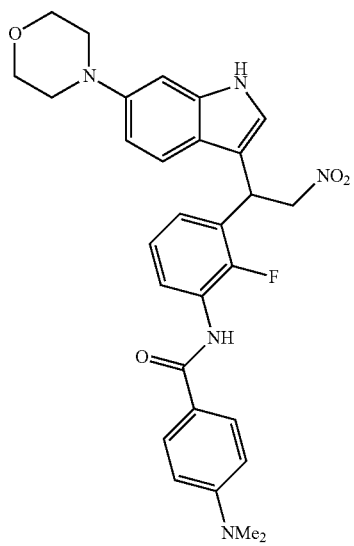

A mixture of 4-(1H-indol-6-yl)morpholine (0.393 g, 1.943 mmol), (E)-4-(dimethylamino)-N-(2-fluoro-3-(2-nitrovinyl)phenyl)benzamide (0.400 g, 1.215 mmol), and tris(trifluoromethylsulfonyloxy)ytterbium (0.075 g, 0.121 mmol) in acetonitrile (25 mL) was heated at 50° C. for 20 h. The acetonitrile was removed under vacuum. The residue was diluted with ethyl acetate (180 mL), washed with 10% NaHCO₃ solution (2×40 mL) and brine (40 mL), and dried over anhydrous MgSO₄. The desired product (0.412 g, 0.750 mmol, 61.8% yield) was isolated with ISCO (80 g silica gel, 30-80% ethyl acetate/hexane) as a pale yellow solid.

5. N-(3-(2-Amino-1-(6-morpholino-1H-indol-3-yl)ethyl)-2-fluorophenyl)-4-(dimethylamino)benzamide

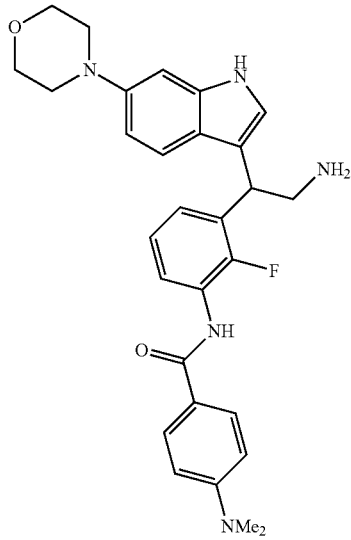 [SMILES: CN(C)c1ccc(C(=O)Nc2cccc(C(C[N+](=O)[O-])c3c[nH]c4cc(N5CCOCC5)ccc34)c2F)cc1]

A mixture of 4-(dimethylamino)-N-(2-fluoro-3-(1-(6-morpholino-1H-indol-3-yl)-2-nitroethyl)phenyl)benzamide (0.388 g, 0.730 mmol) and Raney Ni (a small amount) in MeOH (35 mL) was treated with hydrogen at 55 psi a Parr shaker apparatus for 3 hr. The catalyst was removed by suction filtration. The filtrate was concentrated under vacuum, diluted with CH₂Cl₂ (100 mL), washed with brine (25 mL) and dried over anhydrous MgSO₄. Removal of solvent under vacuum provided the desired product (0.321 g, 0.599 mmol, 82% yield) as an off-white solid.

6. Ethyl 4-(3-(4-(dimethylamino)benzamido)-2-fluorophenyl)-7-morpholino-9H-pyrido[3,4-b]indole-1-carboxylate

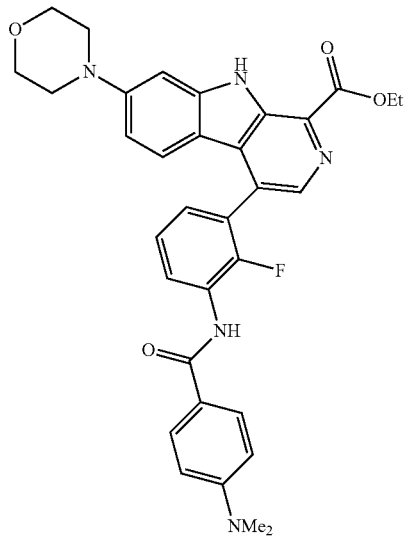 [SMILES: CCOC(=O)c1ncc(-c2cccc(NC(=O)c3ccc(N(C)C)cc3)c2F)c2c1[nH]c1cc(N3CCOCC3)ccc12]

To a solution of N-(3-(2-amino-1-(6-morpholino-1H-indol-3-yl)ethyl)-2-fluorophenyl)-4-(dimethylamino)benzamide (0.321 g, 0.640 mmol) and ethyl 2-oxoacetate in toluene (50%) (0.279 mL, 1.408 mmol) in 1,4-dioxane (30 mL) at room temperature was added hydrogen chloride (4 N in 1,4-dioxane) (0.480 mL, 1.92 mmol). The mixture turned to heterogeneous and it was stirred room temperature for 16 hr. The volatiles were removed under vacuum. The residue was diluted with water (30 mL), basified with NaHCO$_3$ solution to pH 10, and extracted with ethyl acetate (4×40 mL). The combined extract was washed with brine (30 ml), dried over anhydrous MgSO$_4$, and concentrated to dryness under vacuum. To the residue were added 1,4-dioxane (1 mL) and p-xylem (15 mL) and 10% Pd/C (0.4 g), and the mixture was heated at 140° C. under an ambient atmosphere for 4.5 hr. The solid phase was removed by suction filtration. The filtrate was diluted with ethyl acetate (120 ml), washed with brine (25 ml), and dried over anhydrous MgSO$_4$. Removal of solvent under vacuum, followed by triturating with Et$_2$O (8 mL), provided the desired product (0.144 g, 0.238 mmol, 37.1% yield) as a tan solid.

7. 4-(3-(4-(Dimethylamino)benzamido)-2-fluorophenyl)-7-morpholino-9H-pyrido[3,4-b]indole-1-carboxylic acid

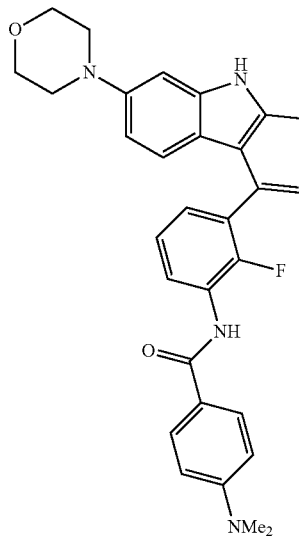

To a suspension of ethyl 4-(3-(4-(dimethylamino)benzamido)-2-fluorophenyl)-7-morpholino-9H-pyrido[3,4-b]indole-1-carboxylate (0.138 g, 0.237 mmol) in methanol (4 mL) at room temperature was added sodium hydroxide (1.068 mL, 1.068 mmol). The mixture was heated at reflux for 45 min. The methanol was removed under vacuum. To the residue was added water (5 mL), and the mixture was acidified with 1 N HCl to pH 5. The insoluble product (0.110 g, 0.199 mmol, 84% yield) was collected as a tan solid with suction filtration and dried at 50° C. under vacuum.

8. 4-(3-(4-(Dimethylamino)benzamido)-2-fluorophenyl)-7-morpholino-9H-pyrido[3,4-b]indole-1-carboxamide A mixture of 4-(3-(4-(dimethylamino)benzamido)-2-fluorophenyl)-7-morpholino-9H-pyrido[3,4-b]indole-1-carboxylic acid (105 mg, 0.190 mmol), ammonium chloride (40.6 mg, 0.759 mmol), N,N-diisopropylethylamine (0.159 mL, 0.910 mmol), BOP (109 mg, 0.247 mmol), N-methylmorpholine (0.081 mL, 0.740 mmol) in DMF (0.5 mL) was stirred at room temperature for 1.5 hr. The mixture was diluted with MeOH (4 mL), divided into three portions, and purified by reverse phase HPLC. The correct fractions were concentrated under vacuum and basified with saturated NaHCO$_3$ solution to pH 10. The precipitating product (24.7 mg, 0.044 mmol, 23.09% yield) was collected as a yellow solid by suction filtration and dried at 50° C. under vacuum. LCMS (M+H)$^+$=553.32. $^1$H NMR (500 z, DMSO-d$_6$) δ: 11.52 (s, 1H), 9.86 (s, 1H), 8.31 (s, 1H), 8.20 (s, 1H), 7.90 (d, J=9.0 Hz, 2H), 7.84 (m, 1H), 7.76 (s, 1H), 7.45-7.40 (m, 2H), 7.32 (d, J=8.0 Hz, 1H), 7.29 (d, J=2.0 Hz, 1H), 6.86 (dd, J1=9.0 Hz, J2=2.0 Hz, 1H), 6.77 (d, J=9.0 Hz, 2H), 3.79-3.77 (m, 4H), 3.22-3.19 (m, 4H), 2.51 (m, 6H).

EXAMPLE 29

7-(2-Hydroxypropan-2-yl)-4-(2-methyl-3-(4-oxoquinazolin-3(4H)-yl)phenyl)-9H-pyrido[3,4-b]indole-1-carboxamide

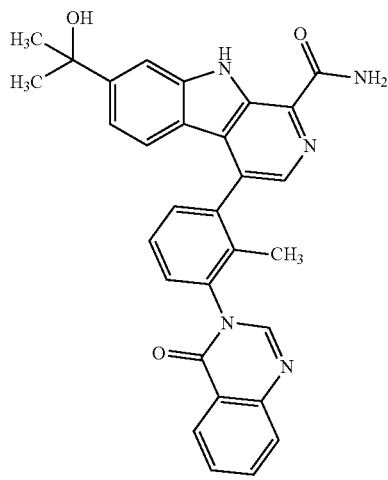 [SMILES: Cc1c(-c2cnc(C(N)=O)c3[nH]c4cc(C(C)(C)O)ccc4c23)cccc1-n1cnc2ccccc2c1=O]

1. Benzyl 3-(1-(6-bromo-1H-indol-3-yl)-2-nitroethyl)-2-methylphenylcarbamate

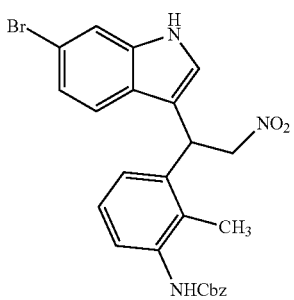

A mixture of 6-bromo-1H-indole (2.82 g, 14.41 mmol) and (E)-benzyl 2-methyl-3-(2-nitrovinyl)phenylcarbamate (3.0 g, 9.61 mmol) was dissolved in THF (50 mL) and NMP (0.5 mL). The THF was removed under vacuum, and the residue was heated at 120° C. for 16 hr and then at 125° C. for 6 hr. Upon cooling to room temperature, the mixture was dissolved in THF (50 mL). The resulting solution was diluted with ethyl acetate (250 mL), washed with water (3×80 mL) and brine (60 mL), and dried over anhydrous MgSO$_4$. The desired product (3.00 g, 5.90 mmol, 61.4% yield) was isolated as a beige solid by ISCO (300 g silica gel, 25-60 ethyl acetate/hexane).

2. Benzyl 3-(2-amino-1-(6-bromo-1H-indol-3-yl)ethyl)-2-methylphenylcarbamate

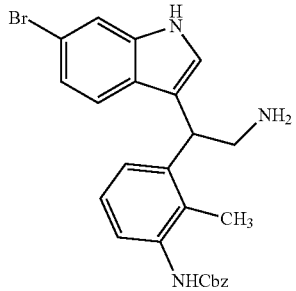 [SMILES: Cc1c(NC(=O)OCc2ccccc2)cccc1C(C[N+](=O)[O-])c1c[nH]c2cc(Br)ccc12]

To a mixture of benzyl 3-(1-(6-bromo-1H-indol-3-yl)-2-nitroethyl)-2-methylphenylcarbamate (3.00 g, 5.90 mmol) and ammonium chloride (4.42 g, 83 mmol) in methanol (100 mL) and tetrahydrofuran (100 mL) at 0° C. was added zinc dust (5.40 g, 83 mmol) in one portion. The mixture was stirred at room temperature for 7 hr, then diluted with ethyl acetate (100 mL) and filtered through CELITE®. The filtrate was concentrated under vacuum. To the residue was added water (60 mL), and the mixture was extracted with ethyl acetate (4×80 mL). The combined extract was washed with brine (60 mL) and dried over anhydrous MgSO₄. Removal of solvent under vacuum provided the desired product (2.82 g, 5.89 mmol, 100% yield) as a beige solid.

3. Ethyl 4-(3-(benzyloxycarbonylamino)-2-methylphenyl)-7-bromo-9H-pyrido[3,4-b]indole-1-carboxylate

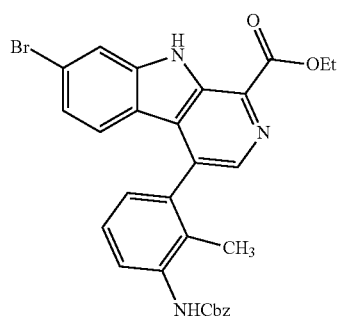 [SMILES: CCOC(=O)c1ncc(-c2cccc(NC(=O)OCc3ccccc3)c2C)c2c1[nH]c1cc(Br)ccc12]

To a mixture of benzyl 3-(2-amino-1-(6-bromo-1H-indol-3-yl)ethyl)-2-methylphenylcarbamate (2.320 g, 4.85 mmol) and 4 angstrom molecular sieves (powder, activated, <5 mesh, 1.80 g) in tetrahydrofuran (100 mL) at room temperature was added ethyl 2-oxoacetate in toluene (1.923 mL, 9.70 mmol), followed by hydrogen chloride in 1,4-dioxane (1.334 mL, 5.33 mmol). The mixture was stirred at room temperature for 24 h. The solid phase was removed by suction filtration through CELITE®, and the filtrate was concentrated under vacuum. The residue was diluted with water (60 mL), basified with saturated NaHCO₃ solution, and extracted with ethyl acetate (3×80 mL). The combined extract was washed with brine (60 mL) and dried over anhydrous MgSO₄. The solvent was removed under vacuum. To the residue was added p-xylene (200 mL) and 10% Pd/C (1.5 g), and the mixture was heated under atmosphere at 125° C. for 16 hr. The solid phase was removed by suction filtration through CELITE®. The filtrate was concentrated under vacuum, and the residue was purified by ISCO (220 g silica gel, solid loading, 20-50% ethyl acetate/hexane) to provide the desired product (0.977 g, 36% yield) as a beige solid.

4. 4-(3-(Benzyloxycarbonylamino)-2-methylphenyl)-7-bromo-9H-pyrido[3,4-b]indole-1-carboxylic acid

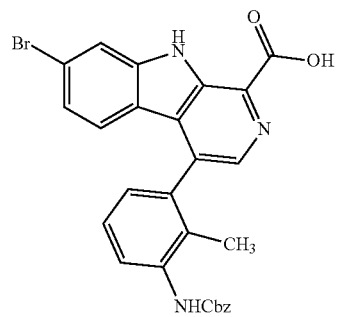 [SMILES: Cc1c(NC(=O)OCc2ccccc2)cccc1-c1cnc(C(=O)O)c2[nH]c3cc(Br)ccc3c12]

To a solution of ethyl 4-(3-(benzyloxycarbonylamino)-2-methylphenyl)-7-bromo-9H-pyrido[3,4-b]indole-1-carboxylate (1.338 g, 2.396 mmol) in tetrahydrofuran (48 mL) and methanol (16 mL) at room temperature was added a solution of lithium hydroxide hydrate (0.402 g, 9.58 mmol) in water (10 mL). The resulting solution was stirred at room temperature for 1.5 hr, and then concentrated under vacuum to a volume of about 10 mL. The residue was diluted with water (5 mL) and neutralized with 1 N HCl solution to pH 5-6. The precipitating product (1.177 g, 2.219 mmol, 93% yield) was collected as a beige solid by suction filtration and dried over Drierite under vacuum.

5. Benzyl 3-(7-bromo-1-carbamoyl-9H-pyrido[3,4-b]indol-4-yl)-2-methylphenylcarbamate

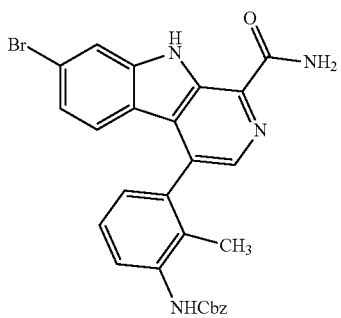 [SMILES: Cc1c(NC(=O)OCc2ccccc2)cccc1-c1cnc(C(N)=O)c2[nH]c3cc(Br)ccc3c12]

A mixture of 4-(3-(benzyloxycarbonylamino)-2-methylphenyl)-7-bromo-9H-pyrido[3,4-b]indole-1-carboxylic acid (1.174 g, 2.214 mmol), ammonium chloride (0.474 g, 8.85 mmol), N,N-diisopropylethylamine (1.856 mL, 10.63 mmol), BOP (1.273 g, 2.88 mmol), and N-methylmorpholine (0.949 mL, 8.63 mmol) in DMF (Volume: 10 mL) was stirred at room temperature for 2 hr. To the mixture was added water (120 mL), and the resulting mixture was stirred at room temperature for 20 min. The precipitating product (1.23 g) was collected as a beige solid by suction filtration and dried over Drierite at 50° C. This product was 80% pure, but was used in the next step without further purification.

6. 4-(3-Amino-2-methylphenyl)-7-bromo-9H-pyrido[3,4-b]indole-1-carboxamide

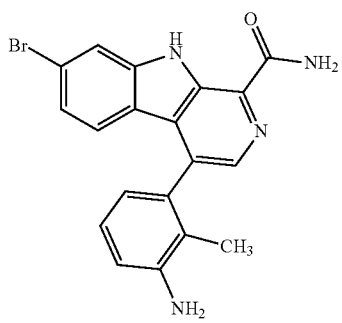 [SMILES: Cc1c(N)cccc1-c1cnc(C(N)=O)c2[nH]c3cc(Br)ccc3c12]

To a solution of benzyl 3-(7-bromo-1-carbamoyl-9H-pyrido[3,4-b]indol-4-yl)-2-methylphenylcarbamate (0.65 g, crude from the previous step) in acetonitrile (80 mL) at 0° C. was added iodotrimethylsilane (0.67 mL, 4.91 mmol) dropwise. The mixture was stirred at room temperature for 1.5 hr, and then concentrated under vacuum. To the residue was added diethylamine (2 mL) and ethyl acetate (150 ml). The mixture was washed with water (2×40 mL) and brine (40 mL), and dried over anhydrous MgSO$_4$. The desired product (0.243 g, 52.6% yield over two steps) was isolated as a beige solid by ISCO (40 g silica gel, solid loading, 40-70% ethyl acetate/hexane).

7. 7-Bromo-4-(2-methyl-3-(4-oxoquinazolin-3(4H)-yl)phenyl)-9H-pyrido[3,4-b]indole-1-carboxamide

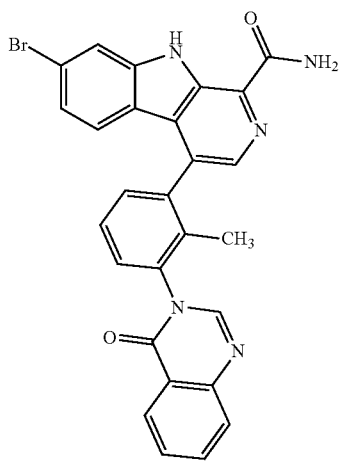 [SMILES: Cc1c(-c2cnc(C(N)=O)c3[nH]c4cc(Br)ccc4c23)cccc1-n1cnc2ccccc2c1=O]

A mixture of 4-(3-amino-2-methylphenyl)-7-bromo-9H-pyrido[3,4-b]indole-1-carboxamide (0.243 g, 0.615 mmol), 1H-benzo[d][1,3]oxazine-2,4-dione (0.251 g, 1.537 mmol), tris(nitrooxy)lanthanum, 6H$_2$O (0.080 g, 0.184 mmol), and trimethoxymethane (2.020 mL, 18.44 mmol) in tetrahydrofuran (2 mL) was heated at 90° C. for 16 hr. The mixture was diluted with ethyl acetate (120 mL), washed with water (2×30 mL) and brine (30 mL), and dried over anhydrous MgSO$_4$. The desired product (0.198 g, 0.378 mmol, 61.4% yield) was isolated as a yellow solid by ISCO (40 g silica gel, solid loading, 40-80% ethyl acetate/hexane).

8. 7-Acetyl-4-(2-methyl-3-(4-oxoquinazolin-3(4H)-yl)phenyl)-9H-pyrido[3,4-b]indole-1-carboxamide

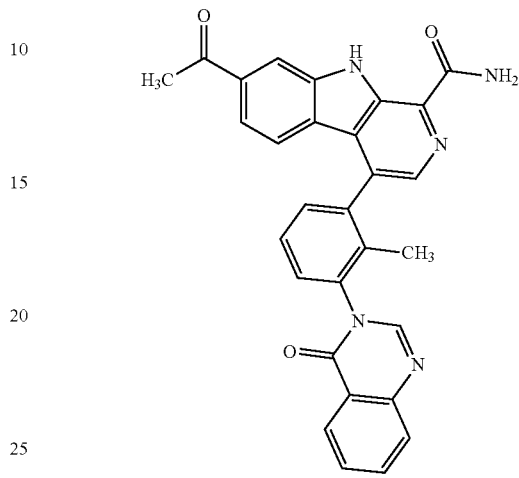

A mixture of 7-bromo-4-(2-methyl-3-(4-oxoquinazolin-3(4H)-yl)phenyl)-9H-pyrido[3,4-b]indole-1-carboxamide (0.198 g, 0.378 mmol), tributyl(1-ethoxyvinyl)stannane (0.299 mL, 0.906 mmol), bis(triphenylphosphine)palladium(II) chloride (0.037 g, 0.053 mmol), triethylamine (0.068 mL, 0.491 mmol) in 1,4-dioxane (Volume: 15 mL) was heated at 95° C. for 24 hr. No reaction occurred. The starting bromo compound remained unchanged. Upon cooling to room temperature, some yellow precipitate formed. The clear solution was transferred to a pressure tube. Additional tributyl(1-ethoxyvinyl)stannane (0.6 mL, 1.82 mmol), bis(triphenylphosphine)palladium(II) chloride (0.080 g, 0.114 mmol), and triethylamine (0.11 mL, 0.789 mmol) were added. The mixture was heated at 125° C. for 16 hr. Upon cooling to room temperature, the reaction mixture was filtered through CELITE®, and the filtrate was concentrated under vacuum. The residue was diluted with THF (30 mL) and stirred with 1 N HCl solution (10 mL) at room temperature for 2 hr. The solution was concentrated under vacuum, basified with 1 N NaOH solution, and extracted with ethyl acetate (3×40 mL). The combined extract was dried over anhydrous MgSO$_4$. The desired product (90 mg, 0.185 mmol, 48.9% yield) was isolated as a yellow solid by ISCO (24 g silica gel, solid loading, 60-90% ethyl acetate/hexane).

9. 7-(2-Hydroxypropan-2-yl)-4-(2-methyl-3-(4-oxoquinazolin-3(4H)-yl)phenyl)-9H-pyrido[3,4-b]indole-1-carboxamide To a solution of 7-acetyl-4-(2-methyl-3-(4-oxoquinazolin-3(4H)-yl)phenyl)-9H-pyrido[3,4-b]indole-1-carboxamide (45 mg, 0.092 mmol) in tetrahydrofuran (10 mL) at 0° C. was added methylmagnesium bromide (0.154 mL, 0.462 mmol). The mixture was stirred at room temperature for 30 min. Additional methylmagnesium bromide (0.100 mL, 0.300 mmol) was added at 0° C., and the mixture was stirred at room temperature for another 30 min. The reaction was quenched with water (10 mL) and the mixture was extracted with ethyl acetate (3×30 mL). The combined extract was washed with brine (25 mL) and dried over anhydrous MgSO$_4$. The organic solution was concentrated under vacuum, and the residue was purified by reverse phase HPLC. The correct fraction was concentrated under vacuum, basified with saturated NaHCO$_3$ solution, and extracted with ethyl acetate (3×35 mL). The combined extract was washed with brine (30 mL) and dried over anhydrous MgSO$_4$. Removal of solvent under vacuum provided the desired product (20.9 mg, 0.041 mmol, 44.1% yield) as a pale yellow solid. LCMS (M+H)$^+$=504.0. $^1$H NMR (500 MHz, DMSO-d$_6$) (recognizable peaks for the major atropisomer) δ: 11.74 (s, 1H), 8.44 (s, 1H), 8.23 (s, 1H), 8.30 (s, 1H), 7.98 (m, 1H), 7.92 (m, 1H), 7.80 (m, 1H), 7.75 (m, 1H), 7.58 (m, 1H), 7.24 (m, 1H), 5.12 (s, 1H), 1.83 (s, 3H), 1.50 (s, 6H).

EXAMPLE 30

7-(1-Hydroxyethyl)-4-(2-methyl-3-(4-oxoquinazolin-3(4H)-yl)phenyl)-9H-pyrido[3,4-b]indole-1-carboxamide

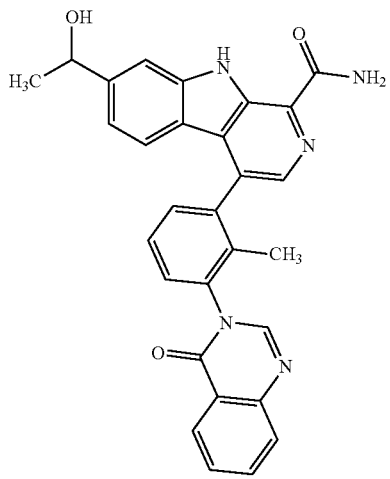 [SMILES: Cc1c(-c2cnc(C(N)=O)c3[nH]c4cc(C(C)O)ccc4c23)cccc1-n1cnc2ccccc2c1=O]

To a cloudy solution of 7-acetyl-4-(2-methyl-3-(4-oxoquinazolin-3(4H)-yl)phenyl)-9H-pyrido[3,4-b]indole-1-carboxamide (45 mg, 0.092 mmol) in tetrahydrofuran (4 mL) and methanol (12 mL) at 0° C. was added sodium borohydride (17.46 mg, 0.462 mmol) in one portion. The mixture was stirred at room temperature for 20 min and then the reaction was quenched with ice cold water (15 mL). The resulting mixture was extracted with ethyl acetate (3×30 mL). The combined extract was washed with brine (25 mL) and dried over anhydrous MgSO$_4$. The organic solution was concentrated under vacuum, and the residue was purified by reverse phase HPLC. The correct fraction was concentrated under vacuum, basified with saturated NaHCO$_3$ solution, and extracted with dichloromethane (3×35 mL). The combined extract was washed with brine (30 mL) and dried over anhydrous MgSO$_4$. Removal of solvent under vacuum provided the desired product (10.9 mg, 0.022 mmol, 23.5% yield) as a white solid. LCMS (M+H)$^+$=490.1. $^1$H NMR (500 MHz, DMSO-d$_6$) (recognizable peaks for the major atropisomer) δ: 11.78 (s, 1H), 8.44 (s, 1H), 8.30 (s, 1H), 8.28 (dd, J1=8.0 Hz, J2=1.4 Hz, 1H), 8.25 (s, 1H), 8.24 (s, 1H), 7.30 (m, 1H), 7.12 (m, 1H), 5.25 (s, 1H), 4.85 (m, 1H), 1.82 (s, 3H),

EXAMPLE 31

7-(1-Hydroxyethyl)-4-(3-(6-methoxy-1-oxoisoindolin-2-yl)-2-methylphenyl)-9H-pyrido[3,4-b]indole-1-carboxamide

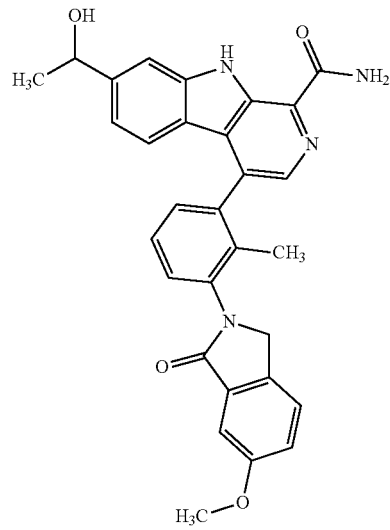 [SMILES: COc1ccc2c(c1)C(=O)N(c1cccc(-c3cnc(C(N)=O)c4[nH]c5cc(C(C)O)ccc5c34)c1C)C2]

1. 2-((3-(7-Bromo-1-carbamoyl-9H-pyrido[3,4-b]indol-4-yl)-2-methylphenylamino)methyl)-5-methoxybenzoic acid

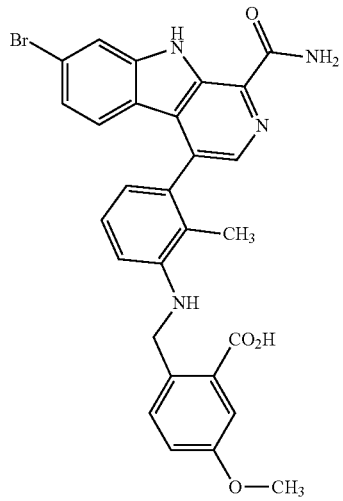 [SMILES: COc1ccc(CNc2cccc(-c3cnc(C(N)=O)c4[nH]c5cc(Br)ccc5c34)c2C)c(C(=O)O)c1]

A mixture of 4-(3-amino-2-methylphenyl)-7-bromo-9H-pyrido[3,4-b]indole-1-carboxamide (0.184 g, 0.466 mmol), 2-formyl-5-methoxybenzoic acid (0.210 g, 1.164 mmol), sodium triacetoxyborohydride (0.296 g, 1.397 mmol), and acetic acid (0.067 mL, 1.164 mmol) in dichloromethane (14 mL) and tetrahydrofuran (14 mL) was stirred at room temperature for 16 hr. The reaction was quenched with water (30 mL) and the mixture was extracted with ethyl acetate (3×40 mL). The combined extract was washed with brine (30 ml) and dried over anhydrous MgSO$_4$. Removal of solvent under vacuum provided the crude desired product (0.425 g, 0.760 mmol, 163% yield) as a beige solid. The crude product was used in the next step without further purification.

2. 7-Bromo-4-(3-(6-methoxy-1-oxoisoindolin-2-yl)-2-methylphenyl)-9H-pyrido[3,4-b]indole-1-carboxamide

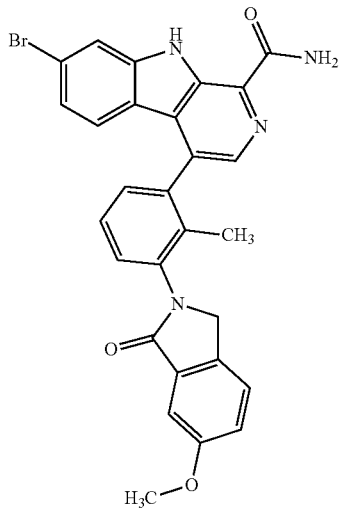 [SMILES: COc1ccc2c(c1)C(=O)N(c1cccc(-c3cnc(C(N)=O)c4[nH]c5cc(Br)ccc5c34)c1C)C2]

A mixture of 2-((3-(7-bromo-1-carbamoyl-9H-pyrido[3,4-b]indol-4-yl)-2-methylphenylamino)methyl)-5-methoxybenzoic acid (0.425 g, the crude product from the previous step), BOP (1.008 g, 2.279 mmol), and N-methylmorpholine (0.752 mL, 6.84 mmol) in DMF (Volume: 5 mL) was stirred at 50° C. for 1 hr. The mixture was diluted with ethyl acetate (100 mL), washed with water (2×25 mL) and brine (25 mL), and dried over anhydrous MgSO$_4$. The desired product (0.198 g, 78% yield over 2 steps), was isolated as a yellow solid by ISCO (40 g silica gel, solid loading, 40-80% ethyl acetate/hexane).

3. 7-Acetyl-4-(3-(6-methoxy-1-oxoisoindolin-2-yl)-2-methylphenyl)-9H-pyrido[3,4-b]indole-1-carboxamide

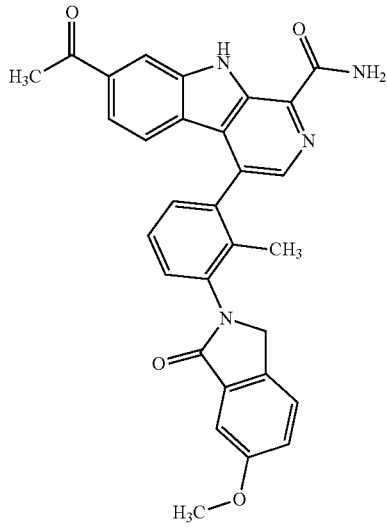 [SMILES: COc1ccc2c(c1)C(=O)N(c1cccc(-c3cnc(C(N)=O)c4[nH]c5cc(C(C)=O)ccc5c34)c1C)C2]

A mixture of 7-bromo-4-(3-(6-methoxy-1-oxoisoindolin-2-yl)-2-methylphenyl)-9H-pyrido[3,4-b]indole-1-carboxamide (0.198 g, 0.366 mmol), tributyl(1-ethoxyvinyl)stannane (0.301 mL, 0.914 mmol), bis(triphenylphosphine)palladium(II) chloride (0.039 g, 0.055 mmol), triethylamine (0.071 mL, 0.512 mmol) in 1,4-Dioxane (12 mL) was heated at 125° C. for 16 hr. Upon cooling to room temperature, the reaction mixture was filtered through CELITE®, and the filtrate was concentrated under vacuum. The residue was diluted with THF (40 mL) and stirred with 1 N HCl solution (10 mL) at 50° C. for 1 hr. The solution was concentrated under vacuum, basified with 1 N NaOH solution, and extracted with ethyl acetate (3×40 mL). The combined extract was dried over anhydrous MgSO$_4$. The desired product (0.112 g, 0.222 mmol, 60.7% yield) was isolated as a pale yellow solid by ISCO (40 g silica gel, solid loading, 50-90% ethyl acetate/hexane).

4. 7-(1-Hydroxyethyl)-4-(3-(6-methoxy-1-oxoisoindolin-2-yl)-2-methylphenyl)-9H-pyrido[3,4-b]indole-1-carboxamide To a cloudy solution of 7-acetyl-4-(3-(6-methoxy-1-oxoisoindolin-2-yl)-2-methylphenyl)-9H-pyrido[3,4-b]indole-1-carboxamide (62 mg, 0.123 mmol) in tetrahydrofuran (5 mL) and methanol (15 mL) at 0° C. was added sodium borohydride (23.25 mg, 0.614 mmol) in one portion. The mixture was stirred at room temperature for 30 min and then the reaction was quenched with ice cold water (15 mL). The resulting mixture was extracted with ethyl acetate (3×30 mL). The combined extract was washed with brine (25 mL) and dried over anhydrous MgSO$_4$. The organic solution was concentrated under vacuum, and the residue was purified by reverse phase HPLC. The correct fraction was concentrated under vacuum, basified with saturated NaHCO$_3$ solution, and extracted with dichloromethane (3×35 mL). The combined extract was washed with brine (30 mL) and dried over anhydrous MgSO$_4$. Removal of solvent under vacuum provided the desired product (24.8 mg, 0.047 mmol, 38.6% yield) as a white solid. LCMS (M+H)$^+$=507.24. $^1$H NMR (500 MHz, DMSO-d$_6$) δ: 11.77 (s, 1H), 8.32 (s, 1H), 8.23 (s, 1H), 7.83 (d, J=11.6 Hz, 1H), 7.75 (s, 1H), 7.67 (d, J=6.9 Hz, 1H), 7.60 (d, J=8.3 Hz, 1H), 7.54 (m, 1H), 7.43 (d, J=7.5 Hz, 1H), 7.32 (m, 1H), 7.27-7.23 (m, 2H), 7.08 (dd, J1=12.9 Hz, J2=8.5 Hz, 1H), 5.26 (m, 1H), 4.85 (m, 1H), 4.96 (d, J=16.9 Hz, 1H), 4.86 (d, J=16.9 Hz, 1H), 3.86 (s, 3H), 1.88 (s, 3H), 1.38 (d, J=6.4 Hz, 3H).

EXAMPLE 32

1-(3-(6-Chloro-1-oxoisoindolin-2-yl)-2-methylphenyl)-7-(2-methoxyethoxy)-5H-pyridazino[4,5-b]indole-4-carboxamide

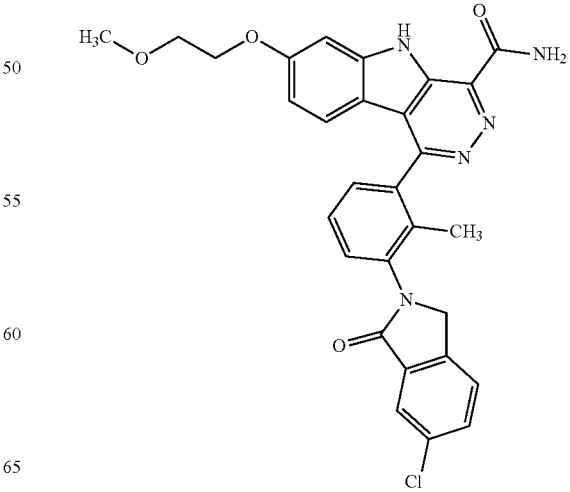

1. Methyl 6-(2-methoxyethoxy)-1H-indole-2-carboxylate

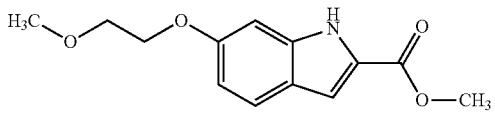

To a light brown, homogeneous solution of methyl 6-hydroxy-1H-indole-2-carboxylate (1.4862 g, 7.77 mmol) and 1-bromo-2-methoxyethane (0.731 mL, 7.77 mmol) in DMF (38.9 mL) under nitrogen was added cesium carbonate (2.53 g, 7.77 mmol). The reaction was heated to 55° C. and stirred overnight. The reaction was cooled to room temperature, diluted with EtOAc (200 mL) and filtered through CELITE®. The filtrate was washed with water (4×50 mL) and brine (2×50 mL), dried over $MgSO_4$, and concentrated in vacuo to give a residue which was purified by flash chromatography using an ISCO 120 g column eluting with 20-60% EtOAc/hexanes. Appropriate fractions were collected and concentrated in vacuo to give desired product (0.8592 g) as a white solid. Mixed fractions were combined and concentrated in vacuo to give a residue which was purified by flash chromatography using an ISCO 80 g column eluting with 20-60% EtOAc/hexanes to give another crop of desired product (0.1673 g) as a white solid.

2. Methyl 6-(2-methoxyethoxy)-3-(2-methyl-3-nitrobenzoyl)-1H-indole-2-carboxylate

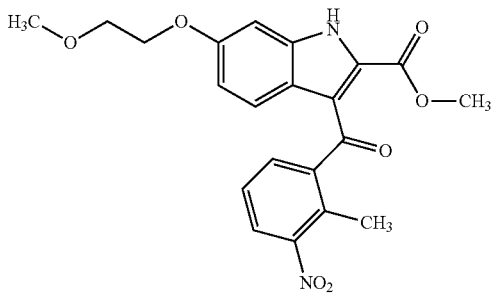

To a homogeneous, colorless solution of methyl 6-(2-methoxyethoxy)-1H-indole-2-carboxylate (0.934 g, 3.75 mmol) in dichloromethane (18.74 mL) at 0° C. under nitrogen was added 1M perchlorostannane/$CH_2Cl_2$ (4.87 mL, 4.87 mmol) over 10 min. After 5 min, the cold bath was removed, and the yellow, heterogeneous solution was stirred to room temperature for 30 min. A solution of 2-methyl-3-nitrobenzoyl chloride (0.897 g, 4.50 mmol) in nitromethane (18.74 mL, previously dried over $MgSO_4$ overnight) was added over 20 min. After 3.25 hr, additional acid chloride (0.350 g) in nitromethane (3 mL) was added to the reaction. Thirty minutes later, the reaction was poured into ice water (50 mL) and stirred for 15 min. It was diluted with EtOAc (150 mL) and washed with water (50 mL), sat. aq. $NaHCO_3$ (50 mL) and brine (25 mL). The organic solution was dried over $MgSO_4$ and concentrated in vacuo to give the desired product (1.6103 g, 3.90 mmol, 104% yield) as a solid.

3. 7-(2-Methoxyethoxy)-1-(2-methyl-3-nitrophenyl)-3H-pyridazino[4,5-b]indol-4(5H)-one

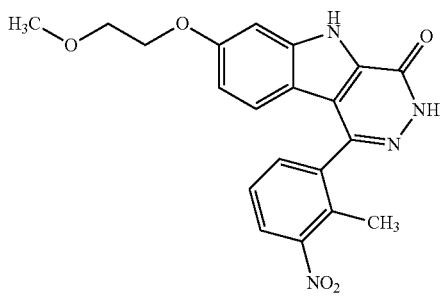 [SMILES: COCCOc1ccc2c(c1)[nH]c1c(=O)[nH]nc(-c3cccc([N+](=O)[O-])c3C)c12]

A yellow, homogeneous solution of methyl 6-(2-methoxyethoxy)-3-(2-methyl-3-nitrobenzoyl)-1H-indole-2-carboxylate (1.546 g, 3.75 mmol) and hydrazine hydrate (0.982 mL, 13.13 mmol) in ethanol (55.1 mL) under nitrogen was refluxed overnight. The reaction was cooled to room temperature and concentrated in vacuo. It was dissolved in EtOAc (150 mL) and washed with water (40 mL) and brine (40 mL), dried over $MgSO_4$, and concentrated in vacuo to give a residue which was purified by flash chromatography using an ISCO 120 g column eluting with 0-100% EtOAc/hexanes. Appropriate fractions were collected and concentrated in vacuo to give the desired product (0.7461 g, 1.892 mmol, 50.4% yield) as a light yellow solid.

4. 4-Chloro-7-(2-methoxyethoxy)-1-(2-methyl-3-nitrophenyl)-5H-pyridazino[4,5-b]indole

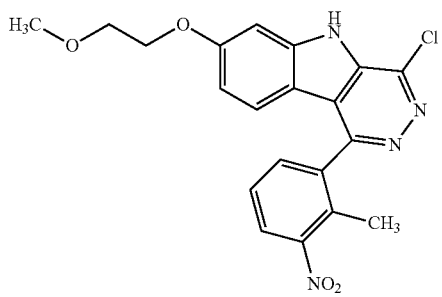 [SMILES: COCCOc1ccc2c(c1)[nH]c1c(Cl)nnc(-c3cccc([N+](=O)[O-])c3C)c12]

A yellow, homogeneous solution of 7-(2-methoxyethoxy)-1-(2-methyl-3-nitrophenyl)-3H-pyridazino[4,5-b]indol-4 (5H)-one (0.2510 g, 0.636 mmol) in phosphoryl trichloride (20 mL, 0.636 mmol) under nitrogen was heated at 100° C. After 1 h, the reaction was cooled to room temperature and concentrated in vacuo. The residue was dissolved in cold EtOAc (250 mL) and was with ice-cold water (40 mL), ice-cold saturated aqueous $NaHCO_3$ (40 mL), ice-cold water (40 mL) and ice-cold brine (40 mL), successively. The organic solution was dried over MgSO₄ and concentrated in vacuo to give the desired product (0.2115 g, 0.512 mmol, 80% yield) as a light orange solid.

5. Methyl 1-(3-amino-2-methylphenyl)-7-(2-methoxyethoxy)-5H-pyridazino[4,5-b]indole-4-carboxylate

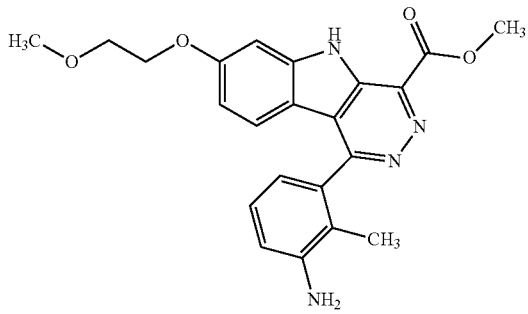

A steel bomb containing a solution of 4-chloro-7-(2-methoxyethoxy)-1-(2-methyl-3-nitrophenyl)-5H-pyridazino[4,5-b]indole (0.5862 g, 1.420 mmol), DPPF (0.118 g, 0.213 mmol), palladium(II) acetate (0.048 g, 0.213 mmol) and sodium acetate (0.233 g, 2.84 mmol) in DMA (10 mL) and methanol (20 mL, 494 mmol) was evacuated and flushed with nitrogen twice. It was then evacuated, filled with CO (g) to 70 psi and heated at 90° C. overnight. The oil bath was removed, and the bomb was cooled to room temperature followed by immersion in dry ice; valve was then released. The cold bath was removed, and the reaction was warmed to room temperature. The solution was filtered through a pad of CELITE® and rinsed with MeOH. The filtrate was concentrated in vacuo, diluted with EtOAc (200 mL) and saturated aqueous NaHCO₃ (40 mL). After separation of the layers, the organic layer was washed with brine (40 mL), dried over MgSO₄, and concentrated in vacuo to give the desired product (0.600 g, 1.476 mmol, 104% yield) as a light burgundy solid.

6. 5-Chloro-2-((3-(4-(methoxycarbonyl)-7-(2-methoxyethoxy)-5H-pyridazino[4,5-b]indol-1-yl)-2-methylphenylamino)methyl)benzoic acid

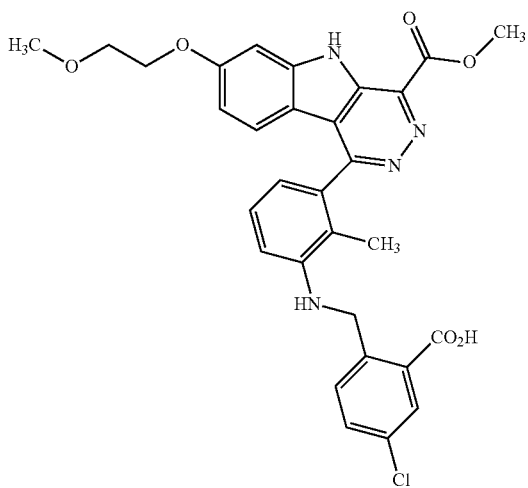

To a homogeneous, burgundy solution of methyl 1-(3-amino-2-methylphenyl)-7-(2-methoxyethoxy)-5H-pyridazino[4,5-b]indole-4-carboxylate (0.1603 g, 0.394 mmol), 5-chloro-2-formylbenzoic acid (0.182 g, 0.986 mmol) and acetic acid (0.056 mL, 0.986 mmol) in dichloromethane (7.89 mL) and tetrahydrofuran (5.26 mL) under nitrogen was added sodium triacetoxyborohydride (0.251 g, 1.183 mmol), and the reaction was stirred overnight. More sodium triacetoxyborohydride (146.2 mg) was added. After 1 hr, water (6 mL) was added, and the reaction was stirred for 30 min. It was dissolved in EtOAc (100 mL) and washed with water (3×30 mL) and brine (30 mL), dried over MgSO₄, and concentrated in vacuo to give a crude product, which was used in the subsequent step.

7. Methyl 1-(3-(6-chloro-1-oxoisoindolin-2-yl)-2-methylphenyl)-7-(2-methoxyethoxy)-5H-pyridazino[4,5-b]indole-4-carboxylate

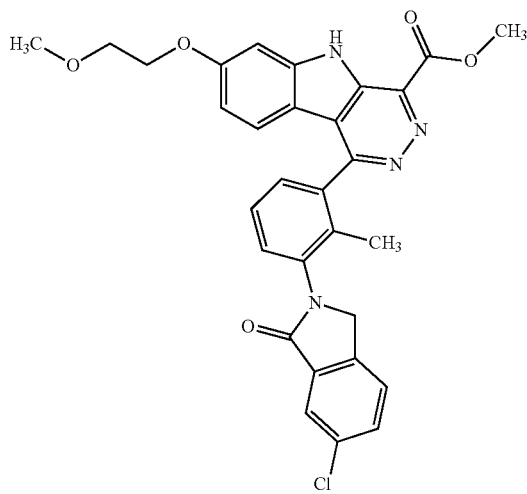

A solution of 5-chloro-2-((3-(4-(methoxycarbonyl)-7-(2-methoxyethoxy)-5H-pyridazino [4,5-b]indol-1-yl)-2-methylphenylamino)methyl)benzoic acid (0.227 g, 0.394 mmol), BOP (0.366 g, 0.827 mmol), and N-methylmorpholine (0.273 mL, 2.482 mmol) in DMF (3.94 mL) under nitrogen was heated at 45° C. After 6 hr, the reaction was cooled to room temperature, dissolved in EtOAc (100 mL) and washed with water (3×25 mL) and brine (25 mL), dried over MgSO₄, filtered and concentrated in vacuo to give a residue which was purified by flash chromatography using an ISCO 24 g column eluting with 0-5% MeOH/CH₂Cl₂. Appropriate fractions were collected and concentrated in vacuo to give the desired product (0.0384 g, 0.069 mmol, 17.5% yield) as a light orange solid.

8. 1-(3-(6-Chloro-1-oxoisoindolin-2-yl)-2-methylphenyl)-7-(2-methoxyethoxy)-5H-pyridazino[4,5-b]indole-4-carboxylic acid

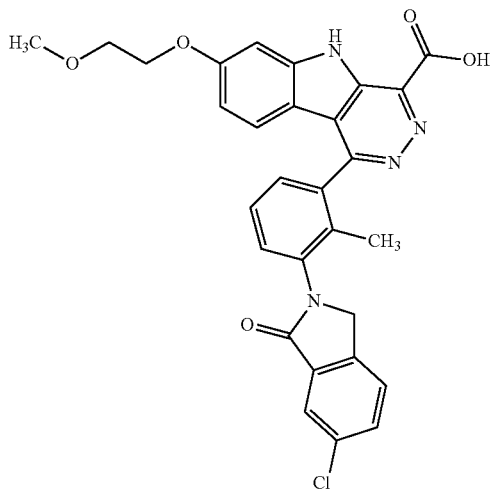 [SMILES: COCCOc1ccc2c(c1)[nH]c1c(C(=O)O)nnc(-c3cccc(N4Cc5ccc(Cl)cc5C4=O)c3C)c12]

To a yellow, homogeneous solution of methyl 1-(3-(6-chloro-1-oxoisoindolin-2-yl)-2-methylphenyl)-7-(2-methoxyethoxy)-5H-pyridazino [4,5-b]indole-4-carboxylate (0.05 g, 0.090 mmol) in THF (1.924 mL) and MeOH (0.641 mL) was added a solution of lithium hydroxide hydrate (0.015 g, 0.359 mmol) in water (0.5 mL). After 2.25 hr, the reaction was concentrated in vacuo, acidified with aqueous 1 N HCl to pH ~4-5 by litmus paper. The precipitate was filtered and dried over Drierite to give the desired product (0.0206 g, 0.038 mmol, 42.3% yield) as a light tan solid.

9. 1-(3-(6-Chloro-1-oxoisoindolin-2-yl)-2-methylphenyl)-7-(2-methoxyethoxy)-5H-pyridazino[4,5-b]indole-4-carboxamide A yellow, homogeneous solution of 1-(3-(6-chloro-1-oxoisoindolin-2-yl)-2-methylphenyl)-7-(2-methoxyethoxy)-5H-pyridazino[4,5-b]indole-4-carboxylic acid (0.0206 g, 0.038 mmol), ammonium chloride (8.12 mg, 0.152 mmol), DIPEA (0.032 mL, 0.182 mmol), N-methylmorpholine (5.42 µL, 0.049 mmol) and BOP (0.065 g, 0.148 mmol) in DMF (0.379 mL) was stirred for 1 hr. It was diluted with MeOH (1 mL) and purified by reverse phase HPLC. The appropriate fractions were collected, basified with NaHCO$_3$ (solid), and concentrated in vacuo. The residue was extracted with CH$_2$Cl$_2$ (3×). The combined extract was dried over Na$_2$SO$_4$ and concentrated in vacuo to give the desired product (0.0064 g, 0.012 mmol, 30.9% yield) as a white solid. LC/MS (M+H)= 542.15; $^1$H NMR (500 MHz, DMSO-d$_6$) (recognizable peaks for major atropoisomer) δ ppm 12.22 (s, 1H), 8.71 (s, 1H), 7.98 (s, 1H), 7.80-7.85 (m, 1H), 7.74-7.76 (m, 2H), 7.73 (d, J=1.1 Hz, 1H), 7.58 (s, 1H), 7.53 (d, J=1.1 Hz, 1H), 7.41 (d, J=2.2 Hz, 1H), 7.19 (d, J=8.9 Hz, 1H), 6.87 (d, J=2.2 Hz, 1H), 5.05 (d, J=17.8 Hz, 1H), 4.98 (d, J=17.5 Hz, 1H), 4.14-4.21 (m, 2H), 3.72 (dd, J1=5.4 Hz, J2=3.8 Hz, 2H), 3.32 (s, 3 H), 1.88 (s, 3 H).

EXAMPLE 33

7-(2-Methoxyethoxy)-1-(2-methyl-3-(4-oxoquinazolin-3(4H)-yl)phenyl)-5H-pyridazino[4,5-b]indole-4-carboxamide

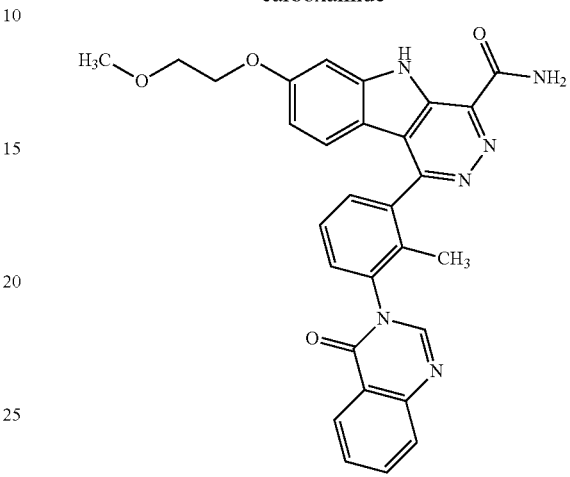

1. Methyl 1-(3-amino-2-methylphenyl)-7-(2-methoxyethoxy)-5H-pyridazino[4,5-b]indole-4-carboxylate

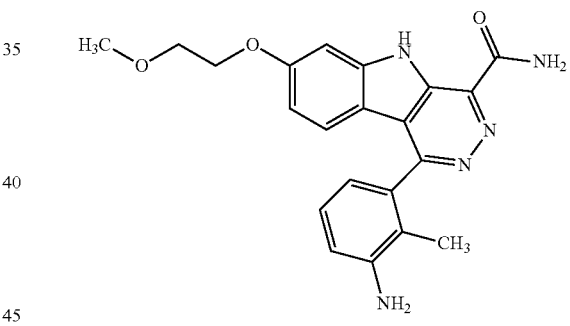

A sealed pressure tube containing methyl 1-(3-amino-2-methylphenyl)-7-(2-methoxyethoxy)-5H-pyridazino[4,5-b]indole-4-carboxylate (0.2838 g, 0.698 mmol) in 7N NH$_3$/MeOH (5.0 mL, 35.0 mmol) was heated at 100° C. for 6.5 hr. After cooling to room temperature, the reaction was stirred without the cap for 20 min and concentrated in vacuo to give the desired product (0.316 g, 0.807 mmol, 116% yield) as a dark solid.

2. 7-(2-Methoxyethoxy)-1-(2-methyl-3-(4-oxoquinazolin-3(4H)-yl)phenyl)-5H-pyridazino[4,5-b]indole-4-carboxamide A sealed pressure tube containing 1-(3-amino-2-methylphenyl)-7-(2-methoxyethoxy)-5H-pyridazino[4,5-b]indole-4-carboxamide (0.2785 g, 0.712 mmol), trimethoxymethane (0.701 mL, 6.40 mmol), 1H-benzo[d][1,3]oxazine-2,4-dione (0.232 g, 1.423 mmol), and lanthanum nitrate hexahydrate (0.092 g, 0.213 mmol) in tetrahydrofuran (3.56 mL) was heated at 95° C. for 6 hr and cooled to room temperature. EtOAc (100 mL) was added, and the resulting mixture was washed with water (20 mL), 1N aq. NaOH (20 mL), water (20 mL) and brine (20 mL) successively. It was then dried over MgSO₄ and concentrated in vacuo to give a residue which was purified by flash chromatography using an ISCO 24 g column eluting with 1-10% MeOH/CH₂Cl₂ to give crude product. This crude was dissolved in DMSO (0.2 mL) and MeOH (0.6 mL) and purified by reverse phase HPLC. The appropriate fractions were collected, basified with NaHCO₃ (solid), and concentrated in vacuo. The residue was extracted with CH₂Cl₂ (3×). The combined extract was dried over Na₂SO₄ and concentrated in vacuo to give (0.0163 g, 0.031 mmol, 4.4% yield) as a light yellow solid. LC/MS (M+H)=521.18; ¹H NMR (500 MHz, DMSO-d₆) (recognizable peaks for the major atropoisomer) δ ppm 12.24 (s, 1H), 8.76 (br. S, 1H), 8.71 (br. S, 1H), 8.53 (s, 1H), 8.48 (s, 1H), 8.26 (t, J=6.9 Hz, 1H), 8.00 (br. S, 1H), 7.89-7.94 (m, 1H), 7.80 (s, 1H), 7.74 (d, J=5.6 Hz, 1H), 7.60-7.70 (m, 2H), 7.41 (d, J=2.2 Hz, 1H), 6.88 (d, J=8.9 Hz, 1H), 4.15-4.21 (m, 2H), 3.72 (t, J=4.3 Hz, 2 H), 3.33 (s, 3H), 1.81 (s, 3H).

EXAMPLE 34

7-(2-Hydroxyethoxy)-1-(2-methyl-3-(4-oxoquinazolin-3(4H)-yl)phenyl)-5H-pyridazino[4,5-b]indole-4-carboxamide

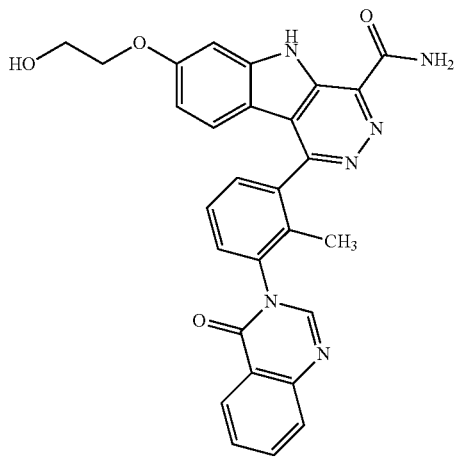 [SMILES: Cc1c(-c2nnc(C(N)=O)c3[nH]c4cc(OCCO)ccc4c23)cccc1-n1cnc2ccccc2c1=O]

To a homogeneous, light orange solution of 7-(2-methoxyethoxy)-1-(2-methyl-3-(4-oxoquinazolin-3(4H)-yl)phenyl)-5H-pyridazino[4,5-b]indole-4-carboxamide (0.0973 g, 0.155 mmol) in dichloromethane (5 ml) under nitrogen at 0° C. was added 1M tribromoborane/dichoromethane (0.496 ml, 0.496 mmol) over 5 min. After 5 min, the cold bath was removed, and the heterogeneous solution was stirred to room temperature. One hour later, the reaction was immersed in an icewater bath and ice water (15 mL) was added. The resulting mixture was basified with 1 N aqueous NaOH solution to pH ~10 by litmus paper. EtOAc (50 mL) was added, and the layers were separated. The aqueous layer was extracted with EtOAc (2×50 mL). The combined extract was dried over MgSO₄ and concentrated in vacuo to give a residue which was diluted with MeOH (1 mL) and purified by reverse phase HPLC. The appropriate fractions were collected, basified with NaHCO₃ (solid), and concentrated in vacuo. The residue was extracted with CH₂Cl₂ (3×). The combined extract was dried over Na₂SO₄ and concentrated in vacuo to give the desired product (0.0148 g, 0.029 mmol, 18.8% yield) as a light yellow solid. LC/MS (M+H)=507.21; ¹H NMR (500 MHz, DMSO-d₆) (recognizable peaks for the major atropoisomer) δ ppm 12.23 (s, 1H), 8.71 (br. S, 1H), 8.48 (s, 1H), 8.26 (t, J=6.2 Hz, 1H), 8.00 (br. S, 1H), 7.88-7.94 (m, 1H), 7.79 (d, J=8.0 Hz, 1H)), 7.72-7.77 (m, 1H), 7.58-7.70 (m, 3H), 7.41 (d, J=2.2 Hz, 1H), 7.29 (d, J=8.6 Hz, 1H), 6.88 (dd, J1=8.9, J2=2.2 Hz, 1H), 4.84-4.97 (m, 1H), 4.01-4.14 (m, 2H), 3.71-3.85 (m, 2H), 1.81 (s, 3H).

EXAMPLE 35

7-Acetyl-1-(3-(6-methoxy-1-oxoisoindolin-2-yl)-2-methylphenyl)-5H-pyridazino[4,5-b]indole-4-carboxamide

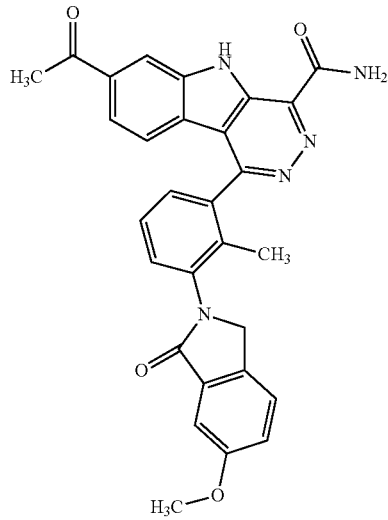 [SMILES: COc1ccc2c(c1)C(=O)N(c1cccc(-c3nnc(C(N)=O)c4[nH]c5cc(C(C)=O)ccc5c34)c1C)C2]

1. Ethyl 6-bromo-3-(2-methyl-3-nitrobenzoyl)-1H-indole-2-carboxylate

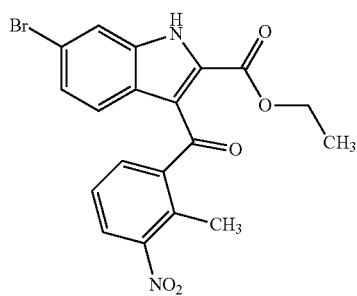 [SMILES: CCOC(=O)c1[nH]c2cc(Br)ccc2c1C(=O)c1cccc([N+](=O)[O-])c1C]

To a solution of ethyl 6-bromo-1H-indole-2-carboxylate (4.40 g, 16.41 mmol) in dichloromethane (70 mL) at 0° C. was added tin (IV) chloride in dichloromethane (20.51 mL, 20.51 mmol) over 15 min. The resulting yellow heterogeneous mixture was stirred at room temperature for 30 min before a solution 2-methyl-3-nitrobenzoyl chloride (4.42 g, 22.16 mmol) in nitromethane (70 mL) was added over 20 min. The mixture was stirred at room temperature for 4 hr and then poured into ice-cold water (200 mL). The resulting mixture was stirred at room temperature for 20 min and diluted with ethyl acetate (800 ml). The mixture was washed with water (100 mL), saturated NaHCO₃ solution (2×100 ml), water (100 mL), and brine (100 mL). The organic solution was dried over anhydrous MgSO₄. Removal of solvent under vacuum gave the desired product (7.04 g, 16.33 mmol, 99% yield) as yellow solid.

2. 7-Bromo-1-(2-methyl-3-nitrophenyl)-3H-pyridazino[4,5-b]indol-4(5H)-one

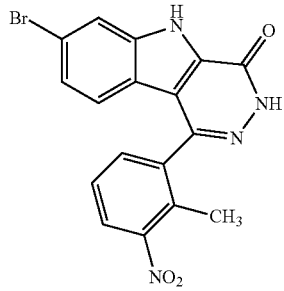 [SMILES: Cc1c(-c2n[nH]c(=O)c3[nH]c4cc(Br)ccc4c23)cccc1[N+](=O)[O-]]

A solution of ethyl 6-bromo-3-(2-methyl-3-nitrobenzoyl)-1H-indole-2-carboxylate (6.02 g, 13.96 mmol) and hydrazine hydrate (2.446 g, 48.9 mmol) in ethanol (200 mL) was heated at reflux for 16 hr. The mixture was concentrated under vacuum to a volume of approximate 30 mL. The insoluble product (4.56 g, 11.42 mmol, 82% yield) was collected by suction filtration and dried under vacuum at 50° C.

3. 7-Acetyl-1-(2-methyl-3-nitrophenyl)-3H-pyridazino[4,5-b]indol-4(5H)-one

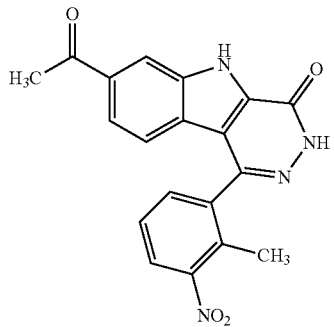 [SMILES: CC(=O)c1ccc2c(c1)[nH]c1c(=O)[nH]nc(-c3cccc([N+](=O)[O-])c3C)c12]

A mixture of 7-bromo-1-(2-methyl-3-nitrophenyl)-3H-pyridazino [4,5-b]indol-4(5H)-one (2.00 g, 5.01 mmol), tributyl (1-ethoxyvinyl)stannane (4.06 mL, 12.02 mmol), dichlorobis(triphenylphosphine)-palladium(II) (0.422 g, 0.601 mmol), and triethylamine (0.908 mL, 6.51 mmol) in 1,4-Dioxane (100 mL) was heated at 95° C. for 24 hr. Upon cooling to room temperature, the mixture was filtered through CELITE®. The filtrate was concentrated under vacuum to dryness. To the residue was added THF (100 mL) and 1 N HCl solution (100 mL), and the mixture was stirred at 60° C. for 1.5 hr. It was concentrated under vacuum to a volume of 100 mL, neutralized with 1 N NaOH solution to pH 4-5, and extracted with ethyl acetate (3×150 mL). The combined, cloudy organic solution was concentrated under vacuum to dryness. To the residue was added hexane (100 mL), and the mixture was stirred at room temperature for 1 hr. The clear solution was decanted and the residue was repeated with this operation for two more times. The solid material was collected by suction filtration to give a crude product (1.98 g, 5.46 mmol, >100% yield) as a beige solid.

4. 1-(4-Chloro-1-(2-methyl-3-nitrophenyl)-5H-pyridazino[4,5-b]indol-7-yl)ethanone

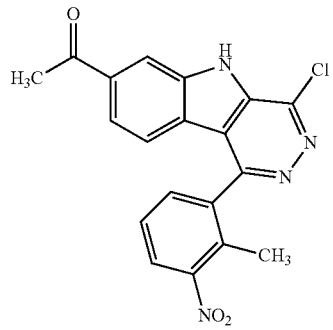 [SMILES: CC(=O)c1ccc2c(c1)[nH]c1c(Cl)nnc(-c3cccc([N+](=O)[O-])c3C)c12]

To 7-acetyl-1-(2-methyl-3-nitrophenyl)-3H-pyridazino[4,5-b]indol-4(5H)-one (1.88 g, 91.7% pure, 4.75 mmol) at room temperature was added phosphoryl trichloride (350 mL, 3755 mmol), and the mixture was heated at 110° C. for 1 hr. The excess of phosphoryl trichloride was removed under vacuum. The residue was dissolved in ice cold ethyl acetate (900 mL), washed with water (100 mL), saturated NaHCO₃ solution (2×100 mL), water (100 mL), and brine (100 mL). The organic solution was dried over anhydrous MgSO₄ and concentrated under vacuum to dryness to provide the desired product (1.57 g, 4.12 mmol, 86% yield over 2 steps) as a beige solid.

5. Methyl 7-acetyl-1-(3-amino-2-methylphenyl)-5H-pyridazino[4,5-b]indole-4-carboxylate

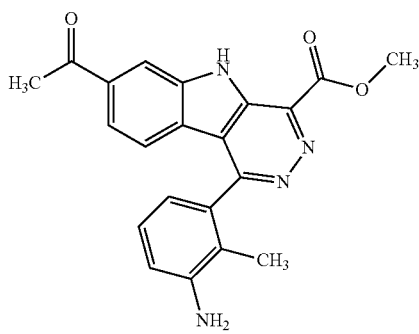 [SMILES: COC(=O)c1nnc(-c2cccc(N)c2C)c2c1[nH]c1cc(C(C)=O)ccc12]

1-(4-Chloro-1-(2-methyl-3-nitrophenyl)-5H-pyridazino[4,5-b]indol-7-yl)ethanone (0.90 g, 2.364 mmol), methanol (30 mL, 740 mmol), DPPF (0.197 g, 0.355 mmol), palladium (II) acetate (0.080 g, 0.355 mmol), and sodium acetate (0.388 g, 4.73 mmol) were placed into a steel bomb. The bomb was evacuated and refilled with nitrogen. This operation was once repeated. The bomb was vacuumed again and then charged with CO (g) at 50 psi. The bomb was then heated at 95° C. for 20 hr. Upon cooling to room temperature, the bomb was further cooled at −78° C. and the excess CO (g) was released. The reaction mixture was diluted with ethyl acetate (20 mL) and filtered through CELITE®. The filtrate was concentrated under vacuum. The residue was diluted with ethyl acetate (180 mL), washed with water (2×40 mL) and brine (40 mL), and dried over anhydrous. The desired product, methyl 7-acetyl-1-(3-amino-2-methylphenyl)-5H-pyridazino[4,5-b]

indole-4-carboxylate (0.539 g, 1.440 mmol, 60.9% yield), was isolated as a beige solid by ISCO (120 g silica gel, 1-5% methanol/CH$_2$Cl$_2$).

6. 7-Acetyl-1-(3-amino-2-methylphenyl)-5H-pyridazino[4,5-b]indole-4-carboxamide

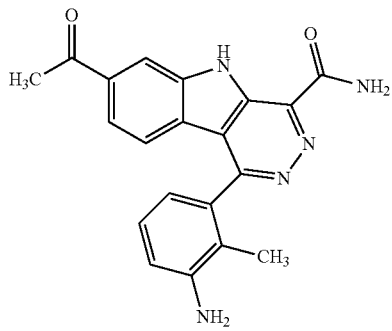 [SMILES: CC(=O)c1ccc2c(c1)[nH]c1c(C(N)=O)nnc(-c3cccc(N)c3C)c12]

A mixture of methyl 7-acetyl-1-(3-amino-2-methylphenyl)-5H-pyridazino[4,5-b]indole-4-carboxylate (0.520 g, 1.389 mmol) and ammonia in methanol (30 ml, 210 mmol) was heated in a sealed bottle at 100° C. for 2 hr. Removal of the volatiles under vacuum gave a crude product (0.501 g) as a tan solid. This crude was 82% pure, but was used in the next step without further purification.

7. 2-(3-(7-Acetyl-4-carbamoyl-5H-pyridazino [4,5-b]indol-1-yl)-2-methylphenylcarbamoyl)-4-methoxybenzoic acid

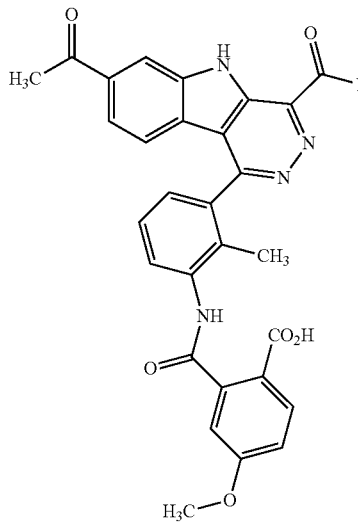

A mixture of 7-acetyl-1-(3-amino-2-methylphenyl)-5H-pyridazino[4,5-b]indole-4-carboxamide (0.250 g, crude product from the previous step), 2-formyl-5-methoxybenzoic acid (0.251 g, 1.391 mmol), sodium triacetoxyborohydride (0.442 g, 2.087 mmol), and acetic acid (0.100 mL, 1.739 mmol) in dichloromethane (18 mL) and tetrahydrofuran (18 mL) was stirred at room temperature for 3 hr. Additional sodium triacetoxyborohydride (0.442 g, 2.087 mmol) was added and the reaction mixture was stirred at rt. Three hours later, another portion of sodium triacetoxyborohydride (0.442 g, 2.087 mmol) was added, and the mixture was stirred at room temperature overnight. The reaction was quenched with water (30 mL) and the mixture was extracted with ethyl acetate (4×40 mL). The combined extract was dried over anhydrous MgSO$_4$. Removal of solvent under vacuum provided the crude desired product (0.336 g) as a beige solid.

8. 7-Acetyl-1-(3-(6-methoxy-1-oxoisoindolin-2-yl)-2-methylphenyl)-5H-pyridazino[4,5-b]indole-4-carboxamide A mixture of 2-((3-(7-acetyl-4-carbamoyl-5H-pyridazino[4,5-b]indol-1-yl)-2-methylphenylamino)methyl)-5-methoxybenzoic acid (0.336 g, the crude product from previous step), BOP (0.852 g, 1.925 mmol), and N-methylmorpholine (0.635 mL, 5.78 mmol) in DMF (4 mL) was stirred at 45° C. for 1 hr. The mixture was diluted with ethyl acetate (100 mL), washed with water (2×25 mL) and brine (25 mL), and dried over anhydrous MgSO$_4$. After solvent was removed under vacuum, the residue were divided into 4 portions and purified by reverse phase HPLC. The correct fractions were combined and concentrated under vacuum, basified with saturated NaHCO$_3$ solution, and extracted with ethyl acetate (3×35 mL). The combined extract was washed with brine (30 mL) and dried over anhydrous MgSO$_4$. Removal of solvent under vacuum provided the desired product (40 mg, 0.077 mmol, 11% yield over 3 steps) as a yellow solid. LCMS (M+H)$^+$= 506.29. $^1$H NMR (500 MHz, DMSO-d$_6$) δ: 12.67 (s, 1H), 8.83 (s, 1H), 8.52 (s, 1H), 8.09 (s, 1H), 7.83 (dd, J1=8.5 Hz, J2=1.5 Hz, 1H), 7.77 (dd, J1=7.8 Hz, J2=1.1 Hz, 1H), 7.63-7.60 (m, 2H), 7.55 (d, J=6.4 Hz, 1H), 7.47 (d, J=8.3 Hz, 1H), 7.33 (d, J=2.5 Hz, 1H), 7.27 (dd, J1=8.3 Hz, J2=2.5 Hz, 1H), 5.02 (d, J=17.2 Hz, 1H), 4.91 (d, J=17.2 Hz, 1H), 3.86 (s, 3H), 2.68 (s, 3H), 1.89 (s, 3H).

EXAMPLE 36

7-(2-Hydroxypropan-2-yl)-1-(3-(6-methoxy-1-oxoisoindolin-2-yl)-2-methylphenyl)-5H-pyridazino[4,5-b]indole-4-carboxamide

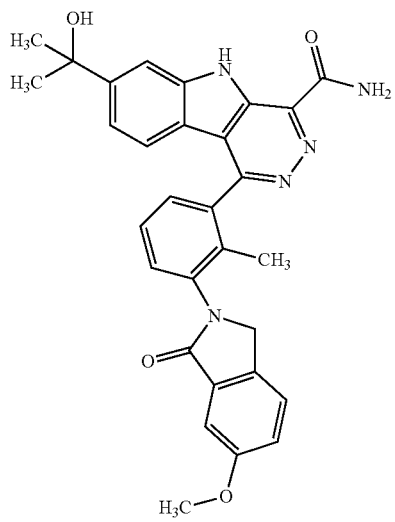 [SMILES: COc1ccc2c(c1)C(=O)N(c1cccc(-c3nnc(C(N)=O)c4[nH]c5cc(C(C)(C)O)ccc5c34)c1C)C2]

To a solution of 7-acetyl-1-(3-(6-methoxy-1-oxoisoindolin-2-yl)-2-methylphenyl)-5H-pyridazino[4,5-b]indole-4-carboxamide (36.0 mg, 0.071 mmol) in tetrahydrofuran (8 mL) at 0° C. was added methylmagnesium bromide (0.119 mL, 0.356 mmol). The mixture was stirred at room temperature for 20 min. Additional methylmagnesium bromide (0.119 mL, 0.356 mmol) was added at 0° C. and the mixture was stirred at room temperature for another 20 min. The reaction was quenched with water (15 mL). The resulting mixture was extracted with ethyl acetate (3×30 mL). The combined extract was washed with brine (25 mL) and dried over anhydrous MgSO₄. After solvent was removed under vacuum, the residue was purified by reverse phase HPLC. The correct fraction was concentrated under vacuum, basified with saturated NaHCO₃ solution, and extracted with ethyl acetate (3×35 mL). The combined extract was washed with brine (30 mL) and dried over anhydrous MgSO₄. Removal of solvent under vacuum provided the desired product (11.4 mg, 0.021 mmol, 30.1% yield) as a white solid. LCMS (M+H)⁺= 522.20. ¹H NMR (500 MHz, DMSO-d₆) δ: 12.34 (s, 1H), 8.75 (s, 1H), 8.07 (s, 1H), 8.00 (s, 1H), 7.73 (d, J=6.9 Hz, 1H), 7.61-7.57 (m, 2H), 7.51 (d, J=6.4 Hz, 1H), 7.35-7.33 (m, 2H), 7.27-7.25 (m, 2H), 5.19 (s, 1H), 4.98 (d, J=16.9 Hz, 1H), 4.90 (d, J=16.9 Hz, 1H), 3.86 (s, 3H), 1.90 (s, 3H), 1.49 (s, 6H).

EXAMPLE 37

7-(2-Methoxyethoxy)-3-methyl-4-(2-methyl-3-(4-oxoquinazolin-3(4H)-yl)phenyl)-9H-pyrido[3,4-b]indole-1-carboxamide

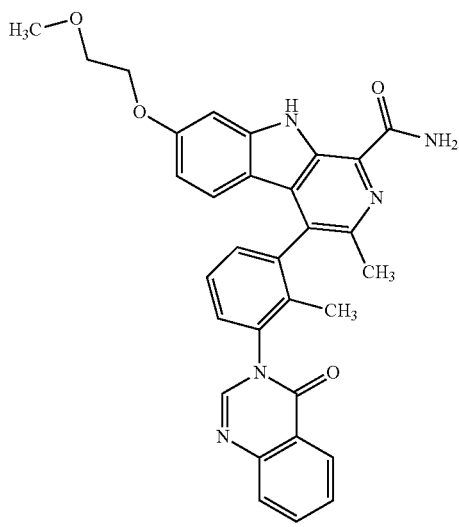 [SMILES: COCCOc1ccc2c(c1)[nH]c1c(C(N)=O)nc(C)c(-c3cccc(-n4cnc5ccccc5c4=O)c3C)c12]

1. (E)-Benzyl 2-methyl-3-(2-nitroprop-1-enyl)phenylcarbamate

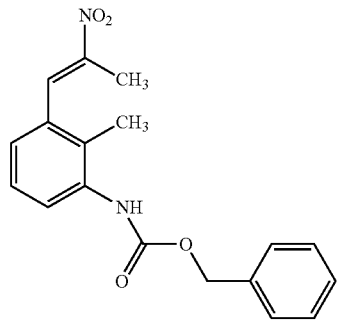 [SMILES: C/C(=C\c1cccc(NC(=O)OCc2ccccc2)c1C)[N+](=O)[O-]]

A solution of benzyl 3-formyl-2-methylphenylcarbamate (5.1667 g, 19.19 mmol), nitroethane (6.89 ml, 96 mmol) and ammonium acetate (7.39 g, 96 mmol) in acetic acid (Volume: 64.0 ml) under nitrogen was heated at 95° C. After 3 h, the reaction was cooled to room temperature and concentrated in vacuo. The residue was dissolved in water (40 mL) and CH₂Cl₂ (75 mL), and basified with Na₂CO₃ (s). The layers were separated, and the aqueous layer was extracted with CH₂Cl₂ (2×75 mL). The organic layers were combined, dried over MgSO₄, filtered and concentrated in vacuo. The residue was purified by flash chromatography using an ISCO 330 g column eluting with 50-100% hexane/CH₂Cl₂. Appropriate fractions were collected and concentrated in vacuo to give (E)-benzyl 2-methyl-3-(2-nitroprop-1-enyl)phenylcarbamate (2.4714 g, 39.5% yield) as a yellow solid, LC/MS (M+H)= 327.16. 0.6875 g of desired product (75% pure by HPLC) was also collected.

2. Benzyl 3-(1-(6-(2-methoxyethoxy)-1H-indol-3-yl)-2-nitropropyl)-2-methylphenylcarbamate

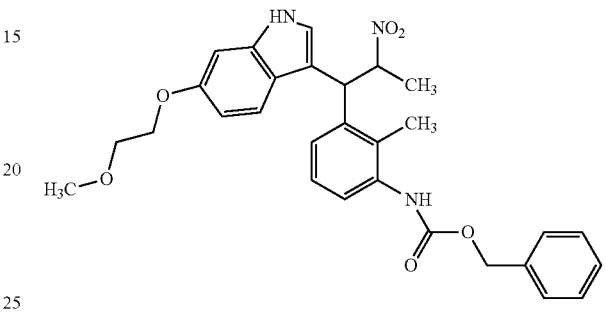

(E)-Benzyl 2-methyl-3-(2-nitroprop-1-enyl)phenylcarbamate (0.6849 g, 1.574 mmol) and 6-(2-methoxyethoxy)-1H-indole (0.602 g, 3.15 mmol) were dissolved in THF (50 mL), concentrated in vacuo, and melted at 140° C. for 12 h. After cooling to room temperature, the crude product was purified by flash chromatography using an ISCO 40 g column (solid loading) eluting with 20-75% EtOAc/hexane. Appropriate fractions were collected and concentrated in vacuo to give benzyl 3-(1-(6-(2-methoxyethoxy)-1H-indol-3-yl)-2-nitropropyl)-2-methylphenylcarbamate (0.4102 g, 0.793 mmol, 50.4% yield, mixture of 2 isomers) as a yellow oil, LC/MS (M+H)=518.12, 518.13.

3. Benzyl 3-(2-amino-1-(6-(2-methoxyethoxy)-1H-indol-3-yl)propyl)-2-methylphenylcarbamate

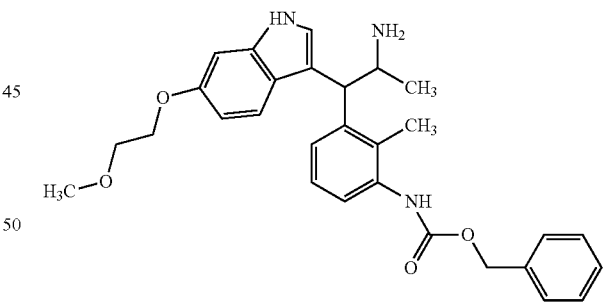

A solution of benzyl 3-(1-(6-(2-methoxyethoxy)-1H-indol-3-yl)-2-nitropropyl)-2-methylphenylcarbamate (1.6194 g, 3.13 mmol), ammonium acetate (2.51 g, 46.9 mmol) and zinc (3.07 g, 46.9 mmol) in methanol (Ratio: 1.000, Volume: 57.9 ml) and tetrahydrofuran (Ratio: 1.000, Volume: 57.9 ml) was stirred under nitrogen. After 5 h, the reaction was diluted with EtOAc and filtered through a wad of CELITE®. The filtrate was concentrated in vacuo, and the residue was dissolved in EtOAc (75 mL) and saturated aqueous NaHCO₃ (30 mL). The layers were separated, and the aqueous layer was extracted with EtOAc (2×75 mL). The organic layers were combined, dried over MgSO₄, filtered and concentrated in vacuo to give benzyl 3-(2-amino-1-(6-(2-methoxyethoxy)-

1H-indol-3-yl)propyl)-2-methylphenylcarbamate (1.3975 g, 2.87 mmol, 92% yield, mixture of 2 isomers) as a colorless oil, LC/MS (M+H)=488.30, 488.30.

4. Ethyl 4-(3-(benzyloxycarbonylamino)-2-methylphenyl)-7-(2-methoxyethoxy)-3-methyl-9H-pyrido[3,4-b]indole-1-carboxylate

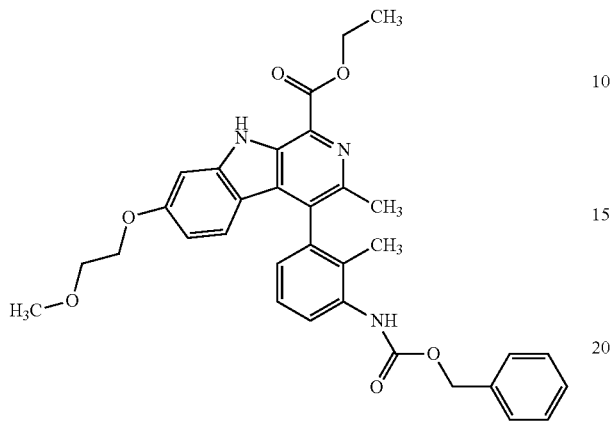

To a homogeneous, colorless solution of benzyl 3-(2-amino-1-(6-(2-methoxyethoxy)-1H-indol-3-yl)propyl)-2-methylphenylcarbamate (1.3975 g, 2.87 mmol) in dioxane (Volume: 143 ml) under nitrogen were added 50% ethyl 2-oxoacetate/toluene (1.136 ml, 5.73 mmol) and 4 N hydrochloric acid/1,4-dioxane (1.433 ml, 5.73 mmol). After stirring overnight, the reaction was concentrated in vacuo, dissolved in EtOAc (75 mL) and saturated aqueous NaHCO₃ (30 mL). The layers were separated, and the aqueous layer was extracted with EtOAc (2×75 mL). the organic layers were combined, dried over MgSO₄, filtered and concentrated in vacuo to give crude cyclized product as a burgundy oil which was used in the next step. p-Xylene (Volume: 82 ml) and 10% palladium on carbon (0.916 g, 0.861 mmol) were added, and the reaction was heated at 120° C. After 3 h, the reaction was cooled to room temperature, diluted with EtOAc (200 mL) and filtered through a wad of CELITE®. The filtrate was concentrated in vacuo, dissolved in EtOAc (125 mL) and washed with water (25 mL). The layers were separated, and the organic layer was dried over MgSO₄, filtered and concentrated in vacuo. The residue was purified by flash chromatography using an ISCO 80 g column eluting with 20-75% EtOAc/hexane. Appropriate fractions were collected and concentrated in vacuo to give ethyl 4-(3-(benzyloxycarbonylamino)-2-methylphenyl)-7-(2-methoxyethoxy)-3-methyl-9H-pyrido[3,4-b]indole-1-carboxylate (0.6232 g, 1.098 mmol, 38.3% yield) as a tan solid, LC/MS (M+H)=568.24.

5. Benzyl 3-(1-carbamoyl-7-(2-methoxyethoxy)-3-methyl-9H-pyrido[3,4-b]indol-4-yl)-2-methylphenylcarbamate

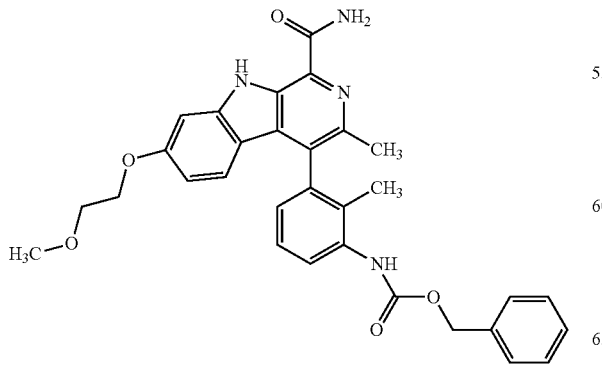

A solution of 4-(3-(benzyloxycarbonylamino)-2-methylphenyl)-7-(2-methoxyethoxy)-3-methyl-9H-pyrido[3,4-b]indole-1-carboxylic acid (0.5025 g, 0.931 mmol), ammonium chloride (0.199 g, 3.73 mmol), BOP (0.535 g, 1.211 mmol), DIPEA (0.781 ml, 4.47 mmol) and N-methylmorpholine (0.399 ml, 3.63 mmol) in DMF (Volume: 4.66 ml) was stirred under nitrogen for 2.5 h. Water (50 mL) was added, and the solution was stirred for 1 h. The precipitate was filtered, rinsed with water and dried over Drierite to give benzyl 3-(1-carbamoyl-7-(2-methoxyethoxy)-3-methyl-9H-pyrido[3,4-b]indol-4-yl)-2-methylphenylcarbamate (0.4856 g, 0.902 mmol, 97% yield) as a tan solid, LC/MS (M+H)=539.24.

6. 4-(3-Amino-2-methylphenyl)-7-(2-methoxyethoxy)-3-methyl-9H-pyrido[3,4-b]indole-1-carboxamide

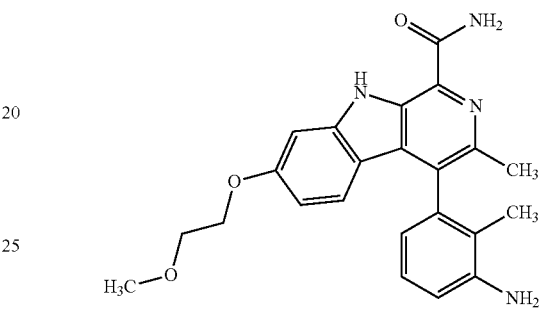

A solution of benzyl 3-(1-carbamoyl-7-(2-methoxyethoxy)-3-methyl-9H-pyrido[3,4-b]indol-4-yl)-2-methylphenylcarbamate (0.4846 g, 0.900 mmol) and 10% palladium on carbon (0.192 g, 0.180 mmol) in tetrahydrofuran (Ratio: 1.000, Volume: 23.99 ml) and methanol (Ratio: 1.5, Volume: 36.0 ml) was hydrogenated. After 1.5 h, the reaction was flushed with nitrogen, filtered through a wad of CELITE®, and rinsed. The filtrate was concentrated in vacuo, dissolved in EtOAc (100 mL), dried over MgSO₄, filtered and concentrated in vacuo to give 4-(3-amino-2-methylphenyl)-7-(2-methoxyethoxy)-3-methyl-9H-pyrido[3,4-b]indole-1-carboxamide (0.3800 g, 0.846 mmol, 94% yield) as a solid, LC/MS (M+H)=405.18.

7. 7-(2-Methoxyethoxy)-3-methyl-4-(2-methyl-3-(4-oxoquinazolin-3(4H)-yl)phenyl)-9H-pyrido[3,4-b]indole-1-carboxamide

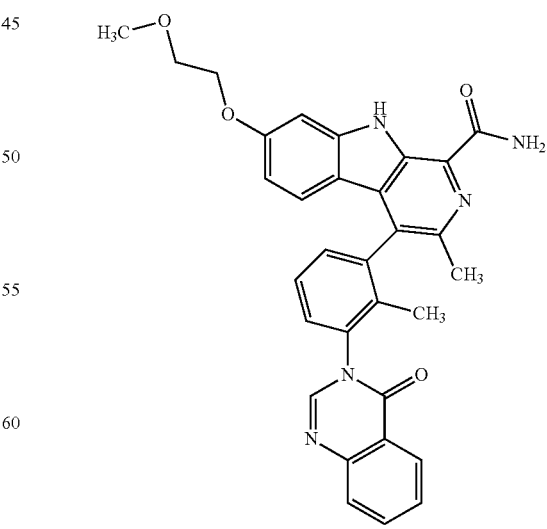

A sealed pressure tube containing 4-(3-amino-2-methylphenyl)-7-(2-methoxyethoxy)-3-methyl-9H-pyrido[3,4-b]

indole-1-carboxamide (0.364 g, 0.9 mmol), 1H-benzo[d][1,3]oxazine-2,4-dione (0.367 g, 2.250 mmol), trimethoxymethane (0.887 ml, 8.10 mmol) and lanthanum nitrate hexahydrate (0.117 g, 0.270 mmol) in tetrahydrofuran (Volume: 4.50 ml) was heated at 95° C. overnight. The reaction was cooled to room temperature, diluted with EtOAc (100 mL) and water (30 mL); the insolubles were filtered, and the layers were separated. The organic layer was washed with water (30 mL) and brine (30 mL), dried over MgSO$_4$, filtered and concentrated in vacuo. The residue was purified by flash chromatography using an ISCO 40 g column eluting with 30-100% EtOAc/hexane (solid loading). Appropriate fractions were collected and concentrated in vacuo to give impure product It was diluted with MeOH (3 mL) and DMSO (0.1 mL) and subjected to autoprep HPLC. The appropriate fractions were collected; NaHCO$_3$ (solid) was added, and the fractions were concentrated in vacuo not to dryness. It was extracted with CH$_2$Cl$_2$ (3×); the organic layers were combined, dried over Na$_2$SO$_4$, filtered and concentrated in vacuo to give 7-(2-methoxyethoxy)-3-methyl-4-(2-methyl-3-(4-oxoquinazolin-3(4H)-yl)phenyl)-9H-pyrido[3,4-b]indole-1-carboxamide (0.0372 g, 0.070 mmol, 7.75% yield) as a light tan solid, LC/MS (M+H)=534.18; $^1$H NMR (500 MHz, DMSO-d$_6$) (recognizable peaks for the major atropoisomer) δ ppm 11.44 (d, J=5.8 Hz, 1H), 8.46 (s, 1H), 8.24 (ddd, J=7.9, 3.3, 1.2 Hz, 1H), 8.12-8.17 (m, 1H), 7.85-7.93 (m 1H), 7.79 (dd, J=7.9, 2.6 Hz, 1H), 7.71 (br d, J=2.5 Hz, 1H), 7.51-7.68 (m, 2H), 7.46 (br ddd, J=7.1, 5.3, 1.4 Hz, 1H), 7.28 (d, J=2.2 Hz, 1H), 6.83 (d, J=8.9 Hz, 1 H), 6.59-6.70 (m, 2H), 4.10-4.16 (m, 2H), 3.69 (br q, J=4.7 Hz, 2H), 3.33 (s, 3H), 2.42 (s, 3H), 1.70 (s, 3H).

EXAMPLE 38

7-(2-Hydroxypropan-2-yl)-3-methyl-4-(2-methyl-3-(4-oxoquinazolin-3(4H)-yl)phenyl)-9H-pyrido[3,4-b]indole-1-carboxamide

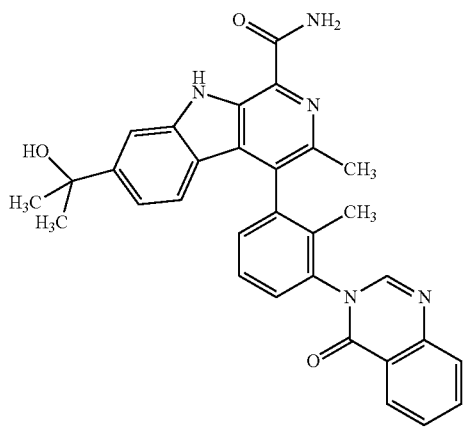 [SMILES: Cc1nc(C(N)=O)c2[nH]c3cc(C(C)(C)O)ccc3c2c1-c1cccc(-n2cnc3ccccc3c2=O)c1C]

1. Benzyl (2-methyl-3-(2-nitroprop-1-en-1-yl)phenyl)carbamate

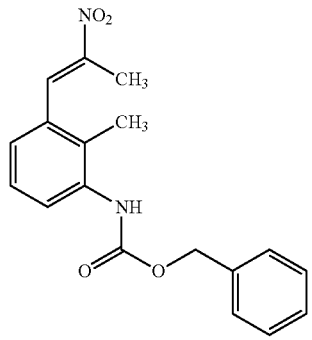 [SMILES: C/C(=C\c1cccc(NC(=O)OCc2ccccc2)c1C)[N+](=O)[O-]]

A solution of benzyl (3-formyl-2-methylphenyl)carbamate (8.00 g, 29.7 mmol), nitroethane (10.7 ml, 149 mmol), and ammonium acetate (11.5 g, 149 mmol) was heated in an oil bath at 95° C. overnight. The reaction mixture was concentrated under reduced pressure, and the residue was diluted with a mixture of dichloromethane (150 mL) and water (75 mL) and basified with solid sodium bicarbonate slowly. The organic layer was collected, and the aqueous layer was extracted with dichloromethane (2×100 mL). The combined organic layers were dried over anhydrous sodium sulfate. Concentration under reduced pressure followed by purification by flash silica gel chromatography using a mixture of ethyl acetate in hexane (20%-35%-50%-65%-75%) afforded benzyl (2-methyl-3-(2-nitroprop-1-en-1-yl)phenyl)carbamate (5.16 g, 15.8 mmol, 53% yield) as a pale yellow solid.

2. Benzyl (3-(1-(6-bromo-1H-indol-3-yl)-2-nitropropyl)-2-methylphenyl)carbamate

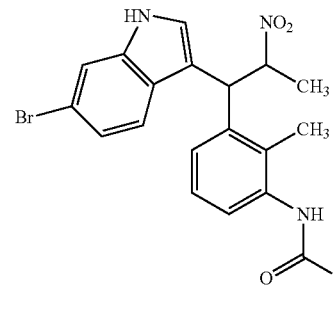

A mixture of (E)-benzyl (2-methyl-3-(2-nitroprop-1-en-1-yl)phenyl)carbamate (5.16 g, 15.8 mmol) and 6-bromo-1H-indole (6.20 g, 31.6 mmol) was heated neat at 140° C. overnight. The crude reaction mixture was purified by flash silica gel chromatography using a mixture of ethyl acetate in hexane (20%-35%-50%) to give benzyl (3-(1-(6-bromo-1H-indol-3-yl)-2-nitropropyl)-2-methylphenyl)carbamate (2.58 g, 4.94 mmol, 31% yield) as a burgundy oil/solid and as a 1:1 mixture of diastereomers.

3. Benzyl (3-(2-amino-1-(6-bromo-1H-indol-3-yl)propyl)-2-methylphenyl)carbamate

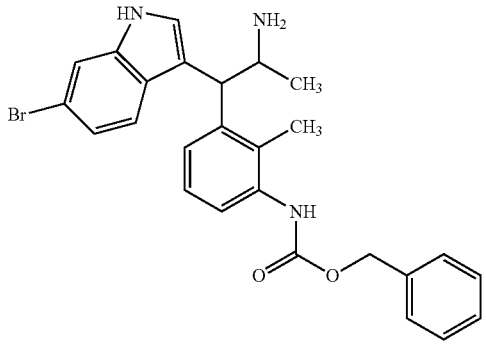 [SMILES: Cc1c(NC(=O)OCc2ccccc2)cccc1C(c1c[nH]c2cc(Br)ccc12)C(C)[N+](=O)[O-]]

A solution of benzyl (3-(1-(6-bromo-1H-indol-3-yl)-2-nitropropyl)-2-methylphenyl)carbamate (4.47 g, 8.56 mmol), ammonium chloride (6.87 g, 128 mmol), and zinc dust (8.40 g, 128 mmol) in methanol (100 mL) and tetrahydrofuran (100 mL) was stirred overnight under nitrogen. The reaction was diluted with ethyl acetate and filtered through a pad of CELITE®. The filtrate was concentrated under reduced pressure, and the residue was diluted with ethyl acetate (150 mL), washed with saturated aqueous sodium bicarbonate (70 mL), and washed with brine (70 mL). The organic layer was collected, and the aqueous layers were sequentially extracted with ethyl acetate (2×100 mL). The combined organic layers were dried over anhydrous sodium sulfate and concentrated under reduced pressure to give benzyl (3-(2-amino-1-(6-bromo-1H-indol-3-yl)propyl)-2-methylphenyl)carbamate (4.00 g, 8.12 mmol, 95% yield) as a light brown semi-solid and as a ~1:1 diastereomers. LC/MS M+1=492.1 and 494.1.

4. Ethyl 4-(3-(((benzyloxy)carbonyl)amino)-2-methylphenyl)-7-bromo-3-methyl-2,3,4,9-tetrahydro-1H-pyrido[3,4-b]indole-1-carboxylate

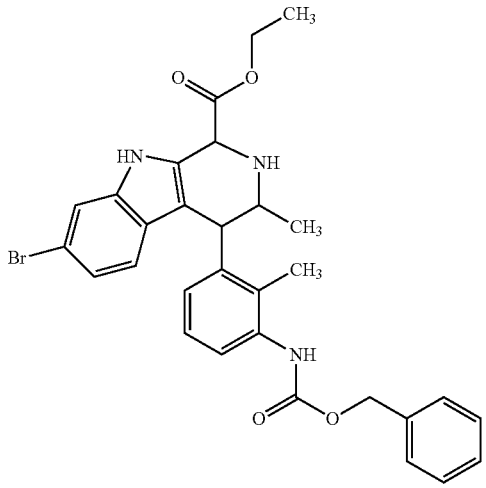 [SMILES: CCOC(=O)C1NC(C)C(c2cccc(NC(=O)OCc3ccccc3)c2C)c2c1[nH]c1cc(Br)ccc21]

To a homogeneous solution of benzyl (3-(2-amino-1-(6-bromo-1H-indol-3-yl)propyl)-2-methylphenyl)carbamate (4.00 g, 8.12 mmol) in dioxane (200 mL) under nitrogen was added 50% ethyl 2-oxoacetate in toluene (3.22 mL, 16.3 mmol) followed by 4 M hydrochloric acid in 1,4-dioxane (4.06 mL, 16.3 mmol). The reaction mixture was stirred at room temperature overnight. The reaction mixture was concentrated under reduced pressure, and the residue was diluted with ethyl acetate (150 mL), washed with saturated aqueous sodium bicarbonate (75 mL), and washed with brine (75 mL). The organic layer was collected, and the aqueous layers were sequentially extracted with ethyl acetate (2×100 mL). The combined organic layers were dried over anhydrous sodium sulfate and concentrated under reduced pressure to give ethyl 4-(3-(((benzyloxy)carbonyl)amino)-2-methylphenyl)-7-bromo-3-methyl-2,3,4,9-tetrahydro-1H-pyrido[3,4-b]indole-1-carboxylate in a quantitative yield as a burgundy solid. The mixture was used in the next step without any further purification. LC/MS M+1=576.2 and 578.2.

5. Ethyl 4-(3-(((benzyloxy)carbonyl)amino)-2-methylphenyl)-7-bromo-3-methyl-9H-pyrido[3,4-b]indole-1-carboxylate

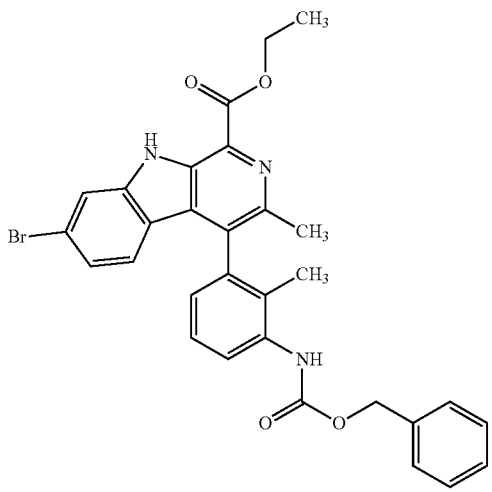 [SMILES: CCOC(=O)c1nc(C)c(-c2cccc(NC(=O)OCc3ccccc3)c2C)c2c1[nH]c1cc(Br)ccc12]

A solution of ethyl 4-(3-(((benzyloxy)carbonyl)amino)-2-methylphenyl)-7-bromo-3-methyl-2,3,4,9-tetrahydro-1H-pyrido[3,4-b]indole-1-carboxylate (4.68 g, 8.12 mmol) and 10% palladium on carbon (2.59 g, 2.44 mmol) in xylene (130 mL) was heated at 120° C. overnight. The reaction mixture was diluted with ethyl acetate and filtered through a pad of CELITE®. The CELITE® pad was washed well with ethyl acetate, and the filtrate was concentrated under reduced pressure. The residue was purified by flash silica gel chromatography using a mixture of ethyl acetate in hexane (20%-35%-50%) to give ethyl 4-(3-(((benzyloxy)carbonyl)amino)-2-methylphenyl)-7-bromo-3-methyl-9H-pyrido[3,4-b]indole-1-carboxylate (1.49 g, 2.60 mmol, 32% yield) as a burgundy solid. LC/MS M+1=572.2 and 574.2.

6. 4-(3-(((Benzyloxy)carbonyl)amino)-2-methylphenyl)-7-bromo-3-methyl-9H-pyrido[3,4-b]indole-1-carboxylic acid

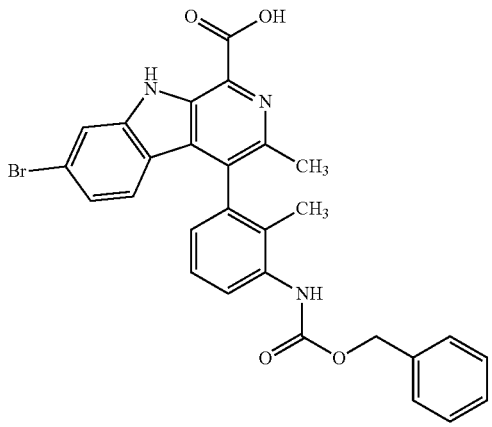 [SMILES: Cc1nc(C(=O)O)c2[nH]c3cc(Br)ccc3c2c1-c1cccc(NC(=O)OCc2ccccc2)c1C]

A mixture of ethyl 4-(3-(((benzyloxy)carbonyl)amino)-2-methylphenyl)-7-bromo-3-methyl-9H-pyrido[3,4-b]indole- 1-carboxylate (1.36 g, 2.38 mmol) and lithium hydroxide, monohydrate (0.399 g, 9.50 mmol) in tetrahydrofuran (30 mL), methanol (10 mL), and water (12 mL) was stirred at room temperature for 4 h. The solvent was removed under reduced pressure, and the residue was suspended in water (~20 mL) and 1N aqueous hydrochloric acid (9.5 mL). The pH was adjusted to 5 with 1N aqueous sodium hydroxide, and the suspension was stirred for 60 min. The solid was collected by vacuum filtration, washed with water, and dried overnight to give 4-(3-(((benzyloxy)carbonyl)amino)-2-methylphenyl)-7-bromo-3-methyl-9H-pyrido[3,4-b]indole-1-carboxylic acid (1.10 g, 2.02 mmol, 85% yield) as a yellow solid. LC/MS M+1=544.3 and 546.3.

7. Benzyl (3-(7-bromo-1-carbamoyl-3-methyl-9H-pyrido[3,4-b]indol-4-yl)-2-methylphenyl)carbamate

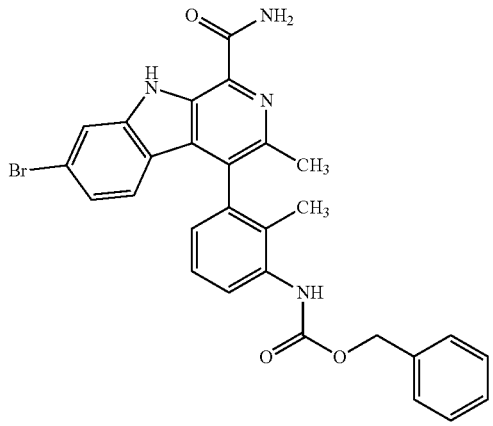 [SMILES: Cc1nc(C(N)=O)c2[nH]c3cc(Br)ccc3c2c1-c1cccc(NC(=O)OCc2ccccc2)c1C]

A mixture of 4-(3-(((benzyloxy)carbonyl)amino)-2-methylphenyl)-7-bromo-3-methyl-9H-pyrido[3,4-b]indole-1-carboxylic acid (1.10 g, 2.02 mmol), ammonium chloride (0.432 g, 8.08 mmol), BOP (1.16 g, 2.63 mmol), N-methylmorpholine (0.866 mL, 7.88 mmol), and diisopropylethylamine (1.69 mL, 9.70 mmol) in N,N-dimethylformamide (10.0 mL) was stirred at room temperature for 4 h. The reaction mixture was added dropwise to rapidly stirring water (100 mL). After stirring for 60 min., the suspension was filtered under reduced pressure, and the solid was washed with water and dried well under reduced pressure to give benzyl (3-(7-bromo-1-carbamoyl-3-methyl-9H-pyrido[3,4-b]indol-4-yl)-2-methylphenyl)carbamate as a light brown solid. LC/MS M+1=543.4 and 545.4. The reaction mixture was used in the next step without any further purification.

8. 4-(3-Amino-2-methylphenyl)-7-bromo-3-methyl-9H-pyrido[3,4-b]indole-1-carboxamide

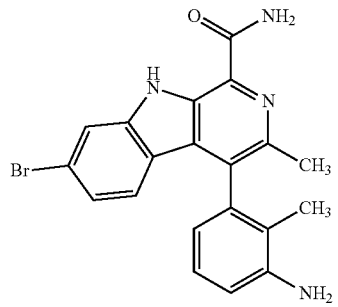 [SMILES: Cc1nc(C(N)=O)c2[nH]c3cc(Br)ccc3c2c1-c1cccc(N)c1C]

To a solution of benzyl (3-(7-bromo-1-carbamoyl-3-methyl-9H-pyrido[3,4-b]indol-4-yl)-2-methylphenyl)carbamate (1.10 g, 2.02 mmol) in acetonitrile (100 mL) at 0° C. was added iodotrimethylsilane (1.10 mL, 8.10 mmol) dropwise. The mixture was stirred at room temperature for 1.5 h. After concentration, diethylamine (2 mL) and ethyl acetate (150 mL) were added to the residue. The mixture was washed with water (2×40 mL), washed with brine (40 mL), and dried over anhydrous sodium sulfate. Concentration under reduced pressure followed by purification by flash silica gel chromatography using a mixture of ethyl acetate in hexane (20%-35%-50%) afforded 4-(3-amino-2-methylphenyl)-7-bromo-3-methyl-9H-pyrido[3,4-b]indole-1-carboxamide (0.411 g, 1.00 mmol, 50% yield) as a tan solid. LC/MS M+1=409.1 and 411.1.

9. 7-Bromo-3-methyl-4-(2-methyl-3-(4-oxoquinazolin-3(4H)-yl)phenyl)-9H-pyrido[3,4-b]indole-1-carboxamide

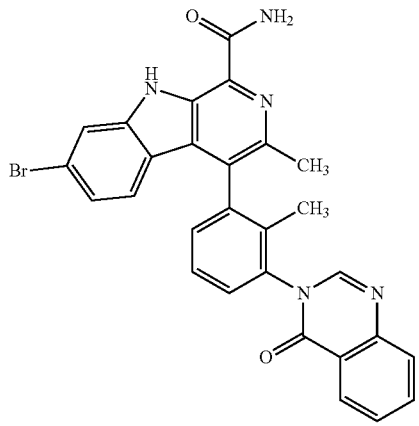 [SMILES: Cc1nc(C(N)=O)c2[nH]c3cc(Br)ccc3c2c1-c1cccc(-n2cnc3ccccc3c2=O)c1C]

A mixture of 4-(3-amino-2-methylphenyl)-7-bromo-3-methyl-9H-pyrido[3,4-b]indole-1-carboxamide (0.042 g, 0.103 mmol), 1H-benzo[d][1,3]oxazine-2,4-dione (0.042 g, 0.257 mmol), tris(nitrooxy)lanthanum, 6H$_2$O (0.013 g, 0.031 mmol), and trimethoxymethane (0.337 mL, 3.08 mmol) in tetrahydrofuran (0.5 mL) in a sealed vial was heated at 90° C. for 12 h. The reaction mixture was then stirred overnight at room temperature. This reaction was repeated two additional times. The combined reaction mixtures were diluted with ethyl acetate, washed with water, washed with brine, and dried over anhydrous sodium sulfate. Concentration under reduced pressure followed by purification by flash silica gel chromatography using a mixture of ethyl acetate and hexane (20%-35%-50%-65%) afforded 7-bromo-3-methyl-4-(2-methyl-3-(4-oxoquinazolin-3(4H)-yl)phenyl)-9H-pyrido[3,4-b]indole-1-carboxamide (0.101 g, 0.188 mmol, 59% yield) as a tan solid. LC/MS M+1=538.1 and 540.1.

10. 7-Acetyl-3-methyl-4-(2-methyl-3-(4-oxoquinazolin-3(4H)-yl)phenyl)-9H-pyrido[3,4-b]indole-1-carboxamide

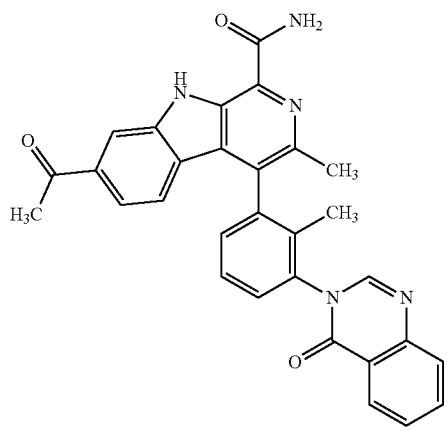 [SMILES: CC(=O)c1ccc2c(c1)[nH]c1c(C(N)=O)nc(C)c(-c3cccc(-n4cnc5ccccc5c4=O)c3C)c12]

To a well degassed mixture of 7-bromo-3-methyl-4-(2-methyl-3-(4-oxoquinazolin-3(4H)-yl)phenyl)-9H-pyrido[3, 4-b]indole-1-carboxamide (0.101 g, 0.188 mmol) and Bis(triphenylphosphine)palladium(II) chloride (0.018 g, 0.026 mmol) in 1,4-dioxane (2.0 mL) in a sealed tube was added tributyl(1-ethoxyvinyl)stannane (0.148 mL, 0.450 mmol) followed by triethylamine (0.052 mL, 0.375 mmol). The resulting mixture was evacuated and charged with nitrogen (2×), immersed in an oil bath at 100° C., and stirred overnight. The mixture was diluted with ethyl acetate, filtered through a pad of CELITE®, and concentrated under reduced pressure. The residue was dissolved in tetrahydrofuran (5 mL) and stirred with 1 N aqueous hydrochloric acid (2 mL) for 2 h. The solution was concentrated under reduced pressure, and the residue was suspended in water. The pH was adjusted to ~6 with 1 N sodium bicarbonate, and the suspension was extracted with ethyl acetate (3×). The combined organic layers were washed with brine and dried over anhydrous sodium sulfate. Concentration under reduced pressure followed by purification by flash silica gel chromatography using a mixture of ethyl acetate and hexane (50%-62%-75%-88%) afforded 7-acetyl-3-methyl-4-(2-methyl-3-(4-oxoquinazolin-3(4H)-yl)phenyl)-9H-pyrido[3,4-b]indole-1-carboxamide (0.051 g, 0.102 mmol, 54% yield) as a pale yellow solid. LC/MS M+1=502.1.

11. 7-(2-Hydroxypropan-2-yl)-3-methyl-4-(2-methyl-3-(4-oxoquinazolin-3(4H)-yl)phenyl)-9H-pyrido[3,4-b]indole-1-carboxamide

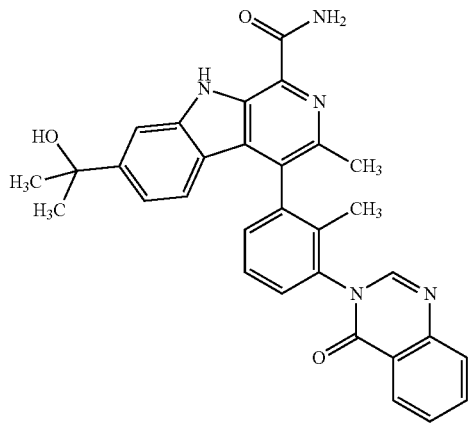 [SMILES: Cc1nc(C(N)=O)c2[nH]c3cc(C(C)(C)O)ccc3c2c1-c1cccc(-n2cnc3ccccc3c2=O)c1C]

To a solution of 7-acetyl-3-methyl-4-(2-methyl-3-(4-oxoquinazolin-3(4H)-yl)phenyl)-9H-pyrido[3,4-b]indole-1-carboxamide (51 mg, 0.102 mmol) in tetrahydrofuran (10.0 mL) at 0° C. was added methylmagnesium bromide (3 M in diethyl ether, 0.169 mL, 0.508 mmol). The mixture was stirred for 30 min. HPLC analysis indicated that there was still a significant amount of starting material remaining. Additional methylmagnesium bromide (0.10 mL) was added, and the reaction mixture was stirred for an additional 30 min. at 0° C. The reaction was slowly quenched with water and extracted with ethyl acetate (3×). The organic layers were combined, washed with brine, and dried over anhydrous sodium sulfate. Concentration under reduced pressure followed by purification by flash silica gel chromatography using a mixture ethyl acetate and hexane (50%-62%-75%-88%-100%) and reverse phase preparative HPLC afforded 7-(2-hydroxypropan-2-yl)-3-methyl-4-(2-methyl-3-(4-oxoquinazolin-3(4H)-yl)phenyl)-9H-pyrido[3,4-b]indole-1-carboxamide (24% yield) as an off-white solid and as a mixture of atropisomers. LC/MS M+1=518.2. $^1$H NMR (500 MHz, MeOD) δ 8.42-8.38 (m, 1H), 8.33 (dt, J=8.0, 1.7 Hz, 1H), 7.93-7.87 (m, 1H), 7.83-7.77 (m, 2H), 7.70-7.59 (m, 3H), 7.53-7.44 (m, 1H), 7.25-7.15 (m, 1H), 7.06 (d, J=8.6 Hz, 0.6H), 6.81 (d, J=8.3 Hz, 0.4H), 2.51-2.46 (m, 3H), 1.81-1.78 (m, 3H), and 1.62-1.56 (m, 6H).

EXAMPLE 39

7-(2-Hydroxypropan-2-yl)-1-(2-methyl-3-(4-oxoquinazolin-3(4H)-yl)phenyl)-5H-pyrido[4,3-b]indole-4-carboxamide

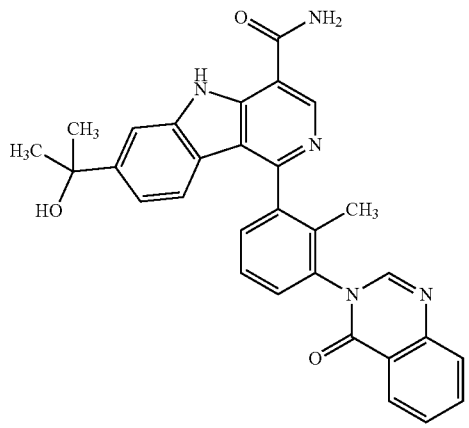 [SMILES: Cc1c(-c2ncc(C(N)=O)c3[nH]c4cc(C(C)(C)O)ccc4c23)cccc1-n1cnc2ccccc2c1=O]

1. 7-Bromo-2,5-dihydro-1H-pyrido[4,3-b]indol-1-one

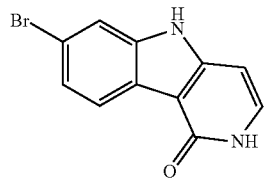

(3-Bromophenyl)hydrazine HCl (20.5730 g, 92.4 mmol) was dissolved in 6.25 N aqueous NaOH (16 mL, 100 mmol), ethanol (80 mL) and water (60 mL), and extracted with EtOAc (200 mL). The organic layer was dried over MgSO$_4$, filtered and concentrated in vacuo. CH$_2$Cl$_2$ (150 mL) was added, dried over MgSO$_4$, filtered and concentrated in vacuo to give (3-bromophenyl)hydrazine as a light orange oil. To a heterogeneous solution of (3-bromophenyl)hydrazine (17.19 g, 92 mmol) in Phenyl ether (82 mL) was added pyridine-2,4-diol (5.11 g, 46.0 mmol). A Dean-Stark trap was set up, and the reaction was heated at 232° C. for 4 hours. A strong effervescence and gas evolution occurred often for 45 min. The solution turned homogeneous with decrease in frequency of strong effervescence and gas evolution. The reaction mixture was cooled to room temperature; precipitation ensued. HPLC and LCMS showed completion of reaction (86784-071-01). Toluene (100 mL) was added, and the mixture stirred overnight at room temperature. The mixture was filtered and the precipitate was collected. Methanol (40 mL) was added, and the solution was stirred for 20 min. The precipitate was filtered and washed with methanol, dried to give 7-bromo-2,5-dihydro-1H-pyrido[4,3-b]indol-1-one as a tan solid. Methanol (60 mL) was added, and the mixture was stirred for 7 h. The precipitate was collected to give 7-bromo-2,5-dihydro-1H-pyrido[4,3-b]indol-1-one (4.4374 g, 16.87 mmol, 36.7% yield) a light tan solid. The precipitate was collected to give 7-bromo-2,5-dihydro-1H-pyrido[4,3-b]indol-1-one (4.4374 g, 16.87 mmol, 36.7% yield) a light tan solid. The product had an HPLC Retention Time=2.585 min [mixture of rotamers] [4 min grad, 10% MeOH/water to 90% MeOH/water, 0.1% TFA, YMC COMBISCREEN® ODS-A, 4.6×50 mm, 220 nM; LC/MS$^{+1}$ 263.04; 265.04

2. Methyl-1-oxo-2,5-dihydro-1H-pyrido[4,3-b]indole-7-carboxylate

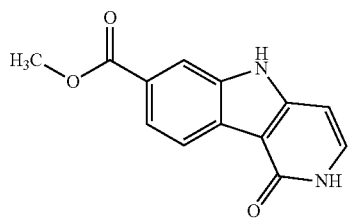 [SMILES: COC(=O)c1ccc2c(c1)[nH]c1cc[nH]c(=O)c12]

A stirred mixture of 7-bromo-2,5-dihydro-1H-pyrido[4,3-b]indol-1-one (1.000 g, 3.80 mmol), 1,1'-Bis(diphenylphosphino)ferrocene (0.319 g, 0.57 mmol), Palladium (II) acetate (0.128 g, 0.57 mmol) and Sodium acetate (0.623 g, 7.600) in a mixture of Methanol (30 mL) and DMA (10 mL) was degassed under vacuum and pressurized with Carbon Monoxide gas [CO] from a lecture bottle to approx. 55 psi in a sealed Steel Reaction vessel. The sealed vessel was heated at 95° C. overnight behind a protective shield. LC-MS showed complete reaction. The reaction mixture was filtered through a pad of CELITE® and the filtrate concentrated under vacuum. The residue was diluted with dichloromethane, filtered and the filtrate concentrated to give methyl-1-oxo-2,5-dihydro-1H-pyrido[4,3-b]indole-7-carboxylate as a tan solid. [0.732 g product, 3.02 mmol, 85% yield]. The product had an HPLC Retention Time=2.192 min [4 min grad, 10% MeOH/water to 90% MeOH/water, 0.1% TFA, YMC COMBISCREEN® ODS-A, 4.6×50 mm, 220 nM]; LC/MS$^{+1}$ 243.06

3. Methyl-4-bromo-1-oxo-2,5-dihydro-1H-pyrido[4,3-b]indole-7-carboxylate

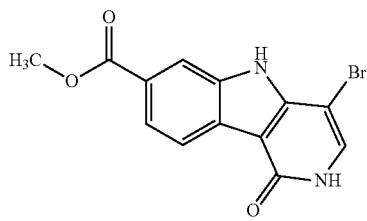 [SMILES: COC(=O)c1ccc2c(c1)[nH]c1c(Br)c[nH]c(=O)c12]

Bromosuccinimide (0.633 g, 3.56 mmol) was quickly added to a stirred mixture of methyl 1-oxo-2,5-dihydro-1H-pyrido[4,3-b]indole-7-carboxylate (0.783 g, 3.23 mmol) in DMF (20 mL) at room temperature. The reaction was exothermic and turned brown. The reaction mixture was stirred for four hours. at room temperature. LC-MS showed complete conversion to the desired product mass. The reaction mixture was poured in to 200 ml water with stirring, then filtered. The residue was washed with water, then slurred in hot methanol, and filtered. The residue was then dried under vacuum overnight to give Methyl-4-bromo-1-oxo-2,5-dihydro-1H-pyrido[4,3-b]indole-7-carboxylate as a light brown solid. [0.898 g, 2.80 mmol, 87% yield]. The product had an HPLC Retention Time=2.703 min [4 min grad, 10% MeOH/water to 90% MeOH/water, 0.1% TFA, YMC COMBISCREEN® ODS-A, 4.6×50 mm, 220 nM]; LC/MS$^{+1}$ 320.86, 322.86

4. Methyl-4-cyano-1-oxo-2,5-dihydro-1H-pyrido[4,3-b]indole-7-carboxylate

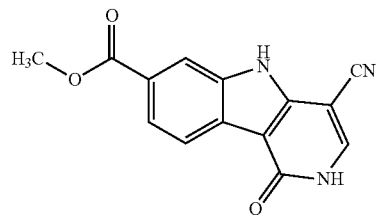 [SMILES: COC(=O)c1ccc2c(c1)[nH]c1c(C#N)c[nH]c(=O)c12]

A stirred mixture of methyl 4-bromo-1-oxo-2,5-dihydro-1H-pyrido[4,3-b]indole-7-carboxylate (0.820 g, 2.55 mmol) and Cuprous cyanide (0.229 g, 2.55 mmol) in N-Methyl-2-pyrrolidinone (25 mL) was heated at 200° C. for 2-4 hours. LC-MS showed complete conversion to the desired product plus minor debrominated product. The reaction mixture was cooled to room temperature then concentrated in vacuo. The residue was slurred in water and filtered. The solid residue was dried overnight under vacuum to give methyl-4-cyano-1-oxo-2,5-dihydro-1H-pyrido[4,3-b]indole-7-carboxylate as a brown solid. [0.672 g product, 2.51 mmol, 98% yield]. The product had an HPLC Retention Time=2.537 min [4 min grad, 10% MeOH/water to 90% MeOH/water, 0.1% TFA, YMC COMBISCREEN® ODS-A, 4.6×50 mm, 220 nM]; LC/MS$^{+1}$ 268.2

5. Methyl-1-chloro-4-cyano-5H-pyrido[4,3-b]indole-7-carboxylate

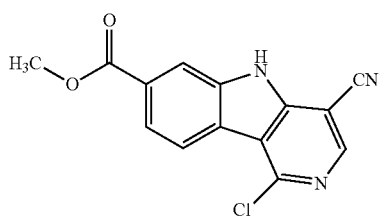 [SMILES: COC(=O)c1ccc2c(c1)[nH]c1c(C#N)cnc(Cl)c12]

A stirred slurry of methyl 4-cyano-1-oxo-2,5-dihydro-1H-pyrido[4,3-b]indole-7-carboxylate (1.000 g, 3.74 mmol) in Dioxane (Volume: 25 mL) was heated to 93° C. Phosphorus oxychloride (1.713 mL, 18.71 mmol) was added slowly dropwise over 30 minutes. After complete addition the reaction mixture was stirred at 93° C. for 5 hours then at room temperature overnight. LC-MS showed complete conversion to the desired product mass with minor by-products. The reaction mixture was diluted with 25 ml ethyl acetate and filtered. The filtrate was concentrated under vacuum to give 1.311 g crude solid tan product. The crude product was washed with diethyl ether, then triturated with acetonitrile and filtered to give Methyl-1-chloro-4-cyano-5H-pyrido[4,3-b]indole-7-carboxylate as a tan solid [0.855 g, 2.99 mmol, 80% yield]. The product had an HPLC Retention Time=3.658 min [4 min grad, 10% MeOH/water to 90% MeOH/water, 0.1% TFA, YMC COMBISCREEN® ODS-A, 4.6×50 mm, 220 nM]; LC/MS+1 286.1

6. Methyl-4-cyano-1-(2-methyl-3-(4-oxoquinazolin-3(4H)-yl)phenyl)-5H-pyrido[4,3-b]indole-7-carboxylate

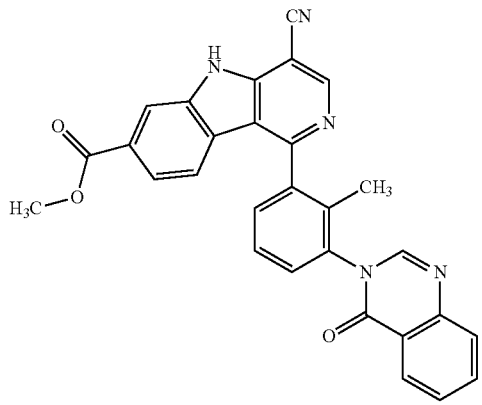 [SMILES: COC(=O)c1ccc2c(c1)[nH]c1c(C#N)cnc(-c3cccc(-n4cnc5ccccc5c4=O)c3C)c12]

A stirred mixture of methyl 1-chloro-4-cyano-5H-pyrido[4,3-b]indole-7-carboxylate (0.285 g, 0.998 mmol), 3-(2-methyl-3-(4,4,5,5-tetramethyl-1,3,2-dioxaborolan-2-yl)phenyl)quinazolin-4(3H)-one (0.361 g, 0.998 mmol), Tetrakis(triphenylphosphine)palladium(0) (0.058 g, 0.050 mmol) and Sodium carbonate[2M] (0.499 mL, 0.998 mmol) in Dioxane (2 mL) was heated at 110° C. for 16 hours overnight. LC-MS showed complete conversion to the desired product mass plus residual starting material[boronic ester] and a byproduct. The reaction mixture was concentrated. The residue was taken up in 10 ml DMF, stirred and filtered. The filtrate was concentrated; the residue triturated with methanol and filtered. The solid residue was dried overnight. LC-MS showed the solid residue to be the desired product methyl-4-cyano-1-(2-methyl-3-(4-oxoquinazolin-3(4H)-yl)phenyl)-5H-pyrido[4,3-b]indole-7-carboxylate as a tan solid [0.192 g, 0.395 mmol, 39% yield]. The product had an HPLC Retention Time=3.521 min [mixture of rotamers][4 min grad, 10% MeOH/water to 90% MeOH/water, 0.1% TFA, YMC COMBISCREEN® ODS-A, 4.6×50 mm, 220 nM]; LC/MS+1 486.2

7. Methyl-4-carbamoyl-1-(2-methyl-3-(4-oxoquinazolin-3(4H)-yl)phenyl)-5H-pyrido[4,3-b]indole-7-carboxylate

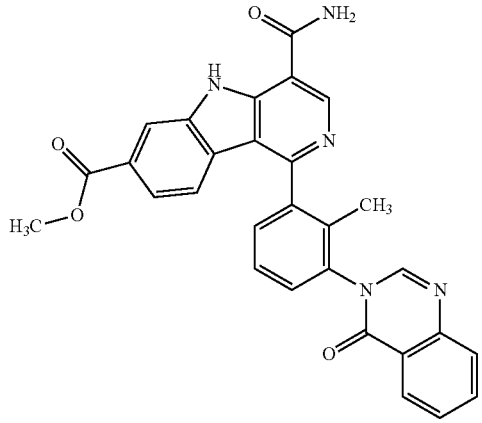 [SMILES: COC(=O)c1ccc2c(c1)[nH]c1c(C(N)=O)cnc(-c3cccc(-n4cnc5ccccc5c4=O)c3C)c12]

A stirred mixture of methyl 4-cyano-1-(2-methyl-3-(4-oxoquinazolin-3(4H)-yl)phenyl)-5H-pyrido[4,3-b]indole-7-carboxylate (0.192 g, 0.395 mmol) and 90% aqueous Sulfuric acid (2.000 ml, 36.8 mmol) was heated at 60° C. for 15-30 minutes. HLC-MS showed complete conversion to the desired product plus the corresponding carboxylic acid. The reaction mixture was cooled to 0° C. and neutralized to approx. pH=5-6 with 50% NaOH solution then stirred overnight. The reaction mixture was filtered and the residue dried overnight under vacuum to give methyl-4-carbamoyl-1-(2-methyl-3-(4-oxoquinazolin-3(4H)-yl)phenyl)-5H-pyrido[4,3-b]indole-7-carboxylate a tan/brown solid [0.111 g, 0.220 mmol, 56% yield]. The product had an HPLC Retention Time=2.798 minutes[mixture of isomers] [4 min grad, 10% MeOH/water to 90% MeOH/water, 0.1% TFA, YMC Comb screen ODS-A, 4.6×50 mm, 220 nM]; LC/MS+1 504.4

8. 7-(2-Hydroxypropan-2-yl)-1-(2-methyl-3-(4-oxoquinazolin-3(4H)-yl)phenyl)-5H-pyrido[4,3-b]indole-4-carboxamide

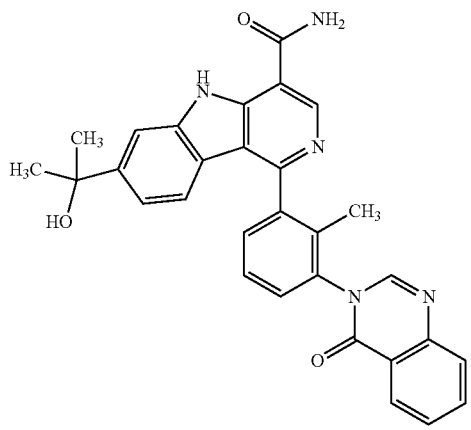 [SMILES: Cc1c(-c2ncc(C(N)=O)c3[nH]c4cc(C(C)(C)O)ccc4c23)cccc1-n1cnc2ccccc2c1=O]

A solution of methyl 4-carbamoyl-1-(2-methyl-3-(4-oxoquinazolin-3(4H)-yl)phenyl)-5H-pyrido[4,3-b]indole-7-carboxylate (0.078 g, 0.155 mmol) in THF (20 mL) and HMPA (1.000 mL) was cooled with stirring to −78° C. Methyllithium [1,6M in diethyl ether] (0.620 mL, 0.929 mmol) was added quickly drop wise and the resulting reaction mixture stirred at −78° C. for fifteen minutes. The reaction mixture was allowed to warm to room temperature and quenched with 1N HCl solution [5 ml]. The resulting mixture was concentrated under high vacuum. The crude product mixture was chromatographed using Reverse-Phase PREP LC. The desired product was obtained as a minor product with two major by-products. Fractions containing the desired product were combined and concentrated to give 7.2 mg product plus residual DMF which was pulled off under high vacuum to give 7-(2-hydroxypropan-2-yl)-1-(2-methyl-3-(4-oxoquinazolin-3(4H)-yl)phenyl)-5H-pyrido[4,3-b]indole-4-carboxamide as a tan solid product. [0.0055 g, 0.011 mmol, 7.3% yield] The product had an HPLC Retention Time=3.461 min[mixture of rotamers] [4 min grad, 10% MeOH/water to 90% MeOH/water, 0.1% TFA, YMC COMBISCREEN® ODS-A, 4.6×50 mm, 220 nM]; LC/MS+1 504.3. $^1$H NMR (400 MHz, methanol-$d_4$) δ 7.97 (s, 1H), 7.85 (dd, J=7.9, 1.3 Hz, 2H), 7.75 (d, J=7.9 Hz, 1H), 7.72-7.61 (m, 1H), 7.58 (d, J=0.9 Hz, 1H), 7.50 (dd, J=8.5, 1.4 Hz, 1H), 7.42 (t, 2H), 7.33 (d, J=8.4 Hz, 1H), 6.92

(d, J=8.4 Hz, 1H), 6.79 (s, 1H), 5.55 (s, 1H), 5.26 (s, 1H), 3.90-3.64 (m, —OH), 2.25 (s, 3H), 2.10 (s, 3H), 1.40-1.12 (m, 6H).

EXAMPLE 40

1-(3-(8-Fluoro-4-oxoquinazolin-3(4H)-yl)-2-methylphenyl)-7-(2-hydroxypropan-2-yl)-5H-pyrido[4,3-b]indole-4-carboxamide

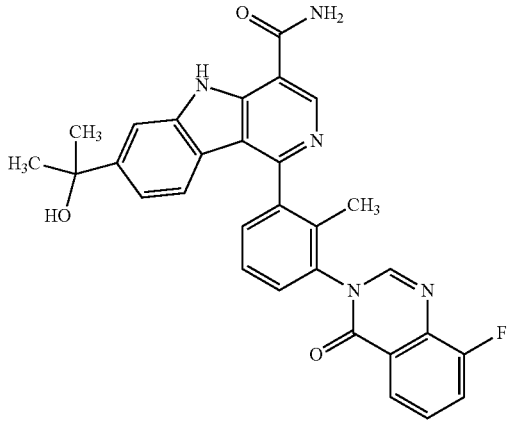 [SMILES: Cc1c(-c2ncc(C(N)=O)c3[nH]c4cc(C(C)(C)O)ccc4c23)cccc1-n1cnc2c(F)cccc2c1=O]

1. Methyl-4-cyano-1-(3-(8-fluoro-4-oxoquinazolin-3(4H)-yl)-2-methylphenyl)-5H-pyrido[4,3-b]indole-7-carboxylate

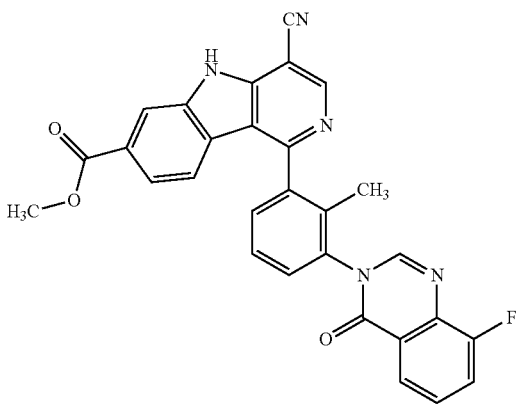 [SMILES: COC(=O)c1ccc2c(c1)[nH]c1c(C#N)cnc(-c3cccc(-n4cnc5c(F)cccc5c4=O)c3C)c12]

A stirred mixture of methyl 1-chloro-4-cyano-5H-pyrido[4,3-b]indole-7-carboxylate (0.285 g, 0.998 mmol), 8-fluoro-3-(2-methyl-3-(4,4,5,5-tetramethyl-1,3,2-dioxaborolan-2-yl)phenyl)quinazolin-4(3H)-one (0.379 g, 0.998 mmol), Tetrakis(triphenylphosphine)palladium(0) (0.058 g, 0.050 mmol) and Sodium carbonate[2M aqueous] (0.499 mL, 0.998 mmol) in Dioxane (2 mL) was heated at 110° C. for 16 hours overnight. LC-MS showed complete conversion to the desired product mass plus residual starting material[boronic ester] and a byproduct. The reaction mixture was concentrated. The residue was taken up in 10 ml DMF, stirred and filtered. The filtrate was concentrated; the residue triturated with methanol and filtered. The solid residue labeled 89040-079-04 was dried overnight. LC-MS showed the solid residue to be the desired product Methyl-4-cyano-1-(3-(8-fluoro-4-oxoquinazolin-3(4H)-yl)-2-methylphenyl)-5H-pyrido[4,3-b]indole-7-carboxylate as a tan solid [0.172 g, 0.342 mmol, 34% yield]. The product had an HPLC Retention Time=3.510 min [mixture of rotamers][4 min grad, 10% MeOH/water to 90% MeOH/water, 0.1% TFA, YMC COMBISCREEN® ODS-A, 4.6×50 mm, 220 nM]; LC/MS$^{+1}$ 504.3.

2. Methyl-4-carbamoyl-1-(3-(8-fluoro-4-oxo-quinazolin-3(4H)-yl)-2-methylphenyl)-5H-pyrido[4,3-b]indole-7-carboxylate

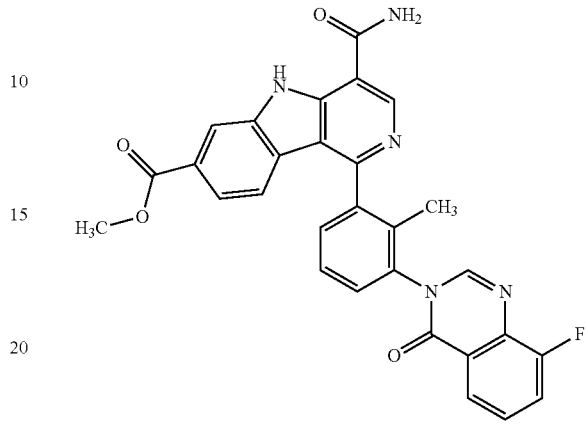

A stirred mixture of methyl 4-cyano-1-(3-(8-fluoro-4-oxoquinazolin-3(4H)-yl)-2-methylphenyl)-5H-pyrido[4,3-b]indole-7-carboxylate (0.172 g, 0.342 mmol) and 90% aqueous Sulfuric acid (2.000 ml, 36.8 mmol) was heated at 60° C. for 15-30 minutes. LC-MS showed complete conversion to the desired product plus the corresponding carboxylic acid as a minor product. The reaction mixture was cooled to 0° C. and carefully neutralized to approx. pH=5-6 with 50% NaOH solution then stirred overnight. The reaction mixture was filtered and the residue dried under vacuum overnight to give methyl-4-carbamoyl-1-(3-(8-fluoro-4-oxoquinazolin-3(4H)-yl)-2-methylphenyl)-5H-pyrido[4,3-b]indole-7-carboxylate as a tan solid. [0.143 g, 0.274 mmol, 80% yield] The product had an HPLC Retention Time=2.798 minutes[mixture of isomers] [4 min grad, 10% MeOH/water to 90% MeOH/water, 0.1% TFA, YMC COMBISCREEN® ODS-A, 4.6×50 mm, 220 nM]; LC/MS$^{+1}$ 522.4.

3. 1-(3-(8-Fluoro-4-oxoquinazolin-3(4H)-yl)-2-methylphenyl)-7-(2-hydroxypropan-2-yl)-5H-pyrido[4,3-b]indole-4-carboxamide In order to overcome the general insolubility of the substrate, a solution of methyl 4-carbamoyl-1-(3-(8-fluoro-4-oxoquinazolin-3(4H)-yl)-2-methylphenyl)-5H-pyrido[4,3-b]indole-7-carboxylate (0.100 g, 0.192 mmol) in 0.5 ml DMF concentrated on the rotary evaporator to product a more amorphous solid. This "amorphous paste" was dissolved in THF (5 mL) and HMPA (0.500 mL), then cooled with stirring to −78° C. Methyllithium[1.6 M in diethyl ether] (0.615 mL, 0.983 mmol) was added quickly drop wise. An exothermic reaction took place. The resulting reaction mixture stirred at −78° C. for 15 minutes, then allowed to warm to 0° C. and quenched with 1N HCl solution and concentrated under vacuum. The residue was chromatographed using Reverse-Phase PREP LC. to give 1-(3-(8-fluoro-4-oxoquinazolin-3(4H)-yl)-2-methylphenyl)-7-(2-hydroxypropan-2-yl)-5H-pyrido[4,3-b]indole-4-carboxamide as a tan solid product. [0.0083 g, 0.015 mmol, 8% yield]. The product had an HPLC Retention Time=2.623 min[mixture of rotamers] [4 min grad, 10% MeOH/water to 90% MeOH/water, 0.1% TFA, YMC COMBISCREEN® ODS-A, 4.6×50 mm, 220 nM; LC/MS$^{+1}$ 522.1. $^1$H NMR (400 MHz, methanol-d$_4$) δ 9.11 (s, 1H), 8.07 (br. s., 1H), 7.93-7.87 (m, 2H), 7.86-7.64, 2H), 7.64-7.44 (m, 2H), 7.38-7.03 (m, 2H), 6.97-6.39 (m, 1H), 2.26-1.96 (m, 3H), 1.77-1.53 (m, 6H).

EXAMPLE 41

1-(3-(6-Fluoro-1-oxoisoindolin-2-yl)-2-methylphentl)-7-(2-hydroxypropan-2-yl)-5H-pyrido[4,3-b]indole-4-carboxamide

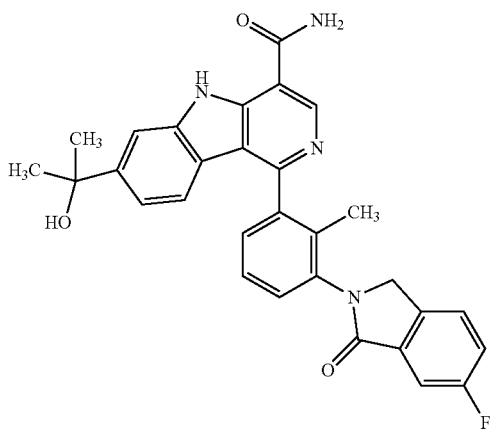 [SMILES: Cc1c(-c2ncc(C(N)=O)c3[nH]c4cc(C(C)(C)O)ccc4c23)cccc1N1Cc2ccc(F)cc2C1=O]

1. Methyl-4-cyano-1-(3-(6-fluoro-1-oxoisoindolin-2-yl)-2-methylphenyl)-5H-pyrido[4,3-b]indole-7-carboxylate

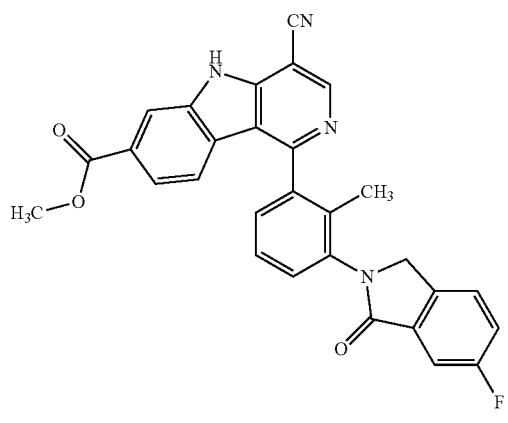 [SMILES: COC(=O)c1ccc2c(c1)[nH]c1c(C#N)cnc(-c3cccc(N4Cc5ccc(F)cc5C4=O)c3C)c12]

A stirred mixture of methyl 1-chloro-4-cyano-5H-pyrido[4,3-b]indole-7-carboxylate (0.285 g, 0.998 mmol), Tetrakis(triphenylphosphine)palladium(0) (0.058 g, 0.050 mmol) and Sodium carbonate[2M] (0.499 mL, 0.998 mmol) in Dioxane (10 mL) was heated at 110° C. for 4 hours. LC-MS showed complete conversion to the desired product mass plus residual starting material[boronic ester] and a byproduct. The reaction mixture was concentrated. The residue was taken up in 10 ml DMF, stirred and filtered. The filtrate was concentrated; the residue triturated with methanol and filtered. The solid residue labeled 89040-080-04 was dried overnight to give methyl-4-cyano-1-(3-(6-fluoro-1-oxoisoindolin-2-yl)-2-methylphenyl)-5H-pyrido[4,3-b]indole-7-carboxylate as a tan solid. [0.216 g, 0.440 mmol, 44% yield]. The product had an HPLC Retention Time=3.498, 3.3.590 min [mixture of rotamers] [4 min grad, 10% MeOH/water to 90% MeOH/water, 0.1% TFA, YMC COMBISCREEN® ODS-A, 4.6×50 mm, 220 nM]; LC/MS[+1] 491.2.

2. Methyl-4-carbamoyl-1-(3-(6-fluoro-1-oxoisoindolin-2-yl)-2-methylphenyl)-5H-pyrido[4,3-b]indole-7-carboxylate

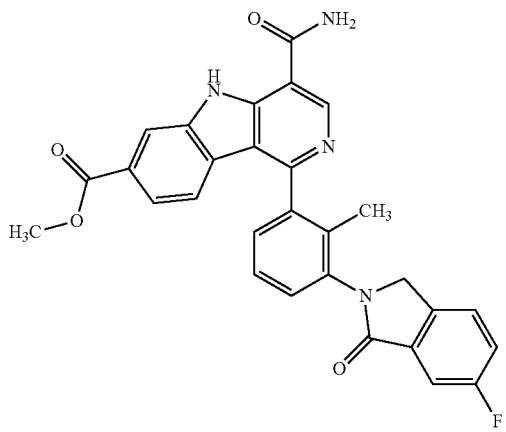 [SMILES: COC(=O)c1ccc2c(c1)[nH]c1c(C(N)=O)cnc(-c3cccc(N4Cc5ccc(F)cc5C4=O)c3C)c12]

A stirred mixture of [Reactants] and 90% aqueous Sulfuric acid (1.000 ml, 18.39 mmol) was heated at 60° C. for 15-30 minutes. LC-MS showed complete conversion to the desired product plus the corresponding carboxylic acid as a minor product. The reaction mixture was neutralized to approx. pH=5-6 with 50% NaOH solution then stirred overnight. The reaction mixture was filtered, and the residue dried under vacuum overnight to give methyl-4-carbamoyl-1-(3-(6-fluoro-1-oxoisoindolin-2-yl)-2-methylphenyl)-5H-pyrido[4,3-b]indole-7-carboxylate as a brown solid. [0.223 g, 0.439 mmol, 96% yield]. The product had an HPLC Retention Time=2.746 min[mixture of isomers] [4 min grad, 10% MeOH/water to 90% MeOH/water, 0.1% TFA, YMC COMBISCREEN® ODS-A, 4.6×50 mm, 220 nM]; LC/MS[+1] 508.4.

3. 1-(3-(6-Fluoro-1-oxoisoindolin-2-yl)-2-methylphentl)-7-(2-hydroxypropan-2-yl)-5H-pyrido[4,3-b]indole-4-carboxamide

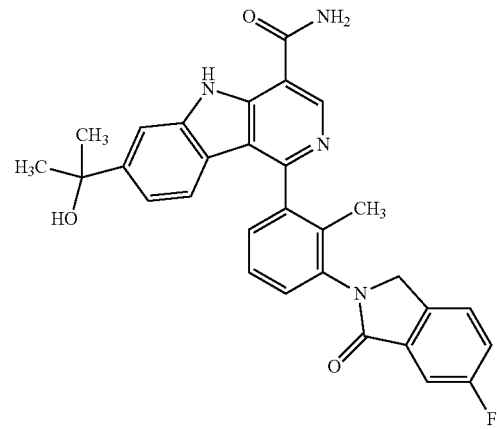 [SMILES: Cc1c(-c2ncc(C(N)=O)c3[nH]c4cc(C(C)(C)O)ccc4c23)cccc1N1Cc2ccc(F)cc2C1=O]

In order to overcome the general insolubility of the substrate, a solution of methyl 4-carbamoyl-1-(3-(6-fluoro-1-oxoisoindolin-2-yl)-2-methylphenyl)-5H-pyrido[4,3-b]indole-7-carboxylate (0.100 g, 0.197 mmol) in 0.5 ml DMF concentrated on the rotary evaporator to product a more amorphous solid. This "amorphous paste" was dissolved in THF (5 mL) and HMPA (0.500 mL) then cooled with stirring to 0° C. Methyllithium [1,6M in diethyl ether](0.615 mL, 0.983 mmol) was added quickly drop wise. An exothermic reaction took place. The resulting reaction mixture stirred at 0° C. for 15 minutes then quenched with 1N HCl solution. LC-MS showed disappearance of starting material. The reaction mixture was concentrated under vacuum and the residue chromatographed using Reverse-Phase PREP LC. Fractions containing product were combined and concentrated to give 1-(3-(6-fluoro-1-oxoisoindolin-2-yl)-2-methylphentl)-7-(2-hydroxypropan-2-yl)-5H-pyrido[4,3-b]indole-4-carboxamide as a tan solid [0.0016 g, 0.031 mmol, 16% yield]. The product had an HPLC Retention Time=2.403-2.48 min[mixture of rotamers] [4 min grad, 10% MeOH/water to 90% MeOH/water, 0.1% TFA, YMC COMBISCREEN® ODS-A, 4.6×50 mm, 220 nM; LC/MS[+1] 509.07. $^1$H NMR (400 MHz, methanol-$d_4$) δ 9.09 (s, 1H), 8.07 (br. s., 1H), 7.94-7.86, (m, 2H), 7.84-7.66 (m, 2H), 7.65-7.46 (m, 2H), 7.40-7.05 (m, 2H), 4.86 (s, 2H), 2.04 (bs, 4H), 1.63 (bs, 6H).

EXAMPLE 42

9-(2-Methyl-3-(4-oxoquinazolin-3(4H)-yl)phenyl)-2,3,4,5-tetrahydro-1H-pyrido[4,3-b]indole-6-carboxamide

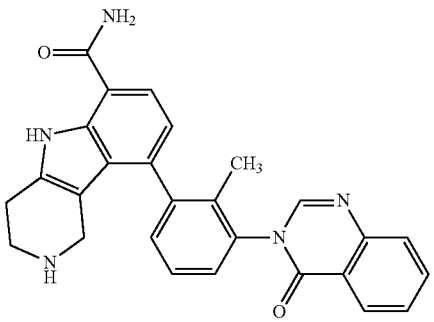 [SMILES: Cc1c(-c2ccc(C(N)=O)c3[nH]c4c(c23)CNCC4)cccc1-n1cnc2ccccc2c1=O]

1. Ethyl 6,9-dibromo-3,4-dihydro-1H-pyrido[4,3-b]indole-2(5H)-carboxylate

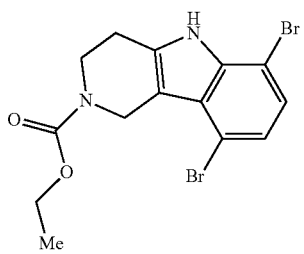 [SMILES: CCOC(=O)N1CCc2[nH]c3c(Br)ccc(Br)c3c2C1]

A solution of (2,5-dibromophenyl)hydrazine (prepared according to the procedure of Benniston, A. C. et al., *J. Org. Chem.*, 72:888-897 (2007), 5.00 g, 18.80 mmol) in ethanol (150 mL) was treated with ethyl 4-oxopiperidine-1-carboxylate (3.22 g, 18.80 mmol) and hydrogen chloride, 4 M in dioxane (4.70 mL, 18.80 mmol). The resulting brown solution was heated at 80-85° C. on an oil bath for 119.5 h. After stirring overnight at room temperature, the solution was concentrated under vacuum. The residue was sonicated in ethyl acetate and the insoluble material was collected by filtration, rinsed with EtOAc and dried under vacuum to provide a reddish-brown solid (2.58 g). The filtrate was concentrated under vacuum to provide a dark red semisolid (6.23 g) which was sonicated and triturated in a small amount (10-20 mL) of EtOAc. The resulting solid was collected by filtration, rinsed with a small amount of EtOAc and dried to provide a pink solid (1.473 g). Both batches of solid were combined and sonicated in water (with a small amount of methanol to promote wetting of the solid). The solid was collected by filtration, rinsed with water and dried under vacuum to provide a pinkish-tan solid (3.262 g). The original EtOAc filtrate was subjected to column chromatography on silica gel (220 g), eluting with EtOAc-hexane (gradient from 15:85 to 80:20). The isolated material was slurred in hexane with a small amount of ethyl acetate, and the precipitate was collected by filtration and dried under vacuum to provide a light tan solid (802 mg). The solids were combined to provide the desired product (4.064 g, 51%). LCMS (M+H[+]) m/z 401, 403, 405.

2. 6,9-Dibromo-2,3,4,5-tetrahydro-1H-pyrido[4,3-b]indole

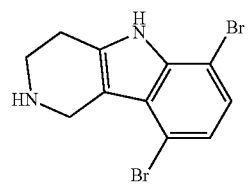 [SMILES: Brc1ccc(Br)c2c3c([nH]c12)CCNC3]

A suspension of ethyl 6,9-dibromo-3,4-dihydro-1H-pyrido[4,3-b]indole-2(5H)-carboxylate (2.70 g, 6.72 mmol) in ethanol (25 mL) was treated with a solution of potassium hydroxide (15.07 g, 269 mmol) in water (15 mL) and ethanol (50 mL). The dark brown mixture was bubbled with nitrogen with sonication for 1 min. The mixture was then heated under nitrogen to 90-100° C. for 44 h, then at reflux for 23 h more. The solution was cooled to room temperature and concentrated under vacuum. The residual aqueous sludge was diluted with water (about 100 mL), stirred and intermittently sonicated for 1 h, and the precipitate was collected by filtration, washed thoroughly with water and dried under vacuum to provide the desired product as a light reddish-brown powder (2.123 g, 96% yield). LCMS (M+H[+]) m/z 329, 331, 333).

3. 6,9-Dibromo-2-trityl-2,3,4,5-tetrahydro-1H-pyrido[4,3-b]indole

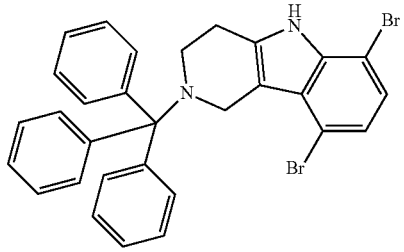 [SMILES: Brc1ccc(Br)c2c3c([nH]c12)CCN(C(c1ccccc1)(c1ccccc1)c1ccccc1)C3]

A suspension of 6,9-dibromo-2,3,4,5-tetrahydro-1H-pyrido[4,3-b]indole (700 mg, 2.121 mmol) in dichloromethane (10 mL) was stirred on an ice-water bath and treated with TEA (0.591 mL, 4.24 mmol), DMAP (25.9 mg, 0.212 mmol) and trityl chloride (1.183 g, 4.24 mmol). The mixture was allowed to warmed to room temperature and stirred for 71 h. The solution was concentrated under vacuum and the residue was subjected to column chromatography on silica gel (120 g), eluting with EtOAc-hexane (gradient from 5:95 to 50:50) to provide the desired product as a yellow glassy foam (1.388 g) contaminated with a trityl derivative (probably trityl chloride or triphenylmethanol), estimated purity 75% (estimated yield of desired product 82%). This material was used without further purification. LCMS m/z 243.2 (trityl cation), 329, 331, 333 (M+H-trityl)⁺.

4. 9-Bromo-2-trityl-2,3,4,5-tetrahydro-1H-pyrido[4,3-b]indole-6-carboxamide

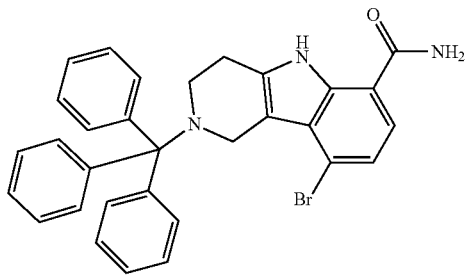 [SMILES: NC(=O)c1ccc(Br)c2c3c([nH]c12)CCN(C(c1ccccc1)(c1ccccc1)c1ccccc1)C3]

A solution of 6,9-dibromo-2-trityl-2,3,4,5-tetrahydro-1H-pyrido[4,3-b]indole (purity about 75%, 650 mg, 0.852 mmol) in THF (10 mL) was stirred at −78° C. and treated with tert-butyllithium, 1.7 M in pentane (2.505 mL, 4.26 mmol) over 2-3 min. After stirring for about 5-10 min at −78° C., the red-orange solution was stirred on an ice-water bath for 2 h. The solution was then cooled again to −78° C. and treated with trimethylsilyl isocyanate (0.922 mL, 6.81 mmol). Stirring was continued while allowing the cooling bath to warm slowly to room temperature. After 19 h, the mixture was treated with water (5 mL) and extracted twice with EtOAc. The combined organic phases were dried and concentrated. The residue was subjected to column chromatography on silica gel (80 g), eluting with EtOAc-hexane (gradient from 20:80 to 100:0) to provide the desired product as an off-white solid (251 mg, 55% yield). LCMS (M+H-trityl)⁺ m/z 294, 296.

5. 9-(2-Methyl-3-(4-oxoquinazolin-3(4H)-yl)phenyl)-2-trityl-2,3,4,5-tetrahydro-1H-pyrido[4,3-b]indole-6-carboxamide

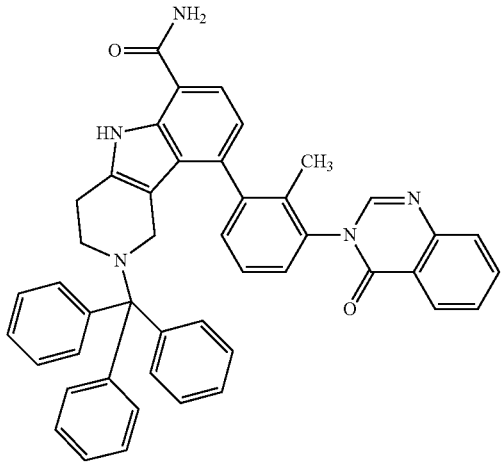 [SMILES: Cc1c(-c2ccc(C(N)=O)c3[nH]c4c(c23)CN(C(c2ccccc2)(c2ccccc2)c2ccccc2)CC4)cccc1-n1cnc2ccccc2c1=O]

A mixture of 9-bromo-2-trityl-2,3,4,5-tetrahydro-1H-pyrido[4,3-b]indole-6-carboxamide (250 mg, 0.466 mmol), 3-(2-methyl-3-(4,4,5,5-tetramethyl-1,3,2-dioxaborolan-2-yl)phenyl)quinazolin-4(3H)-one (186 mg, 0.513 mmol), and 2 M aqueous sodium carbonate (0.699 mL, 1.398 mmol) in toluene (4 mL) and ethanol (1 mL) was degassed by bubbling with argon for ca. 5-10 min (1 minute with sonication). The mixture was treated with tetrakis(triphenylphosphine)palladium (26.9 mg, 0.023 mmol) and heated at 90° C. under argon. After 16 h, the mixture was cooled to room temperature, diluted with EtOAc and a small amount of water and the layers were separated. The aqueous phase was extracted with EtOAc and the combined organic phases were filtered, dried and concentrated. The residue was subjected to column chromatography on silica gel (40 g), eluting with EtOAc-hexane (gradient from 15:85 to 100:0) to provide the desired product as a light yellow glass (243 mg, 70% yield). LCMS (M+H-trityl)⁺ m/z 450.2.

6. 9-(2-Methyl-3-(4-oxoquinazolin-3(4H)-yl)phenyl)-2,3,4,5-tetrahydro-1H-pyrido[4,3-b]indole-6-carboxamide

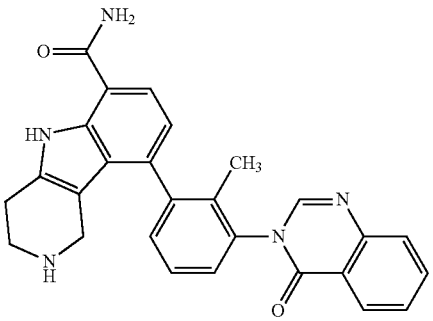 [SMILES: Cc1c(-c2ccc(C(N)=O)c3[nH]c4c(c23)CNCC4)cccc1-n1cnc2ccccc2c1=O]

A suspension of 9-(2-methyl-3-(4-oxoquinazolin-3(4H)-yl)phenyl)-2-trityl-2,3,4,5-tetrahydro-1H-pyrido[4,3-b]indole-6-carboxamide (248.5 mg, 0.359 mmol) in methanol (4 mL) was treated with EtOAc (less than 1 mL) to form a clear solution. This was treated with 1 M aqueous HCl (3 mL), forming a cloudy mixture which was stirred at room temperature. After 30 min, the mixture was concentrated under vacuum, treated with NaHCO₃ (aq) and EtOAc and stirred at room temperature for about 1 h. The precipitate was collected by filtration, washed with water, then with EtOAc, and dried under vacuum to provide the desired product as a white solid (145 mg, 90% yield).

Alternatively, a mixture of 9-bromo-2-trityl-2,3,4,5-tetrahydro-1H-pyrido[4,3-b]indole-6-carboxamide (78.3 mg, 0.146 mmol), 3-(2-methyl-3-(4,4,5,5-tetramethyl-1,3,2-dioxaborolan-2-yl)phenyl)quinazolin-4(3H)-one (52.9 mg, 0.146 mmol), and 2 M aqueous sodium carbonate (0.219 mL, 0.438 mmol) in toluene (1.2 mL) and ethanol (0.3 mL) was degassed by bubbling with argon for ca. 5-10 min (1 minute with sonication). The mixture was treated with tetrakis(triphenylphosphine)palladium (8.4 mg, 0.007 mmol) and heated at 90° C. under argon. After 15.75 h, the mixture was cooled to room temperature and concentrated under vacuum. The residue was stirred in methanol, treated with a small amount of TFA and water and the resulting mixture was sonicated until the gummy insoluble material was replaced by a flocculent precipitate. The mixture was filtered and subjected to purification by preparative HPLC. Fractions containing the desired product by LCMS were combined, treated with saturated aqueous sodium bicarbonate and concentrated under vacuum to provide an aqueous suspension. The precipitate was collected by filtration, washed with water and dried under vacuum to provide the desired product as a white solid (37.7 mg, 56% yield). LCMS (M+H⁺) m/z 450.2. ¹H NMR (400 MHz, DMSO-d₆) δ 10.83-10.93 (1 H, m), 8.19-8.41 (2 H, m), 8.03 (1 H, br. s.), 7.86-7.97 (1 H, m), 7.79 (1 H, t, J=7.3 Hz), 7.58-7.70 (2 H, m), 7.41-7.57 (2 H, m), 7.23-7.41 (2 H, m), 6.74-6.88 (1 H, m), 3.02-3.28 (2 H, m), 2.90 (2 H, br. s.), 2.71 (2 H, br. s.), 1.76 (3 H, s).

EXAMPLE 43

2-Acetyl-9-(2-methyl-3-(4-oxoquinazolin-3(4H)-yl) phenyl)-2,3,4,5-tetrahydro-1H-pyrido[4,3-b]indole-6-carboxamide

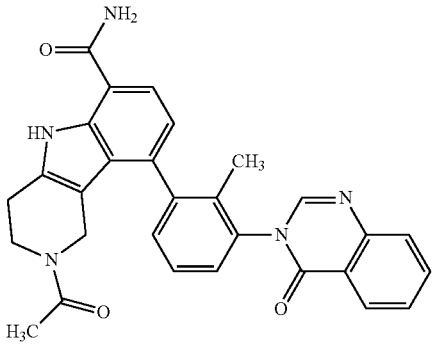 [SMILES: CC(=O)N1CCc2[nH]c3c(C(N)=O)ccc(-c4cccc(-n5cnc6ccccc6c5=O)c4C)c3c2C1]

A cloudy solution of 9-(2-methyl-3-(4-oxoquinazolin-3 (4H)-yl)phenyl)-2,3,4,5-tetrahydro-1H-pyrido[4,3-b]indole-6-carboxamide (20 mg, 0.044 mmol) in THF (0.5 mL) was treated with TEA (0.019 mL, 0.133 mmol) and stirred on an ice-water bath. The mixture was treated with acetic anhydride (nominally 8.40 μl, 0.089 mmol, probably more was added) and the resulting clear solution was stirred at room temperature for 1.5 h. The mixture was concentrated under vacuum, and the residue was purified by preparative HPLC. Effluent fractions containing the desired product were treated with NaHCO$_3$ (aq) and concentrated under vacuum. The resulting aqueous suspension was filtered and the precipitate was washed with water and dried under vacuum to provide the desired product as a white solid (7.0 mg). The filter and aqueous phase were extracted three times with EtOAc, and the organic extracts were dried and concentrated to provide additional desired product as a white solid (1.5 mg) for a total of 8.5 mg (39% yield). LCMS (M+H)$^+$ m/z 492.2, (M+Na)$^+$ 514.2. $^1$H NMR (400 MHz, methanol-d$_4$) δ 8.30-8.55 (2 H, m), 7.87-7.97 (1 H, m), 7.83 (1 H, t, J=7.9 Hz), 7.70 (1 H, dd, J=7.7, 1.3 Hz), 7.61-7.68 (1 H, m), 7.44-7.59 (3 H, m), 6.90-7.05 (1 H, m), 3.58-4.61 (4 H, m), 2.86-3.08 (2 H, m), 1.80-2.21 (6 H, multiple singlets).

EXAMPLE 44

9-(2-Methyl-3-(4-oxoquinazolin-3(4H)-yl)phenyl)-2-(methylsulfonyl)-2,3,4,5-tetrahydro-1H-pyrido[4,3-b]indole-6-carboxamide

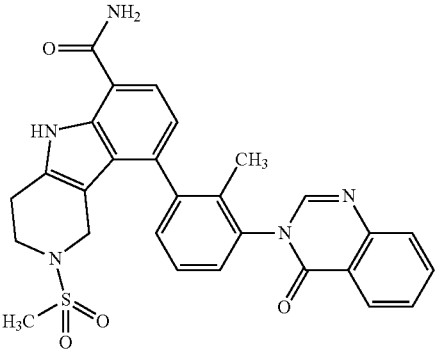 [SMILES: Cc1c(-c2ccc(C(N)=O)c3[nH]c4c(c23)CN(S(C)(=O)=O)CC4)cccc1-n1cnc2ccccc2c1=O]

Using the procedure of Example 43 but substituting methanesulfonyl chloride in place of acetic anhydride, 9-(2-methyl-3-(4-oxoquinazolin-3(4H)-yl)phenyl)-2,3,4,5-tetrahydro-1H-pyrido[4,3-b]indole-6-carboxamide (20 mg, 0.044 mmol) was converted into the desired product as a white solid (8.0 mg, 34% yield). LCMS (M+H)$^+$ m/z 528.2, (M+Na)$^+$ 550.2. $^1$H NMR (400 MHz, DMSO-d$_6$) δ 8.40, 8.15 (1 H, 2s), 8.22 (1 H, ddd, J=13.9, 8.1, 1.3 Hz), 7.92 (1 H, t, J=7.8 Hz), 7.79 (1 H, dd, J=7.6, 4.5 Hz), 7.73 (1 H, t, J=8.3 Hz), 7.54-7.67 (2 H, m), 7.51 (1 H, t, J=7.7 Hz), 7.43 (1 H, dd, J=7.2, 5.6 Hz), 6.83-7.00 (1 H, m), 3.43-3.86 (3 H, m), 3.28-3.34 (3 H, m), 2.89-3.19 (3 H, m), 1.74 (3 H, 2s).

EXAMPLE 45

N2, N2-Dimethyl-9-(2-methyl-3-(4-oxoquinazolin-3 (4H)-yl)phenyl)-3,4-dihydro-1H-pyrido[4,3-b]indole-2,6(5H)-dicarboxamide

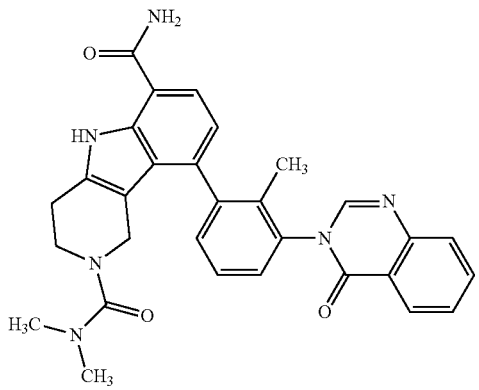 [SMILES: Cc1c(-c2ccc(C(N)=O)c3[nH]c4c(c23)CN(C(=O)N(C)C)CC4)cccc1-n1cnc2ccccc2c1=O]

Using the procedure of Example 43 but substituting dimethylcarbamoyl chloride in place of acetic anhydride, 9-(2-methyl-3-(4-oxoquinazolin-3(4H)-yl)phenyl)-2,3,4,5-tetrahydro-1H-pyrido[4,3-b]indole-6-carboxamide (20 mg, 0.044 mmol) was converted into the desired product as a white solid (10.0 mg, 42% yield). LCMS (M+H)$^+$ m/z 521.3, (M+Na)$^+$543.3. $^1$H NMR (400 MHz, methanol-d$_4$) δ 8.29-8.40 (2 H, m), 7.88-7.98 (1 H, m), 7.77-7.87 (1 H, m), 7.61-7.72 (2 H, m), 7.45-7.60 (3 H, m), 6.90-7.04 (1 H, m), 3.37-4.09 (4 H, m), 2.83-3.08 (2 H, m), 2.65-2.82 (6 H, 2s), 1.87 (3 H, 2s).

EXAMPLE 46

Ethyl 6-carbamoyl-9-(2-methyl-3-(4-oxoquinazolin-3(4H)-yl)phenyl)-3,4-dihydro-1H-pyrido[4,3-b]indole-2(5H)-carboxylate

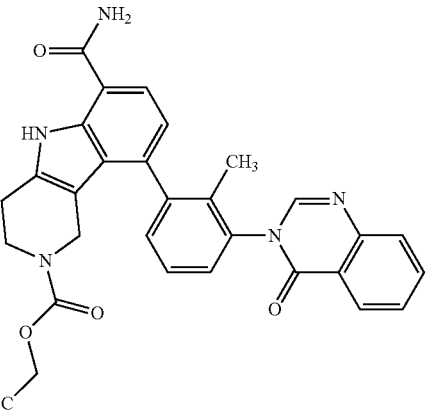

Using the procedure of Example 43 but substituting ethyl chloroformate in place of acetic anhydride, 9-(2-methyl-3-(4- oxoquinazolin-3(4H)-yl)phenyl)-2,3,4,5-tetrahydro-1H-pyrido[4,3-b]indole-6-carboxamide (20 mg, 0.044 mmol) was converted into the desired product as a white solid (14.0 mg, 59% yield). LCMS (M+H)+ m/z 522.3. $^1$H NMR (400 MHz, methanol-d$_4$) δ 8.16-8.56 (2 H, m), 7.87-7.98 (1 H, m), 7.76-7.87 (1 H, m), 7.61-7.73 (2 H, m), 7.42-7.59 (3 H, m), 6.89-7.06 (1 H, m), 3.42-4.22 (6 H, m), 2.79-3.01 (2 H, m), 1.86 (3 H, br. s.), 1.12-1.36 (3 H, m).

EXAMPLE 47

9-(2-Methyl-3-(4-oxoquinazolin-3(4H)-yl)phenyl)-5H-pyrido[4,3-b]indole-6-carboxamide

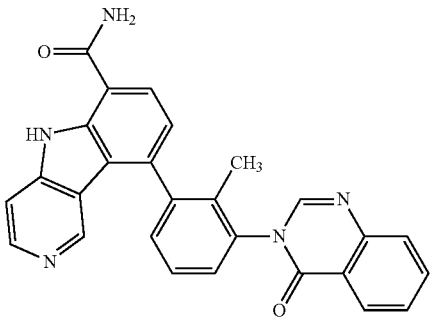 [SMILES: Cc1c(-c2ccc(C(N)=O)c3[nH]c4ccncc4c23)cccc1-n1cnc2ccccc2c1=O]

A mixture of 9-(2-methyl-3-(4-oxoquinazolin-3(4H)-yl)phenyl)-2,3,4,5-tetrahydro-1H-pyrido[4,3-b]indole-6-carboxamide (10 mg, 0.022 mmol) and activated manganese dioxide (19.34 mg, 0.222 mmol) in butyl acetate (0.5 mL) was heated on an oil bath at 110° C. for 5.25 h, then at 90-100° C. for 2.5 days, then at 125° C. for 20 h. The mixture was cooled to room temperature, diluted with methanol, filtered and concentrated under vacuum. The residue was purified by preparative HPLC. The effluent containing the desired product was concentrated under vacuum to provide a fine aqueous suspension. This was extracted three times with EtOAc, and the combined organic phases were dried and concentrated to provide the desired product as an off-white solid (3.5 mg, 33% yield). LCMS (M+H)+ m/z 446.2. $^1$H NMR (400 MHz, methanol-d$_4$) δ 8.31-8.47 (3.6 H, m), 8.06-8.16 (1.4 H, m), 7.87-7.96 (1 H, m), 7.76-7.87 (1 H, m), 7.55-7.70 (5 H, m), 7.24-7.36 (1 H, m), 1.90 (3 H, 2s).

EXAMPLE 48

5-(2-Methyl-3-(4-oxoquinazolin-3(4H)-yl)phenyl)-9H-pyrido[3,4-b]indole-8-carboxamide

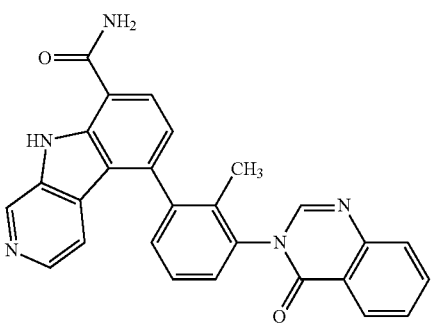 [SMILES: Cc1c(-c2ccc(C(N)=O)c3[nH]c4cnccc4c23)cccc1-n1cnc2ccccc2c1=O]

1. 4,7-Dibromo-1H-indole

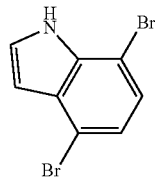 [SMILES: Brc1ccc(Br)c2[nH]ccc12]

To a solution of 1,4-dibromo-2-nitrobenzene (18 g, 64.1 mmol) in THF (200 mL) at −40° C. (dry ice-acetonitrile) was added slowly a solution of vinylmagnesium bromide (1.0 M in THF, 199 mL, 199 mmol). The resulting mixture was stirred at −40° C. for 1.5 h, then was then treated with saturated aqueous NH$_4$Cl (500 mL) and stirred at room temperature for 1 h. HCl (1M) was added to adjust the pH to 7. EtOAc was added and the organic phase was separated, washed with brine, dried and concentrated. The residue was subjected to column chromatography on silica gel (330 g), eluting with EtOAc-hexane (5:95) to provide a light yellow oil which solidified on standing under vacuum. The desired product was obtained as a solid (8.35 g, 47% yield. LCMS showed one major peak with no ionization.

2. 4-Bromo-1H-indole-7-carboxylic acid

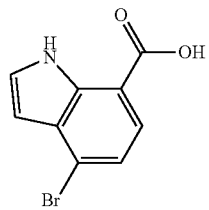 [SMILES: O=C(O)c1ccc(Br)c2cc[nH]c12]

To a solution of 4,7-dibromo-1H-indole (8.53 g, 31.0 mmol) in THF (124 mL) at −78° C. was slowly added n-butyllithium (2.5 M in hexane, 49.6 mL, 124 mmol). The solution was stirred at 0-5° C. for 2 h, then was cooled to −78° C. and bubbled with carbon dioxide gas for 15 min. The reaction mixture was allowed to warm to room temperature for 1 h, then was treated with water and partitioned between EtOAc and 1 M aqueous HCl. The organic phase was washed with brine, dried and concentrated to afford the desired product as a light yellow solid (10.04 g) which was about 75% pure by LCMS, and was used without further purification. LCMS (M−H)−: 238, 240.

3. 4-Bromo-1H-indole-7-carboxamide

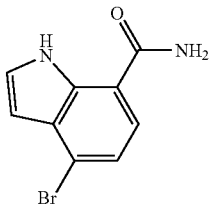 [SMILES: NC(=O)c1ccc(Br)c2cc[nH]c12]

A mixture of 4-bromo-1H-indole-7-carboxylic acid (10.04 g, 75% purity, 31.2 mmol), EDC (8.96 g, 46.7 mmol), and 1-hydroxybenzotriazole hydrate (7.16 g, 46.7 mmol) in THF (198 mL) and CH$_2$Cl$_2$ (247 mL) was stirred at room temperature for 1 h. The mixture was then bubbled with NH$_3$ gas for 15 min and stirred at room temperature for 4 h. LCMS showed residual starting material, so aqueous ammonium hydroxide (4.85 mL, 125 mmol) was added and the mixture was stirred at room temperature overnight. After 20 h, the mixture was concentrated and partitioned between NaHCO$_3$ (aq) and EtOAc. The organic phase was washed with brine, dried and concentrated. The residue was suspended in EtOAc and the solid was collected by filtration and air-dried to provide the desired product. The filtrates were subjected to column chromatography on silica gel (40 g), eluting with EtOAc-hexane (gradient from 20:80 to 50:50) to provide additional desired product for a total of 4.86 g (65% yield) over two steps. LCMS (M−H)$^-$: 237.2, 239.2.

4.
4-Bromo-3-(2-nitrovinyl)-1H-indole-7-carboxamide

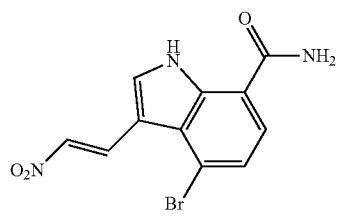 [SMILES: NC(=O)c1ccc(Br)c2c(/C=C/[N+](=O)[O-])c[nH]c12]

A dark red-brown solution of 4-bromo-1H-indole-7-carboxamide (0.79 g, 3.30 mmol) and (E)-N,N-dimethyl-2-nitroethenamine (0.422 g, 3.63 mmol) in TFA (9.44 mL) was stirred at room temperature overnight. After 16 h, LCMS indicated residual starting materials in addition to desired product. Additional (E)-N,N-dimethyl-2-nitroethenamine (77 mg) was added and the mixture was stirred at room temperature for 6 h. The mixture was partitioned between 1 M NaOH (pH was adjusted to ca. 4) and EtOAc. The organic phase was washed with NaHCO$_3$ (aq) and brine, dried and concentrated to afford a bright orange-red solid. The crude product was suspended in EtOAc and the desired product was collected by filtration, washed with EtOAc and air dried to provide a solid (0.89 g, 87% yield). LCMS (M+H)$^+$ m/z 309.7, 311.7.

5.
3-(2-Aminoethyl)-4-bromo-1H-indole-7-carboxamide

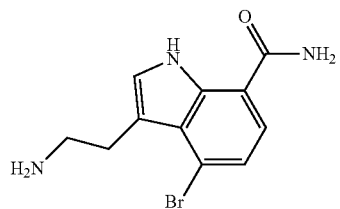 [SMILES: NCCc1c[nH]c2c(C(N)=O)ccc(Br)c12]

To a suspension of (Z)-4-bromo-3-(2-nitrovinyl)-1H-indole-7-carboxamide (0.50 g, 1.612 mmol) in THF (53.7 mL) at 0° C. was slowly added a solution of lithium aluminum hydride (1 M in THF, 8.06 mL, 8.06 mmol). The mixture was stirred at room temperature overnight. After 16 h, the mixture was treated sequentially with water (0.50 mL), 5 M aqueous sodium hydroxide (0.50 mL), and water (1.5 mL), then was diluted with a solvent mixture of THF, methanol, and EtOAc. The resulting mixture was filtered through a CELITE® pad, washed with THF, methanol, and DMSO. The filtrates were concentrated and residue was partitioned between EtOAc and NaHCO$_3$ (aq). The organic phase was washed with brine, dried and concentrated to afford a brown solution which was subjected to preparative HPLC to provide the desired product as the TFA salt (100 mg, 16% yield). LCMS (M+H)$^+$ m/z 281.8, 283.8.

6. 5-Bromo-2,3,4,9-tetrahydro-1H-pyrido[3,4-b]indole-8-carboxamide

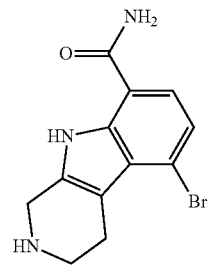 [SMILES: NC(=O)c1ccc(Br)c2c3c([nH]c12)CNCC3]

To a solution of 3-(2-aminoethyl)-4-bromo-1H-indole-7-carboxamide, TFA salt (0.068 g, 0.172 mmol) in methanol (1.2 mL) was added 1 M aqueous HCl (0.933 mL) and 37% aqueous formaldehyde (0.042 mL, 0.515 mmol) and the resulting solution was heated at 80° C. for 18 h. The mixture was concentrated and the residue was purified by preparative HPLC to provide the desired product as the TFA salt (21 mg, 30% yield). LCMS (M+H)$^+$ m/z 2937,295.7.

7. 5-(2-Methyl-3-(4-oxoquinazolin-3(4H)-yl)phenyl)-2,3,4,9-tetrahydro-1H-pyrido[3,4-b]indole-8-carboxamide

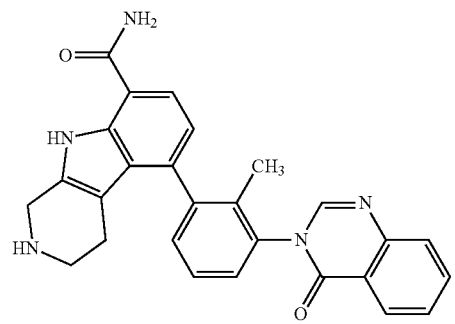 [SMILES: Cc1c(-c2ccc(C(N)=O)c3[nH]c4c(c23)CCNC4)cccc1-n1cnc2ccccc2c1=O]

Using the procedure described in step 5 of Example 42 followed by purification by preparative HPLC, the desired product was obtained from 5-bromo-2,3,4,9-tetrahydro-1H-pyrido[3,4-b]indole-8-carboxamide as the TFA salt (14.5 mg, 40% yield). LCMS (M+H)$^+$ m/z 450.2. $^1$H NMR (400 MHz, methanol-d$_4$) δ 8.38-8.25 (m, 2H), 7.99-7.86 (m, 1H), 7.82 (d, J=8.1 Hz, 1H), 7.78-7.73 (m, 1H), 7.68-7.61 (m, 1H), 7.57-

7.42 (m, 3H), 7.09-6.96 (m, 1H), 4.48 (s, 2H), 3.52-3.34 (m, 2H), 2.77-2.22 (m, 2H), 1.89-1.78 (m, 3H).

8. 5-(2-Methyl-3-(4-oxoquinazolin-3(4H)-yl)phenyl)-9H-pyrido[3,4-b]indole-8-carboxamide

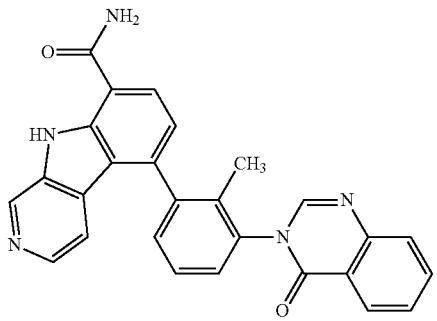 [SMILES: Cc1c(-c2ccc(C(N)=O)c3[nH]c4cnccc4c23)cccc1-n1cnc2ccccc2c1=O]

Using the procedure described in Example 47 followed by purification by preparative HPLC, the desired product was obtained as the TFA salt (7 mg, 34% yield) from 5-(2-methyl-3-(4-oxoquinazolin-3(4H)-yl)phenyl)-2,3,4,9-tetrahydro-1H-pyrido[3,4-b]indole-8-carboxamide. LCMS (M+H)$^+$ m/z 446.1. $^1$H NMR (400 MHz, DMSO-d$_6$) δ 12.75 (br. s., 1H), 9.26 (s, 1H), 8.60-8.29 (m, 4H), 8.27-8.20 (m, 1H), 7.96-7.88 (m, 1H), 7.87-7.71 (m, 3H), 7.65 (dt, J=15.6, 7.5 Hz, 2H), 7.56 (d, J=7.7 Hz, 1H), 7.52-7.23 (m, 2H), 1.80-1.69 (m, 3H).

EXAMPLE 49

3-(Hydroxymethyl)-5-(2-methyl-3-(4-oxoquinazolin-3(4H)-yl)phenyl)-9H-pyrido[3,4-b]indole-8-carboxamide

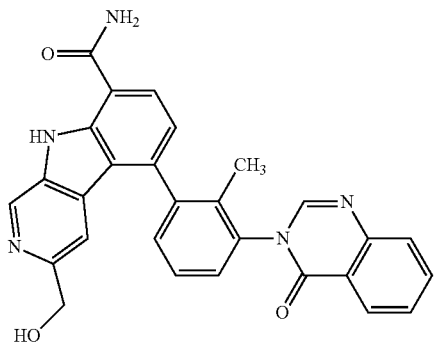 [SMILES: Cc1c(-c2ccc(C(N)=O)c3[nH]c4cnc(CO)cc4c23)cccc1-n1cnc2ccccc2c1=O]

1. 4-Bromo-3-((dimethylamino)methyl)-1H-indole-7-carboxamide

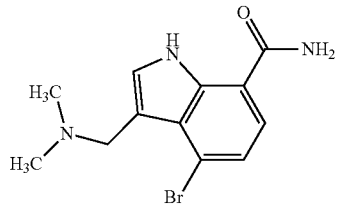 [SMILES: CN(C)Cc1c[nH]c2c(C(N)=O)ccc(Br)c12]

Acetic acid (1.15 mL, 20.08 mmol) was added to a suspension of 4-bromo-1H-indole-7-carboxamide (3 g, 12.55 mmol), paraformaldehyde (0.603 g, 20.08 mmol) and dimethylamine (2 M in methanol, 10 mL, 20.08 mmol) in ethanol (50 mL). The mixture was heated to 80° C. After 2 h, the ethanol was removed under vacuum. The residue was partitioned between NaHCO$_3$ (aq) and EtOAc. The organic phase was washed with brine (15 mL), dried and concentrated to afford the crude desired product as a light brown solid (4.08 g). LCMS (M+H)$^+$ m/z 295.8, 297.8.

2. Ethyl 3-(4-bromo-7-carbamoyl-1H-indol-3-yl)-2-nitropropanoate

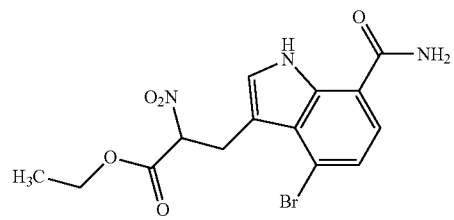 [SMILES: CCOC(=O)C(Cc1c[nH]c2c(C(N)=O)ccc(Br)c12)[N+](=O)[O-]]

Methyl propiolate (2.300 mL, 27.5 mmol) was added slowly to a suspension of crude 4-bromo-3-((dimethylamino)methyl)-1H-indole-7-carboxamide (6.27 g, 21.17 mmol) and ethyl 2-nitroacetate (3.66 g, 27.5 mmol) in dichloromethane (151 mL) and acetonitrile (151 mL). After 30 min, the mixture was concentrated and partitioned between EtOAc and 1 M aqueous HCl. The organic phase was washed with NaHCO$_3$ (aq) and brine, dried and concentrated. The residue was coated subjected to column chromatography on silica gel (80 g), eluting with EtOAc-hexane (gradient from 50:50 to 80:20) to provide the desired product as a solid (4.60 g, 57% yield). LCMS (M+H)$^+$ m/z 383.8, 385.8.

3. Ethyl 2-amino-3-(4-bromo-7-carbamoyl-1H-indol-3-yl)propanoate

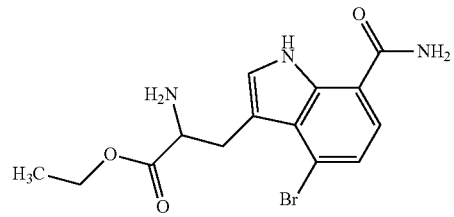

A solution of ethyl 3-(4-bromo-7-carbamoyl-1H-indol-3-yl)-2-nitropropanoate (4.6 g, 11.97 mmol) in isopropanol (200 mL) and THF (100 mL) was cooled in an ice bath and treated portionwise with zinc dust (8.85 g, 135 mmol), followed by 1 M aqueous HCl (150 mL) in portions. The mixture was stirred at room temperature for 3 h, then treated with NaOH pellets and 1 M aqueous NaOH to pH 9-10. The mixture was diluted with THF and EtOAc, stirred for 15 min and filtered through a CELITE® pad. The solids were rinsed with EtOAc, THF, and NaHCO$_3$ (aq). The filtrates were concentrated to remove most of the organic solvents, and the aqueous residue was extracted with EtOAc. The combined extracts were washed with brine, dried and concentrated to provide the desired product as an off-white solid (3.65 g, 86% yield). LCMS (M+H)$^+$ m/z 353.8, 355.8.

4. Ethyl 5-bromo-8-carbamoyl-2,3,4,9-tetrahydro-1H-pyrido[3,4-b]indole-3-carboxylate

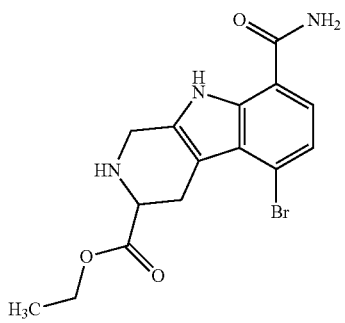 [SMILES: CCOC(=O)C1Cc2c([nH]c3c(C(N)=O)ccc(Br)c23)CN1]

To a solution of ethyl 2-amino-3-(4-bromo-7-carbamoyl-1H-indol-3-yl)propanoate (3.45 g, 9.74 mmol) in methanol (68.8 mL) and 1 M aqueous HCl (52.9 mL) was added 37% aqueous formaldehyde (0.790 mL, 9.74 mmol) and the resulting mixture was heated at 80° C. After 1.5 h, additional formaldehyde (0.79 mL) was added and heating was continued. After 3.5 h, additional formaldehyde (0.79 mL) was again added and heating was continued. After 6 h, the mixture was cooled to room temperature, concentrated, and partitioned between a solvent mixture of CHCl$_3$ and iPrOH (3:1) and 1 M NaOH and NaHCO$_3$ (aq). The organic phase was washed with brine, dried and concentrated to afford the crude product as a light brown solid (3.16 g, 89% yield). LCMS (M+H)$^+$ m/z 365.8, 367.8.

5. Ethyl 5-bromo-8-carbamoyl-9H-pyrido[3,4-b]indole-3-carboxylate

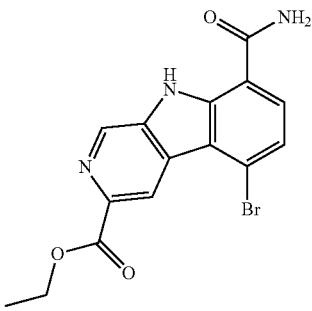 [SMILES: CCOC(=O)c1cc2c(cn1)[nH]c1c(C(N)=O)ccc(Br)c12]

Using the procedure described in Example F, ethyl 5-bromo-8-carbamoyl-2,3,4,9-tetrahydro-1H-pyrido[3,4-b]indole-3-carboxylate was converted to the desired product as a brown solid (0.71 g, 72% yield). LCMS (M+H)$^+$ m/z 361.8, 363.8.

6. 5-Bromo-3-(hydroxymethyl)-9H-pyrido[3,4-b]indole-8-carboxamide

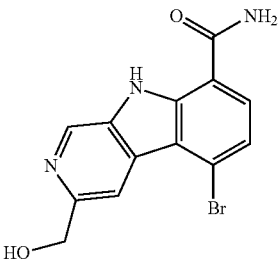 [SMILES: NC(=O)c1ccc(Br)c2c1[nH]c1cnc(CO)cc12]

Using the procedure described in step 5 of Example 48, ethyl 5-bromo-8-carbamoyl-9H-pyrido[3,4-b]indole-3-carboxylate was converted to the desired product as a tan solid (102 mg, 36% yield). LCMS (M+H)$^+$ m/z 319.8, 321.8.

7. 3-(Hydroxymethyl)-5-(2-methyl-3-(4-oxoquinazolin-3(4H)-yl)phenyl)-9H-pyrido[3,4-b]indole-8-carboxamide

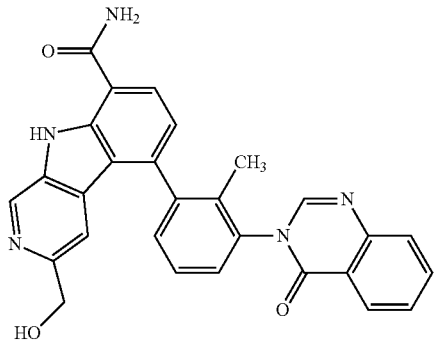 [SMILES: Cc1c(-c2ccc(C(N)=O)c3[nH]c4cnc(CO)cc4c23)cccc1-n1cnc2ccccc2c1=O]

Using the procedure described in step 5 of Example 2, 5-bromo-3-(hydroxymethyl)-9H-pyrido[3,4-b]indole-8-carboxamide was converted to the desired product, isolated as the TFA salt (1.8 mg, 4% yield). LCMS (M+H)$^+$ m/z 475.9. $^1$H NMR (500 MHz, methanol-d$_4$) δ 9.05 (s, 1H), 8.40 (d, J=7.4 Hz, 1H), 8.35-8.29 (m, 2H), 7.93-7.88 (m, 1H), 7.83 (d, J=8.4 Hz, 1H), 7.71-7.60 (m, 5H), 7.45 (d, J=7.4 Hz, 1H), 5.26 (d, J=15.4 Hz, 1H), 5.01 (d, J=15.4 Hz, 1H), 1.86-1.83 (m, 3H).

EXAMPLE 50

3-(2-Hydroxypropan-2-yl)-5-(2-methyl-3-(4-oxoquinazolin-3(4H)-yl)phenyl)-9H-pyrido[3,4-b]indole-8-carboxamide

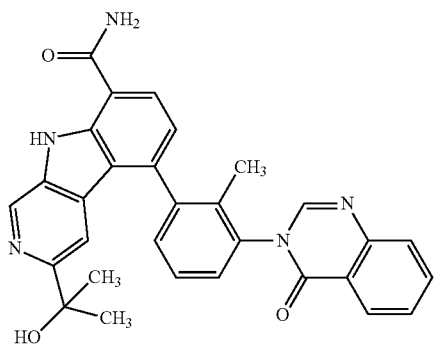 [SMILES: Cc1c(-c2ccc(C(N)=O)c3[nH]c4cnc(C(C)(C)O)cc4c23)cccc1-n1cnc2ccccc2c1=O]

1. 5-Bromo-3-(2-hydroxypropan-2-yl)-9H-pyrido[3,4-b]indole-8-carboxamide

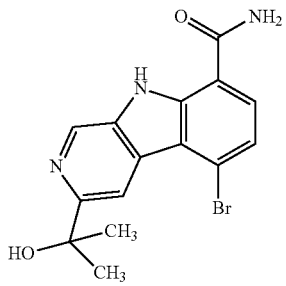 [SMILES: CC(C)(O)c1cc2c(cn1)[nH]c1c(C(N)=O)ccc(Br)c12]

A solution of ethyl 5-bromo-8-carbamoyl-9H-pyrido[3,4-b]indole-3-carboxylate (0.4 g, 1.104 mmol) in THF (31.6 mL) was cooled in a salt-ice bath slowly treated with methyllithium (1.6 M in ether, 3.80 mL, 6.07 mmol). The solution was stirred at −5° C. for 1.5 h, then was treated with ice and 1 M aqueous HCl (7 mL). The mixture was made basic with NaHCO$_3$ (aq) and extracted with chloroform-isopropanol (3:1). The organic phase was washed with brine, dried and concentrated. The residue was subjected to column chromatography on silica gel (40 g), eluting with Methanol-CH$_2$Cl$_2$ (gradient from 2:98 to 10:90) to provide the desired product as a yellow solid (128 mg, 33% yield). LCMS (M+H)$^+$ m/z 347.9, 349.9.

2. 3-(2-Hydroxypropan-2-yl)-5-(2-methyl-3-(4-oxoquinazolin-3(4H)-yl)phenyl)-9H-pyrido[3,4-b]indole-8-carboxamide

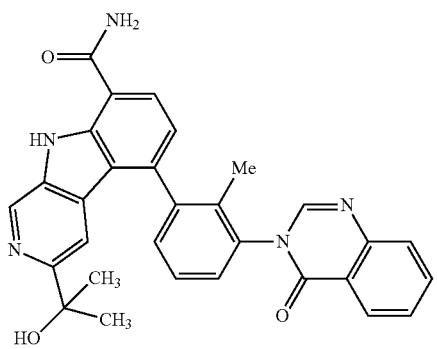 [SMILES: Cc1c(-c2ccc(C(N)=O)c3[nH]c4cnc(C(C)(C)O)cc4c23)cccc1-n1cnc2ccccc2c1=O]

Using the procedure described in step 5 of Example 42, 5-bromo-3-(2-hydroxypropan-2-yl)-9H-pyrido[3,4-b]indole-8-carboxamide was converted to the desired product (14 mg, 33% yield). LCMS (M+H)$^+$ m/z 503.9. $^1$H NMR (500 MHz, methanol-d$_4$) δ 9.00-8.98 (m, 1H), 8.36 (d, J=7.9 Hz, 1H), 8.29-8.22 (m, 2H), 7.90-7.84 (m, 1H), 7.79 (d, J=7.9 Hz, 1H), 7.69-7.64 (m, 1H), 7.62-7.60 (m, 2H), 7.53 (d, J=7.4 Hz, 1H), 7.42-7.35 (m, 2H), 1.83 (s, 3H), 1.73 (s, 3H), 1.62 (s, 3H).

EXAMPLE 51

5-(2-Methyl-3-(4-oxoquinazolin-3(4H)-yl)phenyl)-9H-pyrido[3,4-b]indole-3,8-dicarboxamide

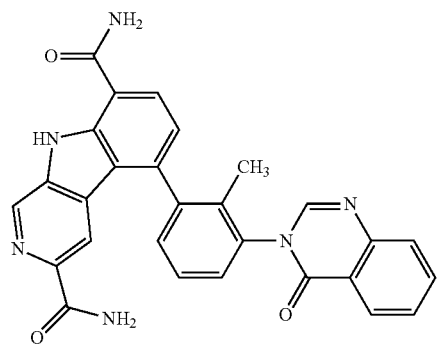

1. Ethyl 8-carbamoyl-5-(2-methyl-3-(4-oxoquinazolin-3(4H)-yl)phenyl)-9H-pyrido[3,4-b]indole-3-carboxylate

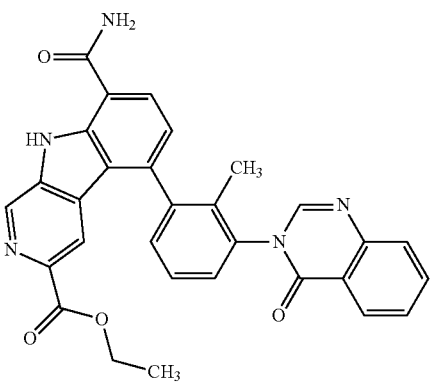 [SMILES: CCOC(=O)c1cc2c(cn1)[nH]c1c(C(N)=O)ccc(-c3cccc(-n4cnc5ccccc5c4=O)c3C)c12]

Using the procedure described in step 5 of Example 42, ethyl 5-bromo-8-carbamoyl-9H-pyrido[3,4-b]indole-3-carboxylate was converted to the desired product (170 mg, 37% yield). LCMS (M+H)$^+$ m/z 517.9.

2. 8-Carbamoyl-5-(2-methyl-3-(4-oxoquinazolin-3(4H)-yl)phenyl)-9H-pyrido[3,4-b]indole-3-carboxylic acid

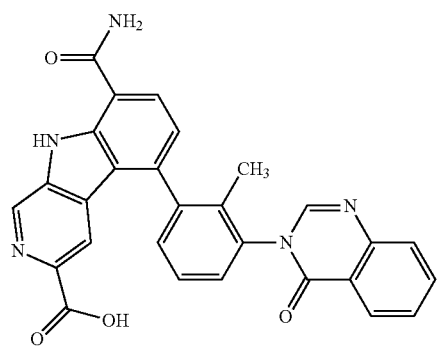 [SMILES: Cc1c(-c2ccc(C(N)=O)c3[nH]c4cnc(C(=O)O)cc4c23)cccc1-n1cnc2ccccc2c1=O]

A solution of ethyl 8-carbamoyl-5-(2-methyl-3-(4-oxoquinazolin-3(4H)-yl)phenyl)-9H-pyrido[3,4-b]indole-3-carboxylate (0.26 g, 0.502 mmol) and lithium hydroxide monohydrate (0.070 g, 1.757 mmol) in THF-ethanol-water (3:1:1, 20.10 mL) was stirred at room temperature overnight. After 18 h, residual starting material was observed by LCMS. The mixture was heated at 50° C. for 2 h, then cooled to room temperature and concentrated. The residue was suspended in water and treated with 1 M aqueous HCl (to pH 1-2). The precipitate was collected by filtration, washed with water and dried to provide the desired product as a pale yellow solid (0.205 g, 76%). LCMS (M+H)+ m/z 490.1.

3. 5-(2-Methyl-3-(4-oxoquinazolin-3(4H)-yl)phenyl)-9H-pyrido[3,4-b]indole-3,8-dicarboxamide

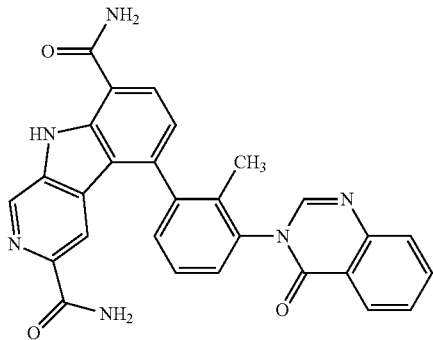 [SMILES: Cc1c(-c2ccc(C(N)=O)c3[nH]c4cnc(C(N)=O)cc4c23)cccc1-n1cnc2ccccc2c1=O]

Using the procedure described in step 3 of Example 48, 8-Carbamoyl-5-(2-methyl-3-(4-oxoquinazolin-3(4H)-yl)phenyl)-9H-pyrido[3,4-b]indole-3-carboxylic acid was converted to the desired product (5.3 mg, 18% yield). LCMS (M+H)+ m/z 488.9. $^1$H NMR (500 MHz, methanol-$d_4$) δ 9.27-8.91 (m, 1H), 8.65-8.14 (m, 3H), 8.03-7.66 (m, 4H), 7.65-7.52 (m, 3H), 7.50-7.30 (m, 1H), 1.89 (m, 3H).

EXAMPLE 52

3-(Hydroxymethyl)-9-(2-methyl-3-(4-oxoquinazolin-3(4H)-yl)phenyl)-5H-pyrido[4,3-b]indole-6-carboxamide

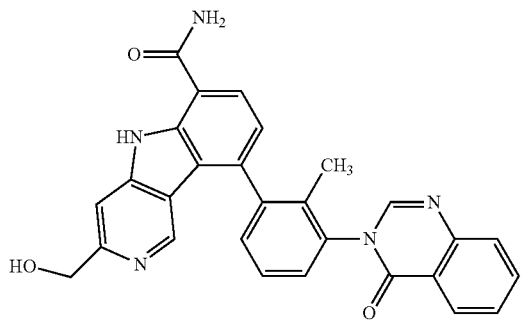 [SMILES: Cc1c(-c2ccc(C(N)=O)c3[nH]c4cc(CO)ncc4c23)cccc1-n1cnc2ccccc2c1=O]

1. 4-Bromo-3-formyl-1H-indole-7-carbonitrile

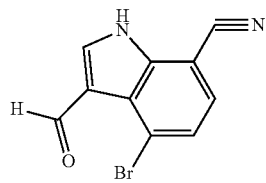 [SMILES: N#Cc1ccc(Br)c2c(C=O)c[nH]c12]

A solution of DMF (8.42 mL, 109 mmol) in CH$_2$Cl$_2$ (105 mL) stirred on a salt-ice bath was treated dropwise with phosphorus oxychloride (2.57 mL, 27.6 mmol). After 15 min, 4-bromo-1H-indole-7-carboxamide (2 g, 8.37 mmol) was added in one portion while maintaining the temperature below −10° C. After addition, the mixture was stirred at room temperature overnight. After 16 h, ice was added, followed by NaHCO$_3$ and 1 M aqueous NaOH added in portions to make the mixture basic. The mixture was extracted with dichloromethane (3 times), and the combined organic phases were washed with brine, dried and concentrated. The residue was subjected to column chromatography on silica gel (80 g), eluting with a gradient from 100% CH$_2$Cl$_2$ to 15% Methanol-85% CH$_2$Cl$_2$, to provide the desired product as a pale solid (1.36 g, 65% yield). LCMS (M+H)+ m/z 248.9, 250.9.

2. Ethyl 2-((4-bromo-7-cyano-1H-indol-3-yl)methylamino)-3,3-diethoxypropanoate

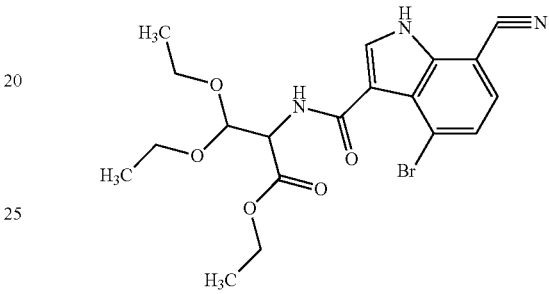

A mixture of 4-bromo-3-formyl-1H-indole-7-carbonitrile (1.08 g, 4.34 mmol), ethyl 2-amino-3,3-diethoxypropanoate (prepared according to the procedure of U.S. Pat. No. 7,470,680; 1.780 g, 6.94 mmol), and molecular sieves (2.17 g, 2 g) in 1,2-dichloroethane (79 mL) and THF (29.6 mL) at 0° C. was treated with sodium triacetoxyborohydride (2.57 g, 12.14 mmol) and the resulting mixture was stirred at room temperature overnight. After 24 h, LCMS residual starting material, so additional sodium triacetoxyborohydride (1.38 g, 1.5 eq.) and molecular sieves (2 g) were added and stirring was continued for 4 h more. The mixture was diluted with EtOAc and filtered through a CELITE® pad and the solids were washed with EtOAc. The filtrates were diluted with EtOAc and washed with NaHCO$_3$ (aq) and brine, dried and concentrated to afford a dark-colored oil. The residue was subjected to column chromatography on silica gel (40 g), eluting with EtOAc-hexane (gradient from 15:85 to 100:0) to provide the desired product as a brown syrup (0.67 g, 35% yield). LCMS (M+H)+ m/z 438.2, 440.2.

3. Ethyl 9-bromo-6-cyano-5H-pyrido[4,3-b]indole-3-carboxylate

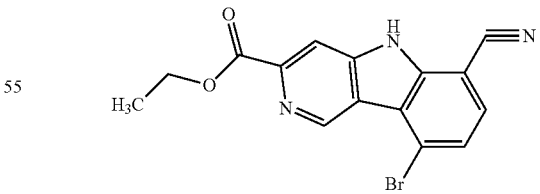

To a solution of ethyl 2-(((4-bromo-7-cyano-1H-indol-3-yl)methyl)amino)-3,3-diethoxypropanoate (1.12 g, 2.56 mmol) in toluene (51.1 mL) at 0° C. was added dropwise titanium tetrachloride (1 M in CH$_2$Cl$_2$, 8.94 mL, 8.94 mmol). The mixture was heated at 90° C. for 3 h. The mixture was cooled to room temperature and partitioned between NaHCO$_3$ (aq) and EtOAc. The organic phase was washed with brine, dried and concentrated. The resulting dark yellow solid was suspended in methanol, then collected by filtration and air-dried to afford the desired product as a yellow solid (300 mg, 29% yield), contaminated with partially aromatized material (ethyl 9-bromo-6-cyano-4,5-dihydro-3H-pyrido[4,3-b]indole-3-carboxylate and/or ethyl 9-bromo-6-cyano-2,5-dihydro-1H-pyrido[4,3-b]indole-3-carboxylate) and ethyl 9-bromo-6-cyano-2,3,4,5-tetrahydro-1H-pyrido[4,3-b]indole-3-carboxylate, which was used without further purification. LCMS (M+H)+ m/z 343.9, 345.9.

4. 9-Bromo-6-carbamoyl-5H-pyrido[4,3-b]indole-3-carboxylic acid

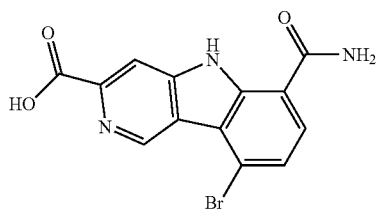 [SMILES: NC(=O)c1ccc(Br)c2c1[nH]c1cc(C(=O)O)ncc12]

A suspension of crude ethyl 9-bromo-6-cyano-5H-pyrido[4,3-b]indole-3-carboxylate (0.78 g, 2.266 mmol) and sodium perborate tetrahydrate (1.395 g, 9.07 mmol) in ethanol-water (3:2, 99 mL) was heated at 100° C. for 3 h. The mixture was cooled to room temperature and the ethanol was removed under vacuum to give a suspension. The pH was adjusted to about 5-6 with 1 M aqueous HCl. The precipitate was collected by filtration, washed with water and air-dried to afford the desired product (0.60 g). The filtrate was concentrated under vacuum to provide additional desired product (70 mg, total of 88% yield). LCMS (M+H)+ m/z 334.0, 335.9.

5. Methyl 9-bromo-6-carbamoyl-5H-pyrido[4,3-b]indole-3-carboxylate

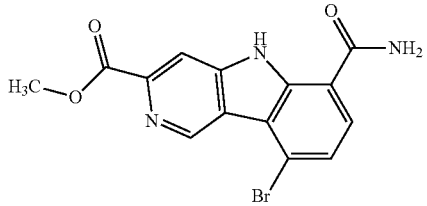 [SMILES: COC(=O)c1cc2[nH]c3c(C(N)=O)ccc(Br)c3c2cn1]

To a mixture of 9-bromo-6-carbamoyl-5H-pyrido[4,3-b]indole-3-carboxylic acid (0.61 g, 1.187 mmol), EDC (0.455 g, 2.373 mmol), 1-hydroxybenzotriazole hydrate (0.363 g, 2.373 mmol), 4-dimethylaminopyridine (0.145 g, 1.187 mmol), and diisopropylethylamine (0.829 mL, 4.75 mmol) in DMF (79 mL) was added methanol (4.80 mL, 119 mmol). The mixture was stirred at room temperature for 20 h, then was partitioned between EtOAc and NaHCO3 (aq). The organic phase was washed with brine, dried and concentrated to afford a yellow oil. This material was subjected to preparative HPLC to provide the desired product as the TFA salt (132 mg, 32% yield). LCMS (M+H)+ m/z 348.0, 350.0.

6. 9-Bromo-3-(hydroxymethyl)-5H-pyrido[4,3-b]indole-6-carboxamide

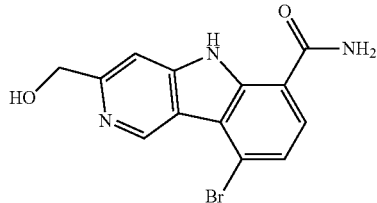 [SMILES: NC(=O)c1ccc(Br)c2c1[nH]c1cc(CO)ncc12]

Using the procedure described in step 5 of Example 48, methyl 9-bromo-6-carbamoyl-5H-pyrido[4,3-b]indole-3-carboxylate was converted to the desired product, isolated by preparative HPLC as the TFA salt (40 mg, 27% yield). LCMS (M+H)+ m/z 320.0, 322.0.

7. 3-(3-Bromo-2-methylphenyl)quinazolin-4(3H)-one

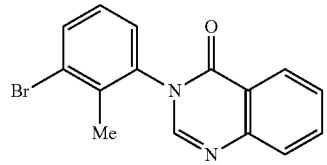 [SMILES: Cc1c(Br)cccc1-n1cnc2ccccc2c1=O]

A mixture of 1H-benzo[d][1,3]oxazine-2,4-dione (200 mg, 1.226 mmol), 3-bromo-2-methylaniline (228 mg, 1.226 mmol), and trimethoxymethane (390 mg, 3.68 mmol) in THF (2 mL) was heated overnight in a sealed tube at 100° C. The mixture was cooled to room temperature and concentrated, and the residue was purified by column chromatography, eluting with EtOAc-hexane (gradient from 10:90 to 50:50) to provide the desired product (140 mg, 36% yield). LCMS (M+H)+ m/z 315, 317.

8. 3-(2-Methyl-3-(4,4,5,5-tetramethyl-1,3,2-dioxaborolan-2-yl)phenyl)quinazolin-4(3H)-one

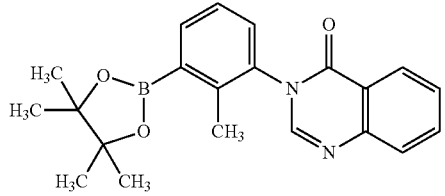 [SMILES: Cc1c(B2OC(C)(C)C(C)(C)O2)cccc1-n1cnc2ccccc2c1=O]

A mixture of 3-(3-bromo-2-methylphenyl)quinazolin-4(3H)-one (0.89 g, 2.82 mmol), 4,4,4',4',5,5,5',5'-octamethyl-2,2'-bi(1,3,2-dioxaborolane) (1.076 g, 4.24 mmol), potassium acetate (0.831 g, 8.47 mmol), and [1,1'-bis(diphenylphosphino)ferrocene]dichloropalladium (II) complex with CH2Cl2 (0.115 g, 0.141 mmol) in dioxane (10 mL) was heated at 110° C. for 5 h. The mixture was cooled to room temperature, diluted with EtOAc and washed with water. The organic phase was filtered, dried and concentrated. The residue was purified by column chromatography on silica gel (40 g), eluting with EtOAc-hexane (gradient from 20:80 to 40:60) to provide 3-(2-methyl-3-(4,4,5,5-tetramethyl-1,3,2-dioxaborolan-2-yl)phenyl)quinazolin-4(3H)-one as a white glassy foam (800 mg, 78% yield). LCMS (M+H)+ m/z 363.2.

9. 3-(Hydroxymethyl)-9-(2-methyl-3-(4-oxoquinazolin-3(4H)-yl)phenyl)-5H-pyrido[4,3-b]indole-6-carboxamide

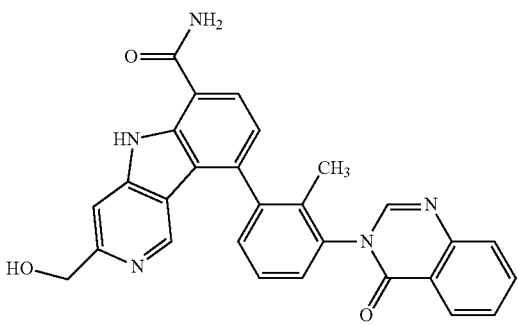 [SMILES: Cc1c(-c2ccc(C(N)=O)c3[nH]c4cc(CO)ncc4c23)cccc1-n1cnc2ccccc2c1=O]

Using the procedure described in step 5 of Example 42, 9-Bromo-3-(hydroxymethyl)-5H-pyrido[4,3-b]indole-6-carboxamide was converted to the desired product (13.7 mg, 31% yield). LCMS (M+H)+ m/z 476.1. $^1$H NMR (500 MHz, DMSO-$d_6$) δ 11.99 (br. s., 1H), 8.46-8.41 (m, 1H), 8.28 (br. s., 1H), 8.26-8.21 (m, 1H), 8.15-7.97 (m, 2H), 7.94-7.88 (m, 1H), 7.82-7.75 (m, 2H), 7.71-7.66 (m, 1H), 7.65-7.58 (m, 3H), 7.57-7.48 (m, 1H), 7.22-7.13 (m, 1H), 5.44 (br. s., 1H), 4.70-4.58 (m, 2H), 1.79 (s, 3H).

Following the procedure for Examples 1-52, additional Examples 53-117 listed in Table 3 were prepared.

TABLE 3

| Example No. | Structure | (M + H)+ |
|---|---|---|
| 53 | 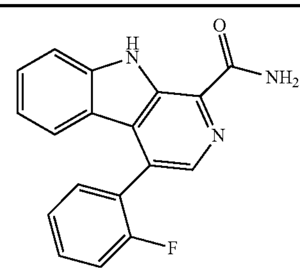 | 306.15 |
| 54 | 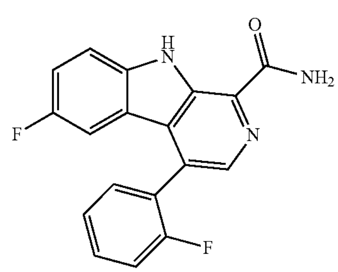 [SMILES: NC(=O)c1ncc(-c2ccccc2F)c2c1[nH]c1ccc(F)cc12] | 324.14 |
| 55 | 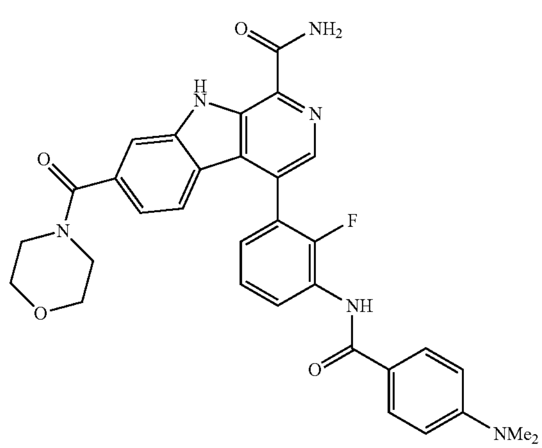 [SMILES: CN(C)c1ccc(C(=O)Nc2cccc(-c3cnc(C(N)=O)c4[nH]c5cc(C(=O)N6CCOCC6)ccc5c34)c2F)cc1] | 581.24 |

TABLE 3-continued
| Example No. | Structure | (M + H)+ |
|---|---|---|
| 56 | 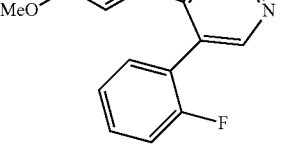 | 336.10 |
| 57 | 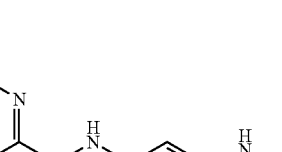 | 427.18 |
| 58 | 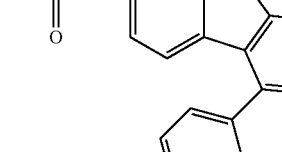 | 529.14 |
| 59 | 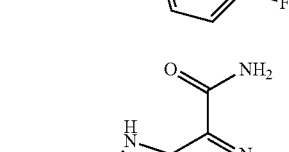 | 528.15 |

TABLE 3-continued

| Example No. | Structure | (M + H)+ |
|---|---|---|
| 60 | 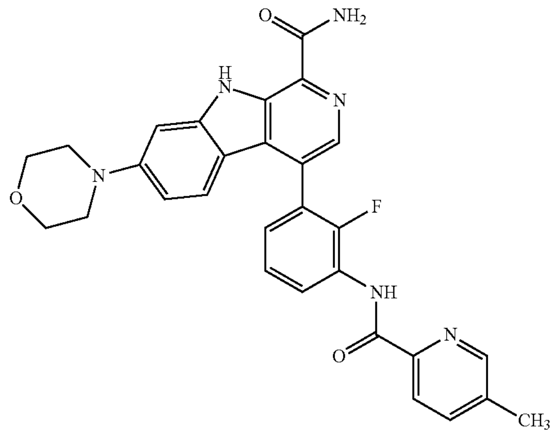 [SMILES: Cc1ccc(C(=O)Nc2cccc(-c3cnc(C(N)=O)c4[nH]c5cc(N6CCOCC6)ccc5c34)c2F)nc1] | 525.20 |
| 61 | 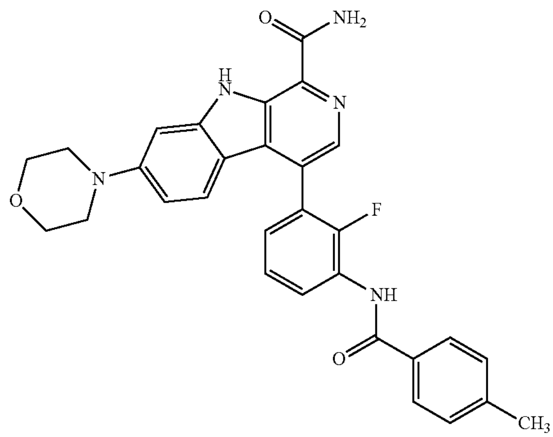 [SMILES: Cc1ccc(C(=O)Nc2cccc(-c3cnc(C(N)=O)c4[nH]c5cc(N6CCOCC6)ccc5c34)c2F)cc1] | 524.21 |
| 62 | 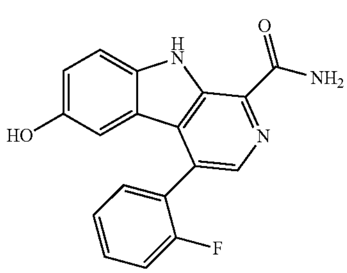 [SMILES: NC(=O)c1ncc(-c2ccccc2F)c2c1[nH]c1ccc(O)cc12] | 322.06 |
| 63 | 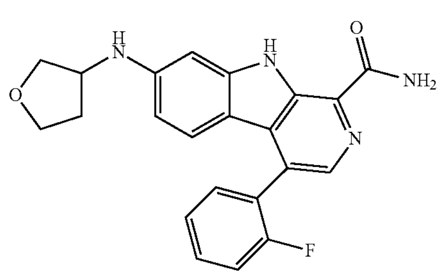 [SMILES: NC(=O)c1ncc(-c2ccccc2F)c2c1[nH]c1cc(NC3CCOC3)ccc12] | 391.13 |

TABLE 3-continued

| Example No. | Structure | (M + H)+ |
|---|---|---|
| 64 | 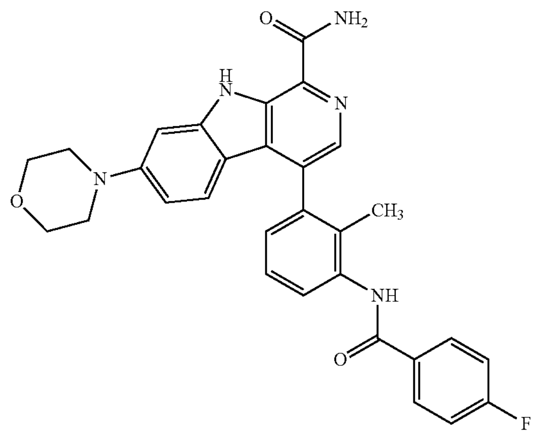 [SMILES: Cc1c(NC(=O)c2ccc(F)cc2)cccc1-c1cnc(C(N)=O)c2[nH]c3cc(N4CCOCC4)ccc3c12] | 524.21 |
| 65 | 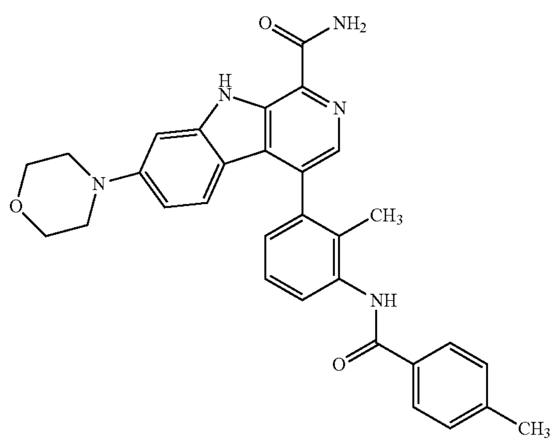 [SMILES: Cc1ccc(C(=O)Nc2cccc(-c3cnc(C(N)=O)c4[nH]c5cc(N6CCOCC6)ccc5c34)c2C)cc1] | 520.12 |
| 66 | 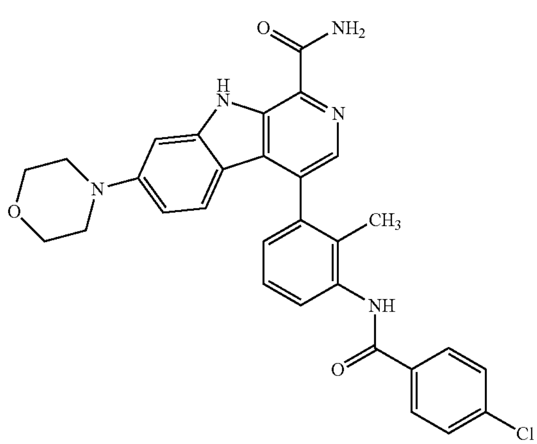 [SMILES: Cc1c(NC(=O)c2ccc(Cl)cc2)cccc1-c1cnc(C(N)=O)c2[nH]c3cc(N4CCOCC4)ccc3c12] | 540.17 |

TABLE 3-continued
| Example No. | Structure | (M + H)⁺ |
|---|---|---|
| 67 | 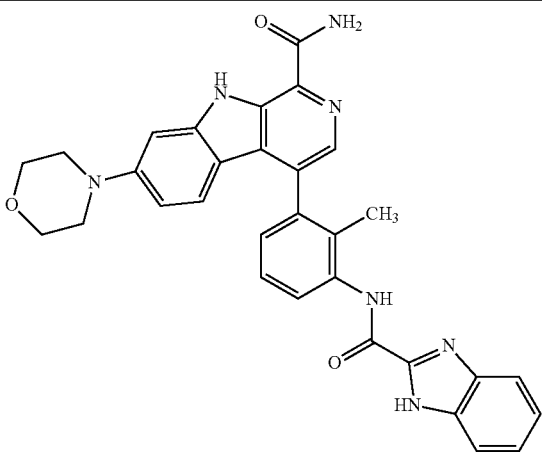 | 546.26 |
| 68 | 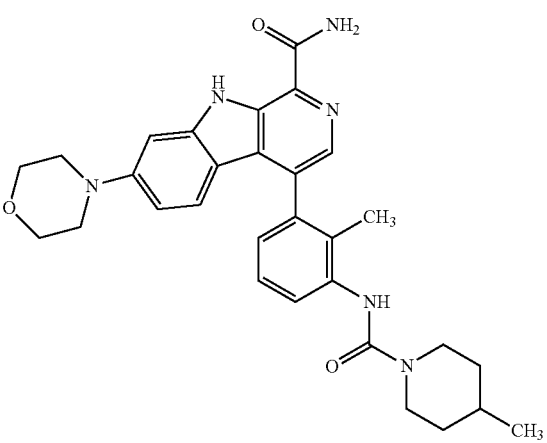 [SMILES: Cc1c(NC(=O)N2CCC(C)CC2)cccc1-c1cnc(C(N)=O)c2[nH]c3cc(N4CCOCC4)ccc3c12] | 527.30 |
| 69 | 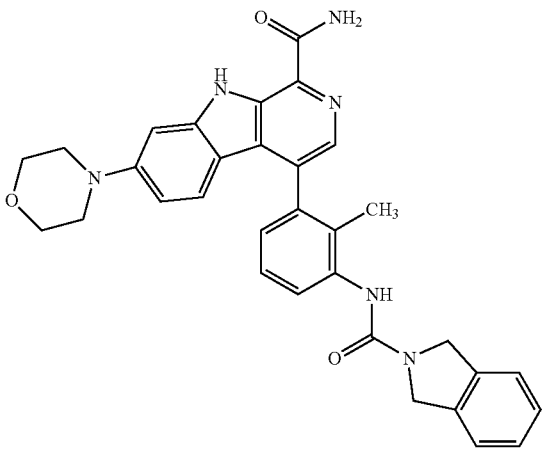 | 547.26 |

TABLE 3-continued

| Example No. | Structure | (M + H)⁺ |
|---|---|---|
| 70 | 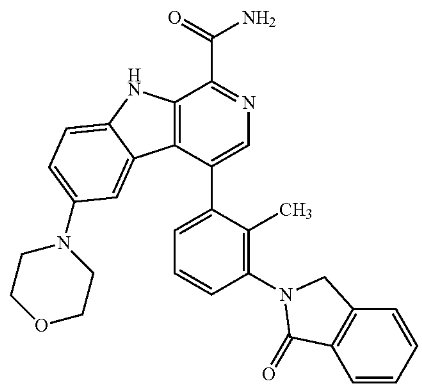 [SMILES: Cc1c(-c2cnc(C(N)=O)c3[nH]c4ccc(N5CCOCC5)cc4c23)cccc1N1Cc2ccccc2C1=O] | 518.23 |
| 71 | 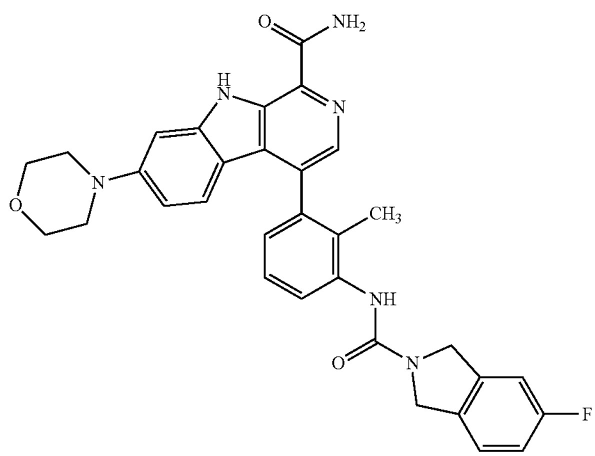 [SMILES: Cc1c(NC(=O)N2Cc3ccc(F)cc3C2)cccc1-c1cnc(C(N)=O)c2[nH]c3cc(N4CCOCC4)ccc3c12] | 565.27 |
| 72 | 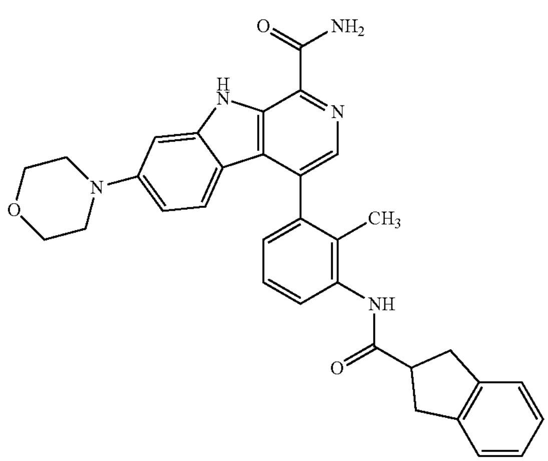 [SMILES: Cc1c(NC(=O)C2Cc3ccccc3C2)cccc1-c1cnc(C(N)=O)c2[nH]c3cc(N4CCOCC4)ccc3c12] | 546.29 |

TABLE 3-continued

| Example No. | Structure | (M + H)+ |
|---|---|---|
| 73 | 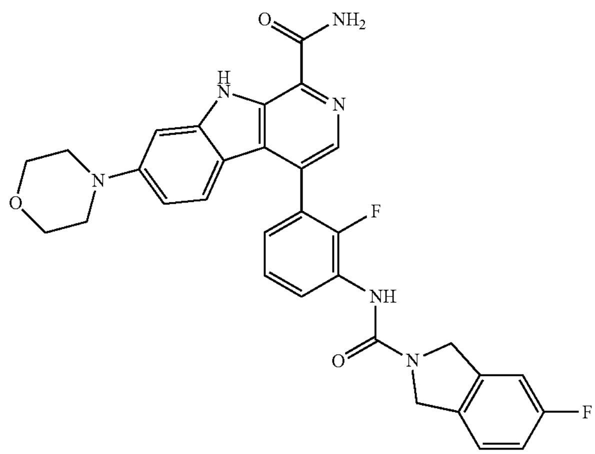 [SMILES: NC(=O)c1ncc(-c2cccc(NC(=O)N3Cc4ccc(F)cc4C3)c2F)c2c1[nH]c1cc(N3CCOCC3)ccc12] | 569.28 |
| 74 | 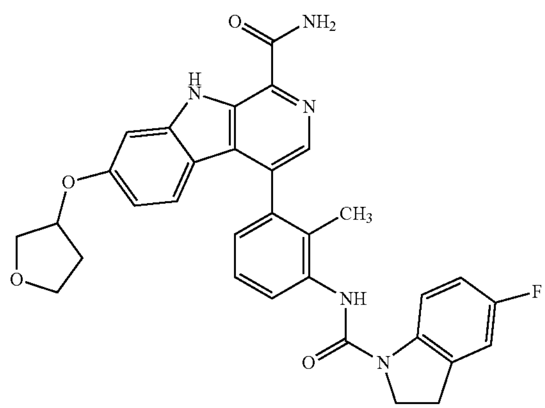 [SMILES: Cc1c(NC(=O)N2CCc3cc(F)ccc32)cccc1-c1cnc(C(N)=O)c2[nH]c3cc(OC4CCOC4)ccc3c12] | 566.35 |
| 75 | 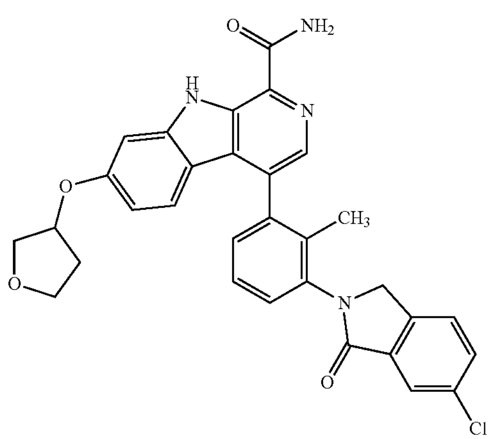 [SMILES: Cc1c(-c2cnc(C(N)=O)c3[nH]c4cc(OC5CCOC5)ccc4c23)cccc1N1Cc2ccc(Cl)cc2C1=O] | 553.38 |

TABLE 3-continued

| Example No. | Structure | (M + H)+ |
|---|---|---|
| 76 | 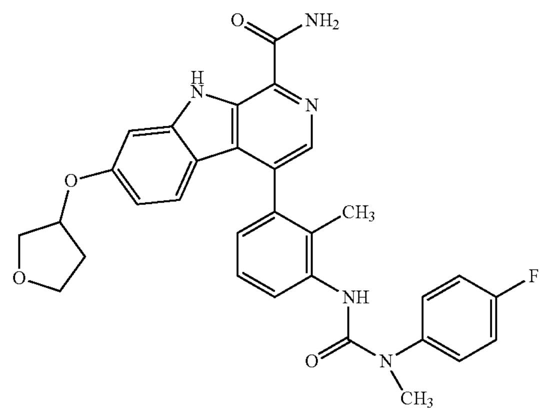 [SMILES: Cc1c(NC(=O)N(C)c2ccc(F)cc2)cccc1-c1cnc(C(N)=O)c2[nH]c3cc(OC4CCOC4)ccc3c12] | 554.36 |
| 77 | 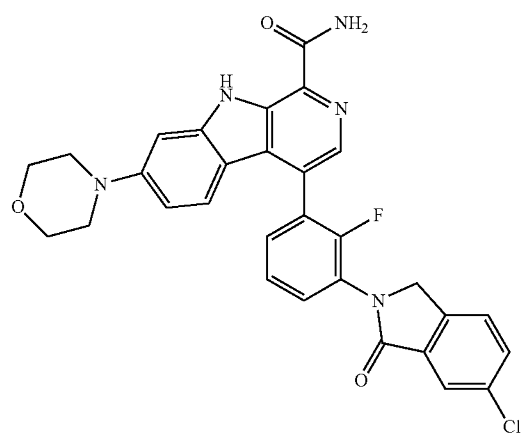 [SMILES: NC(=O)c1ncc(-c2cccc(N3Cc4ccc(Cl)cc4C3=O)c2F)c2c1[nH]c1cc(N3CCOCC3)ccc12] | 556.31 |
| 78 | 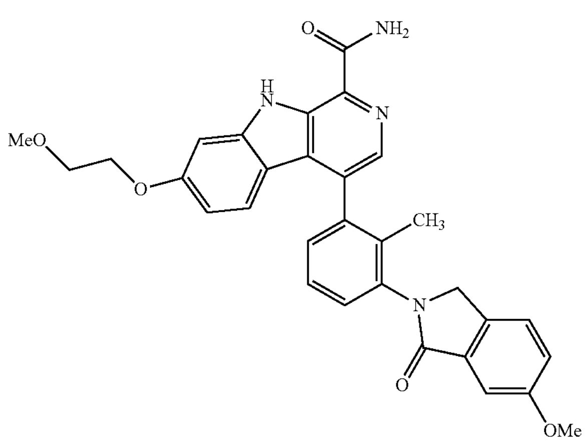 [SMILES: COCCOc1ccc2c(c1)[nH]c1c(C(N)=O)ncc(-c3cccc(N4Cc5ccc(OC)cc5C4=O)c3C)c12] | 537.36 |

TABLE 3-continued
| Example No. | Structure | (M + H)+ |
|---|---|---|
| 79 | 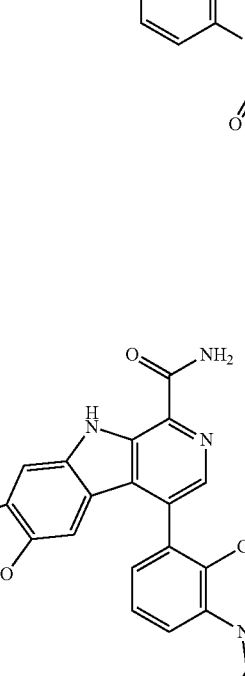 | 511.23 |
| 80 | 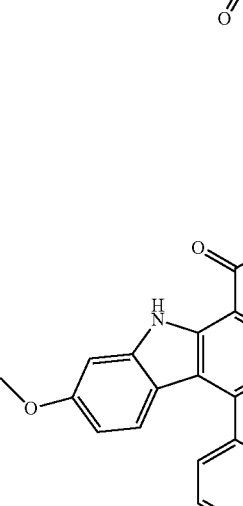 | 507.30 |
| 81 | 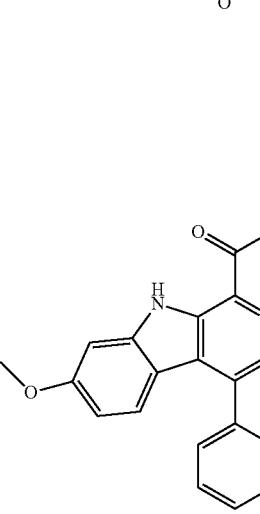 | 527.09 |

TABLE 3-continued

| Example No. | Structure | (M + H)+ |
|---|---|---|
| 82 | 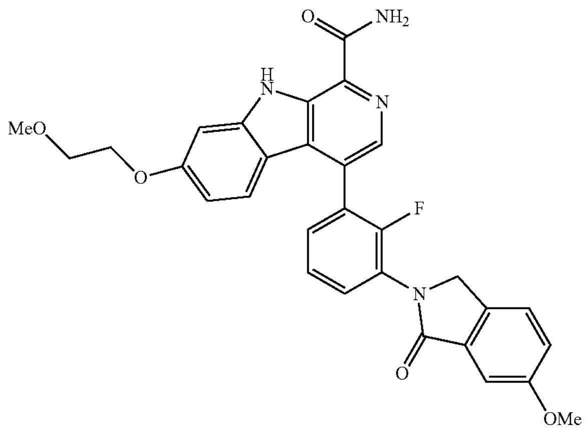 [SMILES: COCCOc1ccc2c(c1)[nH]c1c(C(N)=O)ncc(-c3cccc(N4Cc5ccc(OC)cc5C4=O)c3F)c12] | 541.32 |
| 83 | 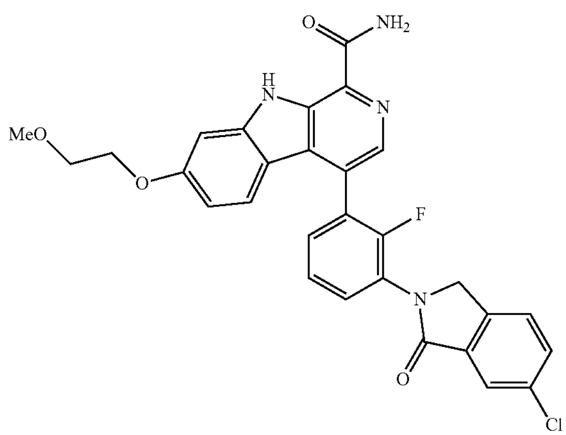 [SMILES: COCCOc1ccc2c(c1)[nH]c1c(C(N)=O)ncc(-c3cccc(N4Cc5ccc(Cl)cc5C4=O)c3F)c12] | 545.25 |
| 84 | 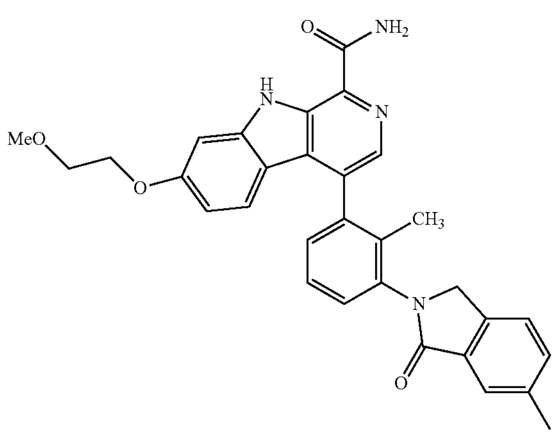 [SMILES: COCCOc1ccc2c(c1)[nH]c1c(C(N)=O)ncc(-c3cccc(N4Cc5ccc(C)cc5C4=O)c3C)c12] | 521.34 |

TABLE 3-continued

| Example No. | Structure | (M + H)+ |
|---|---|---|
| 85 | 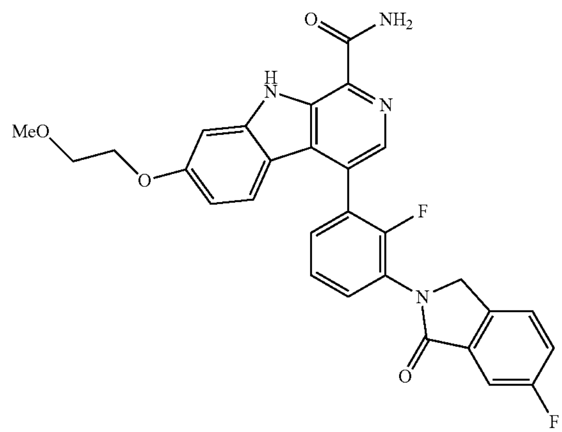 [SMILES: COCCOc1ccc2c(c1)[nH]c1c(C(N)=O)ncc(-c3cccc(N4Cc5ccc(F)cc5C4=O)c3F)c12] | 529.25 |
| 86 | 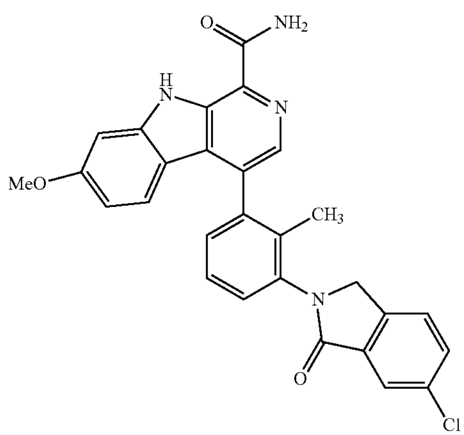 [SMILES: COc1ccc2c(c1)[nH]c1c(C(N)=O)ncc(-c3cccc(N4Cc5ccc(Cl)cc5C4=O)c3C)c12] | 497.19 |
| 87 | 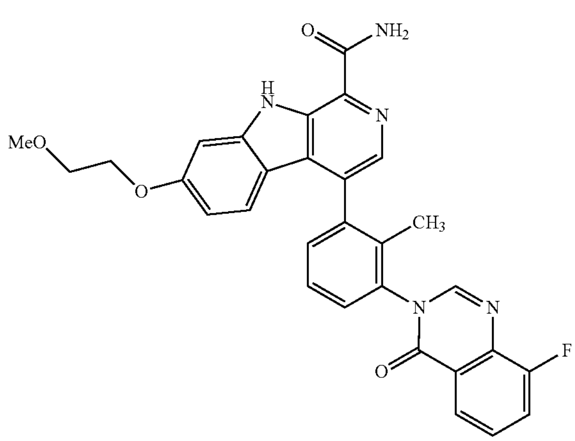 [SMILES: COCCOc1ccc2c(c1)[nH]c1c(C(N)=O)ncc(-c3cccc(-n4cnc5c(F)cccc5c4=O)c3C)c12] | 538.16 |

TABLE 3-continued
| Example No. | Structure | (M + H)+ |
|---|---|---|
| 88 | 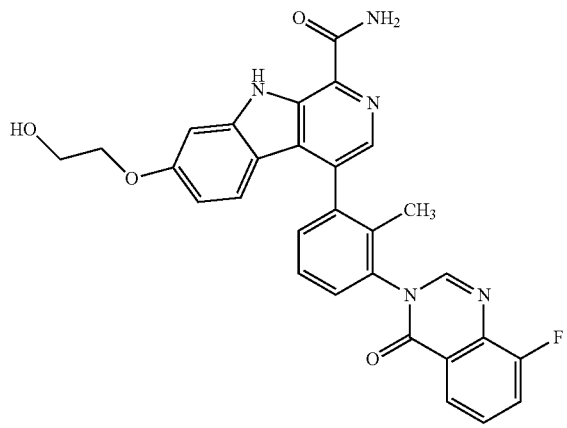 [SMILES: Cc1c(-c2cnc(C(N)=O)c3[nH]c4cc(OCCO)ccc4c23)cccc1-n1cnc2c(F)cccc2c1=O] | 524.17 |
| 89 | 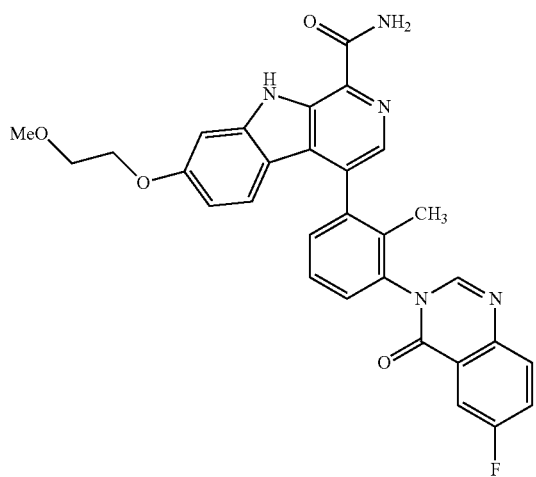 [SMILES: COCCOc1ccc2c(c1)[nH]c1c(C(N)=O)ncc(-c3cccc(-n4cnc5ccc(F)cc5c4=O)c3C)c12] | 538.22 |
| 90 | 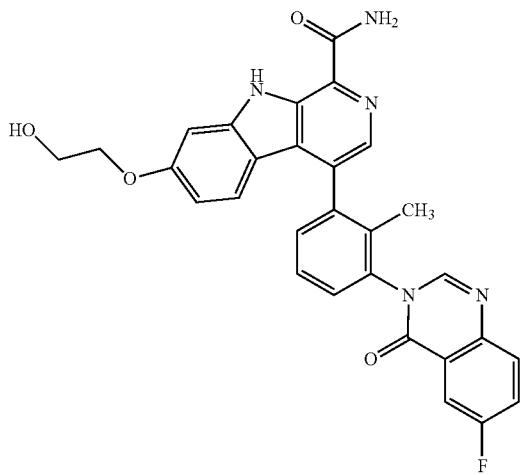 [SMILES: Cc1c(-c2cnc(C(N)=O)c3[nH]c4cc(OCCO)ccc4c23)cccc1-n1cnc2ccc(F)cc2c1=O] | 524.19 |

TABLE 3-continued
| Example No. | Structure | (M + H)+ |
|---|---|---|
| 91 | 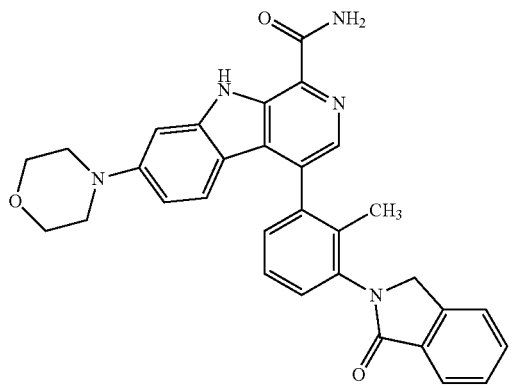 [SMILES: Cc1c(-c2cnc(C(N)=O)c3[nH]c4cc(N5CCOCC5)ccc4c23)cccc1N1Cc2ccccc2C1=O] | 518.22 |
| 92 | 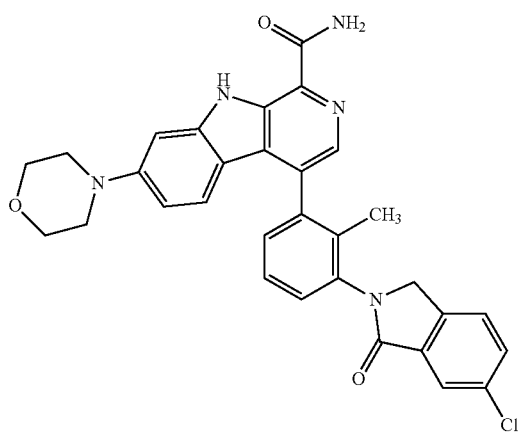 [SMILES: Cc1c(-c2cnc(C(N)=O)c3[nH]c4cc(N5CCOCC5)ccc4c23)cccc1N1Cc2ccc(Cl)cc2C1=O] | 552.26 |
| 93 | 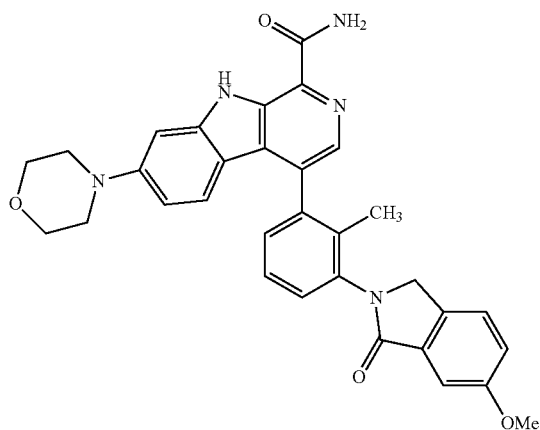 [SMILES: COc1ccc2c(c1)C(=O)N(c1cccc(-c3cnc(C(N)=O)c4[nH]c5cc(N6CCOCC6)ccc5c34)c1C)C2] | 548.32 |

TABLE 3-continued

| Example No. | Structure | (M + H)+ |
| --- | --- | --- |
| 94 | 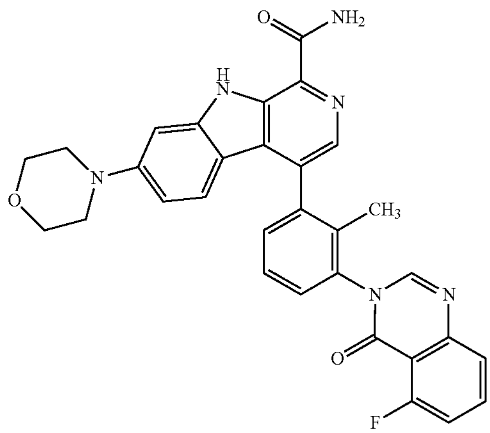 [SMILES: Cc1c(-c2cnc(C(N)=O)c3[nH]c4cc(N5CCOCC5)ccc4c23)cccc1-n1cnc2cccc(F)c2c1=O] | 549.27 |
| 95 | 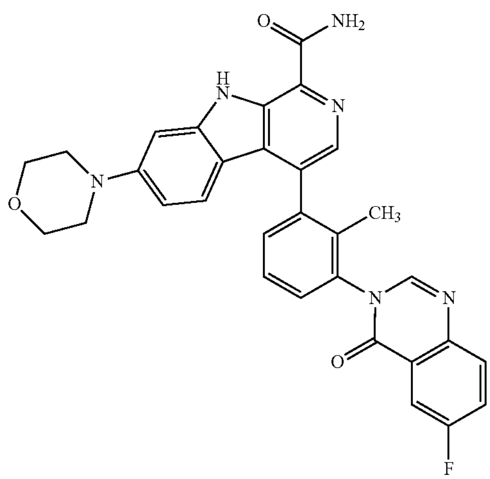 [SMILES: Cc1c(-c2cnc(C(N)=O)c3[nH]c4cc(N5CCOCC5)ccc4c23)cccc1-n1cnc2ccc(F)cc2c1=O] | 549.26 |
| 96 | 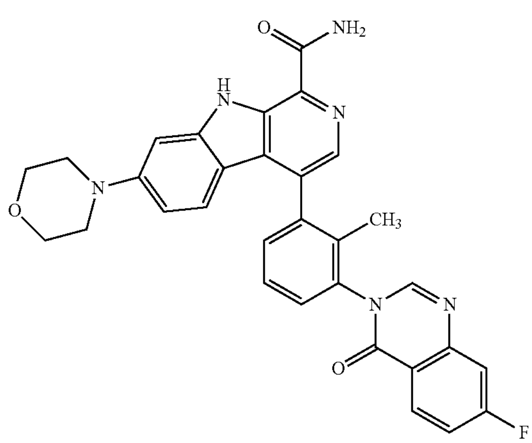 [SMILES: Cc1c(-c2cnc(C(N)=O)c3[nH]c4cc(N5CCOCC5)ccc4c23)cccc1-n1cnc2cc(F)ccc2c1=O] | 549.28 |

TABLE 3-continued

| Example No. | Structure | (M + H)+ |
|---|---|---|
| 97 | 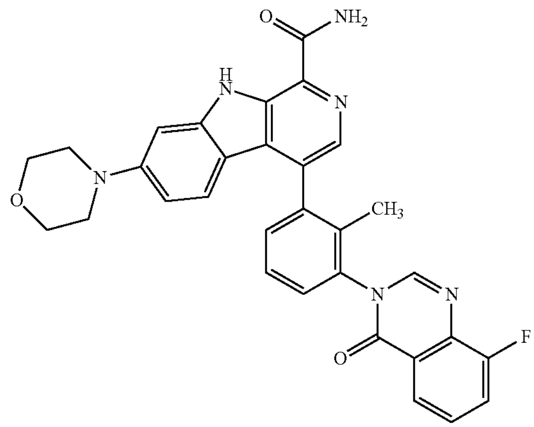 [SMILES: Cc1c(-c2cnc(C(N)=O)c3[nH]c4cc(N5CCOCC5)ccc4c23)cccc1-n1cnc2c(F)cccc2c1=O] | 549.28 |
| 98 | 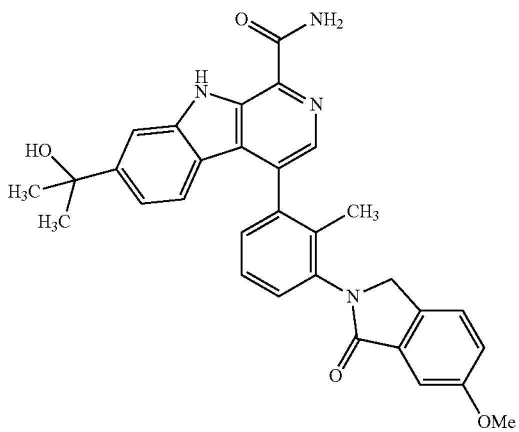 [SMILES: COc1ccc2c(c1)C(=O)N(c1cccc(-c3cnc(C(N)=O)c4[nH]c5cc(C(C)(C)O)ccc5c34)c1C)C2] | 521.21 |
| 99 | 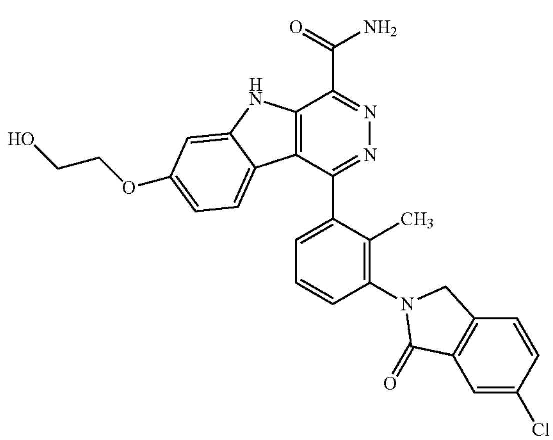 [SMILES: Cc1c(-c2nnc(C(N)=O)c3[nH]c4cc(OCCO)ccc4c23)cccc1N1Cc2ccc(Cl)cc2C1=O] | 528.22 |

TABLE 3-continued
| Example No. | Structure | (M + H)+ |
| --- | --- | --- |
| 100 | 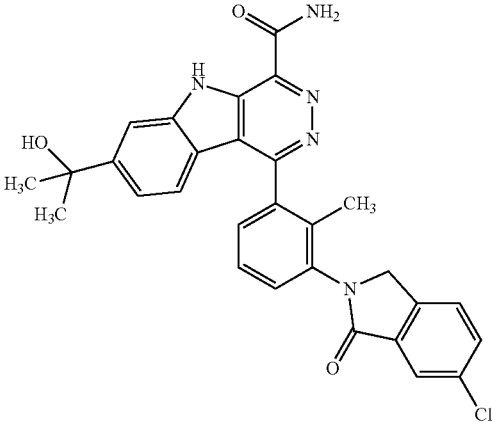 [SMILES: Cc1c(-c2nnc(C(N)=O)c3[nH]c4cc(C(C)(C)O)ccc4c23)cccc1N1Cc2ccc(Cl)cc2C1=O] | 526.16 |
| 101 | 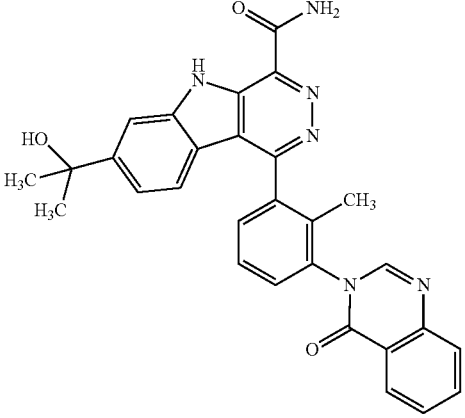 [SMILES: Cc1c(-c2nnc(C(N)=O)c3[nH]c4cc(C(C)(C)O)ccc4c23)cccc1-n1cnc2ccccc2c1=O] | 505.28 |
| 102 | 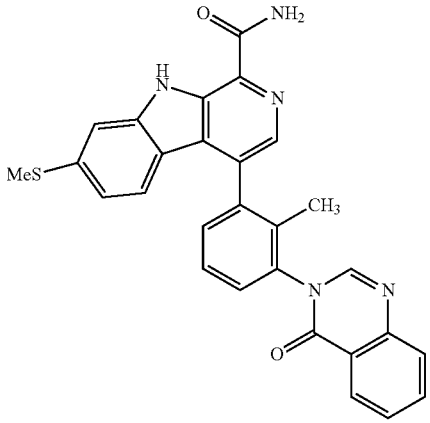 [SMILES: CSc1ccc2c(c1)[nH]c1c(C(N)=O)ncc(-c3cccc(-n4cnc5ccccc5c4=O)c3C)c12] | 492.18 |

TABLE 3-continued
| Example No. | Structure | (M + H)⁺ |
|---|---|---|
| 103 | 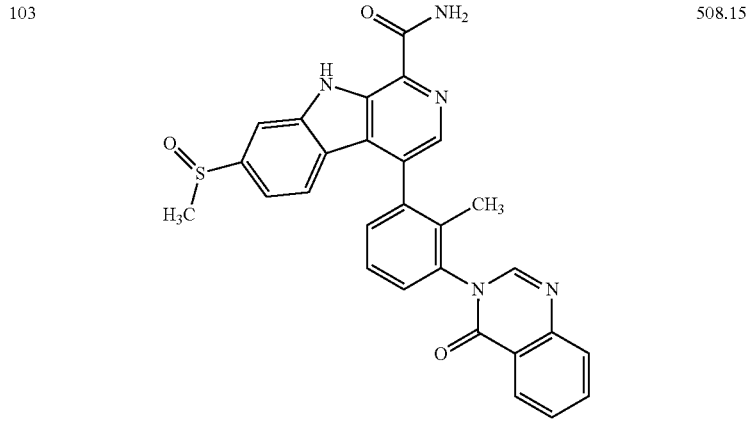 | 508.15 |
| 104 | 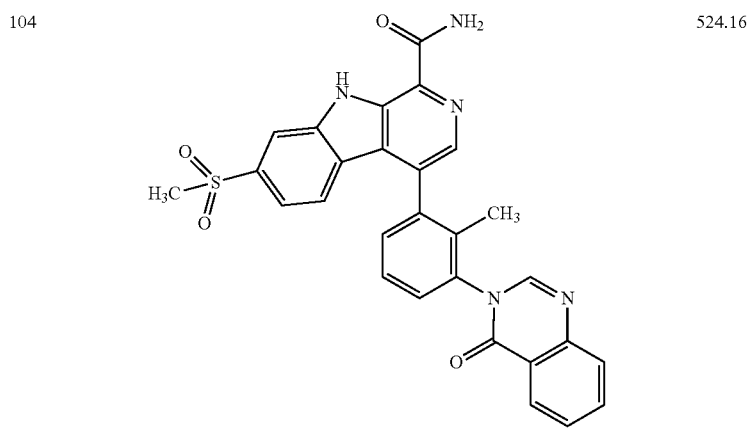 | 524.16 |
| 105 | 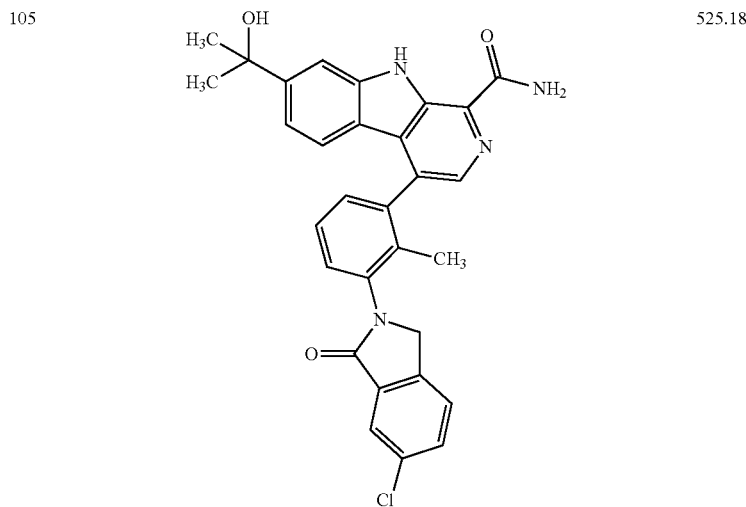 | 525.18 |

TABLE 3-continued

| Example No. | Structure | (M + H)+ |
|---|---|---|
| 106 | 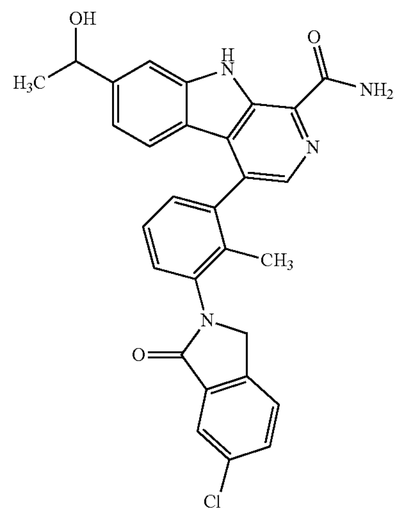 [SMILES: Cc1c(-c2cnc(C(N)=O)c3[nH]c4cc(C(C)O)ccc4c23)cccc1N1Cc2ccc(Cl)cc2C1=O] | 511.15 |
| 107 | 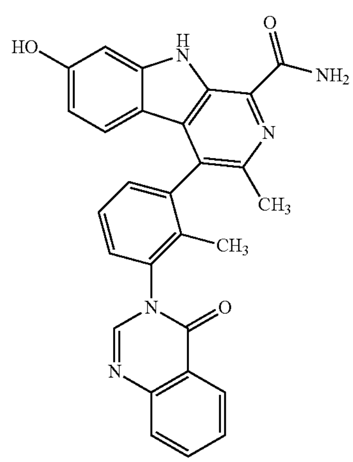 [SMILES: Cc1nc(C(N)=O)c2[nH]c3cc(O)ccc3c2c1-c1cccc(-n2cnc3ccccc3c2=O)c1C] | 476.14 |
| 108 | 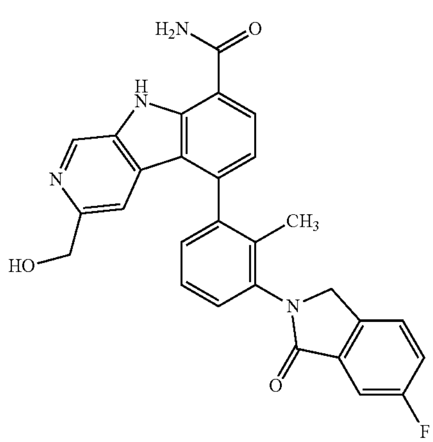 [SMILES: Cc1c(-c2ccc(C(N)=O)c3[nH]c4cnc(CO)cc4c23)cccc1N1Cc2ccc(F)cc2C1=O] | 481.0 (M + H)+ |

TABLE 3-continued
| Example No. | Structure | (M + H)+ |
|---|---|---|
| 109 | 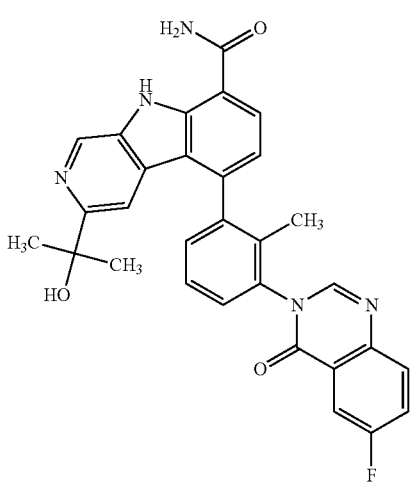 [SMILES: Cc1c(-c2ccc(C(N)=O)c3[nH]c4cnc(C(C)(C)O)cc4c23)cccc1-n1cnc2ccc(F)cc2c1=O] | 522.0 (M + H)+ |
| 110 | 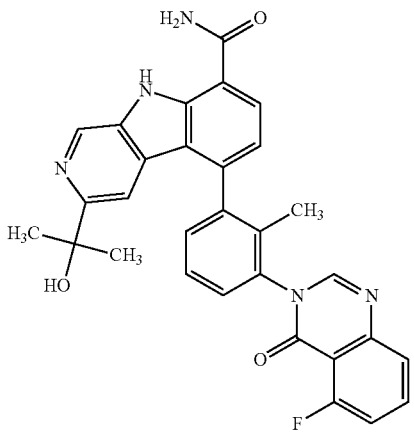 [SMILES: Cc1c(-c2ccc(C(N)=O)c3[nH]c4cnc(C(C)(C)O)cc4c23)cccc1-n1cnc2cccc(F)c2c1=O] | 522.0 (M + H)+ |
| 111 | 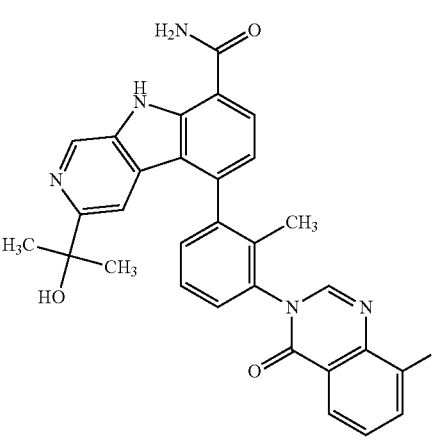 | 522.0 (M + H)+ |

TABLE 3-continued

| Example No. | Structure | (M + H)⁺ |
|---|---|---|
| 112 | 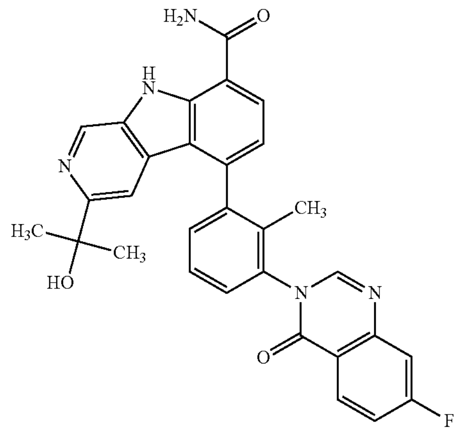 [SMILES: Cc1c(-c2ccc(C(N)=O)c3[nH]c4cnc(C(C)(C)O)cc4c23)cccc1-n1cnc2cc(F)ccc2c1=O] | 522.0 (M + H)⁺ |
| 113 | 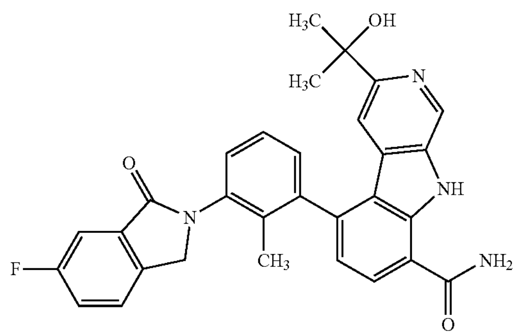 [SMILES: Cc1c(-c2ccc(C(N)=O)c3[nH]c4cnc(C(C)(C)O)cc4c23)cccc1N1Cc2ccc(F)cc2C1=O] | 509.0 (M + H)⁺ |
| 114 | 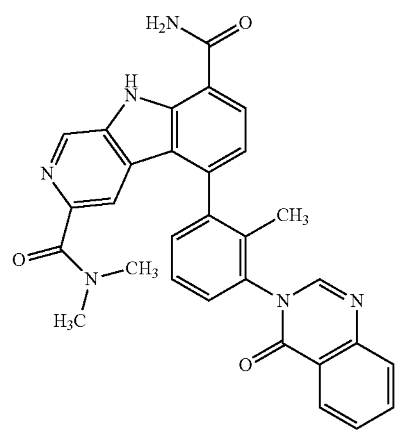 [SMILES: Cc1c(-c2ccc(C(N)=O)c3[nH]c4cnc(C(=O)N(C)C)cc4c23)cccc1-n1cnc2ccccc2c1=O] | 517.1 (M + H)⁺ |
| 115 | 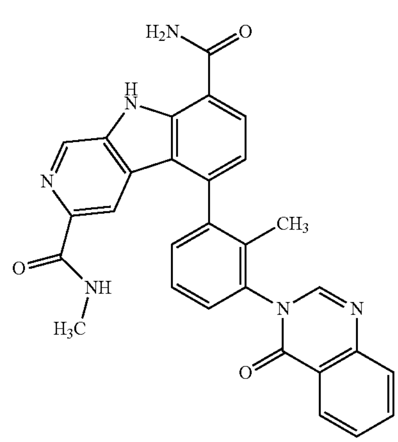 [SMILES: CNC(=O)c1cc2c(cn1)[nH]c1c(C(N)=O)ccc(-c3cccc(-n4cnc5ccccc5c4=O)c3C)c12] | 503.3 (M + H)⁺ |

TABLE 3-continued

| Example No. | Structure | (M + H)⁺ |
|---|---|---|
| 116 | 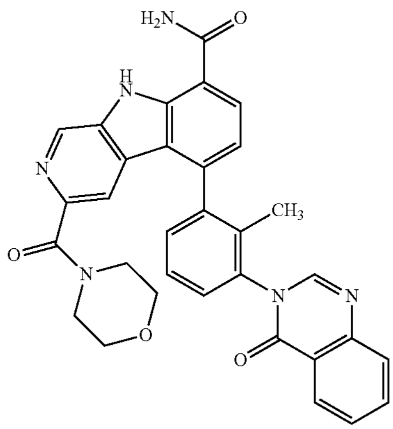 [SMILES: Cc1c(-c2ccc(C(N)=O)c3[nH]c4cnc(C(=O)N5CCOCC5)cc4c23)cccc1-n1cnc2ccccc2c1=O] | 559.0 (M + H)⁺ |
| 117 | 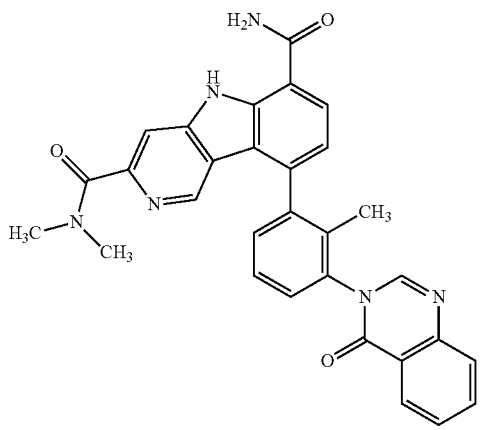 [SMILES: Cc1c(-c2ccc(C(N)=O)c3[nH]c4cc(C(=O)N(C)C)ncc4c23)cccc1-n1cnc2ccccc2c1=O] | 517.2 (M + H)⁺ |

Intermediates

In addition to the intermediates mentioned in preparation of Examples 1-52, additional intermediates shown in Table 4 were synthesized.

Intermediate 1

6-Fluoro-3-(2-methyl-3-(4,4,5,5-tetramethyl-1,3,2-dioxaborolan-2-yl)phenyl)quinazolin-4(3H)-one

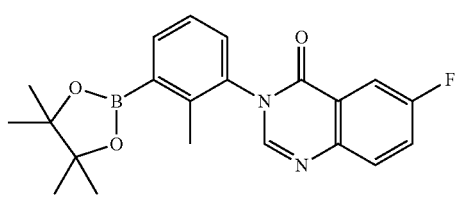 [SMILES: Cc1c(B2OC(C)(C)C(C)(C)O2)cccc1-n1cnc2ccc(F)cc2c1=O]

1. 3-(3-Bromo-2-methylphenyl)-6-fluoroquinazolin-4(3H)-one

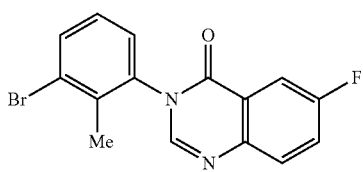 [SMILES: Cc1c(Br)cccc1-n1cnc2ccc(F)cc2c1=O]

A mixture of 2-amino-5-fluorobenzoic acid (1.00 g, 6.45 mmol), 3-bromo-2-methylaniline (1.199 g, 6.45 mmol) and triethoxymethane (0.955 g, 6.45 mmol) in THF (2 mL) was heated at 110° C. overnight in a sealed tube. The mixture was cooled to room temperature and diluted with EtOAc. The solution was washed with NaHCO₃ (aq) and water, then was dried and concentrated. The residue was purified by column chromatography, eluting with EtOAc-hexane (gradient from

2. 2-Fluoro-3-(2-methyl-3-(4,4,5,5-tetramethyl-1,3,2-dioxaborolan-2-yl)phenyl)quinazolin-4(3H)-one

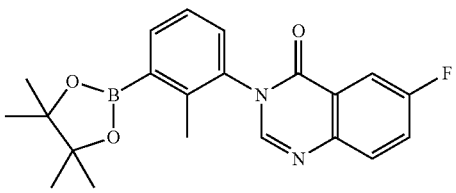 [SMILES: Cc1c(B2OC(C)(C)C(C)(C)O2)cccc1-n1cnc2ccc(F)cc2c1=O]

A mixture of 3-(3-bromo-2-methylphenyl)-6-fluoroquinazolin-4(3H)-one (1.2 g, 3.60 mmol), 4,4,4',4',5,5,5',5'-octamethyl-2,2'-bi(1,3,2-dioxaborolane) (1.372 g, 5.40 mmol), potassium acetate (1.061 g, 10.81 mmol), and [1,1'-bis(diphenylphosphino)ferrocene]dichloropalladium (II) complex with CH$_2$Cl$_2$ (0.147 g, 0.180 mmol) in dioxane (15 mL) was heated in a sealed vial at 110° C. for 3 h. The mixture was cooled to room temperature, diluted with EtOAc and washed with water. The organic phase was filtered, dried and concentrated. The residue was purified by column chromatography on silica gel (40 g) eluting with EtOAc-hexane (gradient from 20:80 to 40:60) to provide 6-Fluoro-3-(2-methyl-3-(4,4,5,5-tetramethyl-1,3,2-dioxaborolan-2-yl)phenyl)quinazolin-4(3H)-one as a white glassy foam (1.25 g, 91% yield). LCMS (M+H)$^+$ m/z 380.9.

Intermediate 1 was used in the preparation of Example 112 in Table 3.

Intermediate 2

6-Fluoro-2-(2-methyl-3-(4,4,5,5-tetramethyl-1,3,2-dioxaborolan-2-yl)phenyl)isoindolin-1-one

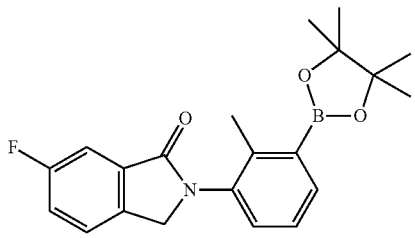 [SMILES: Cc1c(B2OC(C)(C)C(C)(C)O2)cccc1N1Cc2ccc(F)cc2C1=O]

1. 2-(Bromomethyl)-5-fluorobenzoic acid

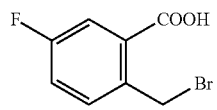

A suspension of 5-fluoro-2-methylbenzoic acid (500 mg, 3.24 mmol), N-bromosuccinimide (606 mg, 3.41 mmol) and benzoyl peroxide (47 mg, 0.195 mmol) in tetrachloromethane (10 mL) was heated at 78° C. for 4 h. The hot mixture was filtered and the filtrate was concentrated to provide crude 2-(bromomethyl)-5-fluorobenzoic acid as a white solid (730 mg), used without further purification. $^1$H NMR (400 MHz, chloroform-d) δ 7.81 (1 H, dd, J=9.2, 2.9 Hz), 7.50 (1 H, dd, J=8.5, 5.4 Hz), 7.23-7.30 (1 H, m), 4.98 (2 H, s).

2. N-(3-Bromo-2-methylphenyl)-2-(bromomethyl)-5-fluorobenzamide

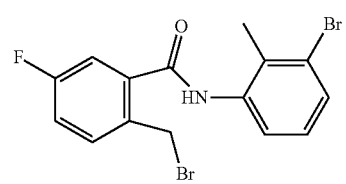 [SMILES: Cc1c(Br)cccc1NC(=O)c1cc(F)ccc1CBr]

A solution of crude 2-(bromomethyl)-5-fluorobenzoic acid (3.05 g, 13.1 mmol) in CH$_2$Cl$_2$ (50 mL) was treated with oxalyl chloride (1.66 g, 13.1 mmol) and 6 drops of DMF. The mixture was stirred at room temperature for 1 h, and then was concentrated. The residue was dissolved in CH$_2$Cl$_2$ (50 mL) and treated with 3-bromo-2-methylaniline (1.705 g, 9.16 mmol). The mixture was stirred at room temperature for 1 h, and then TEA (2.19 mL, 15.7 mmol) was added in portions. The mixture was stirred at room temperature for 2 h, then was diluted with CH$_2$Cl$_2$ (100 mL), washed with NaHCO$_3$ (aq) and water, dried and concentrated. The residue was triturated with CH$_2$Cl$_2$ to provide the desired product as a white solid (0.9 g). The mother liquor was concentrated and the residue was again triturated with CH$_2$Cl$_2$ to provide additional desired product as a white solid (0.46 g). The mother liquor was concentrated and the residue was purified by column chromatography on silica gel, eluting with EtOAc-hexane (gradient from 0:100 to 30:70) to provide additional desired product as a pink solid (1.18 g) for a total of 2.54 g (48% yield). LCMS (M+H)$^+$ m/z 400, 402, 404.

3. 2-(3-Bromo-2-methylphenyl)-6-fluoroisoindolin-1-one

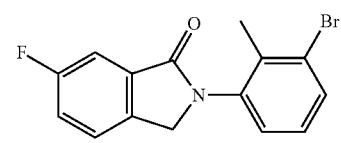 [SMILES: Cc1c(Br)cccc1N1Cc2ccc(F)cc2C1=O]

A mixture of N-(3-bromo-2-methylphenyl)-2-(bromomethyl)-5-fluorobenzamide (2.54 g, 6.33 mmol) and sodium tert-butoxide (0.913 g, 9.50 mmol) in THF (80 mL) was stirred at room temperature for 30 min. The mixture was diluted with water and extracted with twice with CH$_2$Cl$_2$. The combined organic phases were washed with water, dried and concentrated. The residue was purified by column chromatography on silica gel, eluting with EtOAc-hexane to provide the desired product as a white solid (1.18 g, 58% yield). LCMS (M+H)+ m/z 320, 322.

4. 6-Fluoro-2-(2-methyl-3-(4,4,5,5-tetramethyl-1,3, 2-dioxaborolan-2-yl)phenyl)isoindolin-1-one

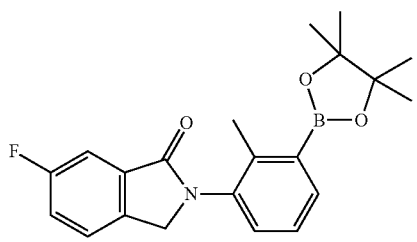 [SMILES: Cc1c(B2OC(C)(C)C(C)(C)O2)cccc1N1Cc2ccc(F)cc2C1=O]

A mixture of 2-(3-bromo-2-methylphenyl)-6-fluoroisoindolin-1-one (1.367 g, 4.27 mmol), 4,4,4',4',5,5,5',5'-octamethyl-2,2'-bi(1,3,2-dioxaborolane) (1.301 g, 5.12 mmol), potassium acetate (0.838 g, 8.54 mmol), and [1,1'-bis(diphenylphosphino)ferrocene]dichloropalladium (II) complex with $CH_2Cl_2$ (0.105 g, 0.128 mmol) in dioxane (30 mL) and DMSO (6 mL) was degassed with nitrogen and heated in equal portions in two sealed vials at 90° C. overnight. The mixtures were cooled to room temperature and combined, diluted with $CH_2Cl_2$ and washed with water. The aqueous phase was extracted twice with $CH_2Cl_2$, and the combined organic phases were dried and concentrated. The residue was purified by column chromatography on silica gel (52 g) eluting with EtOAc-hexane (gradient from 0:100 to 50:50) to provide the desired product as a white solid (1.35 g, 86% yield). LCMS $(M+H)^+$ m/z 368.1.

Intermediates 4, 5, 6 in Table 4 were prepared in the same manner as Intermediate 2 was prepared.

Intermediate 2 was used in the preparation of Examples 108 and 113 in Table 3. Intermediate 3, prepared in the same manner as Intermediate 1, was used in the preparation of Examples 42-51 and 114-117. Intermediate 4 was used to prepare Example 112. Intermediate 6 was used to prepare Example 113.

TABLE 4

| Intermediate No. | Structure | $(M + H)^+$ |
|---|---|---|
| 1 | 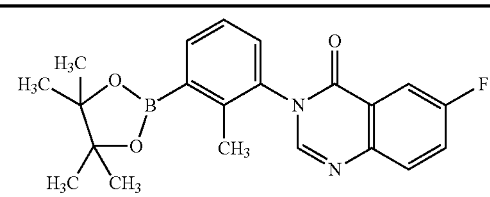 | 380.9 |
| 2 | 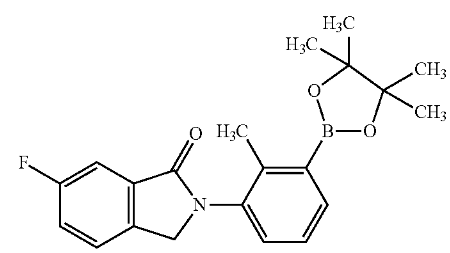 [SMILES: Cc1c(B2OC(C)(C)C(C)(C)O2)cccc1N1Cc2ccc(F)cc2C1=O] | 368.1 |
| 3 | 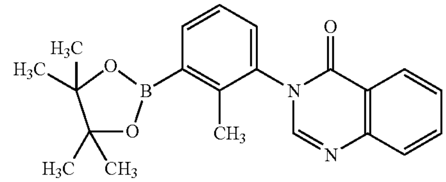 [SMILES: Cc1c(B2OC(C)(C)C(C)(C)O2)cccc1-n1cnc2ccccc2c1=O] | 363.2 |
| 4 | 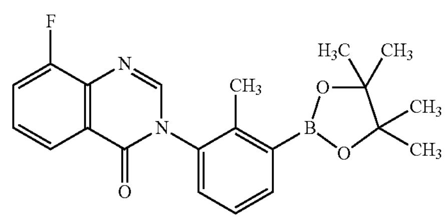 [SMILES: Cc1c(B2OC(C)(C)C(C)(C)O2)cccc1-n1cnc2c(F)cccc2c1=O] | 381.2 |
| 5 | 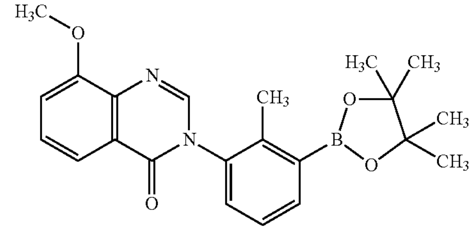 [SMILES: COc1cccc2c(=O)n(-c3cccc(B4OC(C)(C)C(C)(C)O4)c3C)cnc12] | 393.1 |

TABLE 4-continued

| Intermediate No. | Structure | (M + H)+ |
|---|---|---|
| 6 | 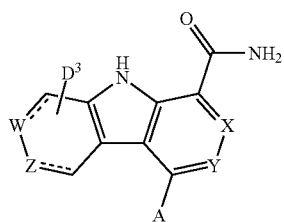 | 381.1 |

What is claimed is:

1. A compound according to formula (I):

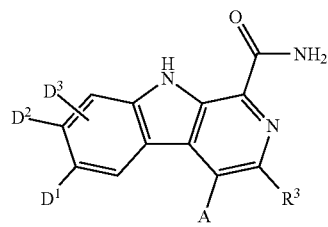
(I)

or an enantiomer, a diastereomer, a stereoisomer thereof, wherein

X is $CR^3$ or N;
Y is $CR^3$ or N;
Z is $CD^1$ or N;
W is $CD^2$ or N;
— is an optional bond; provided when the two optional bonds are absent, Z is $CHD^1$, W is $ND^2$ or Z is $ND^1$, W is $CHD^2$;

wherein said compound of formula (I) is selected from:

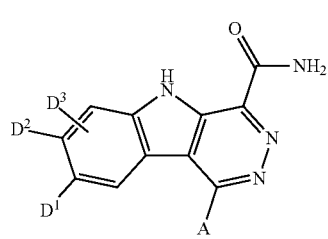
(Ia)

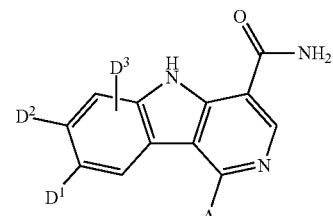 (Ib)

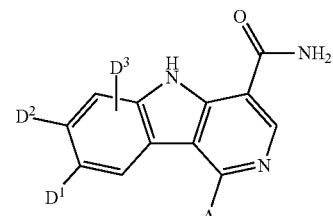 (Ic)

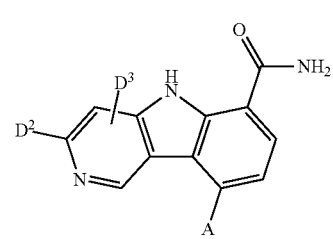 (Id)

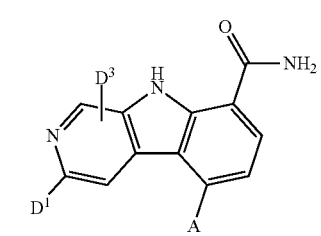 (Ie)

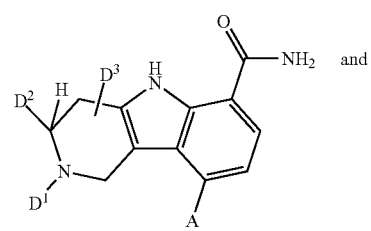 (If) and

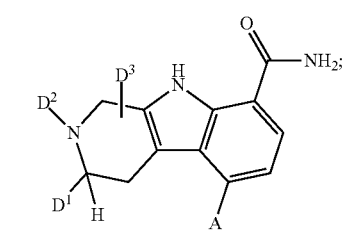 (Ig)

A is $C_{3-10}$ carbocycle substituted with 0-5 B or $C_{6-10}$ mono- or bicyclic aryl substituted with 0-5 B;

B is $R^1$, halogen, cyano, nitro, —$OR^1$, —$C(=O)R^1$, —$C(=O)OR^1$, —$C(=O)NR^{11}R^1$, —$S(=O)_2R^1$, —$NR^1C(=O)R^1$, —$NR^{11}C(=O)NR^{11}R^1$, —$NR^{11}C$ (=O)OR$^1$, —N(C(=O)OR$^1$)$_2$, —NR$^{11}$S(=O)$_2$R$^1$, —N(S(=O)$_2$R$^1$)$_2$, or —NR$^{11}$R$^1$;

R$^1$ is hydrogen, C$_{1-6}$ alkyl substituted with 0-3 R$^{1a}$, C$_{1-6}$ haloalkyl, C$_{2-6}$ alkenyl substituted with 0-3 R$^{1a}$, C$_{2-6}$ alkynyl substituted with 0-3 R$^{1a}$, C$_{3-10}$ cycloalkyl substituted with 0-5 R$^{1a}$, C$_{6-10}$ aryl substituted with 0-5 R$^{1a}$, a 5-10 membered heterocyclyl containing 1-4 heteroatoms selected from N, O, and S, substituted with 0-5 R$^{1a}$, or a 5-10 membered heteroaryl containing 1-4 heteroatoms selected from N, O, and S, substituted with 0-5 R$^{1a}$;

R$^{1a}$ is hydrogen, =O, F, Cl, Br, OCF$_3$, CF$_3$, CHF$_2$, CN, NO$_2$, —(CH$_2$)$_r$OR$^b$, —(CH$_2$)$_r$SR$^b$, —(CH$_2$)$_r$C(O)R$^b$, —(CH$_2$)$_r$C(O)OR$^b$, —(CH$_2$)$_r$OC(O)R$^b$, —(CH$_2$)$_r$NR$^{11}$R$^{11}$, —(CH$_2$)$_r$C(O)NR$^{11}$R$^{11}$, —(CH$_2$)$_r$NR$^b$C(O)R$^c$, —(CH$_2$)$_r$NR$^b$C(O)OR$^c$, —NR$^b$C(O)NR$^{11}$R$^{11}$, —S(O)$_p$NR$^{11}$R$^{11}$, —NR$^b$S(O)$_p$R$^c$, —S(O)R$^c$, S(O)$_2$R$^c$, C$_{1-6}$ alkyl substituted with 0-2 R$^a$, C$_{1-6}$ haloalkyl, —(CH$_2$)$_r$-3-14 membered carbocycle substituted with 0-1 R$^a$, or —(CH$_2$)$_r$-5-7 membered heterocycle comprising carbon atoms and 1-4 heteroatoms selected from N, O, and S(O)$_p$ substituted with 0-1 R$^a$;

D$^1$ and D$^2$ are independently R$^2$, halogen, —(C(R$^{11}$)$_2$)$_r$R$^2$, —OR$^2$, —C(=O)R$^2$, —C(=O)OR$^2$, —C(=O)NR$^{11}$R$^2$, —S(=O)$_2$R$^2$, —S(=O)R$^2$, —SR$^2$, —NR$^{11}$C(=O)R$^2$, —NR$^{11}$C(=O)NR$^{11}$R$^2$, —NR$^{11}$C(=O)OR$^2$, —NR$^{11}$S(=O)$_2$R$^2$, —NR$^{11}$R$^2$, —C(=O)NR$^{11}$OR$^2$, —OC(=O)OR$^2$, —OC(=O)R$^2$, or —CH=N—OH; alternatively D$^1$ and D$^2$ join to form —O—CH$_2$—O—;

D$^3$ is hydrogen, halogen, C$_{1-3}$ alkyl, C$_{1-3}$ alkoxy, or CN;

R$^2$ is hydrogen, C$_{1-6}$ alkyl substituted with 0-3 R$^{2a}$, C$_{2-6}$ alkenyl substituted with 0-3 R$^{2a}$, C$_{2-6}$ alkynyl substituted with 0-3 R$^{2a}$, C$_{3-10}$ cycloalkyl substituted with 0-5 R$^{2a}$, C$_{6-10}$ aryl substituted with 0-5 R$^{2a}$, a 5-10 membered heterocyclyl containing 1-4 heteroatoms selected from N, O, and S, substituted with 0-5 R$^{2a}$, or a 5-10 membered heteroaryl containing 1-4 heteroatoms selected from N, O, and S, substituted with 0-5 R$^{2a}$;

R$^{2a}$ is hydrogen, =O, F, Cl, Br, OCF$_3$, CN, NO$_2$, —(CH$_2$)$_r$OR$^b$, —(CH$_2$)$_r$SR$^b$, —(CH$_2$)$_r$C(O)R$^b$, —(CH$_2$)$_r$C(O)OR$^b$, —(CH$_2$)$_r$OC(O)R$^b$, —(CH$_2$)$_r$NR$^{11}$R$^{11}$, —(CH$_2$)$_r$C(O)NR$^{11}$R$^{11}$, —(CH$_2$)$_r$NR$^b$C(O)R$^c$, —(CH$_2$)$_r$NR$^b$C(O)OR$^c$, —NR$^b$C(O)NR$^{11}$R$^{11}$, —S(O)$_p$NR$^{11}$R$^{11}$, —NR$^b$S(O)$_p$R$^c$, —S(O)R$^c$, —S(O)$_2$R$^c$, C$_{1-6}$ alkyl substituted with 0-2 R$^a$, C$_{1-6}$ haloalkyl, —(CH$_2$)$_r$-3-14 membered carbocycle substituted with 0-1 R$^a$, or —(CH$_2$)$_r$-5-7 membered heterocycle comprising carbon atoms and 1-4 heteroatoms selected from N, O, and S(O)$_p$ substituted with 0-2 R$^a$;

R$^3$ is hydrogen or C$_{1-6}$ alkyl;

R$^{11}$ is independently hydrogen or C$_{1-4}$ alkyl substituted with 0-1 R$^f$, —CH$_2$-phenyl, or —(CH$_2$)$_r$-5-7 membered heterocycle comprising carbon atoms and 1-4 heteroatoms selected from N, O, and S(O)$_p$;

alternatively, R$^{11}$ along with another R$^{11}$, R$^f$, or R$^2$ on the same nitrogen atom may join to form an optionally substituted azetidinyl, pyrrolidinyl, piperidinyl, morpholinyl, or 4-(C$_{1-6}$ alkyl)piperazinyl;

R$^a$ is hydrogen, F, Cl, Br, OCF$_3$, CF$_3$, CHF$_2$, CN, NO$_2$, —(CH$_2$)$_r$OR$^b$, —(CH$_2$)$_r$SR$^b$, —(CH$_2$)$_r$C(O)R$^b$, —(CH$_2$)$_r$C(O)OR$^b$, —(CH$_2$)$_r$OC(O)R$^b$, —(CH$_2$)$_r$NR$^{11}$R$^{11}$, —(CH$_2$)$_r$C(O)NR$^{11}$R$^{11}$, —(CH$_2$)$_r$NR$^b$C(O)R$^c$, —(CH$_2$)$_r$NR$^b$C(O)OR$^c$, —NR$^b$C(O)NR$^{11}$R$^{11}$, —S(O)$_p$NR$^{11}$R$^{11}$, —NR$^b$S(O)$_p$R$^c$, —S(O)R$^c$, —S(O)$_2$R$^c$, C$_{1-6}$ alkyl substituted with 0-1 R$^f$, C$_{1-6}$ haloalkyl, —(CH$_2$)$_r$-3-14 membered carbocycle, or —(CH$_2$)$_r$-5-7 membered heterocycle comprising carbon atoms and 1-4 heteroatoms selected from N, O, and S(O)$_p$, alternatively two R$^a$ on adjacent or the same carbon atom form a cyclic acetal of the formula —O—(CH$_2$)$_n$—O—, or —O—CF$_2$—O—, wherein n is selected from 1 or 2;

R$^b$ is hydrogen, C$_{1-6}$ alkyl substituted with 0-2 R$^d$, C$_{1-6}$ haloalkyl, C$_{3-6}$ cycloalkyl substituted with 0-2 R$^d$, or —(CH$_2$)$_r$-phenyl substituted with 0-2 R$^d$;

R$^c$ is C$_{1-6}$ alkyl substituted with 0-1 R$^f$, C$_{3-6}$ cycloalkyl, or —(CH$_2$)$_r$-phenyl substituted with 0-1 R$^f$;

R$^d$ is hydrogen, F, Cl, Br, OCF$_3$, CF$_3$, CN, NO$_2$, —OR$^e$, —(CH$_2$)$_r$(O)R$^c$, —NR$^e$R$^e$, —NR$^e$C(O)OR$^c$, C$_{1-6}$ alkyl, or —(CH$_2$)$_r$-phenyl;

R$^e$ is hydrogen, C$_{1-6}$ alkyl, C$_{3-6}$ cycloalkyl, or —(CH$_2$)$_r$-phenyl;

R$^f$ is hydrogen, halo, NH$_2$, OH, or OCH$_3$;

r is 0, 1, 2, 3, or 4; and p is 0, 1, or 2.

2. The compound according to claim 1, having formula (Ia), (Ib), or (Ic):

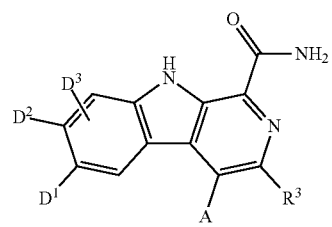

(Ia)

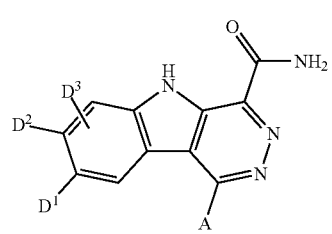

(Ib)

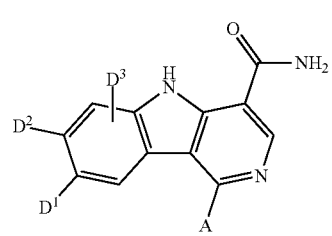

(Ic)

wherein A is C$_{6-10}$ mono- or bicyclic aryl substituted with 0-5 B.

3. The compound according to claim 1, having formula (Id) or (Ie):

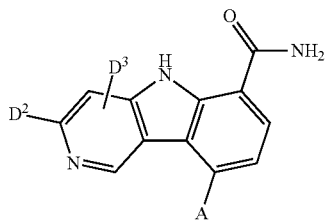
(Id)

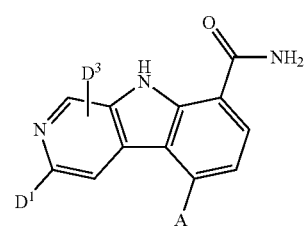
(Ie)

wherein A is $C_{6-10}$ mono- or bicyclic aryl substituted with 0-5 B.

4. The compound according to claim 1, wherein formula (I) is formula (If) or (Ig):

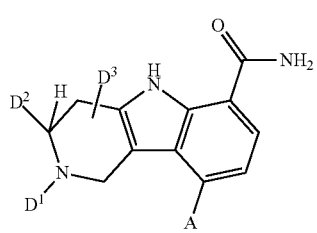
(If)

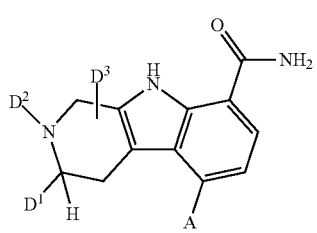
(Ig)

wherein A is $C_{6-10}$ mono- or bicyclic aryl substituted with 0-5 B.

5. The compound according to claim 1, wherein
$D^1$ and $D^2$ are independently $R^2$, —$(CH_2)_rR^2$, —$OR^2$, —C(=O)$R^2$, —C(=O)O$R^2$, —C(=O)N$R^{11}R^2$, —S(O)$_2R^2$, —S(O)$R^2$, —S$R^2$, —$NR^{11}$C(O)$R^2$, —$NR^{11}$C(O)N$R^{11}R^2$, —$NR^{11}$C(=O)O$R^2$, —$NR^{11}$S(=O)$_2R^2$, or —$NR^{11}R^2$;

$R^2$ is hydrogen, $C_{1-6}$ alkyl substituted with 0-3 $R^{2a}$, $C_{2-6}$ alkenyl substituted with 0-3 $R^{2a}$, $C_{3-10}$ cycloalkyl substituted with 0-4 $R^{2a}$, —$C_{6-10}$ aryl substituted with 0-4 $R^{2a}$, a 5-10 membered heterocyclyl containing 1-4 heteroatoms selected from N, O, and S, substituted with 0-4 $R^{2a}$, or a 5-10 membered heteroaryl containing 1-4 heteroatoms selected from N, O, and S, substituted with 0-4 $R^{2a}$;

$R^{2a}$ is hydrogen, =O, F, Cl, Br, OCF$_3$, CF$_3$, CHF$_2$, CN, NO$_2$, OR$^b$, SR$^b$, —C(O)R$^b$, —C(O)OR$^b$, —OC(O)R$^b$, —NR$^{11}$R$^{11}$, —C(O)NR$^{11}$R$^{11}$, —NR$^b$C(O)R$^c$, —NR$^b$C(O)OR$^c$, —NR$^b$C(O)NR$^{11}$R$^{11}$, —S(O)$_p$NR$^{11}$R$^{11}$, —NR$^b$S(O)$_p$R$^c$, —S(O)R$^c$, —S(O)$_2$R$^c$, $C_{1-6}$ alkyl substituted with 0-2 $R^a$, —$(CH_2)_r$-3-14 membered carbocycle substituted with 0-1 $R^a$, wherein the carbocycle is cyclopropyl, cyclobutyl, cyclopentyl or cyclohexyl; or —$(CH_2)_r$-5-7 membered heterocycle comprising carbon atoms and 1-4 heteroatoms selected from N, O, and S(O)$_p$ substituted with 0-2 $R^a$; and r is 0, 1, or 2.

6. The compound according claim 1, or an enantiomer, a diastereomer, a stereoisomer thereof, wherein said compound of formula (I) is selected from:

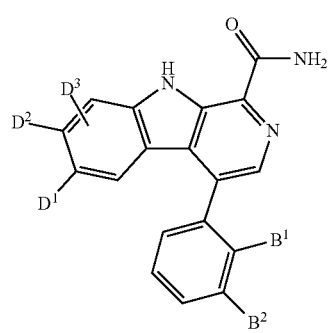
(IIa)

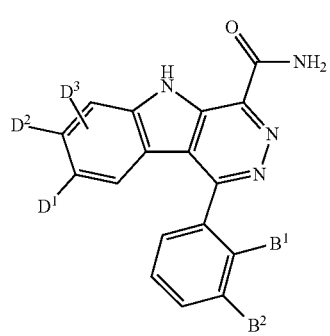
(IIb)

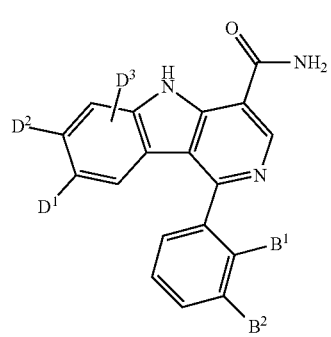
(IIc)

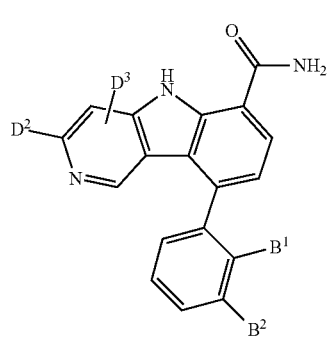
(IId)

-continued

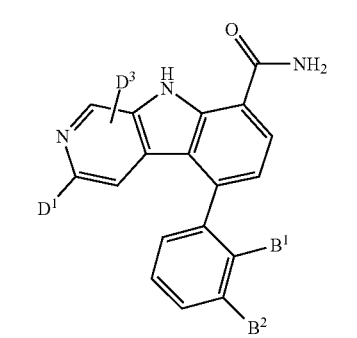

(IIe)

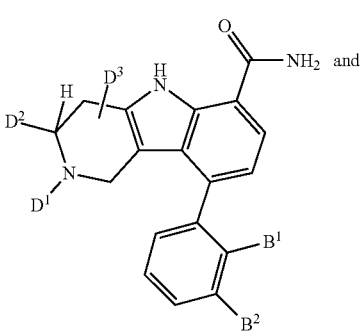

(IIf) and

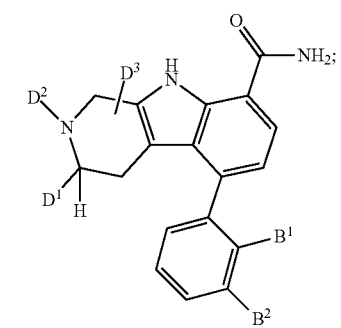

(IIg)

$B^1$ is hydrogen, halogen, cyano, nitro, —OH, or $C_{1-6}$ alkyl substituted with 0-3 $R^{1a}$;

$B^2$ is $R^1$, —C(=O)$R^1$, —C(=O)O$R^1$, —C(=O)N$R^{11}R^1$, —S(=O)$_2R^1$, —N$R^{11}$C(=O)$R^1$, —N$R^{11}$C(=O) N$R^{11}R^1$, —N$R^{11}$C(=O)O$R^1$, —N(C(=O)O$R^1$)$_2$, —N$R^{11}$S(=O)$_2R^1$, —N(S(=O)$_2R^1$)$_2$, or —N$R^{11}R^1$;

$R^1$ is hydrogen, $C_{1-6}$ alkyl substituted with 0-3 $R^{1a}$, $C_{1-6}$ haloalkyl, $C_{2-6}$ alkenyl substituted with 0-3 $R^{1a}$, $C_{2-6}$ alkynyl substituted with 0-3 $R^{1a}$, $C_{3-10}$ cycloalkyl substituted with 0-5 $R^{1a}$, $C_{6-10}$ aryl substituted with 0-5 $R^{1a}$, a 5-10 membered heterocyclyl containing 1-4 heteroatoms selected from N, O, and S, substituted with 0-5 $R^{1a}$, or a 5-10 membered heteroaryl containing 1-4 heteroatoms selected from N, O, and S, substituted with 0-5 $R^{1a}$;

$R^{1a}$ is hydrogen, =O, F, Cl, Br, OCF$_3$, CF$_3$, CHF$_2$, CN, NO$_2$, —(CH$_2$)$_r$OR$^b$, —(CH$_2$)$_r$SR$^b$, —(CH$_2$)$_r$C(O)R$^b$, —(CH$_2$)$_r$C(O)OR$^b$, —(CH$_2$)$_r$OC(O)R$^b$, —(CH$_2$)$_r$NR$^{11}$R$^{11}$, —(CH$_2$)$_r$C(O)NR$^{11}$R$^{11}$, —(CH$_2$)$_r$NR$^b$C(O) R$^c$, —(CH$_2$)$_r$NR$^b$C(O)OR$^c$, —NR$^b$C(O)NR$^{11}$R$^{11}$, —S(O)$_p$NR$^{11}$R$^{11}$, —NR$^b$S(O)$_p$R$^c$, —S(O)R$^c$, —S(O)$_2$R$^c$, $C_{1-6}$ alkyl substituted with 0-2 R$^a$, $C_{1-6}$ haloalkyl, —(CH$_2$)$_r$-3-14 membered carbocycle substituted with 0-1 R$^a$, or —(CH$_2$)$_r$-5-7 membered heterocycle comprising carbon atoms and 1-4 heteroatoms selected from N, O, and S(O)$_p$ substituted with 0-1 R$^a$;

$D^1$ and $D^2$ are independently $R^2$, halogen, —C(R$^{11}$)$_2$)$_r$R$^2$, —(C(R$^{11}$)$_2$)$_r$OR$^2$, —C(=O)R$^2$, —C(=O)OR$^2$, —C(=O)NR$^{11}$R$^2$, —S(=O)$_2$R$^2$, —S(=O)R$^2$, —SR$^2$, —NR$^{11}$C(=O)R$^2$, —NR$^{11}$C(=O)NR$^{11}$R$^2$, —NR$^{11}$C (=O)OR$^2$, —NR$^{11}$S(=O)$_2$R$^2$, —NR$^{11}$R$^2$, —C(=O) NR$^{11}$OR$^2$, —OC(=O)OR$^2$, —OC(=O)R$^2$, or —CH=N—OH; alternatively $D^1$ and $D^2$ join to form —O—CH$_2$—O—;

$D^3$ is hydrogen, halogen, $C_{1-3}$ alkyl, $C_{1-3}$ alkoxy, or CN;

$R^2$ is hydrogen, $C_{1-6}$ alkyl substituted with 0-3 $R^{2a}$, $C_{2-6}$ alkenyl substituted with 0-3 $R^{2a}$, $C_{2-6}$ alkynyl substituted with 0-3 $R^{2a}$, $C_{3-10}$ cycloalkyl substituted with 0-5 $R^{2a}$, $C_{6-10}$ aryl substituted with 0-5 $R^{2a}$, a 5-10 membered heterocyclyl containing 1-4 heteroatoms selected from N, O, and S, substituted with 0-5 $R^{2a}$, or a 5-10 membered heteroaryl containing 1-4 heteroatoms selected from N, O, and S, substituted with 0-5 $R^{2a}$;

$R^{2a}$ is hydrogen, =O, F, Cl, Br, OCF$_3$, CN, NO$_2$, —(CH$_2$)$_r$OR$^b$, —(CH$_2$)$_r$SR$^b$, —(CH$_2$)$_r$C(O)R$^b$, —(CH$_2$)$_r$C(O) OR$^b$, —(CH$_2$)$_r$OC(O)R$^b$, —(CH$_2$)$_r$NR$^{11}$R$^{11}$, —(CH$_2$)$_r$C(O)NR$^{11}$R$^{11}$, —(CH$_2$)$_r$NR$^b$C(O)R$^c$, —(CH$_2$)$_r$NR$^b$C (O)OR$^c$, —NR$^b$C(O)NR$^{11}$R$^{11}$, —S(O)$_p$NR$^{11}$R$^{11}$, —NR$^b$S(O)$_p$R$^c$, —S(O)R$^c$, —S(O)$_2$R$^c$, $C_{1-6}$ alkyl substituted with 0-2 R$^a$, $C_{1-6}$ haloalkyl, —(CH$_2$)$_r$-3-14 membered carbocycle substituted with 0-1 R$^a$, or —(CH$_2$)$_r$-5-7 membered heterocycle comprising carbon atoms and 1-4 heteroatoms selected from N, O, and S(O)$_p$ substituted with 0-2 R$^a$;

$R^{11}$ is independently hydrogen or $C_{1-4}$ alkyl substituted with 0-1 R$^f$, —CH$_2$-phenyl, or —(CH$_2$)$_r$-5-7 membered heterocycle comprising carbon atoms and 1-4 heteroatoms selected from N, O, and S(O)$_p$;

alternatively, $R^{11}$ along with another $R^{11}$, $R^1$, or $R^2$ on the same nitrogen atom may join to form an optionally substituted azetidinyl, pyrrolidinyl, piperidinyl, morpholinyl, or 4-($C_{1-6}$ alkyl)piperazinyl;

$R^3$ is hydrogen or $C_{1-6}$ alkyl;

$R^a$ is hydrogen, F, Cl, Br, OCF$_3$, CF$_3$, CHF$_2$, CN, NO$_2$, —(CH$_2$)$_r$OR$^b$, —(CH$_2$)$_r$SR$^b$, —(CH$_2$)$_r$C(O)R$^b$, —(CH$_2$)$_r$C(O)OR$^b$, —(CH$_2$)$_r$OC(O)R$^b$, —(CH$_2$)$_r$NR$^{11}$R$^{11}$, —(CH$_2$)$_r$C(O)NR$^{11}$R$^{11}$, —(CH$_2$)$_r$NR$^b$C(O) R$^c$, —(CH$_2$)$_r$NR$^b$C(O)OR$^c$, —NR$^b$C(O)NR$^{11}$R$^{11}$, —S(O)$_p$NR$^{11}$R$^{11}$, —NR$^b$S(O)$_p$R$^c$, —S(O)R$^c$, —S(O)$_2$ R$^c$, $C_{1-6}$ alkyl substituted with 0-1 R$^f$, $C_{1-6}$ haloalkyl, —(CH$_2$)$_r$-3-14 membered carbocycle, or —(CH$_2$)$_r$-5-7 membered heterocycle comprising carbon atoms and 1-4 heteroatoms selected from N, O, and S(O)$_p$; alternatively two R$^a$ on adjacent or the same carbon atom form a cyclic acetal of the formula —O—(CH$_2$)$_n$—O—, or —O—CF$_2$—O—, wherein n is selected from 1 or 2;

$R^b$ is hydrogen, $C_{1-6}$ alkyl substituted with 0-2 R$^d$, $C_{1-6}$ haloalkyl, $C_{3-6}$ cycloalkyl substituted with 0-2 R$^d$, or —(CH$_2$)$_r$-phenyl substituted with 0-2 R$^d$;

$R^c$ is $C_{1-6}$ alkyl substituted with 0-1 R$^f$, $C_{3-6}$ cycloalkyl, or —(CH$_2$)$_r$-phenyl substituted with 0-1 R$^f$;

$R^d$ is hydrogen, F, Cl, Br, OCF$_3$, CF$_3$, CN, NO$_2$, —OR$^e$, —(CH$_2$)$_r$C(O)R$^e$, —NR$^e$R$^e$, —NR$^e$C(O)OR$^c$, $C_{1-6}$ alkyl, or —(CH$_2$)$_r$-phenyl;

$R^e$ is hydrogen, $C_{1-6}$ alkyl, $C_{3-6}$ cycloalkyl, or —(CH$_2$)$_r$-phenyl;

$R^f$ is hydrogen, halo, NH$_2$, OH, or OCH$_3$;

r is 0, 1, 2, 3, or 4; and p is 0, 1, or 2.

7. The compound according to claim 6 having formula (IIa), (IIb), or (IIc):

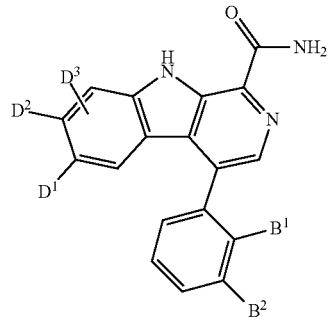
(IIa)

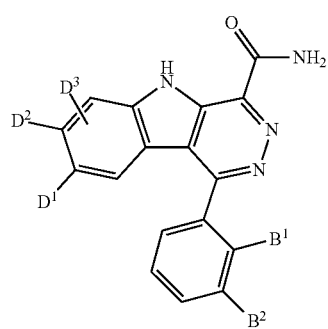
(IIb)

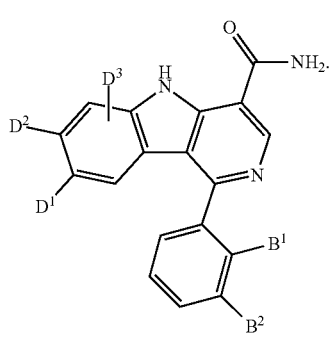
(IIc)

8. The compound according to claim 6 having formula (IId) or (IIe):

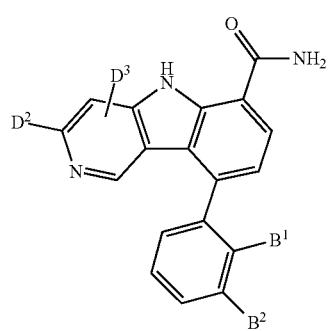
(IId)

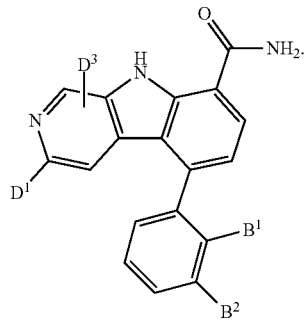
(IIe)

9. The compound according to claim 6 having formula (IIf) or (IIg):

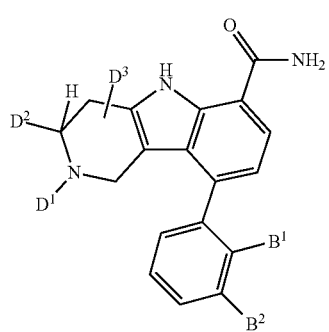
(IIf)

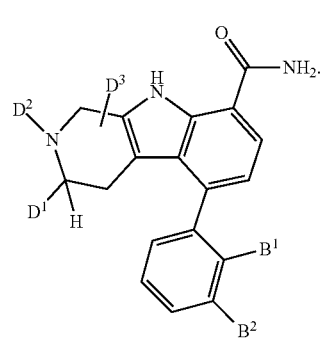
(IIg)

10. The compound according to claim 6 wherein $B^1$ is $C_{1-4}$ alkyl or halogen;

$B^2$ is $R^1$, halogen, $C_{1-4}$ alkyl, —$NR^{11}C(=O)R^1$, —$NR^{11}C(=O)OR^1$, —$NR^{11}C(=O)NR^{11}R^1$, or —$NR^{11}R^1$;

$R^1$ is hydrogen, $C_{1-4}$ alkyl, indane or phenyl substituted with 0-3 $R^{1a}$, a 5-10 membered heterocyclyl containing 1-4 heteroatoms selected from N, O, and S, substituted with 0-3 $R^{1a}$, or a 5-10 membered heteroaryl containing 1-4 heteroatoms selected from N, O, and S, substituted with 0-3 $R^{1a}$, wherein the heterocyclyl or heteroaryl is selected from

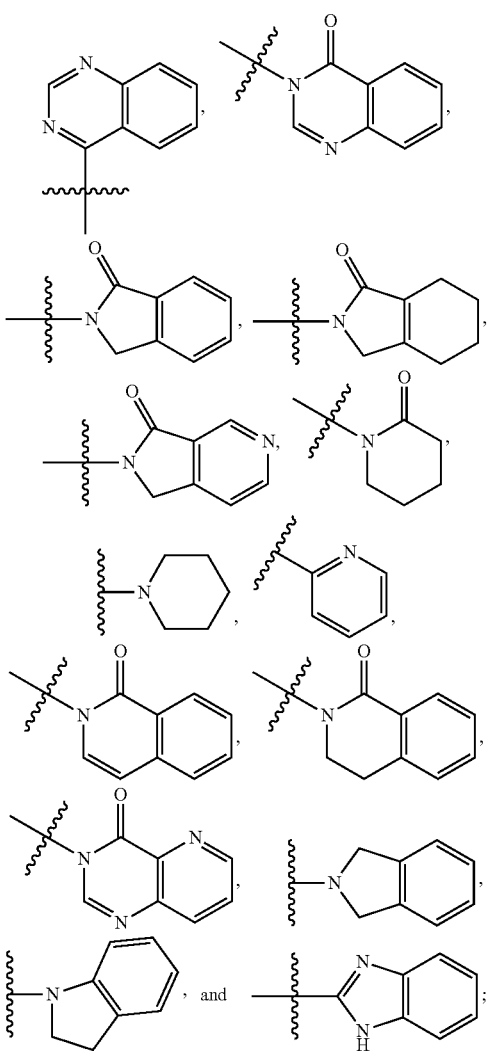

$R^{1a}$ is F, Cl, Br, —NR$^{11}$,R$^{11}$, —OR$^b$, or C$_{1-6}$ alkyl substituted with 0-1 R$^a$;

D$^1$ and D$^2$ are independently R$^2$, halogen, —OR$^2$, —C(=O)R$^2$, —C(=O)OR$^2$, —C(=O)NR$^{11}$R$^2$, —NR$^{11}$C(=O)R$^2$, —NR$^{11}$S(=O)$_2$R$^2$, —SR$^2$, —S(=O)R$^2$, —S(=O)$_2$R$^2$, or —NR$^{11}$R$^2$; alternatively D$^1$ and D$^2$ join to form —O—CH$_2$—O—;

R$^2$ is hydrogen, C$_{1-6}$ alkyl substituted with 0-3 R$^{2a}$, a 5-10 membered heterocyclyl containing 1-4 heteroatoms selected from N, O, and S, substituted with 0-3 R$^{2a}$, wherein the heterocyclyl is selected from pyrimidinyl, morpholinyl, piperidinyl, pyrrolidinyl, pyridinyl, tetrahydropyranyl, or tetrahydrofuranyl;

R$^{2a}$ is hydrogen, CN, C$_{1-6}$ alkyl, —N(CH$_3$)$_2$ or —OR$^b$;

R$^{11}$ is independently hydrogen, C$_{1-4}$ alkyl, or —CH$_2$-phenyl;

R$^a$ is hydrogen, F, Cl, Br, OCF$_3$, CF$_3$, CHF$_2$, CN, NO$_2$, —OR$^b$, —SR$^b$, —C(O)R$^b$, —C(O)OR$^b$, —OC(O)R$^b$, —NR$^{11}$R$^{11}$, —C(O)NR$^{11}$R$^{11}$, —NR$^b$C(O)R$^c$, —NR$^b$C(O)OR$^c$, —NR$^b$C(O)NR$^{11}$R$^{11}$, —S(O)$_p$NR$^{11}$R$^{11}$, —NR$^b$S(O)$_p$R$^c$, —S(O)R$^c$, —S(O)$_2$R$^c$, C$_{1-6}$ alkyl substituted with 0-1 R$^f$, C$_{1-6}$ haloalkyl, —(CH$_2$)$_r$-3-6 membered carbocycle, or —(CH$_2$)$_r$-5-7 membered heterocycle comprising carbon atoms and 1-4 heteroatoms selected from N, O, and S(O)$_p$, wherein the heterocycle is pyrrolidinyl, pyrrolyl, pyrazolyl, imidazolyl, oxazolyl, isoxazolyl, thiazolyl, isothiazolyl, furyl, thienyl, pyridyl, pyrazinyl, pyrimidinyl, morpholinyl, thiamorpholinyl, triazolyl, indolyl, benzothiazolyl, benzoxazolyl, benzothienyl, quinolinyl, isoquinolinyl, tetrahydroisoquinolinyl, benzimidazolyl, benzopyranyl, benzofuryl, benzisothiazolyl, benzisoxazolyl, benzodiazinyl, or benzofurazanyl;

R$^b$ is hydrogen, C$_{1-4}$ alkyl substituted with 0-2 R$^d$, C$_{1-4}$ haloalkyl, C$_{3-6}$ cycloalkyl substituted with 0-2 R$^d$, or —(CH$_2$)$_r$-phenyl substituted with 0-2 R$^d$;

R$^c$ is C$_{1-4}$ alkyl substituted with 0-1 R$^f$, C$_{3-6}$ cycloalkyl, or —(CH$_2$)$_r$-phenyl substituted with 0-1 R$^f$;

R$^d$ is hydrogen, F, Cl, Br, OCF$_3$, CF$_3$, CN, NO$_2$, —OR$^e$, —C(O)R$^e$, —NR$^e$R$^e$, —NR$^e$C(O)OR$^c$, C$_{1-6}$ alkyl, or —(CH$_2$)$_r$-phenyl;

R$^e$ is hydrogen, C$_{1-4}$alkyl, C$_{3-6}$ cycloalkyl, or —(CH$_2$)$_r$-phenyl;

R$^f$ is hydrogen, halo, or NH$_2$; and r is 0 or 1.

11. The compound according to claim 10, wherein

R$^a$ is hydrogen, F, Cl, Br, OCF$_3$, CF$_3$, CHF$_2$, CN, NO$_2$, —OR$^b$, —SR$^b$, —C(O)R$^b$, —C(O)OR$^b$, —OC(O)R$^b$, —NR$^{11}$R$^{11}$, —C(O)NR$^{11}$R$^{11}$, —NR$^b$C(O)R$^c$, —NR$^b$C(O)OR$^c$, —NR$^b$C(O)NR$^{11}$R$^{11}$, —S(O)$_p$NR$^{11}$R$^{11}$, —NR$^b$S(O)$_p$R$^c$, —S(O)R$^c$, —S(O)$_2$R$^c$, C$_{1-6}$ alkyl, C$_{1-6}$ haloalkyl, —(CH$_2$)$_r$-3-6 membered carbocycle phenyl, or —(CH$_2$)$_r$-5-7 membered heterocycle comprising carbon atoms and 1-4 heteroatoms selected from N, O, and S(O)$_p$, wherein the heterocycle is thiazolyl, pyridinyl, piperidinyl, morpholinyl, piperazinyl, pyrrolidinyl, or pyrrolidin-one, R$^b$ is hydrogen, C$_{1-4}$ alkyl substituted with 0-2 R$^d$, C$_{1-4}$ haloalkyl, C$_{3-6}$ cycloalkyl substituted with 0-2 R$^d$, or —(CH$_2$)$_r$-phenyl substituted with 0-2 R$^d$;

R$^c$ is C$_{1-4}$ alkyl, C$_{3-6}$ cycloalkyl, or —(CH$_2$)$_r$-phenyl;

R$^d$ is hydrogen, F, Cl, Br, OCF$_3$, CF$_3$, CN, NO$_2$, —OR$^e$, —C(O)R$^e$, —NR$^e$R$^e$, —NHC(O)OR$^c$, C$_{1-4}$ alkyl, or —(CH$_2$)$_r$-phenyl; and R$^e$ is hydrogen, C$_{1-4}$ alkyl, C$_{3-6}$ cycloalkyl, or —(CH$_2$)$_r$-phenyl.

12. The compound according to claim 10 wherein

B$^1$ is methyl or fluorine;

B$^2$ is hydrogen, R$^{1b}$, —NR$^{11}$C(=O)R$^{1c}$, —NR$^{11}$C(=O)NR$^{11}$R$^{1d}$, or —NR$^{11}$R$^{1e}$;

R$^{1b}$ is

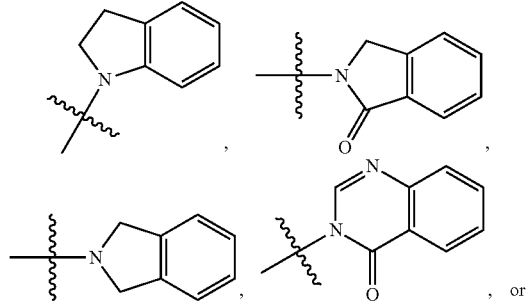

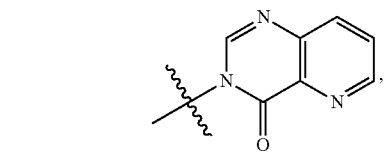

any of which are substituted with 0-3 $R^{1a}$;

$R^{1c}$ is $C_{1-6}$ alkyl,

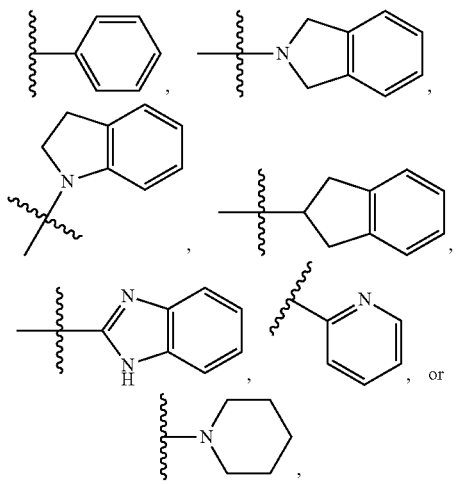

any of which are substituted with 0-2 $R^a$;

$R^{1d}$ is phenyl substituted with 0-1 $R^{1a}$;

$R^{1e}$ is quinazolinyl substituted with 0-1 $R^{1a}$;

$R^{1a}$ is selected from hydrogen, F, Cl, CN, methyl, ethyl, $CF_3$, OH, and O-methyl;

$D^1$ and $D^2$ are independently selected from $R^2$, F, Cl, Br, —$OR^2$, —C(=O)$R^2$, —C(=O)$OR^2$, —C(=O)$NR^{11}R^2$, —S(=O)$_2R^2$, —S(=O)$R^2$, —$SR^2$, —$NR^{11}$C(=O)$R^2$, —$NR^{11}$S(=O)$_2R^2$, and —$NR^{11}R^2$;

$R^2$ is hydrogen, $C_{1-6}$ alkyl substituted with 0-3 $R^{2a}$, piperazinyl, pyrrolidinyl, tetrahydrofuranyl, tetrahydropyranyl, morpholinyl, piperidinyl, pyridinyl, imidazolyl, pyrazinyl, or pyrimidinyl, any of which are substituted with 0-3 $R^{2a}$;

$R^{2a}$ is hydrogen, CN, —$OR^b$, or morpholinyl;

$R^{11}$ is hydrogen or $C_{1-4}$ alkyl;

$R^a$ is hydrogen, F, Cl, $C_{1-4}$ alkyl, —$OR^b$, —$NR^{11}R^{11}$, imidazolyl, or morpholinyl; and $R^b$ is hydrogen or $C_{1-6}$ alkyl.

13. A pharmaceutical composition comprising one or more compounds according to claim 1 and a pharmaceutically acceptable carrier or diluent.

14. A method for treating a disease comprising the administration to a subject in need thereof a therapeutically-effective amount of at least one compound according toclaim 1, wherein said disease is selected from systemic lupus erythematosus (SLE), rheumatoid arthritis, multiple sclerosis (MS), or transplant rejection.

15. A method of inhibiting Bruton's tyrosine kinase (Btk) comprising administering to a subject in need thereof a therapeutically effective amount of at least one compound according to claim 1, wherein said disease is selected from systemic lupus erythematosus (SLE), rheumatoid arthritis, multiple sclerosis (MS), or transplant rejection.

* * * * *

UNITED STATES PATENT AND TRADEMARK OFFICE
CERTIFICATE OF CORRECTION

PATENT NO. : 8,685,969 B2  Page 1 of 1
APPLICATION NO. : 13/704297
DATED : April 1, 2014
INVENTOR(S) : Chunjian Liu et al.

It is certified that error appears in the above-identified patent and that said Letters Patent is hereby corrected as shown below:

In the Claims:

Claim 1, col. 238, line 67, delete "—$NR^1$" and insert -- —$NR^{11}$ --;

Claim 5, col. 241, line 55, delete "—$S(O)_2R^2$ —$S(O)R^2$ —$SR^2$, —$NR^{11}C(O)R^2$" and insert -- —$S(=O)_2R^2$ —$S(=O)R^2$ —$SR^2$, —$NR^{11}C(=O)R^2$ --;

Claim 5, col. 241, line 56, delete "—$NR^{11}C(O)NR^{11}R^2$," and insert -- —$NR^{11}C(=O)NR^{11}R^2$, --;

Claim 6, col. 242, line 11, delete "according claim" and insert -- according to claim --;

Claim 6, col. 244, line 1, delete "—$C(R^{11})_2)_rR^2$," and insert -- —$(C(R^{11})_2)_rR^2$, --;

Claim 10, col. 247, line 43, delete "—$NR^{11}$, $R^{11}$" and insert -- —$NR^{11}R^{11}$ --; and Claim 14, col. 250, line 19, delete "toclaim" and insert -- to claim --, therefor.

Signed and Sealed this
Twenty-fourth Day of February, 2015

Michelle K. Lee
*Deputy Director of the United States Patent and Trademark Office*